United States Patent
Yang et al.

(10) Patent No.: US 11,655,206 B2
(45) Date of Patent: May 23, 2023

(54) NITROGEN-CONTAINING COMPOUND, ELECTRONIC ELEMENT, AND ELECTRONIC DEVICE

(71) Applicant: Shaanxi Lighte Optoelectronics Material Co., Ltd., Xi'an (CN)

(72) Inventors: Min Yang, Xi'an (CN); Peng Nan, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/787,700

(22) PCT Filed: Mar. 22, 2021

(86) PCT No.: PCT/CN2021/082174
§ 371 (c)(1),
(2) Date: Jun. 21, 2022

(87) PCT Pub. No.: WO2021/218491
PCT Pub. Date: Nov. 4, 2021

(65) Prior Publication Data
US 2023/0099039 A1    Mar. 30, 2023

(30) Foreign Application Priority Data

Apr. 27, 2020  (CN) .......................... 202010346414.5
Aug. 20, 2020  (CN) .......................... 202010844829.5

(51) Int. Cl.
*C07C 211/54*   (2006.01)
*H01L 51/00*    (2006.01)
(Continued)

(52) U.S. Cl.
CPC .......... *C07C 211/54* (2013.01); *C07C 255/59* (2013.01); *C07D 209/82* (2013.01);
(Continued)

(58) Field of Classification Search
CPC ............... C07C 211/45; C07C 2603/18; C07C 2603/74
See application file for complete search history.

(56) References Cited

FOREIGN PATENT DOCUMENTS

| CN | 107459466 A | 12/2017 |
|---|---|---|
| CN | 110128279 A | 8/2019 |

(Continued)

OTHER PUBLICATIONS

International Search Report from corresponding International Application No. PCT/CN2021/082174, dated May 17, 2021, 6 pages with translation.

*Primary Examiner* — Vu A Nguyen
(74) *Attorney, Agent, or Firm* — Tucker Ellis LLP

(57) ABSTRACT

Provided are a nitrogen-containing compound, an electronic element, and an electronic device, and the present disclosure belongs to the technical field of organic materials. The structure of the nitrogen-containing compound is as shown in chemical formula (1); and the nitrogen-containing compound can improve the properties of an electronic element.

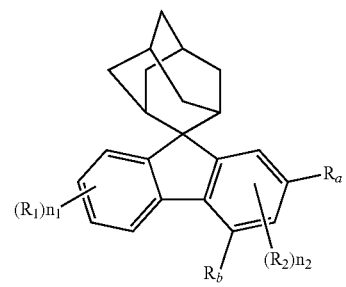

(1)

10 Claims, 2 Drawing Sheets

(51) Int. Cl.
    *H01L 51/50*         (2006.01)
    *C07D 209/82*       (2006.01)
    *C07D 307/91*       (2006.01)
    *C07C 255/59*       (2006.01)
    *C07D 213/38*       (2006.01)
    *C07D 333/76*       (2006.01)

(52) U.S. Cl.
    CPC ......... *C07D 213/38* (2013.01); *C07D 307/91* (2013.01); *C07D 333/76* (2013.01); *H10K 50/18* (2023.02); *H10K 85/615* (2023.02); *H10K 85/622* (2023.02); *H10K 85/633* (2023.02); *H10K 85/652* (2023.02); *H10K 85/654* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| | | | | |
|---|---|---|---|---|
| CN | 111039881 | A | 4/2020 | |
| CN | 111138298 | A | 5/2020 | |
| CN | 111777517 | A | 10/2020 | |
| CN | 111995533 | A | 11/2020 | |
| CN | 112110825 | A | 12/2020 | |
| CN | 112480011 | A | 3/2021 | |
| CN | 112759582 | A | 5/2021 | |
| CN | 113121408 | A | 7/2021 | |
| KR | 20200037732 | A | 4/2020 | |
| WO | WO-2020050623 | A1 * | 3/2020 | ........... C07C 211/61 |
| WO | 2020080872 | A1 | 4/2020 | |
| WO | WO-2020080872 | A1 * | 4/2020 | .............. C07F 5/027 |

\* cited by examiner

NITROGEN-CONTAINING COMPOUND, ELECTRONIC ELEMENT, AND ELECTRONIC DEVICE

CROSS REFERENCE TO RELATED APPLICATIONS

The present application claims the priority of the Chinese patent application No. CN202010346414.5 filed on Apr. 27, 2020 and the Chinese patent application No. CN202010844829.5 filed on Aug. 20, 2020, and the contents of the Chinese patent applications are hereby incorporated by reference in their entirety as a part of the application.

TECHNICAL FIELD

The present disclosure relates to the technical field of organic materials, in particular to a nitrogen-containing compound, an electronic element using the nitrogen-containing compound, and an electronic device using the electronic element.

BACKGROUND

With the development of electronic technology and the progress of material science, the application scope of electronic elements for realizing electroluminescence or photoelectric conversion becomes more and more widely. Such electronic element generally includes a cathode and an anode which are disposed oppositely, and a functional layer disposed between the cathode and the anode. The functional layer is composed of multiple organic or inorganic film layers and generally includes an energy conversion layer, a hole transport layer disposed between the energy conversion layer and the anode and an electron transport layer disposed between the energy conversion layer and the cathode.

For example, when the electronic element is an organic electroluminescent device, the electronic element generally includes an anode, a hole transport layer, an electroluminescent layer as an energy conversion layer, an electron transport layer and a cathode which are sequentially stacked. When a voltage is applied to the cathode and the anode, the two electrodes generate an electric field. Under the action of the electric field, the electrons on a cathode side move towards the electroluminescent layer and the holes on an anode side also move towards the electroluminescent layer, so the electrons and the holes are combined in the electroluminescent layer to form excitons, the excitons are in an excited state and release energy outwards, and then the electroluminescent layer emits light outwards.

At present, in terms of organic electroluminescent materials, the performance of green light materials is relatively good, but the performance of the green light materials and blue light materials does not meet commercialization requirements at present, and the service life of the green light materials and the blue light materials is only dozens of hours in the aspect of colorization. Thus, it is necessary to develop new materials, thus improving the performance of electronic elements.

The information disclosed by the background part is only used for enhancing the understanding of the background of the present disclosure, so the information can include information which does not constitute the prior art known to those of ordinary skill in the art.

SUMMARY

The present disclosure aims to provide a nitrogen-containing compound, an electronic element and an electronic device so as to improve the performance of the electronic element and the electronic device.

In order to realize the above inventive purpose, the present disclosure adopts the following technical solution:

According to a first aspect of the present disclosure, there is provided a nitrogen-containing compound having a structure as shown in a chemical formula 1:

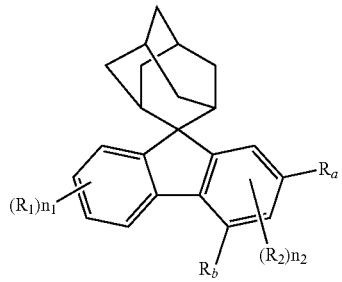

Chemical formula 1

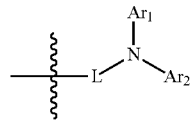

Chemical formula 1-1 wherein

represents a chemical bond;

$R_a$ and $R_b$ are independently selected from hydrogen or a group shown in a chemical formula 1-1, and there is only one of $R_a$ and $R_b$ is the group shown in the chemical formula 1-1;

L is selected from a single bond, substituted or unsubstituted arylene with a total carbon atom number of 6 to 30, or substituted or unsubstituted heteroarylene with a total carbon atom number of 3 to 30;

$R_1$ is selected from deuterium, cyano, halogen group, substituted or unsubstituted alkyl with a total carbon atoms number of 1 to 20, substituted or unsubstituted aryl with a total carbon atoms number of 6 to 30, or substituted or unsubstituted heteroaryl with a total carbon atoms number of 3 to 30, and the $R_1$ is not carbazolyl or N-phenylcarbazolyl;

$R_2$ is selected from deuterium, cyano, halogen group, substituted or unsubstituted alkyl with a total carbon atoms number of 1 to 20, substituted or unsubstituted aryl with a total carbon atoms number of 6 to 30, or substituted or unsubstituted heteroaryl with a total carbon atoms number of 3 to 30; and at least one of the $R_1$ and the $R_2$ is selected from substituted or unsubstituted aryl with a total carbon atoms number of 6 to 30, or substituted or unsubstituted heteroaryl with a total carbon atoms number of 3 to 30;

$n_1$ and $n_2$ are the number of $R_1$ and $R_2$ respectively;

$n_1$ is selected from 0, 1, 2, 3 or 4, and when $n_1$ is greater than 1, any two $R_1$ are the same or different;

$n_2$ is selected from 0, 1, 2 or 3, and when $n_2$ is greater than 1, any two $R_2$ are the same or different;

$n_1+n_2 \geq 1$;

$Ar_1$ and $Ar_2$ are the same or different, and are independently selected from substituted or unsubstituted alkyl with a total carbon atoms number of 1 to 20, substituted or unsubstituted cycloalkyl with a total carbon atoms number of 3 to 20, substituted or unsubstituted aryl with a total carbon atoms number of 6 to 30, or substituted or unsubstituted heteroaryl with a total carbon atoms number of 3 to 30, the $Ar_1$ is not 9,9-diphenylfluorenyl, and the $Ar_2$ is not 9,9-diphenylfluorenyl; and the substituents in the L, $R_1$, $R_2$, $Ar_1$ and $Ar_2$ are the same or different, and are independently selected from deuterium, halogen group, cyano, heteroaryl with 3 to 20 carbon atoms, aryl with 6 to 20 carbon atoms which can be optionally substituted with 0, 1, 2, 3, 4 or 5 substituents selected from deuterium, fluorine, chlorine, cyano, methyl or tert-butyl, haloaryl with 6 to 20 carbon atoms, trialkylsilyl with 3 to 12 carbon atoms, triarylsilyl with 18 to 24 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, or phosphinyloxy with 6 to 18 carbon atoms.

The compound provided in the present disclosure has good hole transport properties, and can be applied between an anode and an energy conversion layer of an organic electroluminescent device and a photoelectric conversion device, so that the hole transport efficiency between the anode and the energy conversion layer is improved; and the luminous efficiency of the organic electroluminescent device and the power generation efficiency of the photoelectric conversion device are further improved.

According to the present disclosure, an arylamine group is introduced into an adamantane spiro-bonded fluorene group, and the adamantane spiro-bonded fluorene group has a substituent group of aryl-type or heteroaryl-type, which can increase the steric hindrance effect of the compound, and the glass transition temperature of the material can be effectively increased; and the adamantyl which is spirobonded to the fluorenyl has a large space volume and strong rigidity, so that the structure has relatively high electron tolerance and film-forming properties, and the efficiency and the service life of the organic electroluminescent device and the photoelectric conversion device can be improved. Secondly, the compound provided by the present disclosure has relatively low working voltage.

Not only that, the compound also has better thermal stability, and can maintain structural stability at high temperature for a long time. Under the same molecular weight, the evaporation temperature decreases, which makes the nitrogen-containing compound of the present disclosure have better physical and thermal stability when being used for mass production, and further facilitates the mass production stability of organic electroluminescent devices.

According to a second aspect of the present disclosure, there is provided an electronic element, including an anode and a cathode disposed oppositely, and a functional layer disposed between the anode and the cathode; wherein the functional layer contains the above nitrogen-containing compound. According to one embodiment of the present disclosure, the electronic element is an organic electroluminescent device. According to another embodiment of the present disclosure, the electronic element is a photoelectric conversion device.

According to a third aspect of the present disclosure, there is provided an electronic device, including the above electronic element.

BRIEF DESCRIPTION OF THE DRAWINGS

The above and other features and advantages of the present disclosure will become more obvious by referring to the drawings to describe embodiments in detail.

DESCRIPTION OF REFERENCE SIGNS

Figure 1:
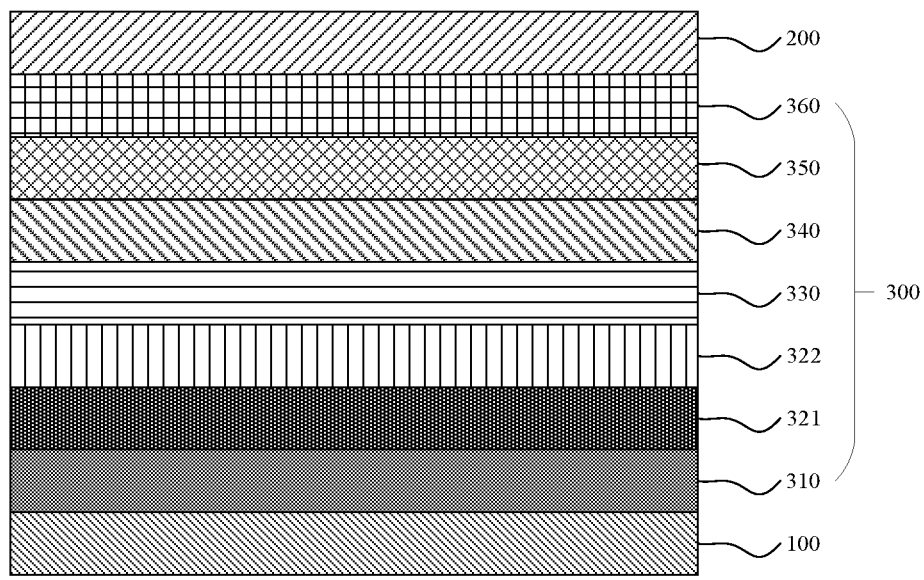
FIG. 1 is a structural schematic diagram of an organic electroluminescent device according to the embodiments of the present disclosure.

100, anode; 200, cathode; 300, functional layer; 310, hole injection layer; 321, hole transport layer; 322, electron blocking layer; 330, organic electroluminescent layer; 340, hole blocking layer; 350, electron transport layer; 360, electron injection layer; 370, photoelectric conversion layer; 400, first electronic device; and 500, second electronic device.

DETAILED DESCRIPTION

Embodiments will now be described more comprehensively with reference to the accompanying drawings. However, the embodiments can be implemented in a variety of forms, and should not be understood as limited to the embodiments set forth herein; and on the contrary, these examples are provided such that the present disclosure will be more comprehensive and complete, and the concepts of the embodiments are comprehensively conveyed to those skilled in the art. The described features, structures, or characteristics may be incorporated in one or more embodiments in any suitable manner. In the following description, many specific details are provided to give a sufficient understanding of the embodiments of the present disclosure.

In the drawings, for clearness, the thickness of regions and layers may be exaggerated. The same reference signs in the drawings represent the same or similar structure, so that detailed description will be omitted.

The described features, structures, or characteristics may be incorporated in one or more embodiments in any suitable manner. In the following description, many specific details are provided to give a sufficient understanding of the embodiments of the present disclosure. However, those skilled in the art will realize that the technical solution of the present disclosure may be practiced without one or more of the specific details, or other methods, components, materials, etc. may be employed. In other cases, well-known structures, materials, or operations are not shown or described in detail to avoid obscuring the primary technical ideas of the present disclosure.

In a first aspect, the present disclosure provides a nitrogen-containing compound, having a structural as shown in a chemical formula 1:

Chemical formula 1

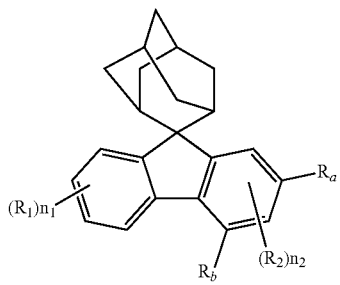

Chemical formula 1-1

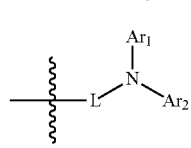

wherein

represents a chemical bond;

$R_a$ and $R_b$ are independently selected from hydrogen or a group shown in a chemical formula 1-1, and there is only one of $R_a$ and $R_b$ is the group shown in the chemical formula 1-1;

L is selected from a single bond, substituted or unsubstituted arylene with a total carbon atoms number of 6 to 30, or substituted or unsubstituted heteroarylene with a total carbon atoms number of 3 to 30;

$R_1$ is selected from deuterium, cyano, halogen group, substituted or unsubstituted alkyl with a total carbon atoms number of 1 to 10, substituted or unsubstituted aryl with a total carbon atoms number of 6 to 30, or substituted or unsubstituted heteroaryl with a total carbon atoms number of 3 to 30, and the $R_1$ is not carbazolyl or N-phenylcarbazolyl;

$R_2$ is selected from deuterium, cyano, halogen group, substituted or unsubstituted alkyl with a total carbon atoms number of 1 to 20, substituted or unsubstituted aryl with a total carbon atoms number of 6 to 30, or substituted or unsubstituted heteroaryl with a total carbon atoms number of 3 to 30; and at least one of the $R_1$ and the $R_2$ is selected from substituted or unsubstituted aryl with a total carbon atoms number of 6 to 30, or substituted or unsubstituted heteroaryl with a total carbon atoms number of 3 to 30;

$n_1$ and $n_2$ are the number of $R_1$ and $R_2$ respectively;

$n_1$ is selected from 0, 1, 2, 3 or 4, and when $n_1$ is greater than 1, any two $R_1$ are the same or different;

$n_2$ is selected from 0, 1, 2 or 3, and when $n_2$ is greater than 1, any two $R_2$ are the same or different;

$n_1+n_2 \geq 1$;

$Ar_1$ and $Ar_2$ are the same or different, and are independently selected from substituted or unsubstituted alkyl with a total carbon atoms number of 1 to 20, substituted or unsubstituted cycloalkyl with a total carbon atoms number of 3 to 20, substituted or unsubstituted aryl with a total carbon atoms number of 6 to 30, or substituted or unsubstituted heteroaryl with a total carbon atoms number of 3 to 30, the $Ar_1$ is not 9,9-diphenylfluorenyl, and the $Ar_2$ is not 9,9-diphenylfluorenyl; and the substituents in the L, $R_1$, $R_2$, $Ar_1$ and $Ar_2$ are the same or different, and are independently selected from deuterium, halogen group, cyano, heteroaryl with 3 to 20 carbon atoms, aryl with 6 to 20 carbon atoms which can be optionally substituted by 0, 1, 2, 3, 4 or 5 substituents selected from deuterium, fluorine, chlorine, cyano, methyl or tert-butyl, haloaryl with 6 to 20 carbon atoms, trialkylsilyl with 3 to 12 carbon atoms, triarylsilyl with 18 to 24 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, or phosphinyloxy with 6 to 18 carbon atoms.

Wherein the "aryl with 6 to 20 carbon atoms which can be optionally substituted by 0, 1, 2, 3, 4 or 5 substituents selected from deuterium, fluorine, chlorine, cyano, methyl or tert-butyl" means that the aryl can be substituted by one or more groups selected from deuterium, fluorine, chlorine, cyano, methyl or tert-butyl, and also can not be substituted by deuterium, fluorine, chlorine, cyano, methyl or tert-butyl, and when the number of substituents on the aryl is greater than or equal to 2, the substituents may be the same or different.

Optionally, the substituents in the L, $R_1$, $R_2$, $Ar_1$ and $Ar_2$ are independently selected from deuterium, halogen group, cyano, heteroaryl with 3 to 18 carbon atoms, aryl with 6 to 18 carbon atoms, haloaryl with 6 to 20 carbon atoms, trialkylsilyl with 3 to 12 carbon atoms, triarylsilyl with 18 to 24 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, or phosphinyloxy with 6 to 18 carbon atoms.

In the present disclosure, since adamantane is of a three-dimensional structure, in a compound structure diagram, due to different drawing angles, different plane shapes can be presented. The ring structures formed on 9,9-dimethylfluorene are all adamantane, and the connection positions are the same. For example:

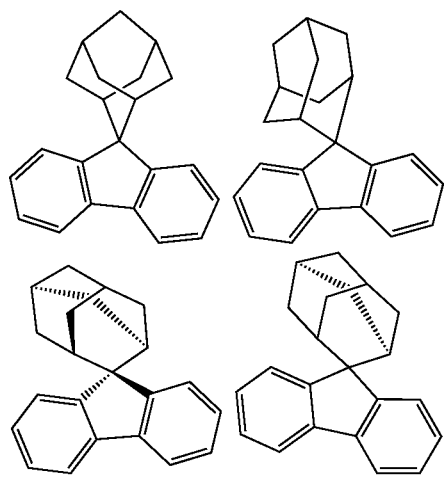

all have the same structure.

The compound provided in the present disclosure has good hole transport properties, and can be applied between an anode and an energy conversion layer of an organic electroluminescent device and a photoelectric conversion device, so that the hole transport efficiency between the anode and the energy conversion layer is improved; and the luminous efficiency of the organic electroluminescent device and the power generation efficiency of the photoelectric conversion device are further improved.

According to the present disclosure, an arylamine group is introduced into an adamantane spiro-bonded fluorene group, and the adamantane spiro-bonded fluorene group has a substituent group of aryl-type or heteroaryl-type, which can increase the steric hindrance effect of the compound, and the glass transition temperature of the material can be effectively increased; and the adamantyl which is spiro-bonded to the fluorenyl has a large space volume and strong rigidity. This structure has higher electron tolerance and film-forming properties, and the efficiency and the service life of the organic electroluminescent device and the photoelectric conversion device can be improved. Not only that, the compound also has better thermal stability and can maintain structural stability at high temperature for a long time, especially, the linking groups L are in para-position connection, so that under the same molecular weight, the evaporation temperature is decreased, the hole transport capability is improved, and the voltage is decreased.

In the present disclosure, the adopted description modes "each . . . are independently", " . . . are respectively and independently" and " . . . are independently selected from" can be interchanged, and should be understood in a broad sense, which means that in different groups, specific options expressed between the same symbols do not influence each other, or in a same group, specific options expressed between the same symbols do not influence each other. For example, the meaning of

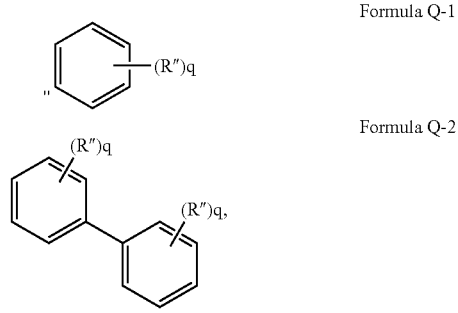

Formula Q-1

Formula Q-2 wherein each q is independently 0, 1, 2 or 3, and each R" is independently selected from hydrogen, deuterium, fluorine or chlorine" is as follows: the formula Q-1 represents that q substituents R" exist on a benzene ring, each R" can be the same or different, and options of each R" do not influence each other; and the formula Q-2 represents that each benzene ring of biphenyl has q substituents R", the number q of the substituents R" on the two benzene rings can be the same or different, each R" can be the same or different, and options of each R" do not influence each other.

In the present disclosure, the total number of substituted or unsubstituted carbon atoms of L, $Ar_1$, $Ar_2$, $R_1$, $R_2$, $R_a$ and $R_b$ refers to the number of all carbon atoms. For example, if L is selected from substituted arylene with a total carbon atoms number of 12, the number of all carbon atoms of the arylene and substituents on the arylene is 12. For example, if $Ar_1$ is

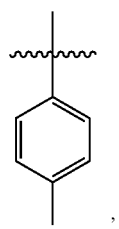 [SMILES: *c1ccc(C)cc1]

the total number of carbon atoms is 7; and if L is

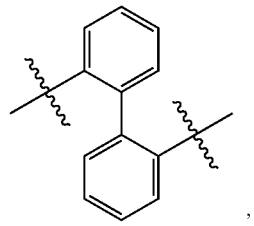 [SMILES: *c1ccccc1-c1ccccc1*]

the total number of carbon atoms is 12.

In the present disclosure, when no specific definition is additionally provided, 'hetero' means that a functional group includes at least one heteroatom such as B, N, O, S, Se, Si or P, and the remaining atoms are carbon and hydrogen. An unsubstituted alkyl may be a "saturated alkyl group" without any double bond or triple bond.

In the present disclosure, the "alkyl" may include linear alkyl or branched alkyl. The alkyl may have 1 to 20 carbon atoms, in the present disclosure, a numerical range such as "1 to 20" refers to each integer in the given range; for example, "1 to 20 carbon atoms" refer to alkyl that may include 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The alkyl may also be medium sized alkyl with 1 to 10 carbon atoms. The alkyl may also be lower alkyl with 1 to 6 carbon atoms. In addition, the alkyl may be substituted or unsubstituted.

Optionally, alkyl is selected from alkyl with 1 to 6 carbon atoms, and specific examples include but are not limited to methyl, ethyl, n-propyl, isopropyl, n-butyl, isobutyl, sec-butyl, tert-butyl, amyl and hexyl.

In the present disclosure, aryl refers to an optional functional group or substituent derived from an aromatic carbocyclic ring. The aryl may be monocyclic aryl or polycyclic aryl. In other words, the aryl can be monocyclic aryl, fused ring aryl, which formed by two or more monocyclic aryl conjugatedly connected through carbon-carbon bonds, formed by a monocyclic aryl and fused ring aryl conjugatedly connected through a carbon-carbon bond, or formed by two or more fused ring aryl conjugatedly connected through carbon-carbon bonds. That is, two or more aromatic groups conjugatedly connected through carbon-carbon bonds can also be regarded as aryl groups in the present disclosure. Among them, the aryl does not contain heteroatoms such as B, N, O, S, P, Si and the like. For example, in the present disclosure, examples of the aryl may include, but are not limited to, phenyl, naphthyl, fluorenyl, anthryl, phenanthryl, biphenyl, terphenyl, quaterphenyl, quinquephenyl, benzo[9,10]phenanthryl, pyrenyl, benzofluoranthenyl, chrysenyl, and the like.

In the present disclosure, the substituted aryl refers to one or two or more hydrogen atoms in the aryl are substituted by a group such as deuterium atom, halogen group, —CN, aryl, heteroaryl, trialkylsilyl, alkyl, cycloalkyl, alkoxy, alkylthio and the like.

In the present disclosure, specific examples of aryl as a substituent include, but are not limited to, phenyl, naphthyl, biphenyl, terphenyl, phenanthryl and fluorenyl.

It should be understood that the number of carbon atoms in the substituted aryl refers to the total number of carbon atoms of the aryl and substituents on the aryl, for example, the substituted aryl with 18 carbon atoms means that the total number of carbon atoms of the aryl and the substituents is 18. That is, in the present disclosure, the number of carbon atoms of the aryl is selected from 6, 7, 8, 9, 10, 11, 12, 13, 14, 15, 16, 17, 18, 19, 20, 21, 22, 23, 24, 25, 26, 27, 28, 29 or 30.

In the present disclosure, the fluorenyl group may be substituted, and two substituents may be combined with each other to form a spiro structure, and specific examples include, but are not limited to, the following structures:

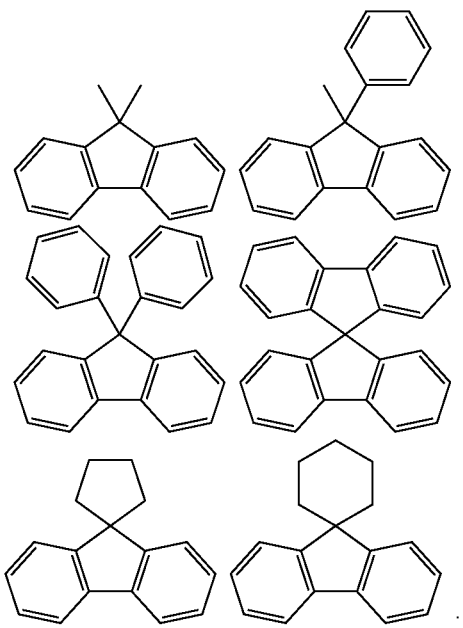

In particular, $Ar_1$ is not

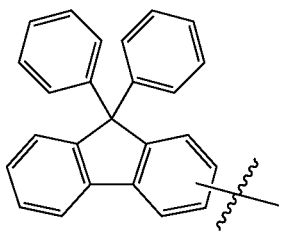

and $Ar_2$ is not

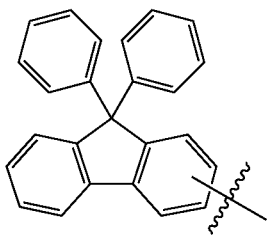

In the present disclosure, the heteroaryl refers to a monovalent aromatic ring containing at least one heteroatom in a ring or its derivative, and the heteroatom can be at least one of B, O, N, P, Si and S. The heteroaryl may be monocyclic heteroaryl or polycyclic heteroaryl. In other words, the heteroaryl may be a single aromatic ring system or a polycyclic ring systems formed by multiple aromatic rings conjugatedly connected through carbon-carbon bonds, where any one aromatic ring system is an aromatic monocyclic ring or one aromatic fused ring. Exemplarily, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited thereto. Wherein the thienyl, furyl, phenanthrolinyl and the like are heteroaryl of the single aromatic ring system, and the N-arylcarbazolyl and N-heteroarylcarbazolyl are heteroaryl of a polycyclic ring systems conjugatedly connected through carbon-carbon bonds.

In the present disclosure, the substituted heteroaryl can be that one or two or more hydrogen atoms in the heteroaryl are substituted by a group such as deuterium atom, halogen group, —CN, aryl, heteroaryl, trialkylsilyl, alkyl, cycloalkyl, alkoxy, alkylthio and the like.

In the present disclosure, specific examples of heteroaryl as a substituent include, but are not limited to, dibenzofuranyl, carbazolyl, dibenzothienyl, pyridyl and the like.

It should be understood that the number of carbon atoms of the substituted heteroaryl refers to the total number of carbon atoms of heteroaryl and substituents on the heteroaryl. That is, in the present disclosure, the number of carbon atoms of the heteroaryl is selected from 3, 4, 5, 6, 7, 8, 9, 10, 11, 12, 13, 14, 15, 16, 17, 18, 19, 20, 21, 22, 23, 24, 25, 26, 27, 28, 29 or 30.

In the present disclosure, the explanation of the aryl may be applied to arylene, and the explanation of the heteroaryl may also be applied to heteroarylene.

In the present disclosure, the halogen group can be fluorine, chlorine, bromine or iodine.

Due to these characteristics of the nitrogen-containing compound of the present application, the nitrogen-containing compound can be used for manufacturing organic electroluminescent devices and photoelectric conversion devices, and is particularly suitable for manufacturing electron blocking layers (also called a hole auxiliary layer, a second hole transport layer and the like) of the organic electroluminescent devices and the photoelectric conversion devices, so that the efficiency and service life of the organic electroluminescent device and the photoelectric conversion device are improved, the working voltage of the organic electroluminescent device is reduced, the open-circuit voltage of the photoelectric conversion device is improved, and the mass production stability of the photoelectric conversion device and the organic electroluminescent device is improved.

According to one embodiment of the present disclosure, L is selected from a single bond, substituted or unsubstituted arylene with a total carbon atoms number of 6 to 20, or substituted or unsubstituted heteroarylene with a total carbon atoms number of 5 to 20.

Preferably, L is selected from a single bond or substituted or unsubstituted arylene with a total carbon atoms number of 6 to 15.

In the present disclosure, the substituent in L is selected from deuterium, halogen group, cyano or alkyl with 1 to 5 carbon atoms. Specifically, the substituent in the L is selected from deuterium, fluorine, cyano, methyl, ethyl, tert-butyl and the like.

According to another embodiment of the present disclosure, L is selected from a single bond or the group consisting of groups represented by chemical formulae j-1 to j-14:

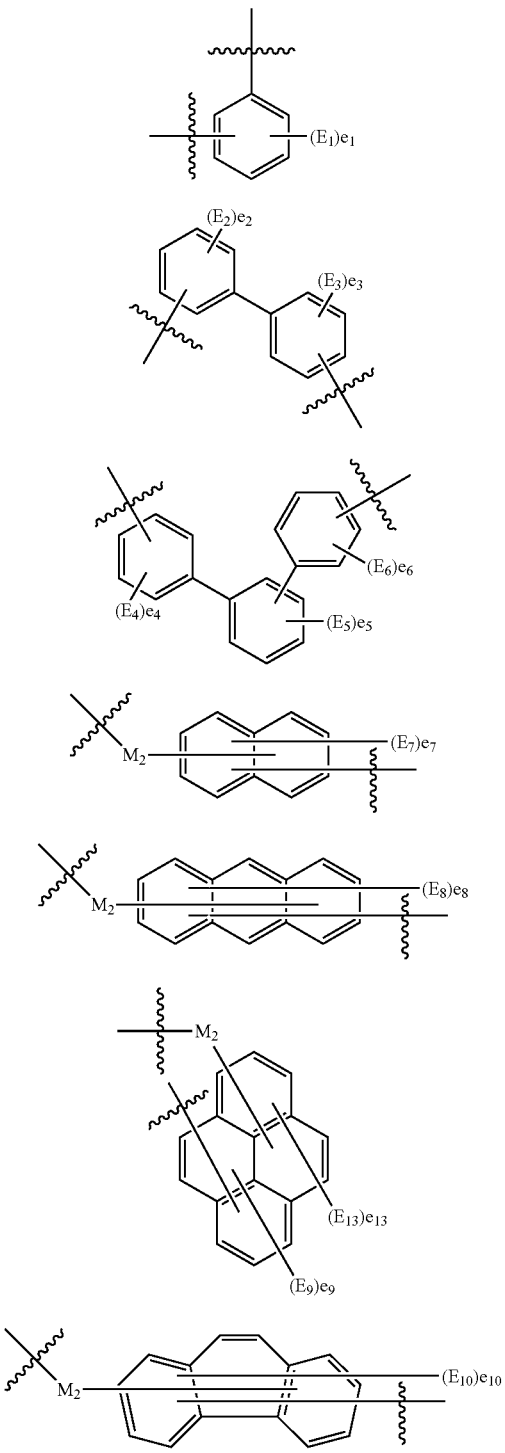

wherein $M_2$ is selected from a single bond or

, and represents a chemical bond;

$Q_1$ to $Q_5$ and $Q'_1$ to $Q'_5$ are each independently selected from N or $C(J_5)$, and at least one of $Q_1$ to $Q_5$ is selected from N; and when two or more of $Q_1$ to $Q_5$ are selected from $C(J_5)$, any two $J_5$ are the same or different, and when two or more of $Q'_1$ to $Q'_4$ are selected from $C(J_5)$, any two $J_5$ are the same or different;

$Q_6$ to $Q_{13}$ are each independently selected from N, C or $C(J_6)$, and at least one of $Q_6$ to $Q_{13}$ is selected from N; and when two or more of $Q_6$ to $Q_{13}$ are selected from $C(J_6)$, any two $J_6$ are the same or different;

$Q_{14}$ to $Q_{23}$ are each independently selected from N, C or $C(J_7)$, and at least one of $Q_{14}$ to $Q_{23}$ is selected from N; and when two or more of $Q_{14}$ to $Q_{23}$ are selected from $C(J_7)$, any two $J_7$ are the same or different;

$Q_{24}$ to $Q_{33}$ are each independently selected from N, C or $C(J_8)$, and at least one of $Q_{24}$ to $Q_{32}$ is selected from N; and when two or more of $Q_{24}$ to $Q_{32}$ are selected from $C(J_8)$, any two $J_8$ are the same or different;

$E_1$ to $E_{14}$ and $J_5$ to $J_9$ are each independently selected from hydrogen, deuterium, halogen group, cyano, heteroaryl with 3 to 20 carbon atoms, aryl with 6 to 20 carbon atoms which can be optionally substituted by 0, 1, 2, 3, 4 or 5 substituents selected from deuterium, fluorine, chlorine, cyano, methyl or tert-butyl, trialkylsilyl with 3 to 12 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, phosphinyloxy with 6 to 18 carbon atoms, or triarylsilyl with 18 to 24 carbon atoms;

$e_1$ to $e_{14}$ are represented by $e_r$, $E_1$ to $E_{14}$ are represented by $E_r$, r is a variable and represents any integer of 1 to 14, and $e_r$ represents the number of substituents $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6 or 7; when r is selected from 8 or 10, $e_r$ is selected from 1, 2, 3, 4, 5, 6, 7 or 8; and when $e_r$ is greater than 1, any two $E_r$ are the same or different;

$K_3$ is selected from O, S, Se, $N(E_{15})$, $C(E_{16}E_{17})$ or $Si(E_{18}E_{19})$; wherein $E_{15}$, $E_{16}$, $E_{17}$, $E_{18}$ and $E_{19}$ are each independently selected from aryl with 6 to 20 carbon atoms, heteroaryl with 3 to 20 carbon atoms, alkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, or heterocloalkenyl with 4 to 10 carbon atoms; or $E_{16}$ and $E_{17}$ are connected with each other to form a saturated or unsaturated ring with 3 to 15 carbon atoms together with atoms to which they are jointly connected, or $E_{18}$ and $E_{19}$ are connected with each other to form a saturated or unsaturated ring with 3 to 15 carbon atoms together with atoms to which they are jointly connected; and $K_4$ is selected from a single bond, O, S, Se, $N(E_{20})$, $C(E_{21}E_{22})$ or $Si(E_{23}E_{24})$; wherein $E_{20}$ to $E_{24}$ are each independently selected from aryl with 6 to 20 carbon atoms, heteroaryl with 3 to 20 carbon atoms, alkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, or heterocloalkenyl with 4 to 10 carbon atoms; or $E_{21}$ and $E_{22}$ are connected with each other to form a saturated or unsaturated ring with 3-15 carbon atoms together with atoms to which they are jointly connected, or $E_{23}$ and $E_{24}$ are connected with each other to form a saturated or unsaturated ring with 3 to 15 carbon atoms together with atoms to which they are jointly connected.

According to one embodiment of the present disclosure, L is selected from a single bond, substituted or unsubstituted phenylene, substituted or unsubstituted naphthylene, substituted or unsubstituted biphenylene, or substituted or unsubstituted fluorenylidene.

Optionally, L is selected from a single bond or the group consisting of the following groups:

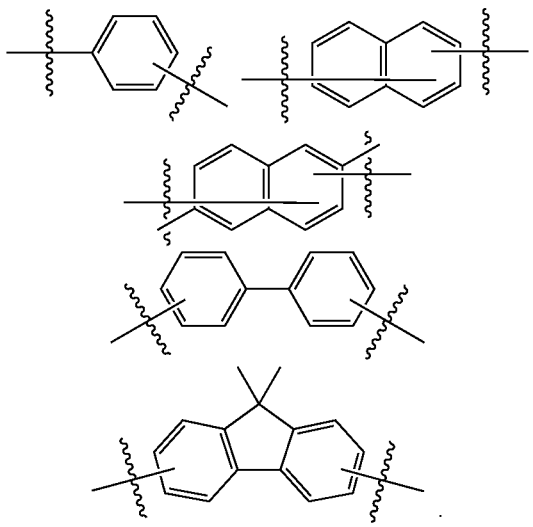

Optionally, L is selected from a single bond or the group consisting of the following groups:

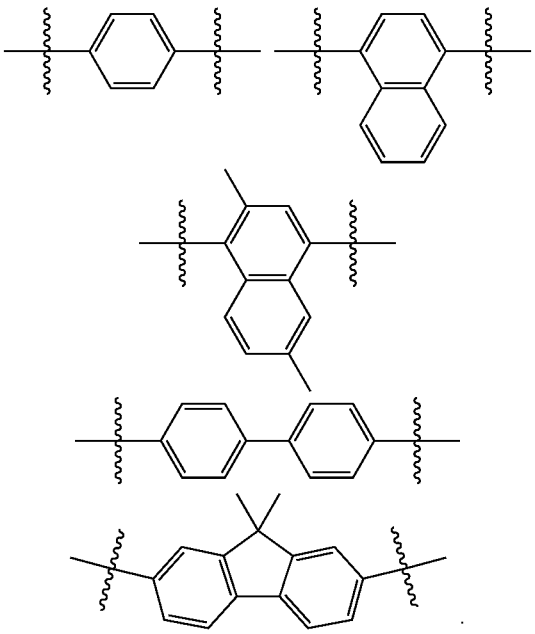

Optionally, the substituent in the L is selected from deuterium, methyl, ethyl or tert-butyl.

According to one embodiment of the present disclosure, $R_1$ and $R_2$ are the same or different, and are independently selected from deuterium, cyano, halogen group, substituted or unsubstituted alkyl with a total carbon atoms number of 1 to 6, substituted or unsubstituted aryl with a total carbon atoms number of 6 to 25, or substituted or unsubstituted heteroaryl with a total carbon atoms number of 5 to 25, and the $R_1$ is not carbazolyl or N-phenylcarbazolyl.

Optionally, $R_1$ is selected from deuterium, cyano, halogen group, substituted or unsubstituted alkyl with a total carbon atoms number of 1 to 6, substituted or unsubstituted aryl with a total carbon atoms number of 6 to 25, or substituted or unsubstituted heteroaryl with a total carbon atoms number of 5 to 12, and the $R_1$ is not carbazolyl or N-phenylcarbazolyl. Specifically, $R_1$ is selected from deuterium, fluorine, cyano, methyl, ethyl, n-propyl, isopropyl, tert-butyl, substituted or unsubstituted phenyl, substituted or unsubstituted biphenyl, substituted or unsubstituted terphenyl, substituted or unsubstituted anthryl, substituted or unsubstituted fluorenyl, substituted or unsubstituted phenanthryl, substituted or unsubstituted pyrenyl, substituted or unsubstituted pyridyl, substituted or unsubstituted naphthyl, or substituted or unsubstituted dibenzofuryl.

Optionally, $R_2$ is selected from deuterium, cyano, halogen group, substituted or unsubstituted alkyl with a total carbon atoms number of 1 to 6, substituted or unsubstituted aryl with a total carbon atoms number of 6 to 25, or substituted or unsubstituted heteroaryl with a total carbon atoms number of 5 to 18. Specifically, $R_2$ is selected from deuterium, fluorine, cyano, methyl, ethyl, n-propyl, isopropyl, tert-butyl, substituted or unsubstituted phenyl, substituted or unsubstituted biphenyl, substituted or unsubstituted terphenyl, substituted or unsubstituted anthryl, substituted or unsubstituted fluorenyl, substituted or unsubstituted phenanthryl, substituted or unsubstituted pyrenyl, substituted or unsubstituted pyridyl, substituted or unsubstituted naphthyl, substituted or unsubstituted dibenzofuranyl, or substituted or unsubstituted carbazolyl.

In one embodiment of the present disclosure, the substituents in $R_1$ and $R_2$ are the same or different, and are independently selected from deuterium, cyano, halogen group, substituted or unsubstituted alkyl with a total carbon atoms number of 1 to 6, aryl 6 to 20 carbon atoms, or heteroaryl with 3 to 20 carbon atoms, and the substituent in the $R_1$ is not carbazolyl.

Optionally, the substituent in the $R_1$ is selected from deuterium, fluorine, methyl, ethyl, tert-butyl, phenyl, naphthyl, biphenyl or cyano.

Optionally, the substituent in the $R_2$ is selected from deuterium, fluorine, methyl, ethyl, tert-butyl, phenyl, naphthyl, biphenyl, carbazolyl, N-phenylcarbazolyl or cyano.

In one embodiment of the present disclosure, $R_1$ is selected from deuterium, halogen group, methyl, ethyl, tert-butyl or the group consisting of, but is not limited to, the following groups:

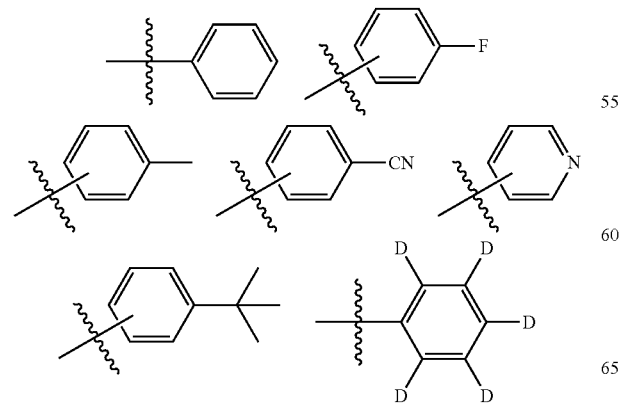

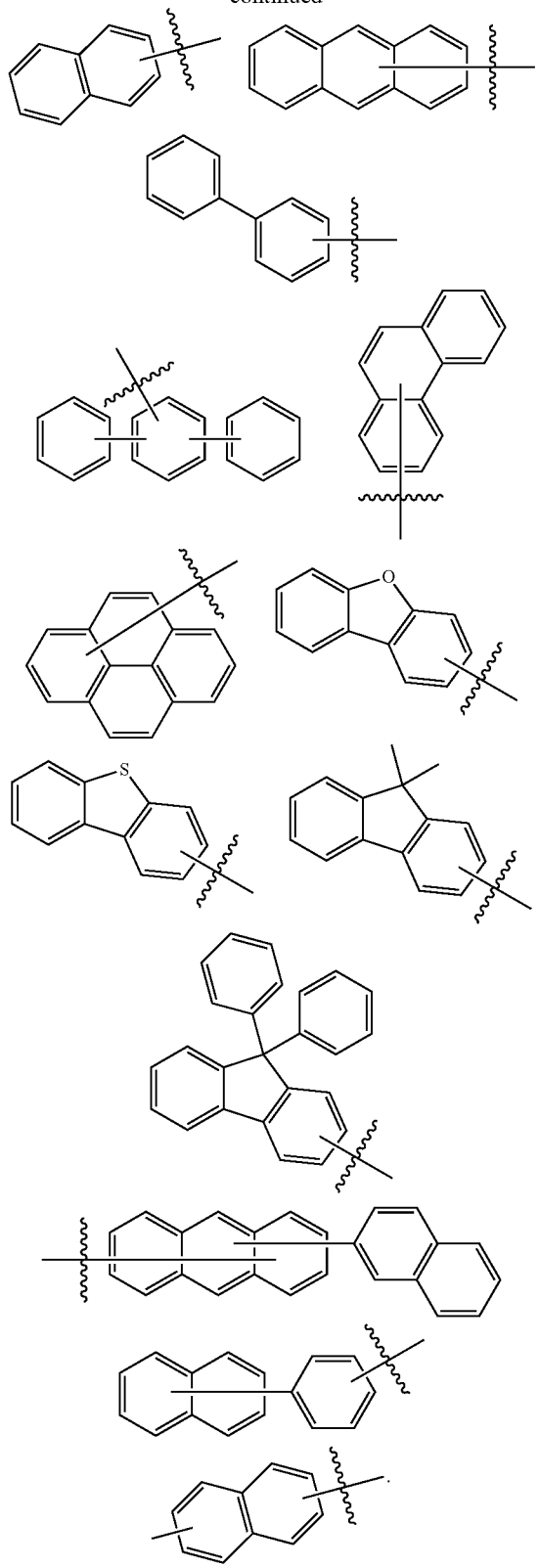

In one embodiment of the present disclosure, $R_2$ is selected from deuterium, halogen group, methyl, ethyl, tert-butyl or the group consisting of, but is not limited to, the following groups:

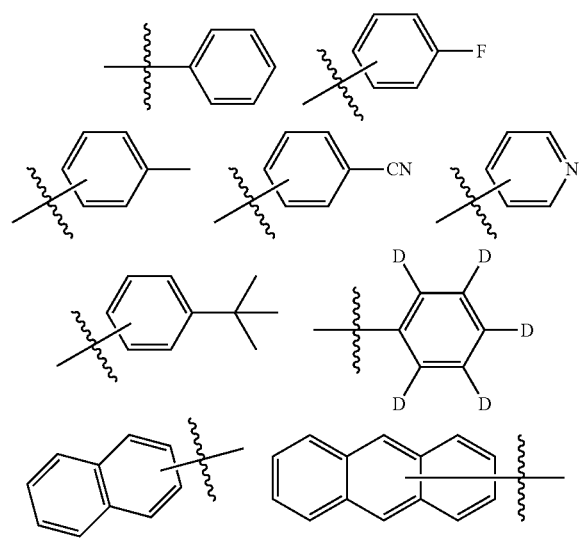
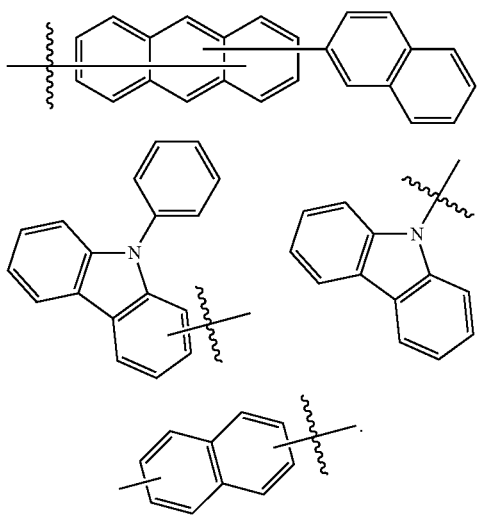
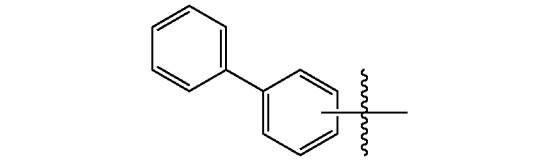
Optionally, $R_1$ is selected from deuterium, halogen group, methyl, ethyl, tert-butyl or the group consisting of the following groups:

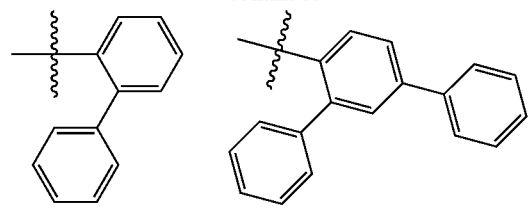
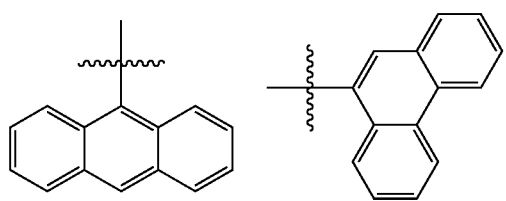
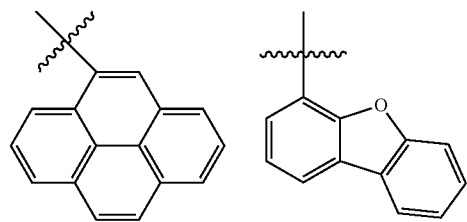
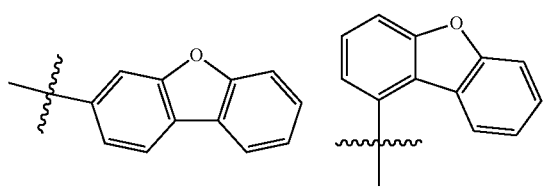
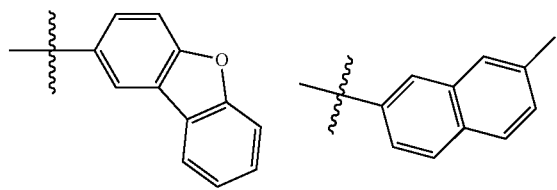
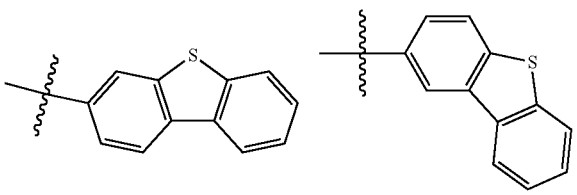
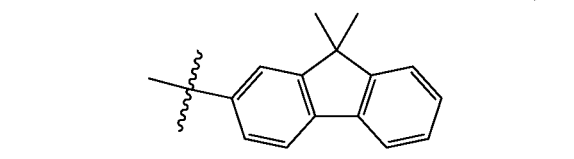
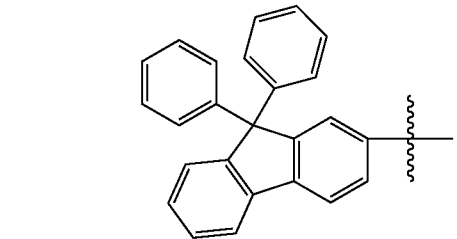
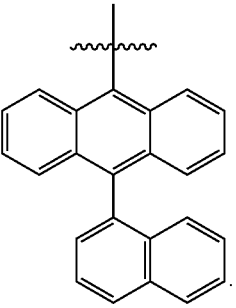
Optionally, $R_2$ is selected from deuterium, halogen group, methyl, ethyl, tert-butyl or the group consisting of the following groups:
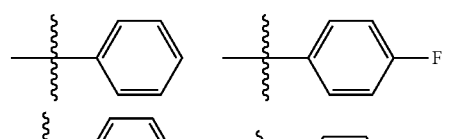
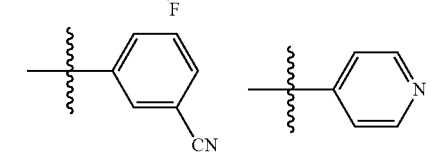
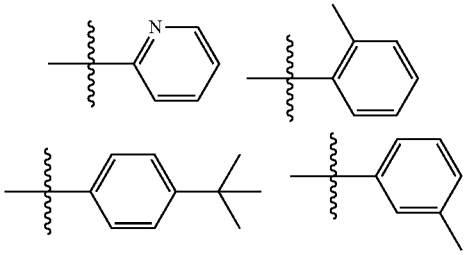
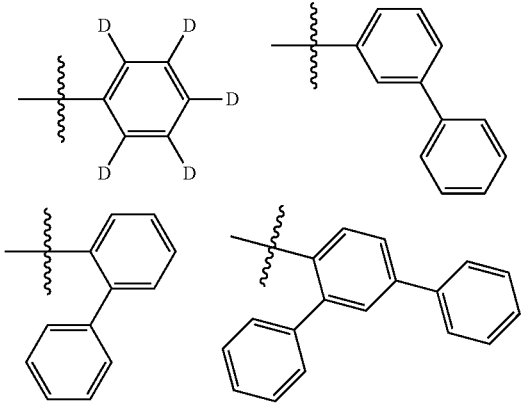

-continued

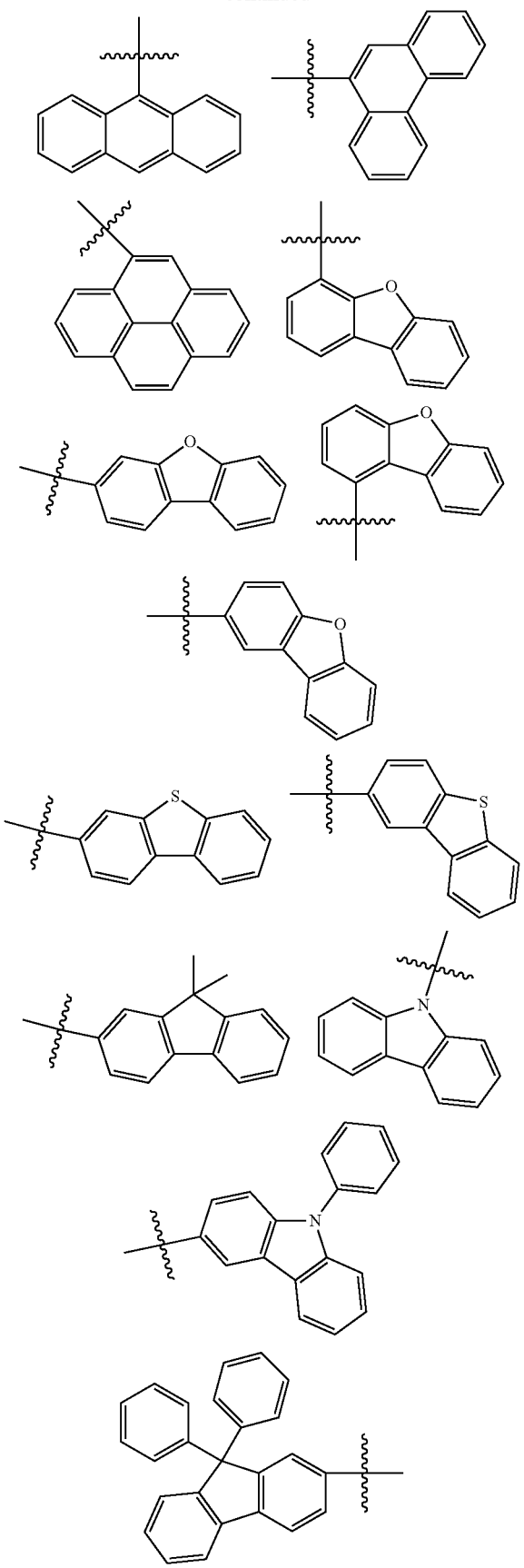

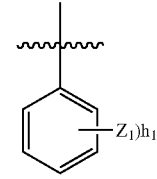

In one embodiment of the present disclosure, $Ar_1$ and $Ar_2$ are the same or different, and are independently selected from substituted or unsubstituted aryl with a total carbon atoms number of 6 to 24 or substituted or unsubstituted heteroaryl with a total carbon atoms number of 3 to 24.

Optionally, the substituents in $Ar_1$ and $Ar_2$ are the same or different, and are independently selected from deuterium, halogen group, cyano, alkyl with 1 to 5 carbon atoms, cycloalkyl with 3 to 15 carbon atoms, aryl with 6 to 18 carbon atoms, or heteroaryl with 12 to 18 carbon atoms. Specifically, the substituents in the $Ar_1$ and the $Ar_2$ are the same or different, and are independently selected from deuterium, fluorine, methyl, ethyl, n-propyl, isopropyl, tert-butyl, cyclohexyl, adamantyl, phenyl, naphthyl, biphenyl, dibenzofuranyl, dibenzothienyl, carbazolyl or N-phenylcarbazolyl.

Preferably, $Ar_1$ and $Ar_2$ are the same or different, and are respectively and independently selected from substituted or unsubstituted aryl with a total carbon atoms number of 6 to 21 or substituted or unsubstituted heteroaryl with a total carbon atoms number of 12 to 24.

In another embodiment of the present disclosure, $Ar_1$ and $Ar_2$ are the same or different, and are independently selected from groups represented by the following chemical formulae i-1 to i-15:

Chemical formula i-1

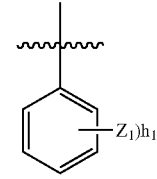

Chemical formula i-2

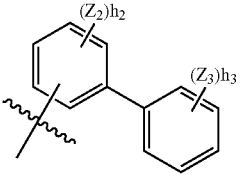

Chemical formula i-3

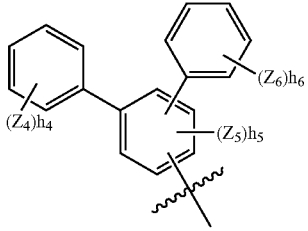

Chemical formula i-4
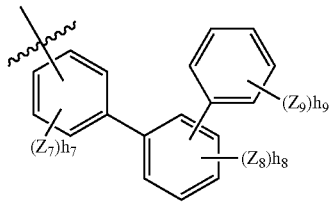

Chemical formula i-5
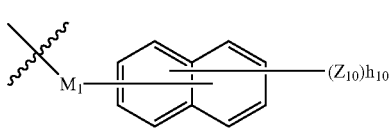

Chemical formula i-6
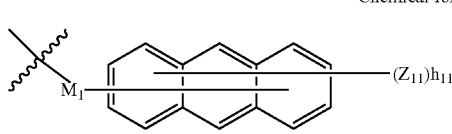

Chemical formula i-7
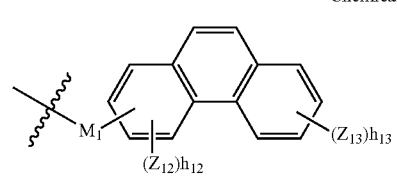

Chemical formula i-8
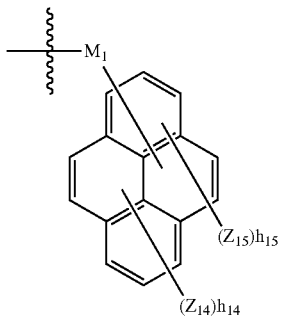

Chemical formula i-9
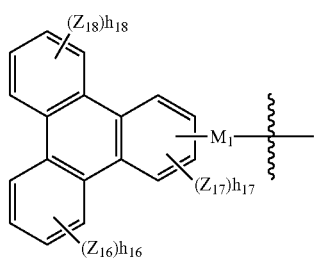

Chemical formula i-10
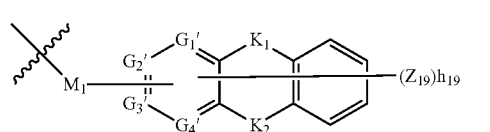

Chemical formula i-11
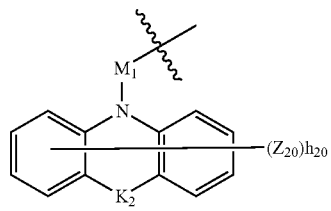

Chemical formula i-12
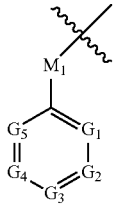

Chemical formula i-13
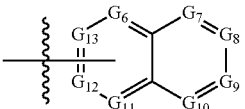

Chemical formula i-14
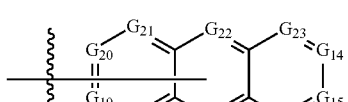

Chemical formula i-15
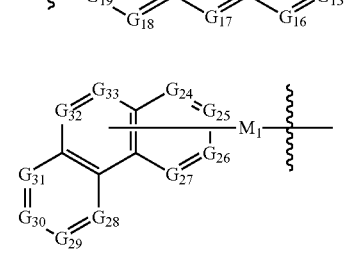

wherein $M_1$ is selected from a single bond or

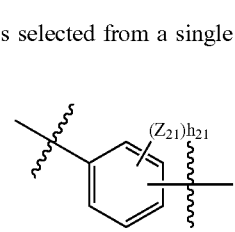
;

$G_1$ to $G_5$ and $G'_1$ to $G'_4$ are each independently selected from N, C or $C(J_1)$, at least one of $G_1$ to $G_5$ is selected from N, and when two or more of $G_1$ to $G_5$ are selected from $C(J_1)$, any two $J_1$ are the same or different;

$G_6$ to $G_{13}$ are each independently selected from N, C or $C(J_2)$, and at least one of $G_6$ to $G_{13}$ is selected from N; and when two or more of $G_6$ to $G_{13}$ are selected from $C(J_2)$, any two $J_2$ are the same or different;

$G_{14}$ to $G_{23}$ are each independently selected from N, C or $C(J_3)$, and at least one of $G_{14}$-$G_{23}$ is selected from N; and when two or more of $G_{14}$ to $G_{23}$ are selected from $C(J_3)$, any two $J_3$ are the same or different;

$G_{24}$ to $G_{33}$ are each independently selected from N, C or $C(J_4)$, and at least one of $G_{24}$ to $G_{33}$ is selected from N; and when two or more of $G_{24}$ to $G_{33}$ are selected from $C(J_4)$, any two $J_4$ are the same or different;

$Z_1$ is selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms or triarylsilyl with 18 to 24 carbon atoms;

$Z_2$ to $Z_9$ and $Z_{21}$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, alkylthio with 1 to 10 carbon atoms, heteroaryl with 3 to 18 carbon atoms or triarylsilyl with 18 to 24 carbon atoms;

$Z_{10}$ to $Z_{20}$ and $J_1$ to $J_4$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms which can be optionally substituted by 0, 1, 2, 3, 4 or 5 substituents selected from deuterium, fluorine, chlorine, cyano, methyl, ethyl or tert-butyl, heteroaryl with 3 to 18 carbon atoms, or triarylsilyl with 18 to 24 carbon atoms;

$h_1$ to $h_{21}$ are represented by $h_k$, $Z_1$ to $Z_{21}$ are represented by $Z_k$, k is a variable and represents any integer of 1 to 21, and $h_k$ represents the number of substituents $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is 20, $h_k$ is selected from 1, 2, 3, 4, 5, 6, 7 or 8; when k is 11, $h_k$ is selected from 1, 2, 3, 4, 5, 6, 7, 8 or 9; and when $h_k$ is greater than 1, any two $Z_k$ are the same or different;

$K_1$ is selected from O, S, N($Z_{22}$), C($Z_{23}Z_{24}$) or Si($Z_{28}Z_{29}$); wherein $Z_{22}$, $Z_{23}$, $Z_{24}$, $Z_{28}$ and $Z_{29}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{23}$ and the $Z_{24}$ are connected with each other to form a saturated or unsaturated ring with 3 to 15 carbon atoms together with atoms to which they are jointly connected, or the $Z_{28}$ and the $Z_{29}$ are connected with each other to form a saturated or unsaturated ring with 3 to 15 carbon atoms together with atoms to which they are jointly connected; and $K_2$ is selected from a single bond, O, S, N($Z_{25}$), C($Z_{26}Z_{27}$), or Si($Z_{30}Z_{31}$); wherein $Z_{25}$, $Z_{26}$, $Z_{27}$, $Z_{30}$ and $Z_{31}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{26}$ and the $Z_{27}$ are connected with each other to form a saturated or unsaturated ring with 3 to 15 carbon atoms together with atoms to which they are jointly connected, or the $Z_{30}$ and the $Z_{31}$ are connected with each other to form a saturated or unsaturated ring with 3 to 15 carbon atoms together with atoms to which they are jointly connected.

In another embodiment of the present disclosure, $Ar_1$ and $Ar_2$ are respectively selected from groups represented by the following chemical formula i-16:

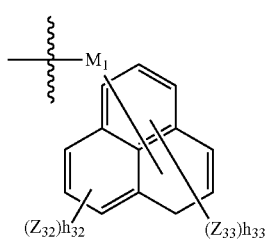

i-16

$Z_{32}$ and $Z_{33}$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms which can be optionally substituted by 0, 1, 2, 3, 4 or 5 substituents selected from deuterium, fluorine, chlorine, cyano, methyl, ethyl or tert-butyl, heteroaryl with 3 to 18 carbon atoms, or triarylsilyl with 18 to 24 carbon atoms;

$h_{32}$ is the number of $Z_{32}$, and $h_{33}$ is the number of $Z_{33}$;

$h_{32}$ is selected from 0, 1, 2 or 3, and when $h_{32}$ is more than 1, any two $Z_{32}$ are the same or different; and $h_{33}$ is selected from 0, 1, 2, 3, 4 or 5, and when $h_{33}$ is greater than 1, any two $Z_{33}$ are the same or different.

In one embodiment of the present disclosure, $Ar_1$ and $Ar_2$ are the same or different, and are independently selected from the group consisting of, but are not limited to, the following groups:

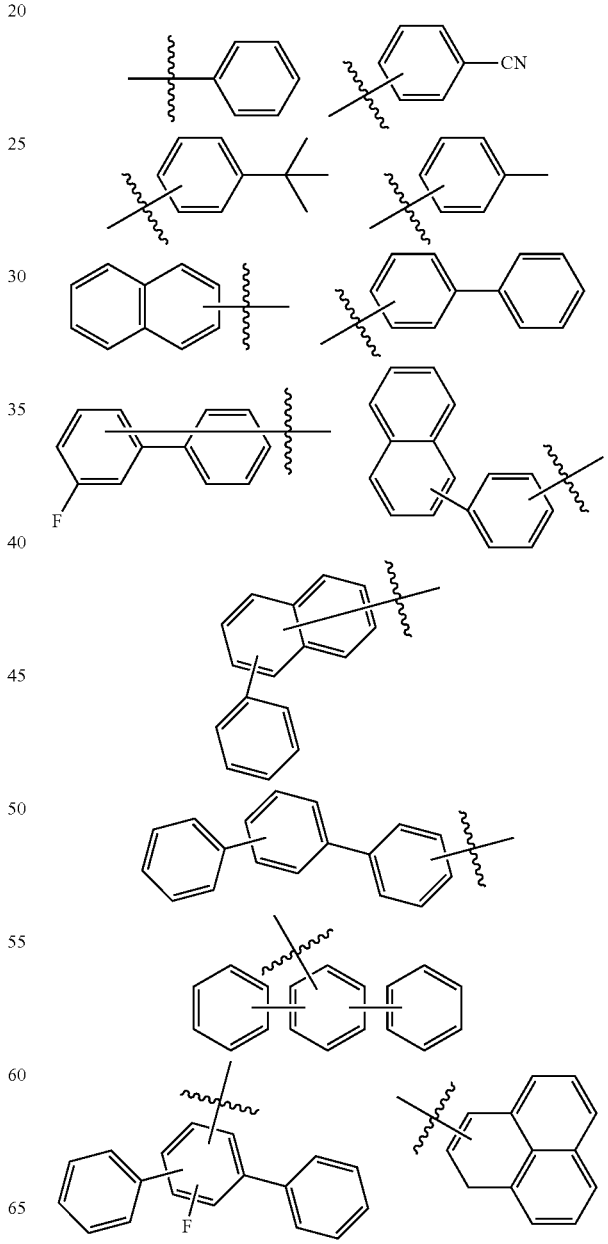

-continued
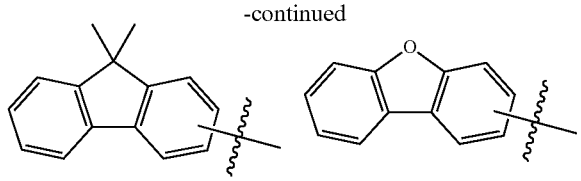
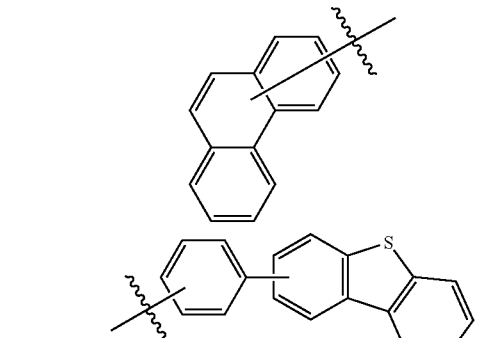
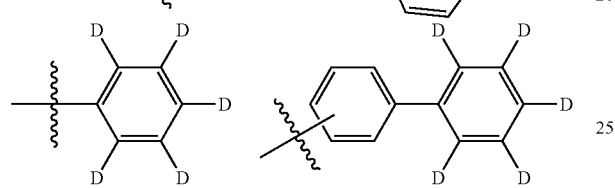
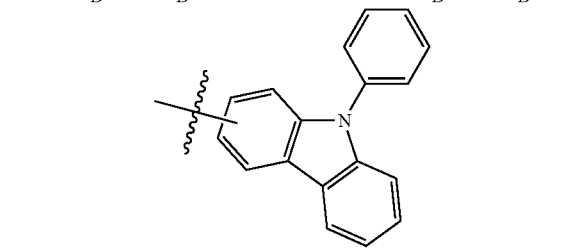
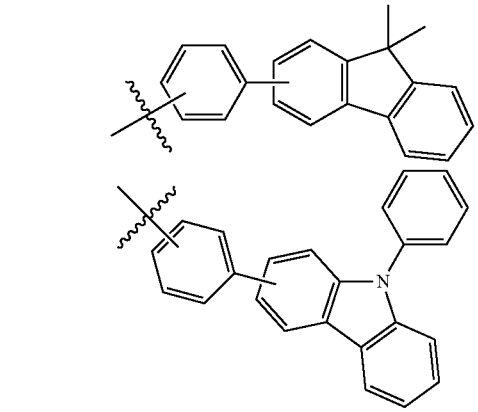
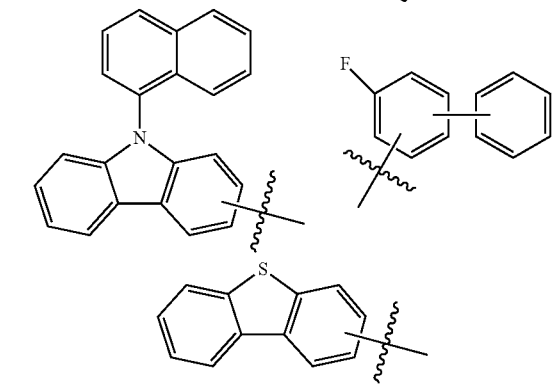
-continued
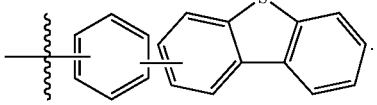
In the present disclosure,
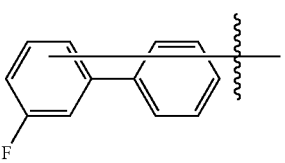
refers to
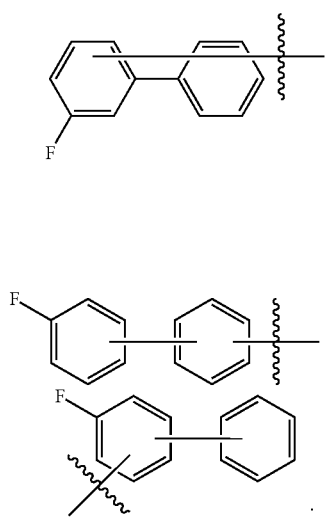
and
Optionally, $Ar_1$ and $Ar_2$ are the same or different, and are independently selected from the group consisting of, but are not limited to, the following groups:
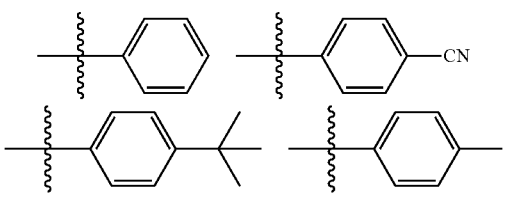
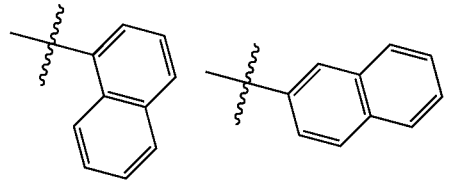
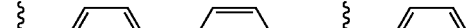
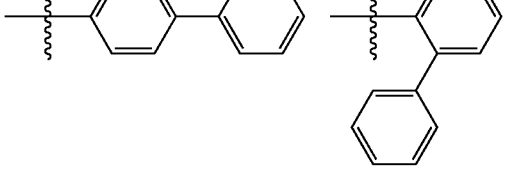
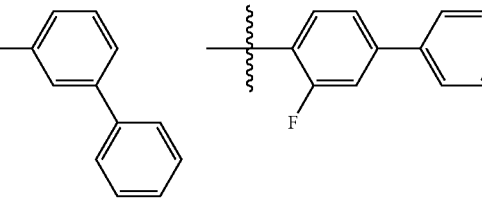

-continued
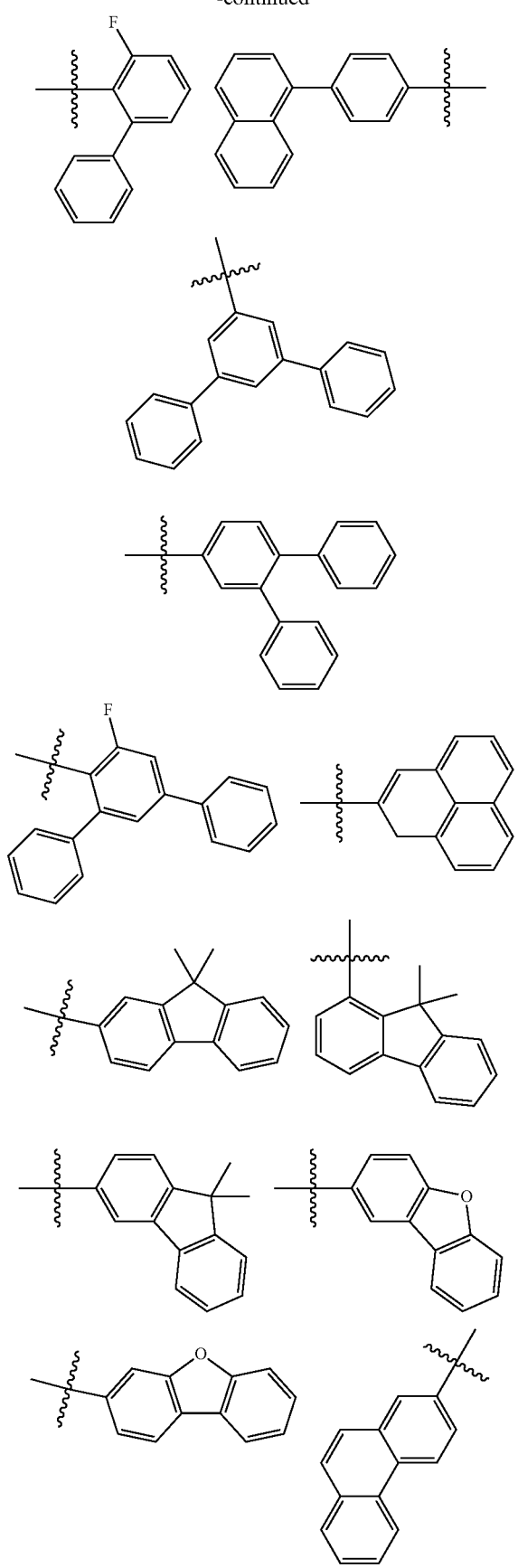
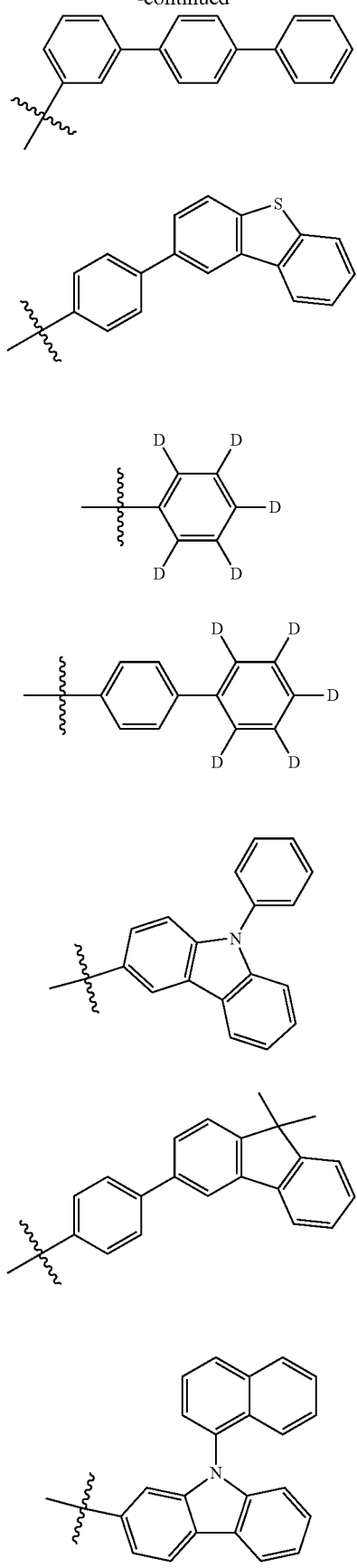

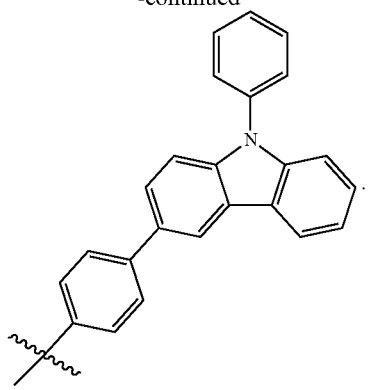
Optionally, the nitrogen-containing compound is selected from the group consisting of, but are not limited to, the following compounds:
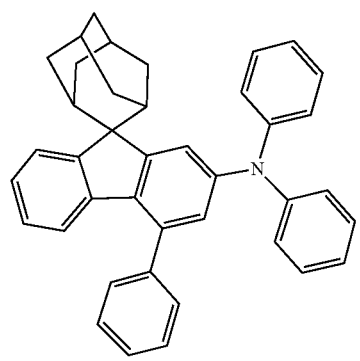
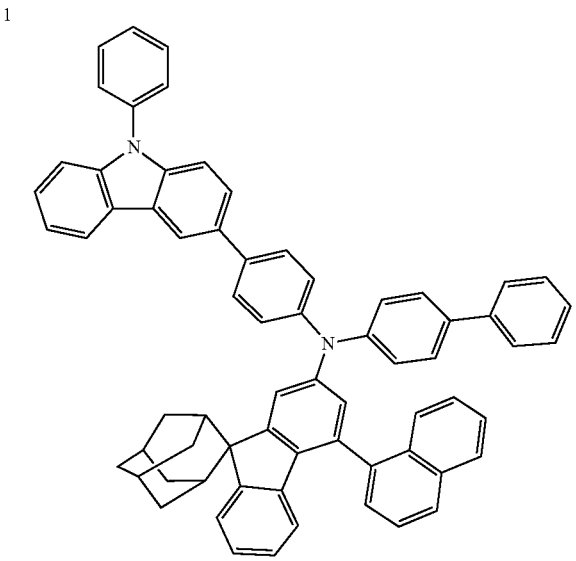
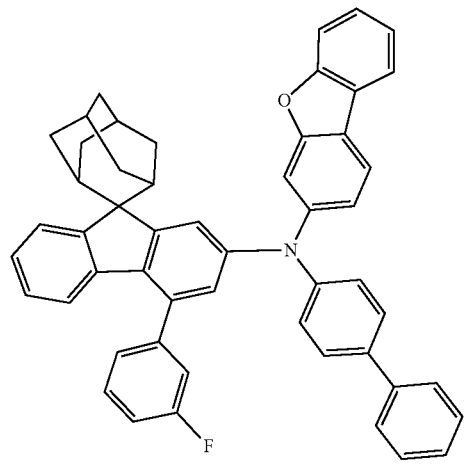
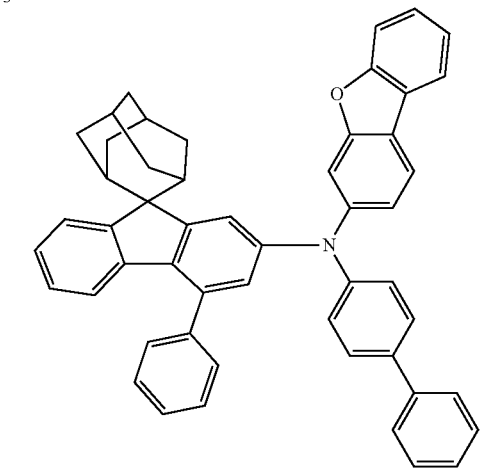

-continued
5
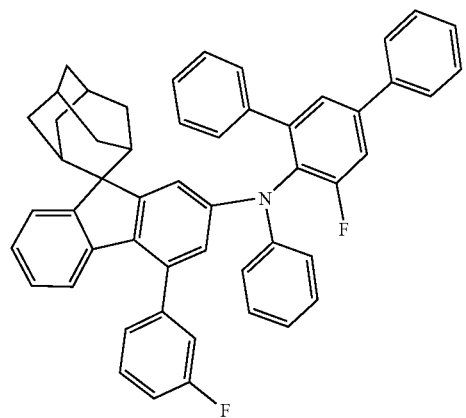
6
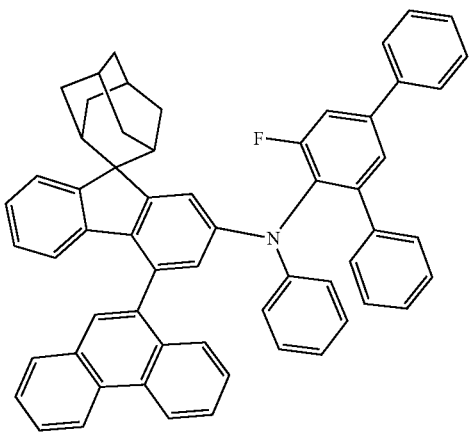
7
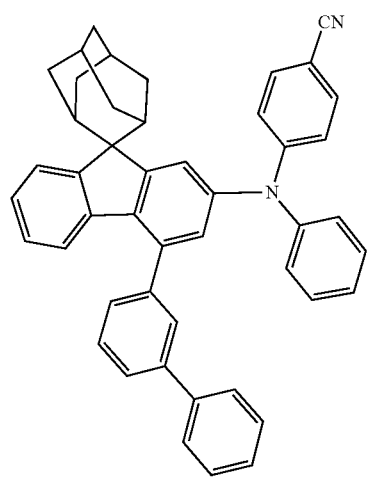
8
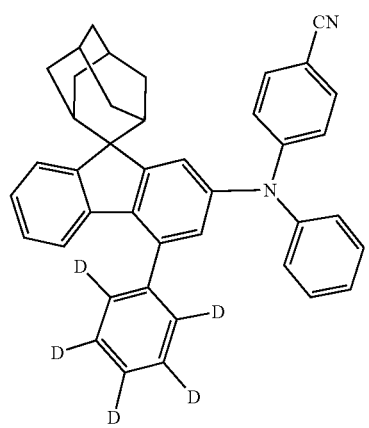
9
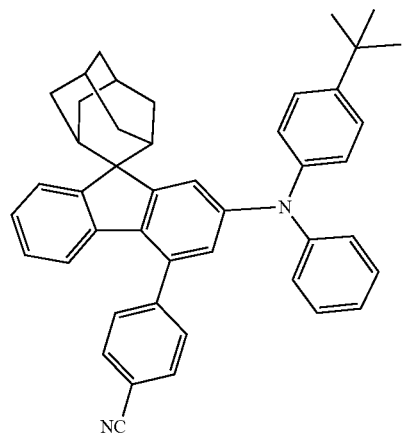
10
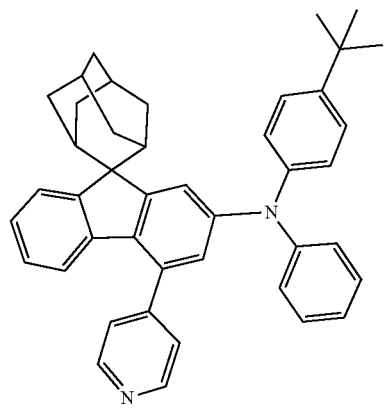

-continued
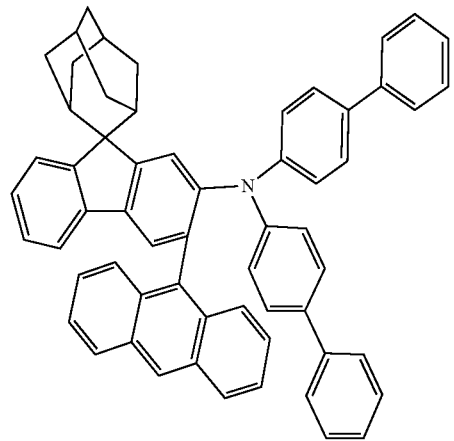
11
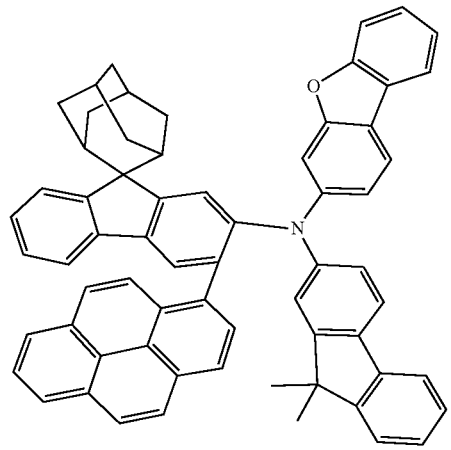
12
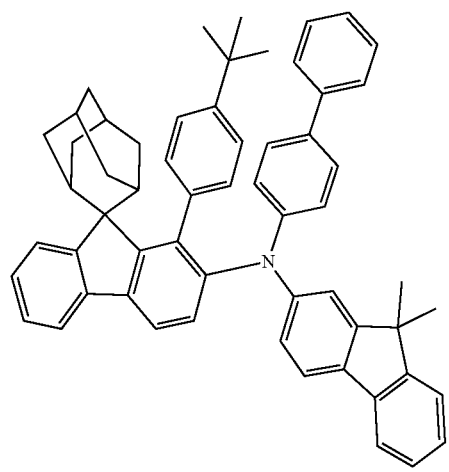
13
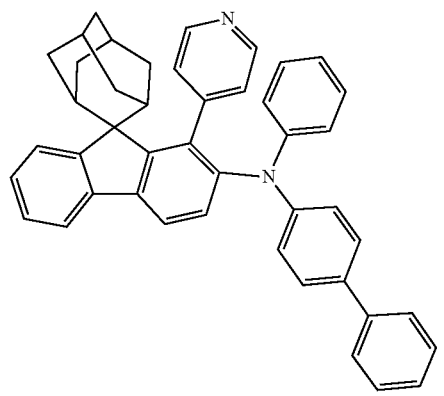
14
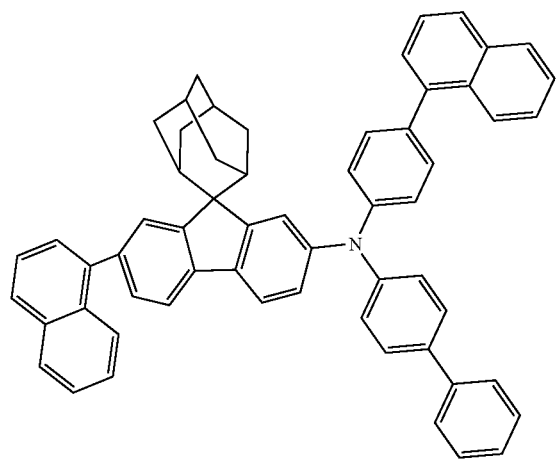
15
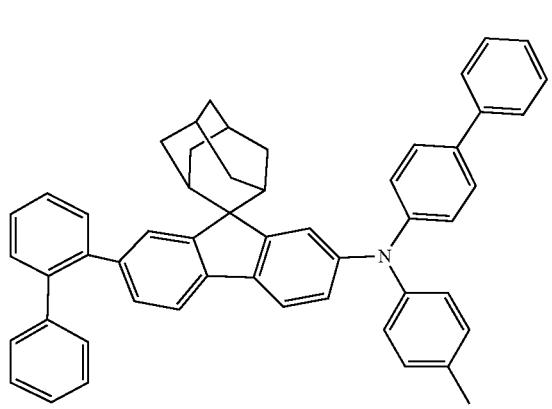
16

-continued
17
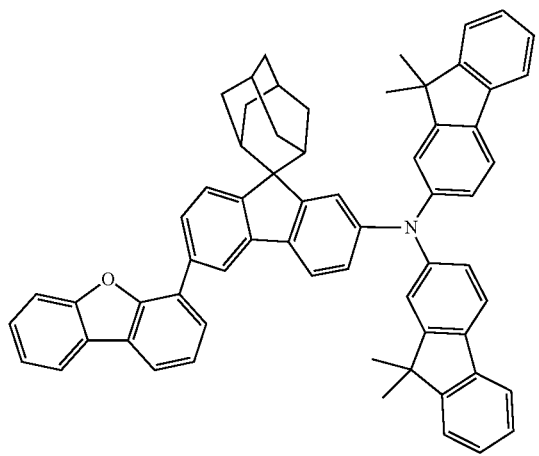
18
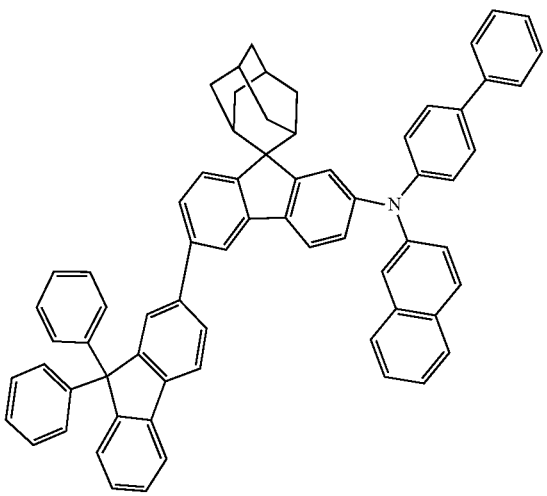
19
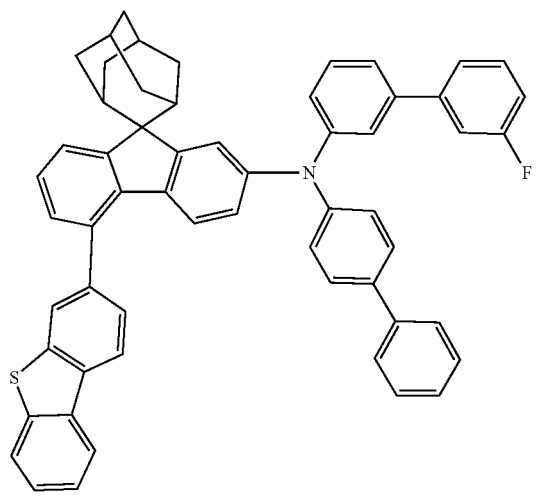
20
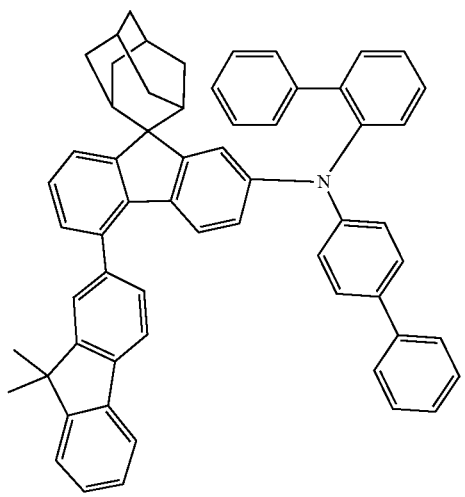
21
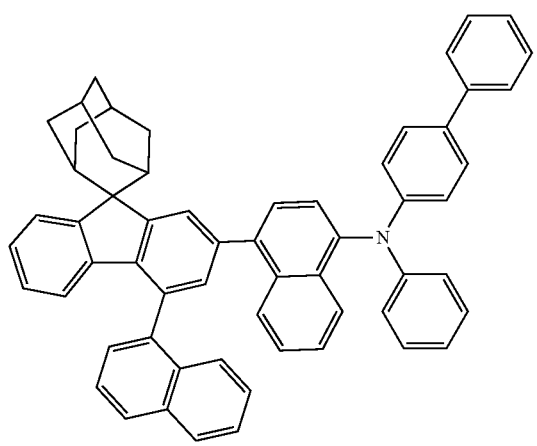
22
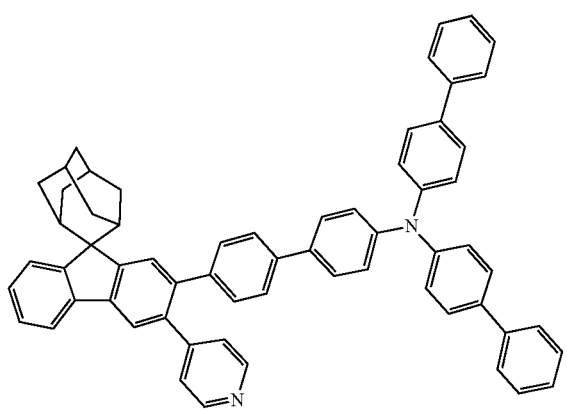

-continued
23
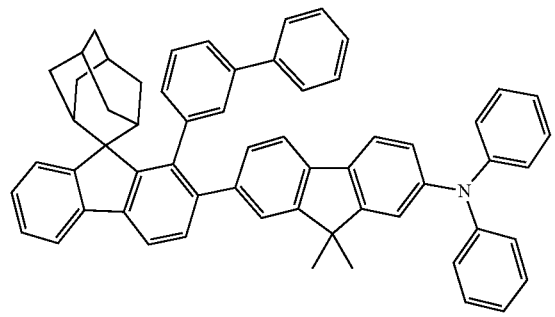
24
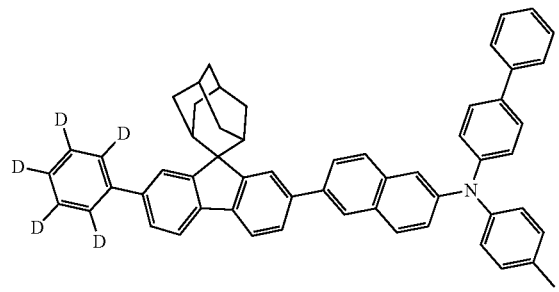
25
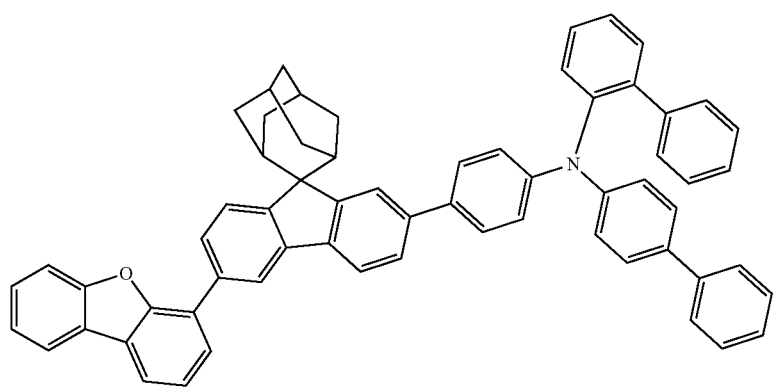
26
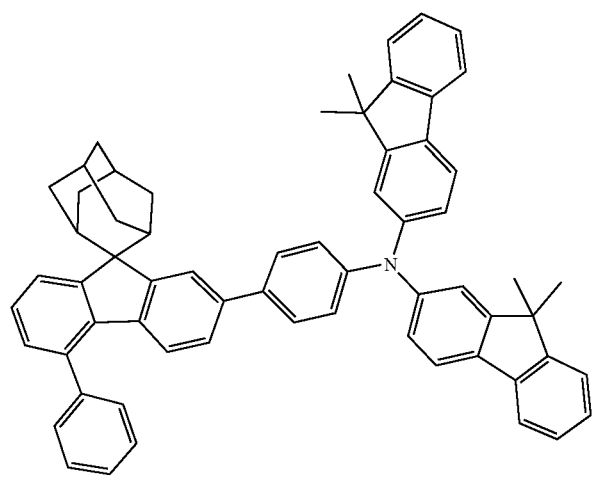
27
28
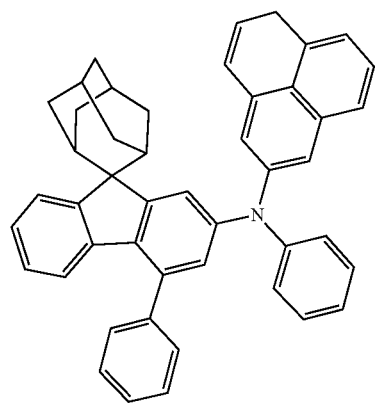
29
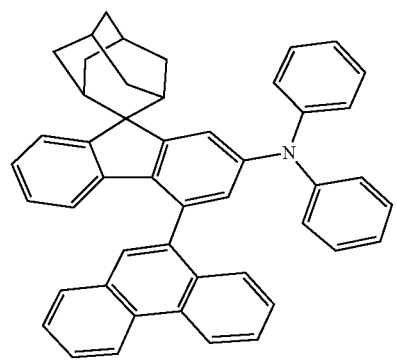

-continued
30
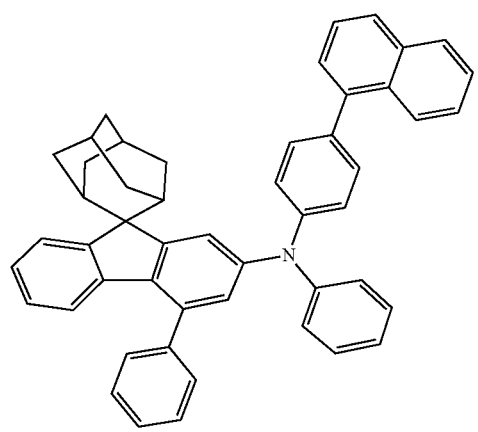
31
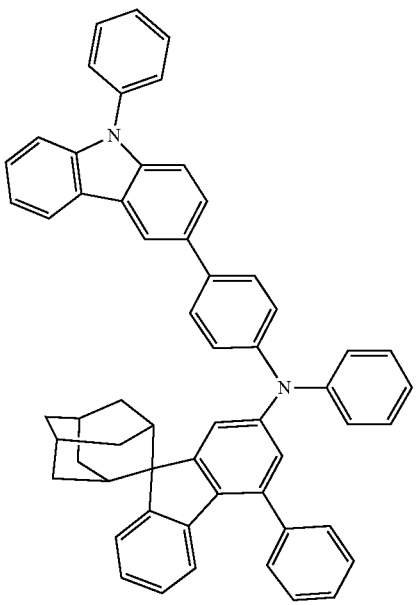
32
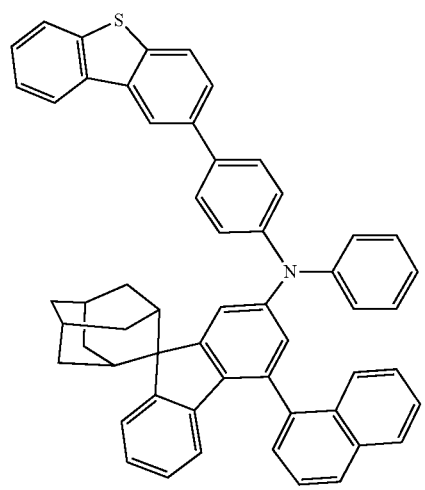
33
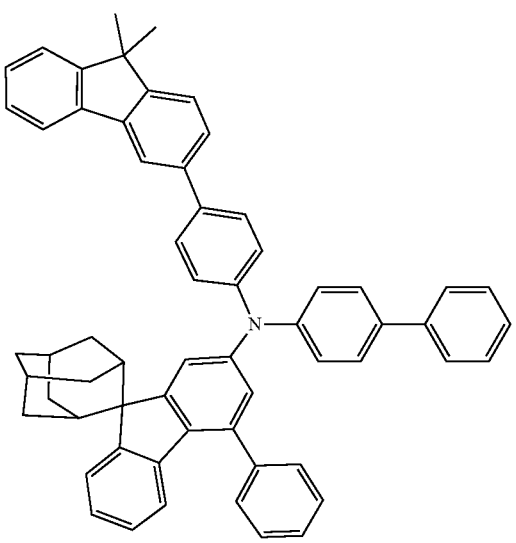
34
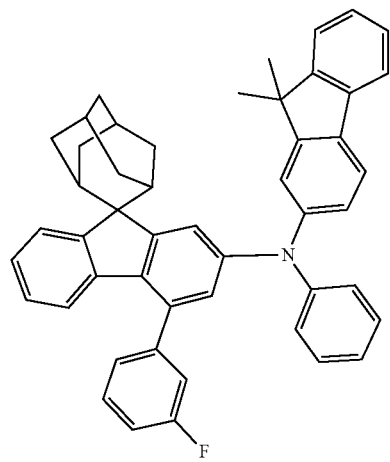
35
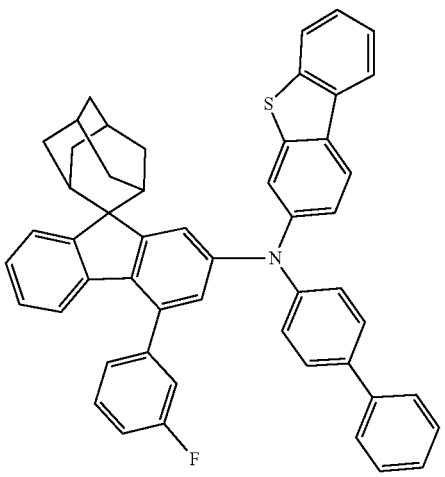

-continued
36
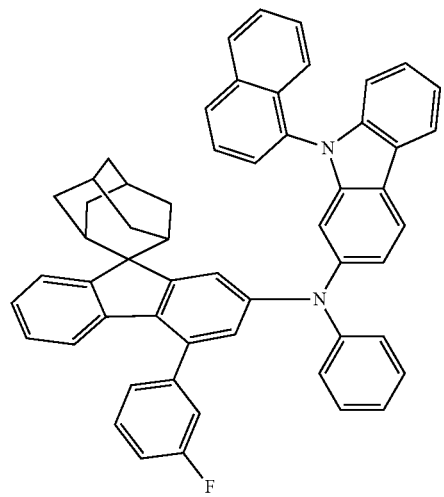
37
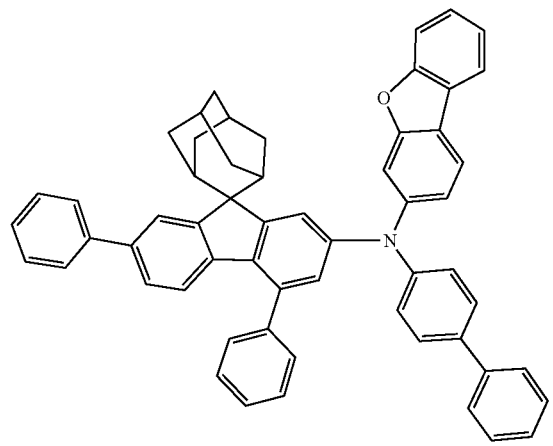
38
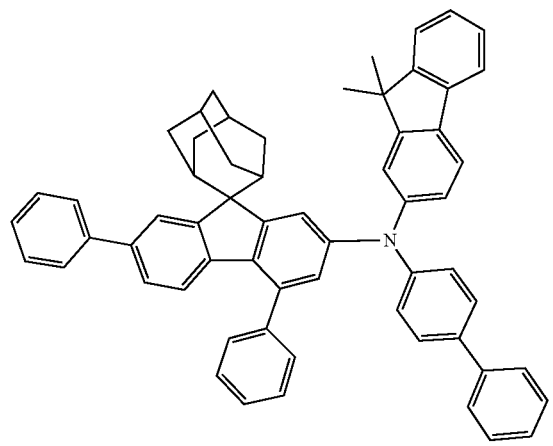
39
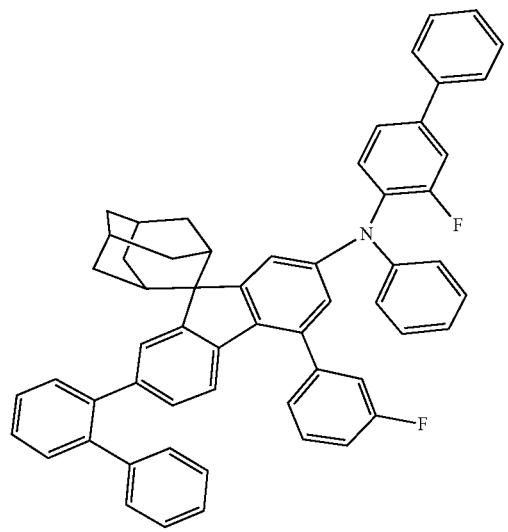
40
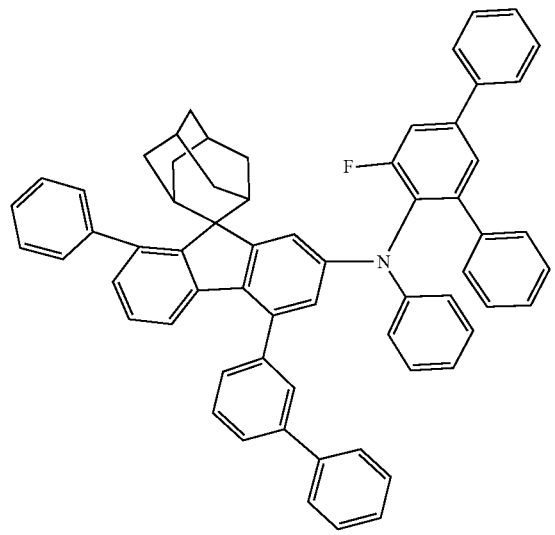
41
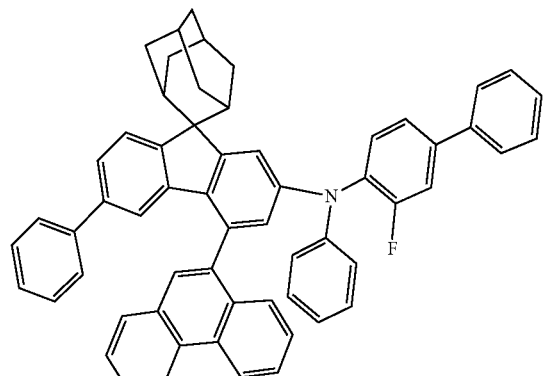

-continued
42
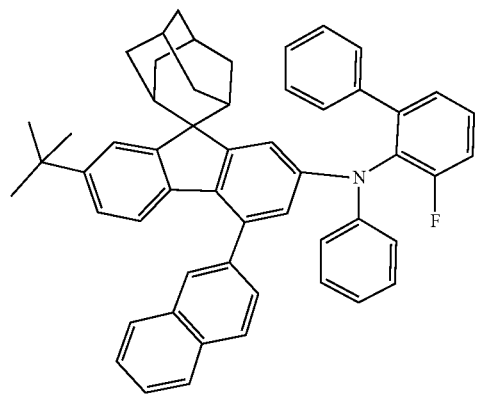
43
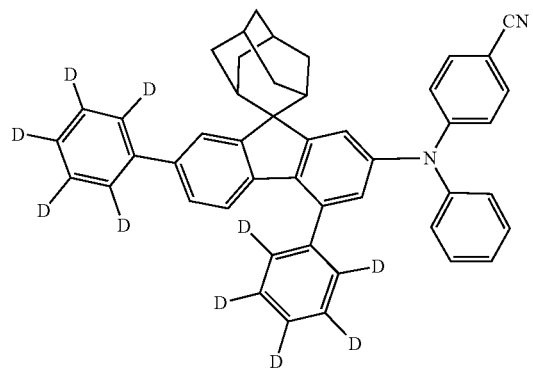
44
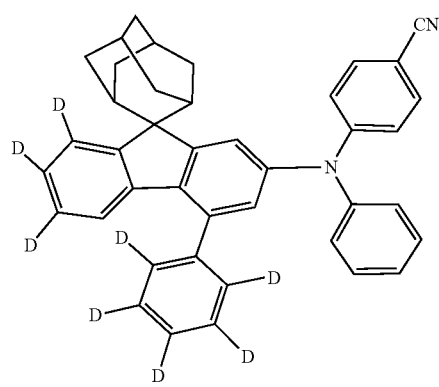
45
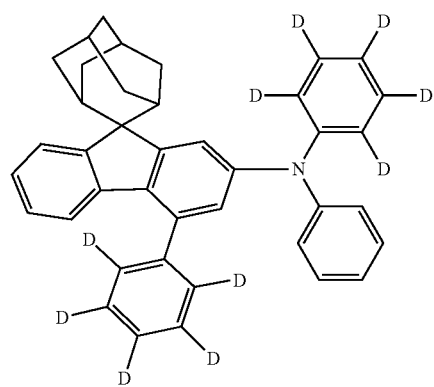
46
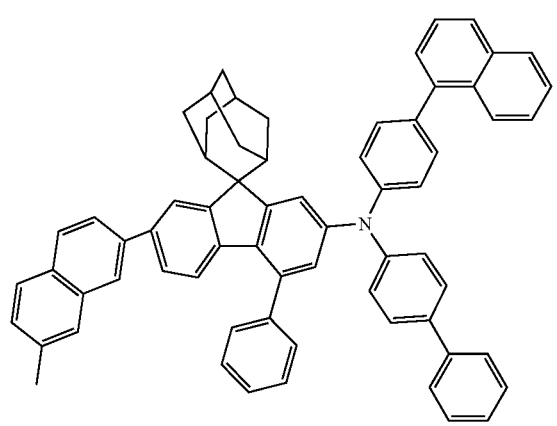
47
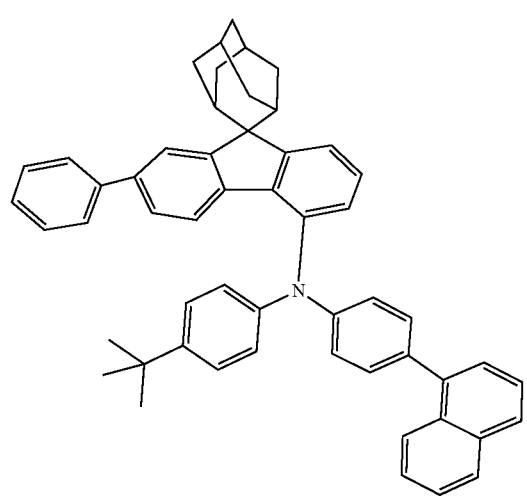

47
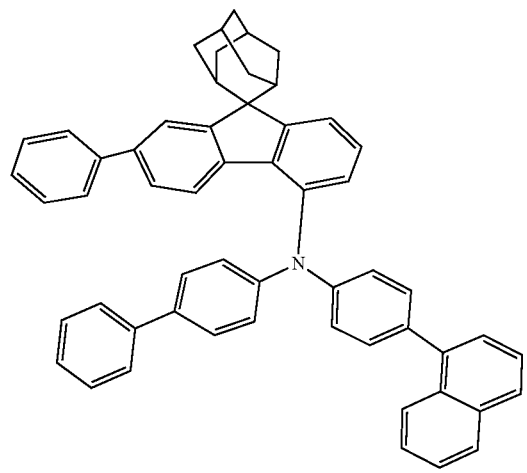
48
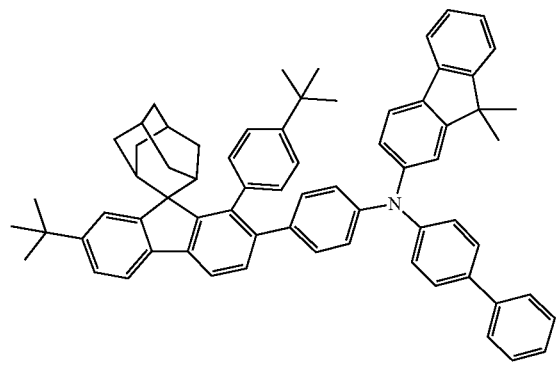
-continued
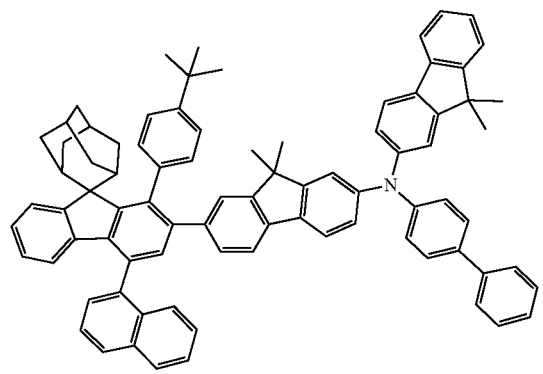
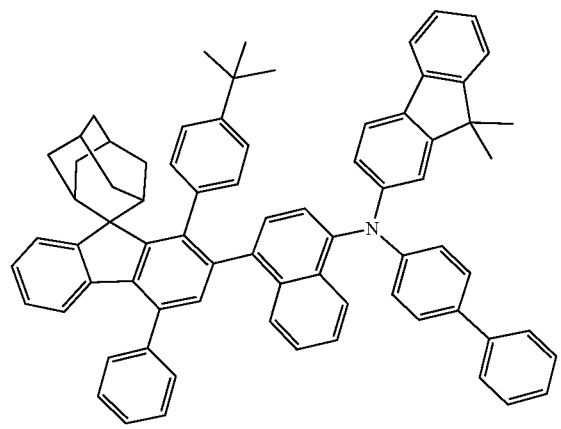
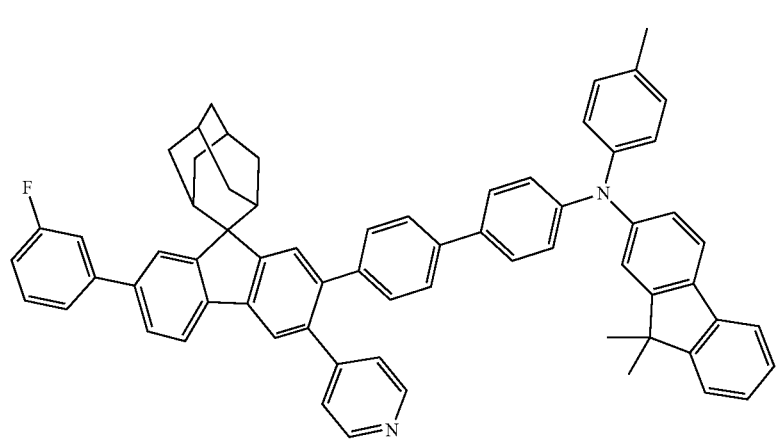

-continued
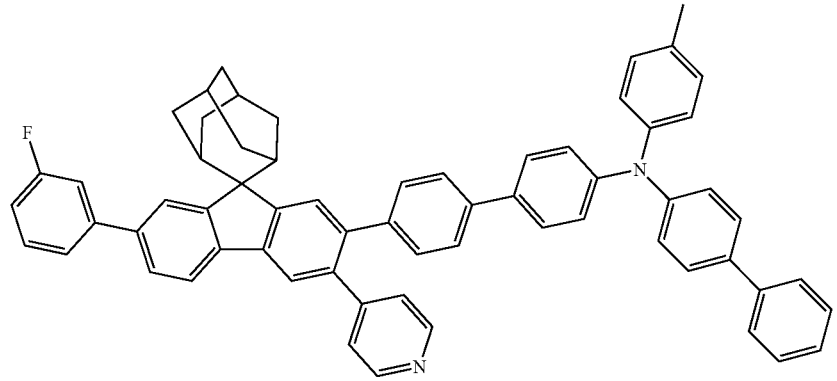
53
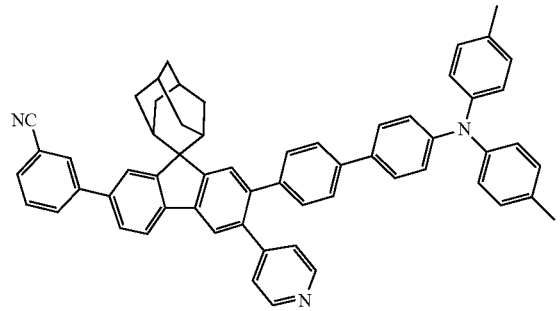
54
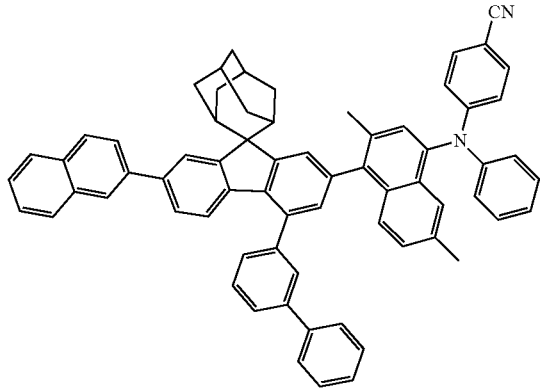
55
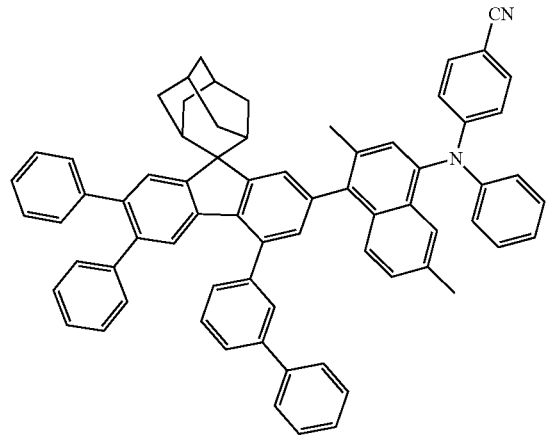
56
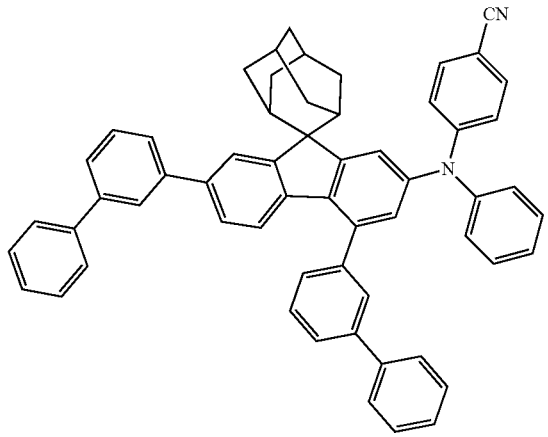
57

58
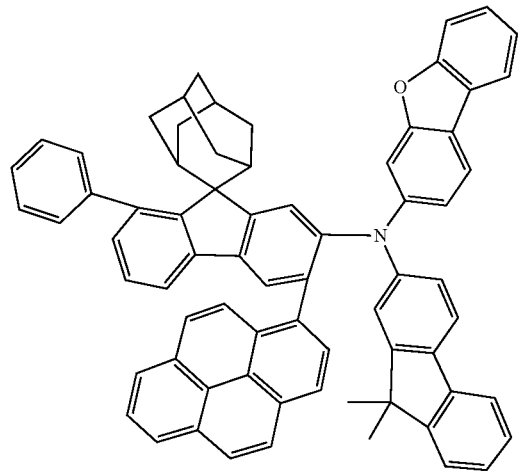
59
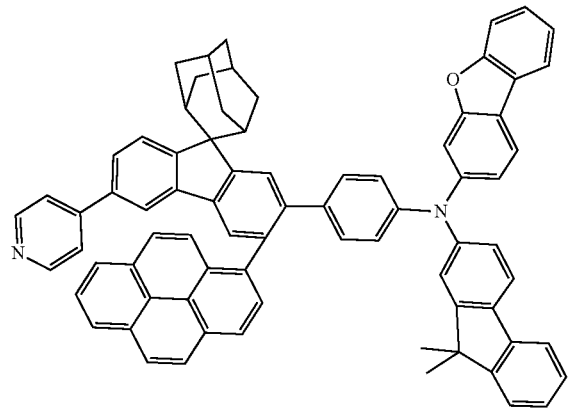
60
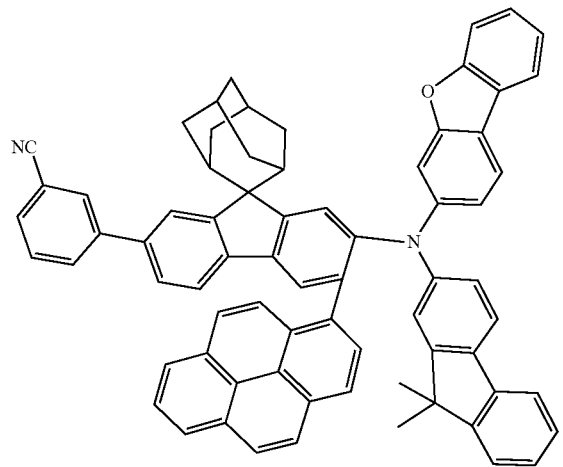
61
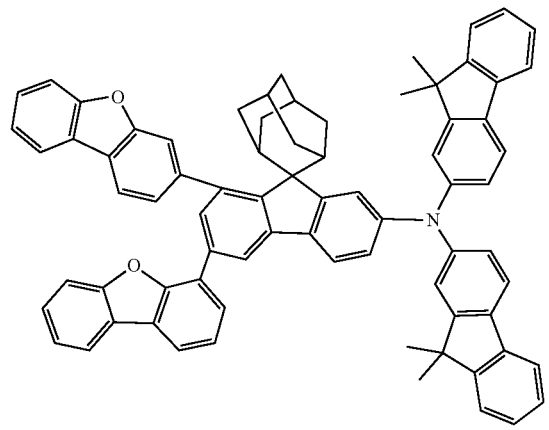
62
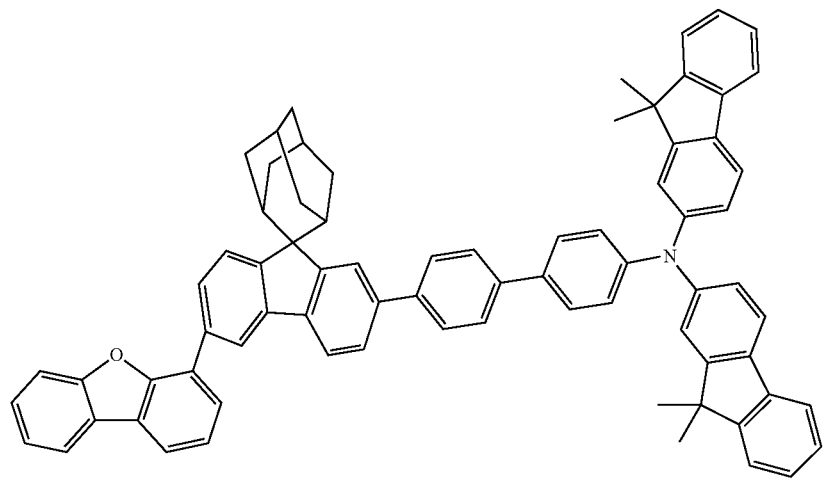

-continued
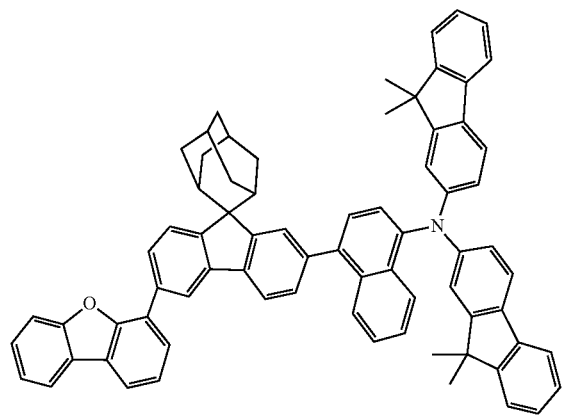
63
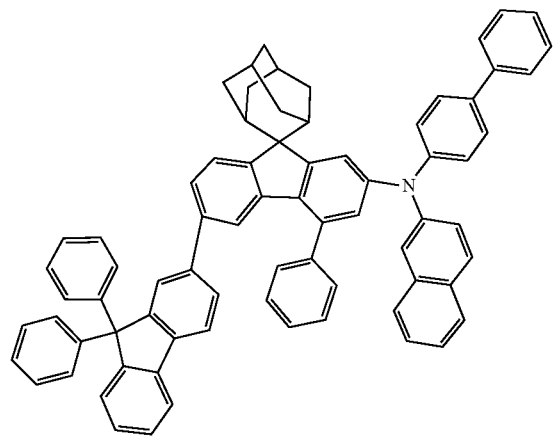
64
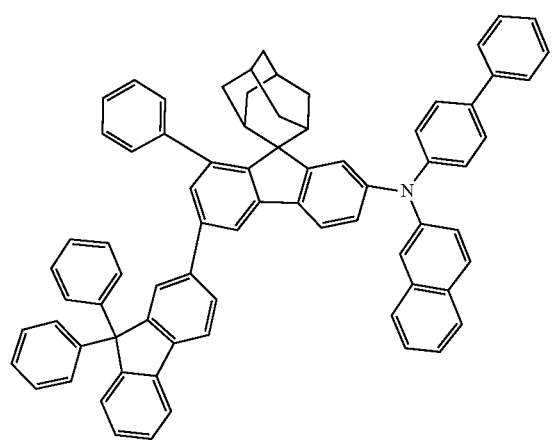
65
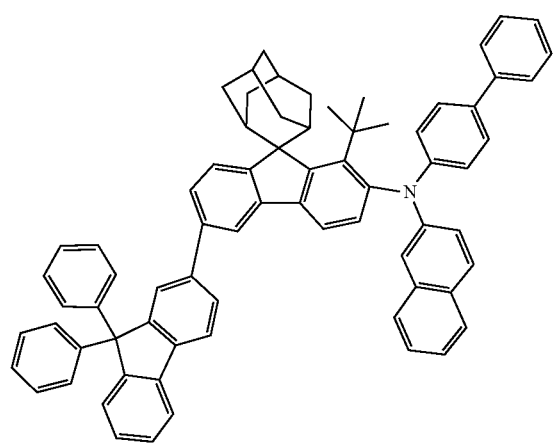
66
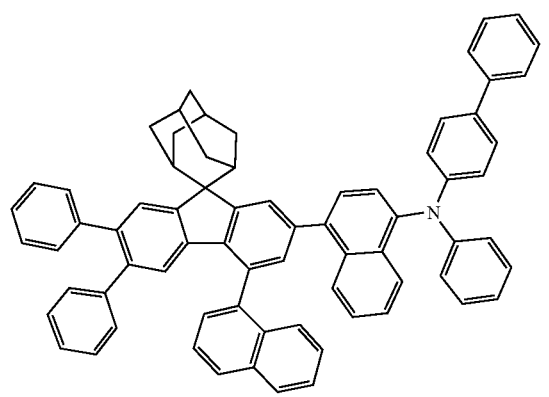
67
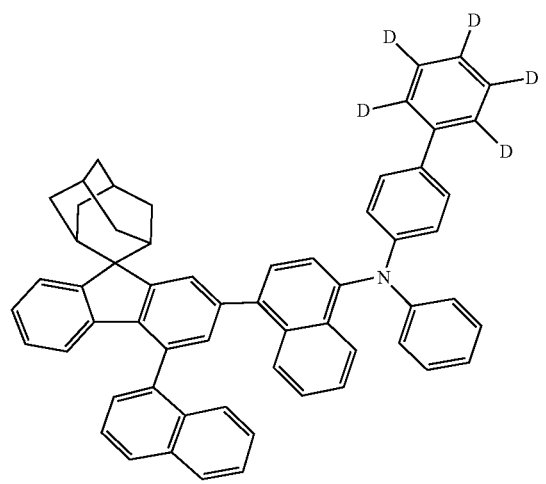
68

-continued
69
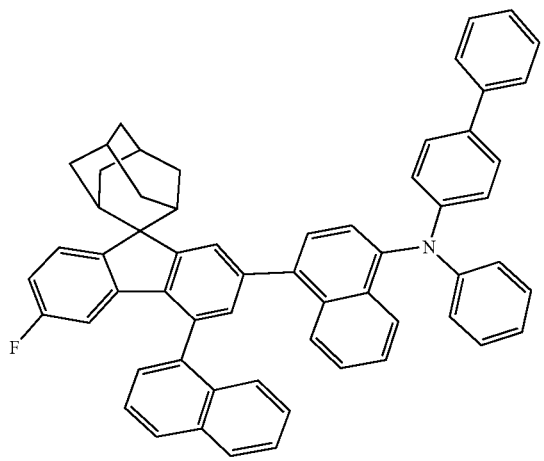
70
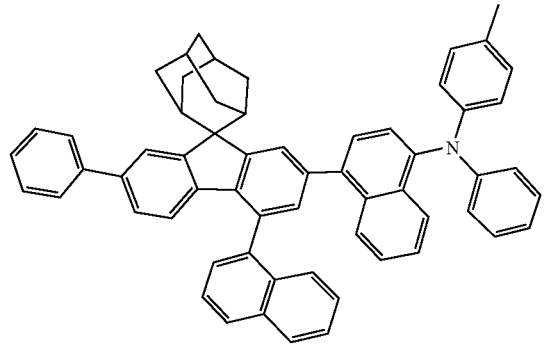
71
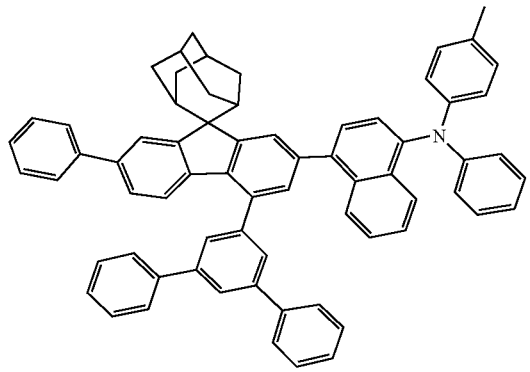
72
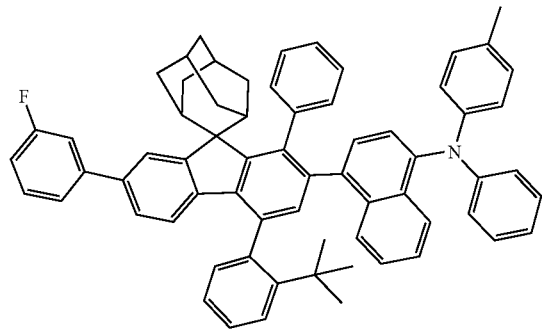
73
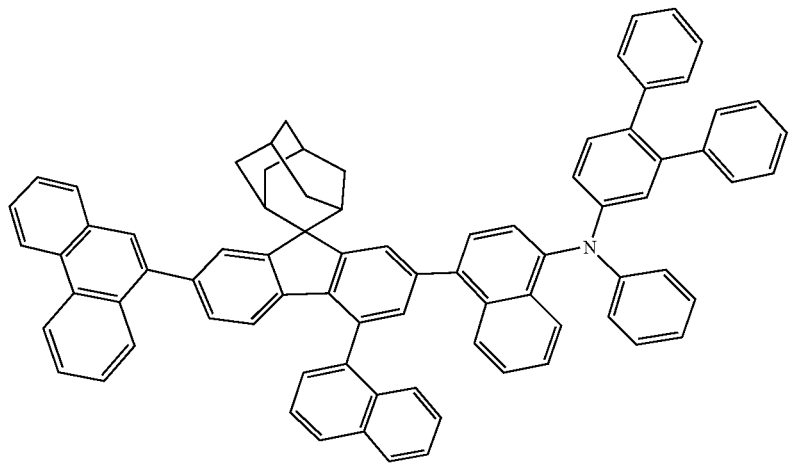

-continued
74
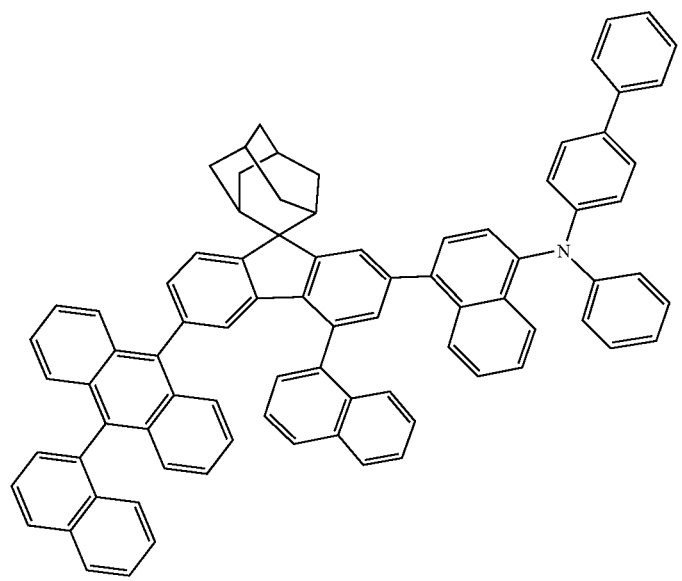
75
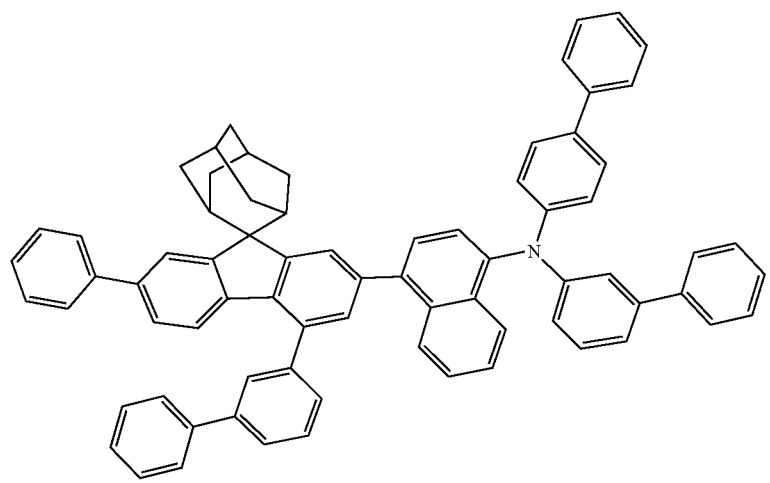
76
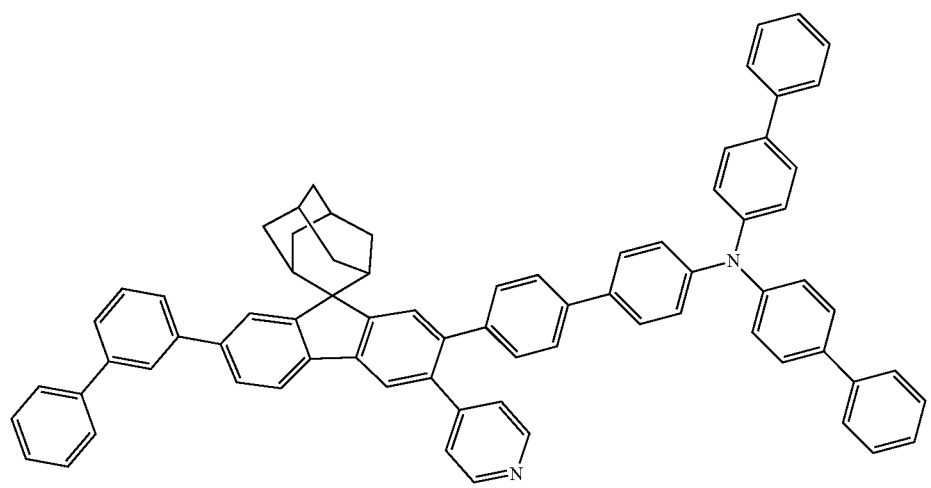

77
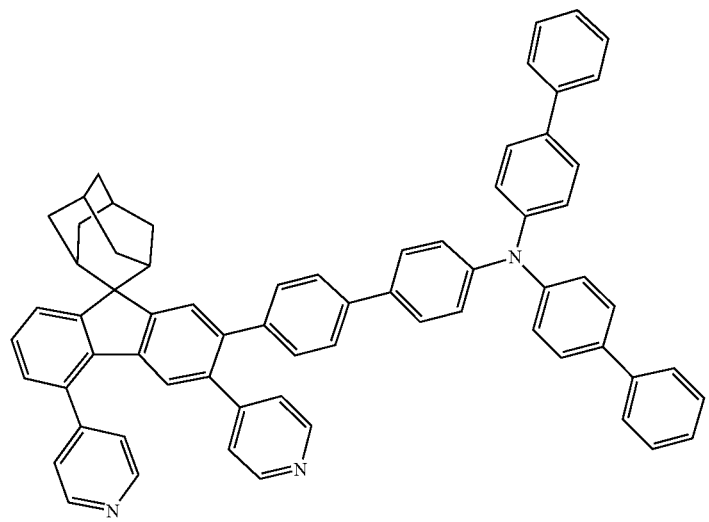
78
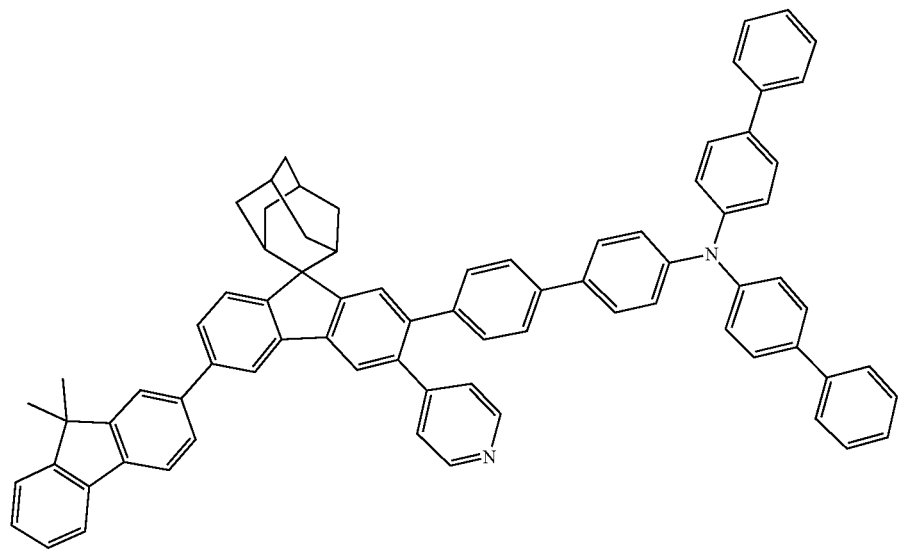
79
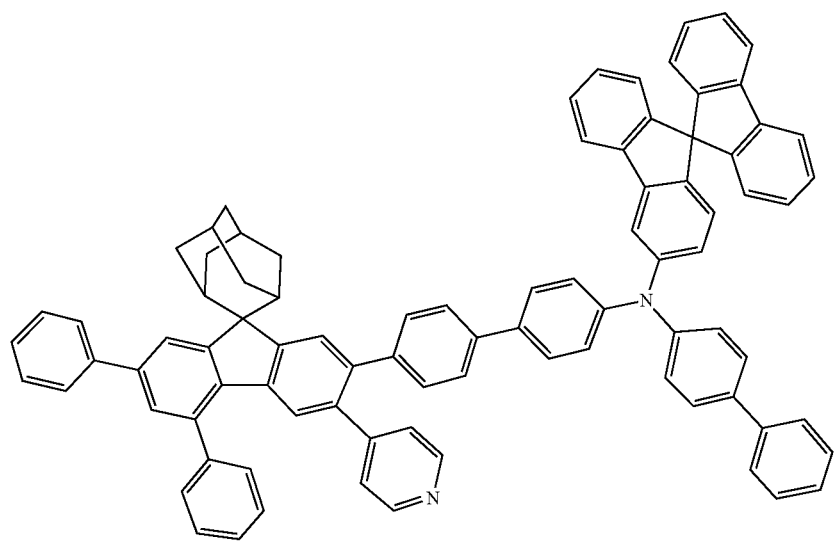

-continued
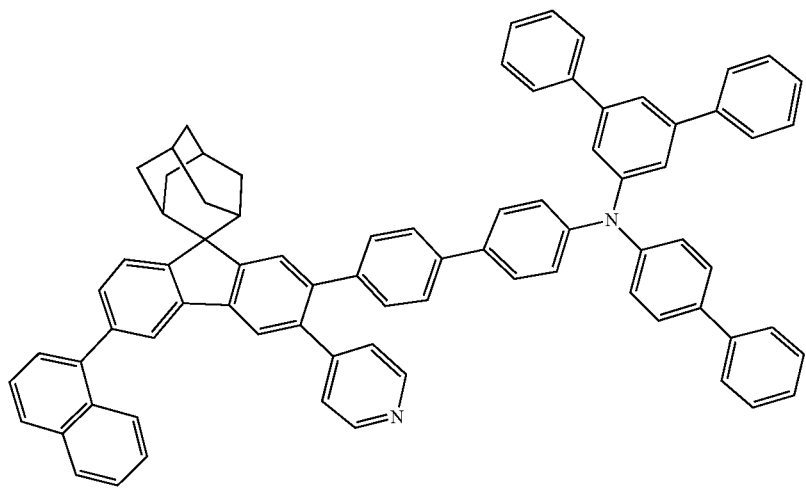
80
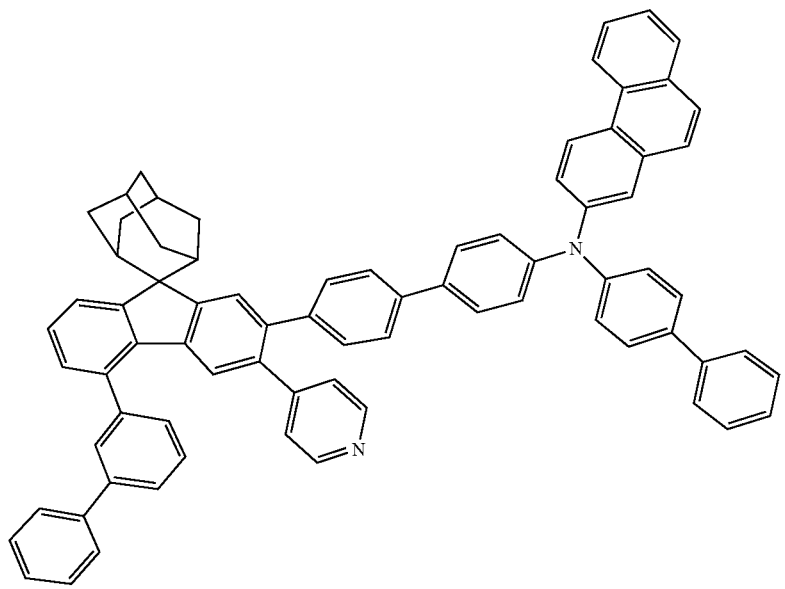
81
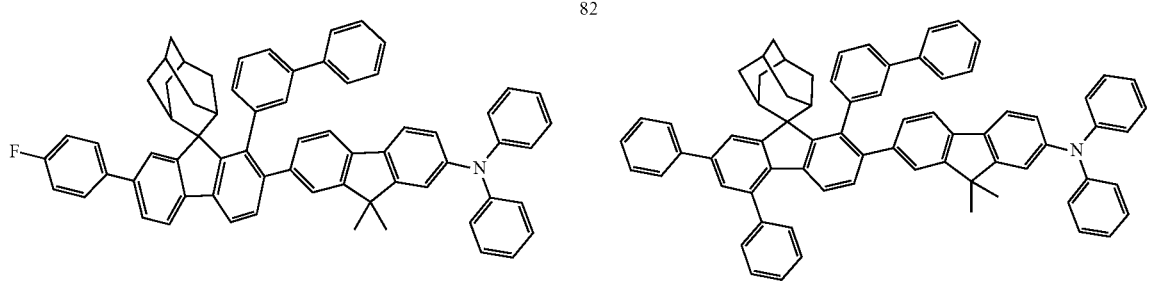
82  83

84
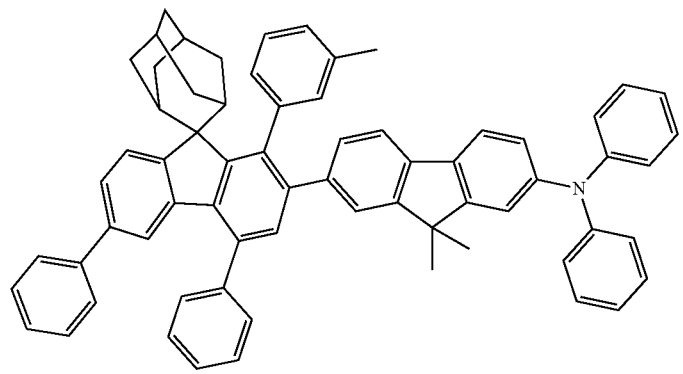
85
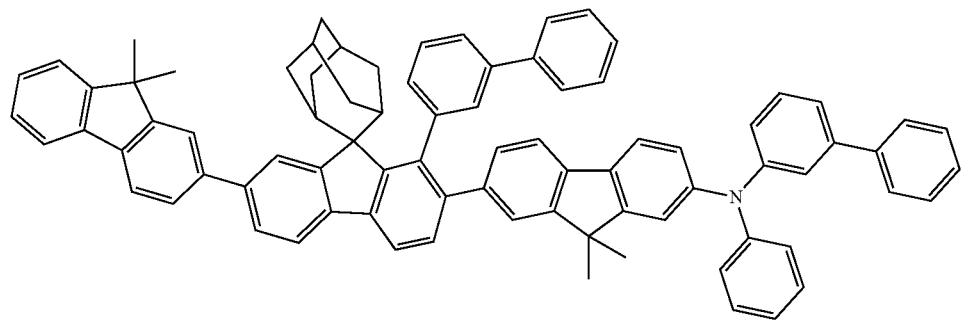
86
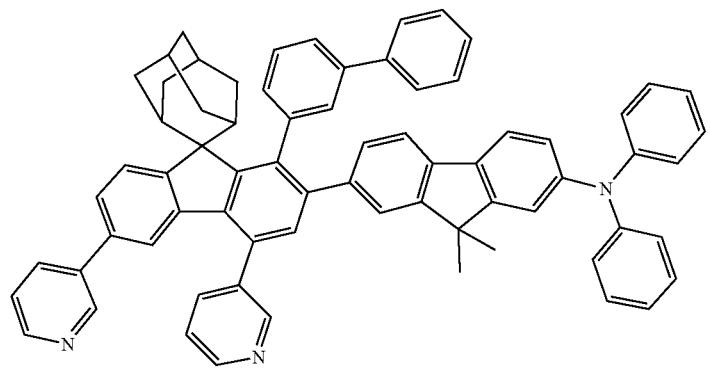
87
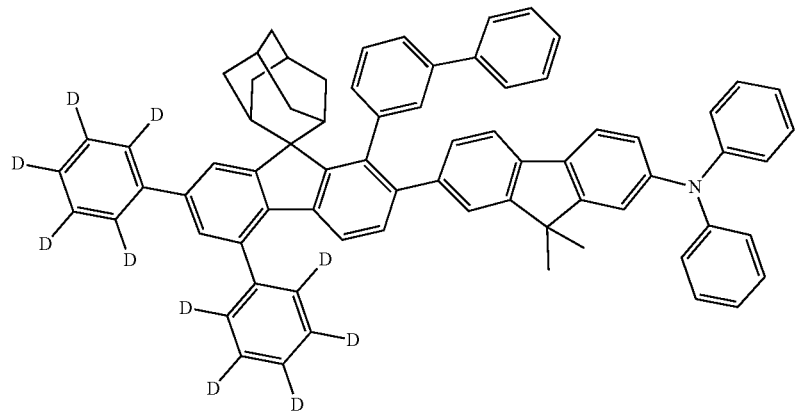

-continued
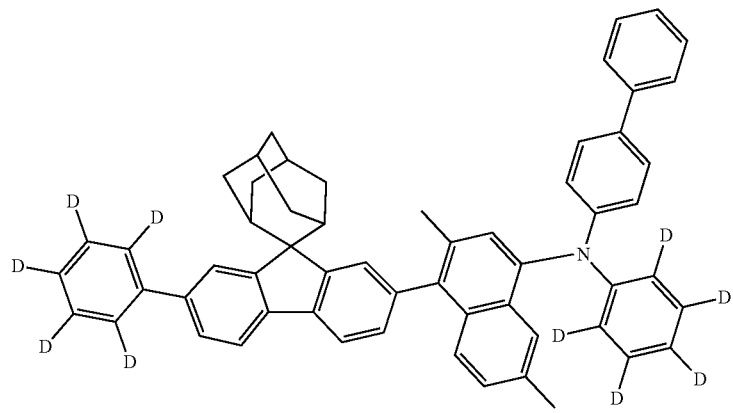
88
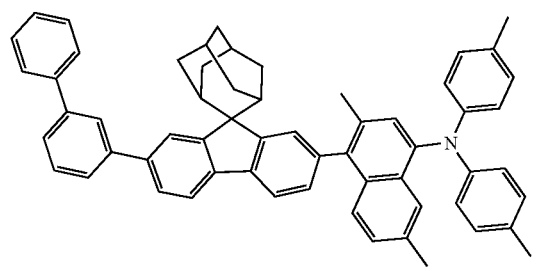
89
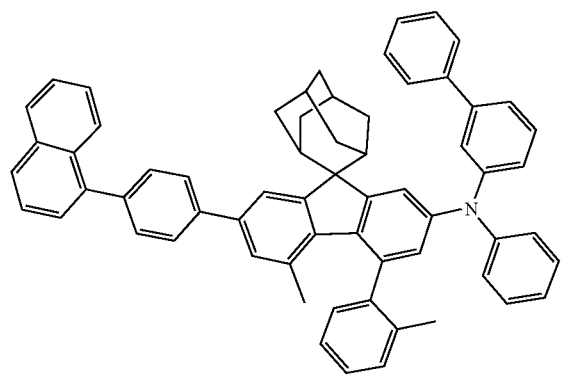
91
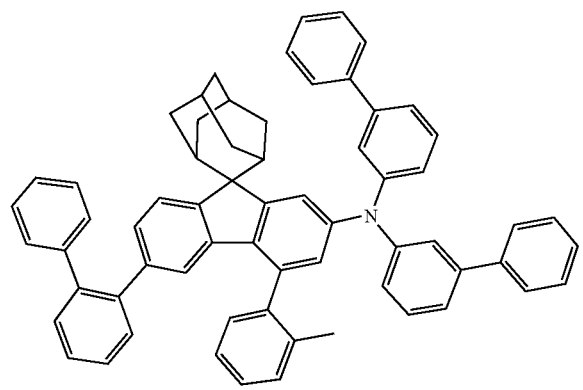
92
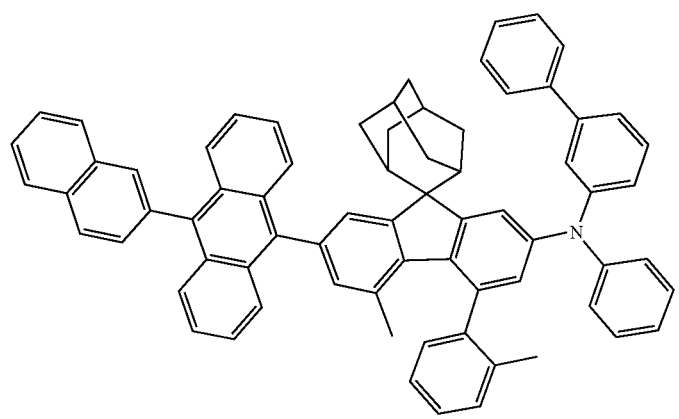
93

-continued
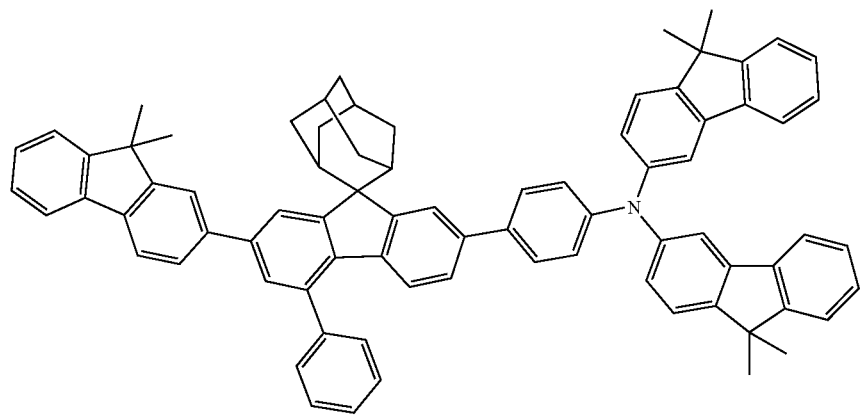
94
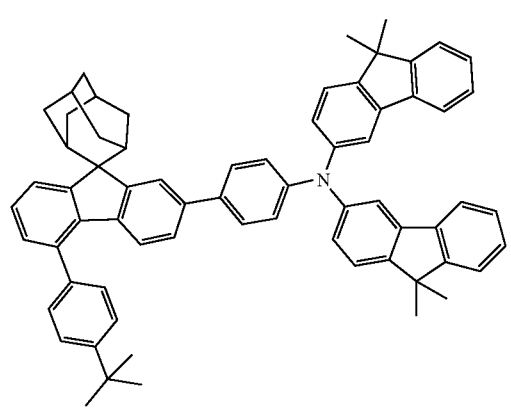
95
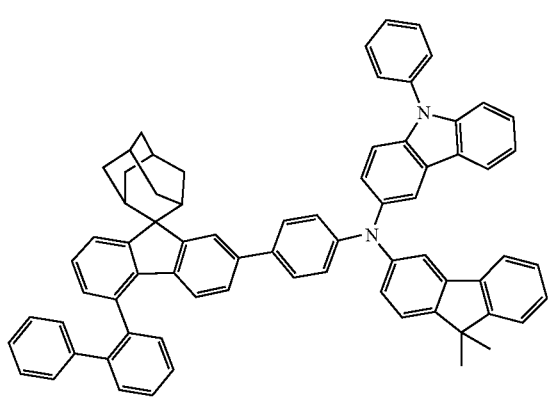
96
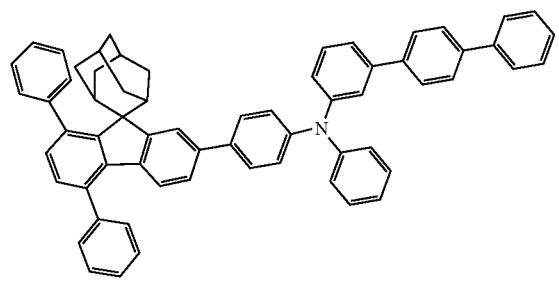
97
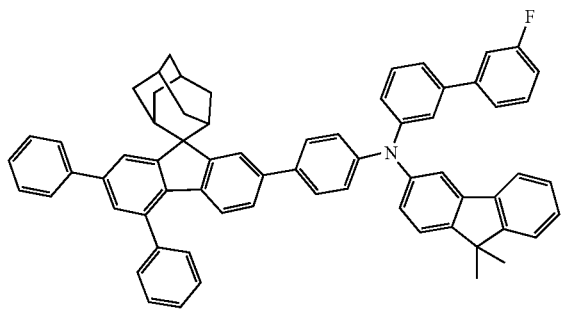
98
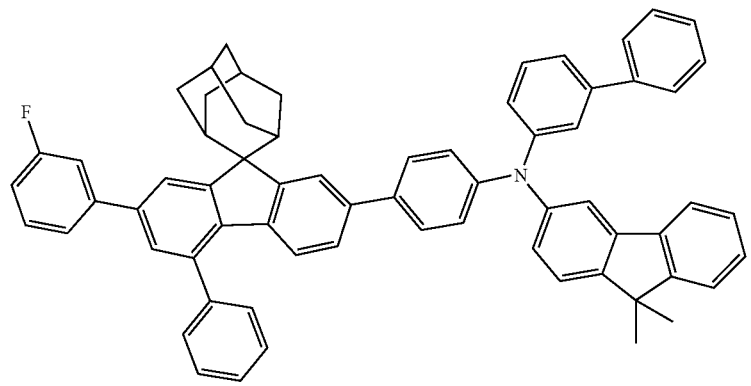
99

-continued
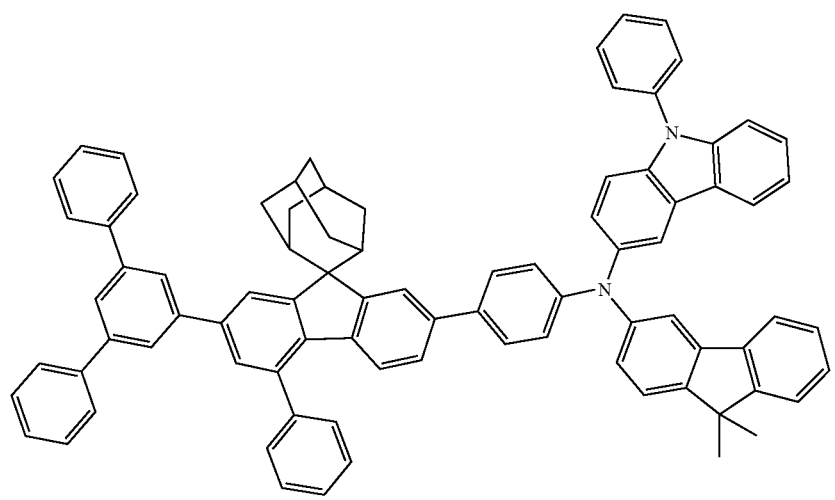
100
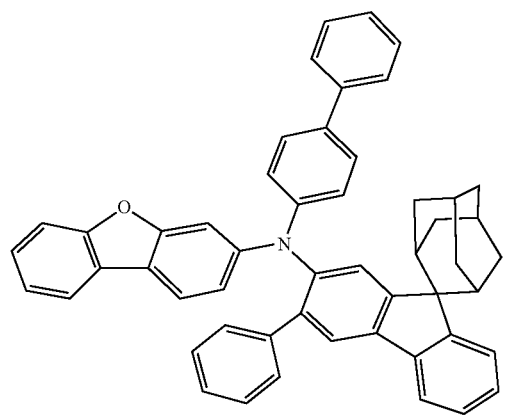
101
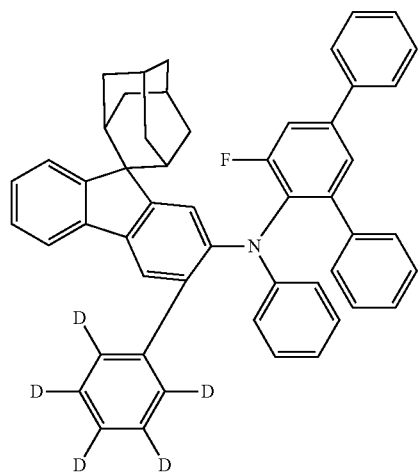
102
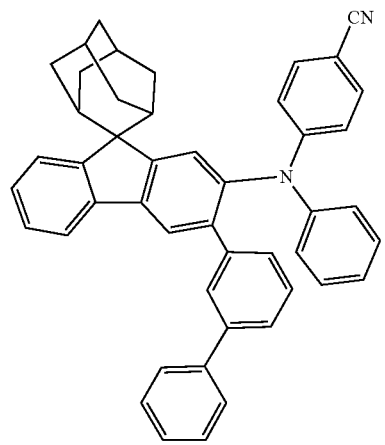
103
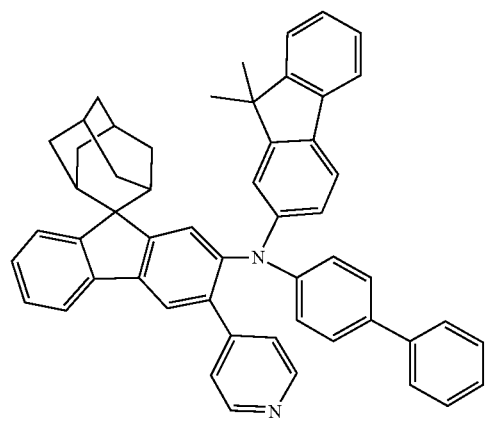
104

-continued
105
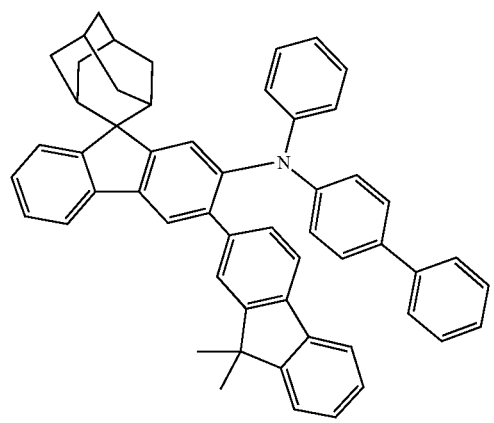
106
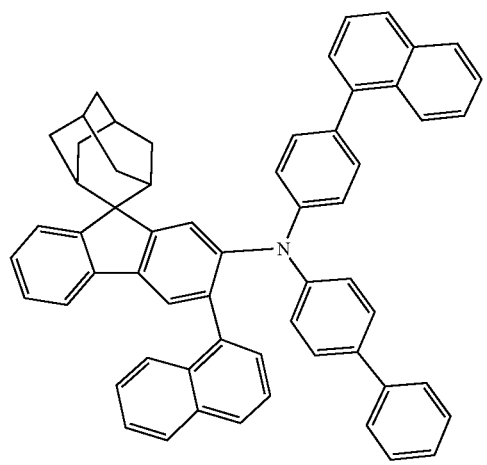
107
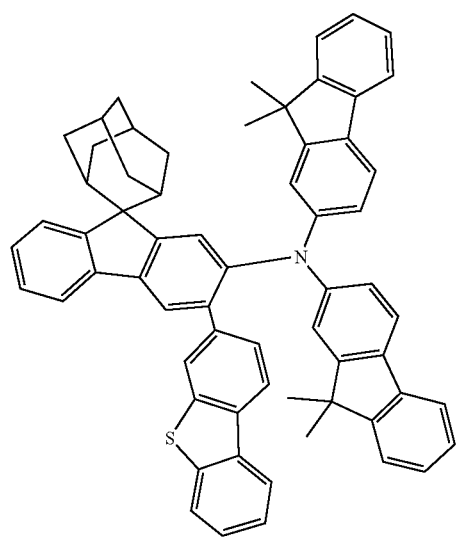
108
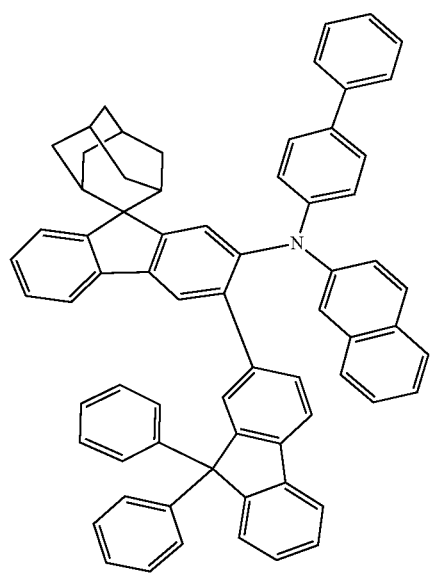
109
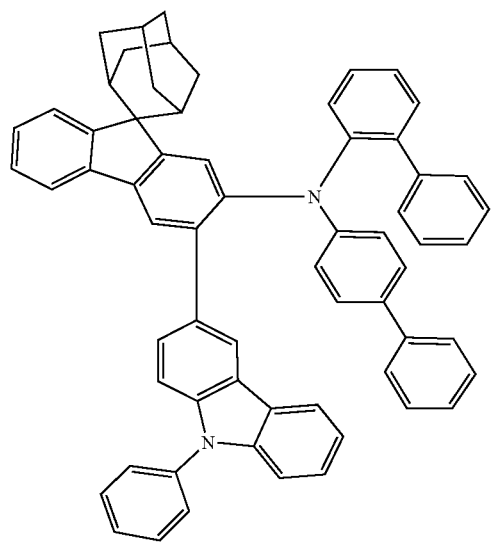
110
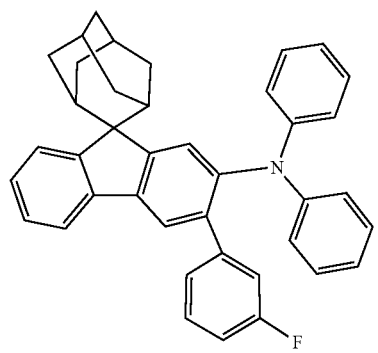

-continued
111
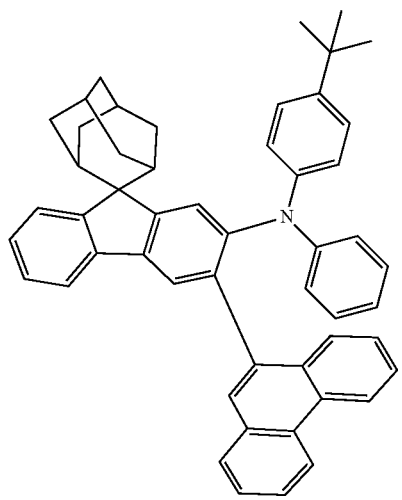
112
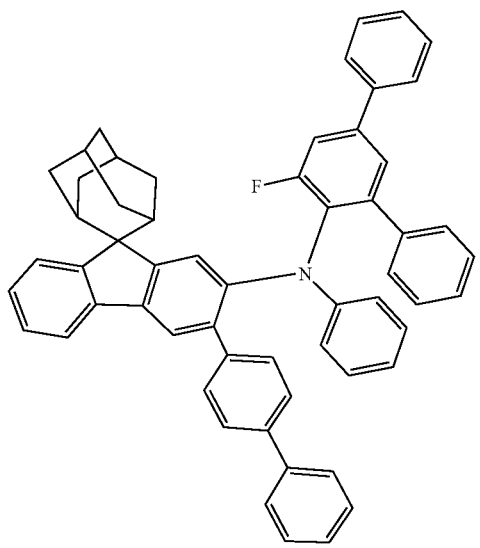
113
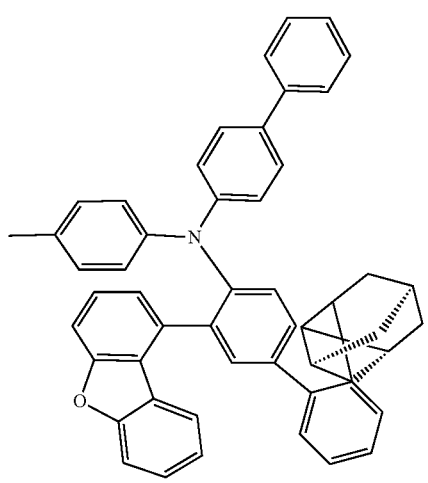
114
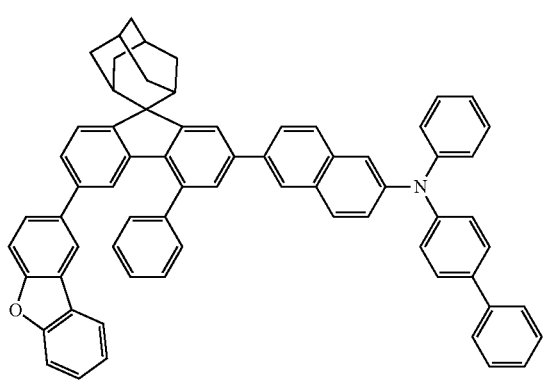
115
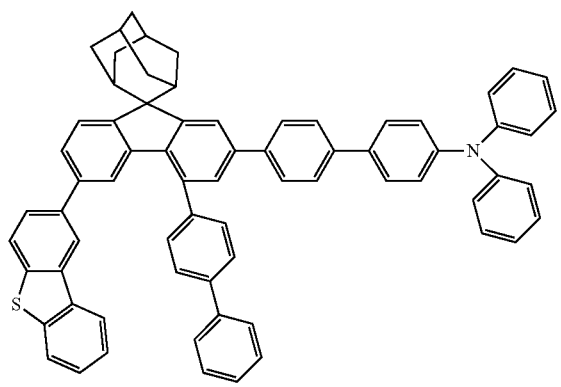
116
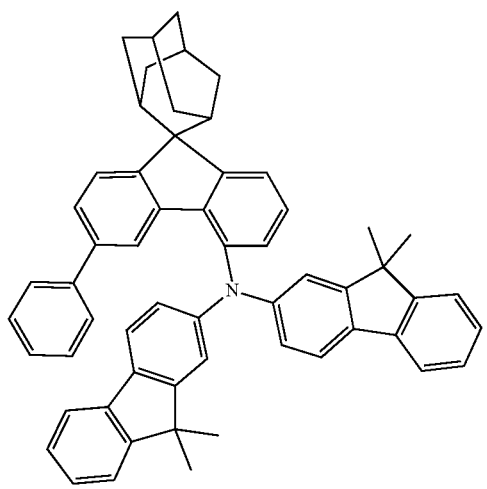

-continued
117
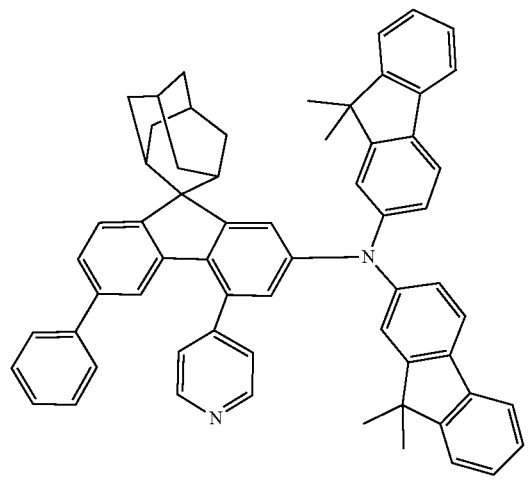
118
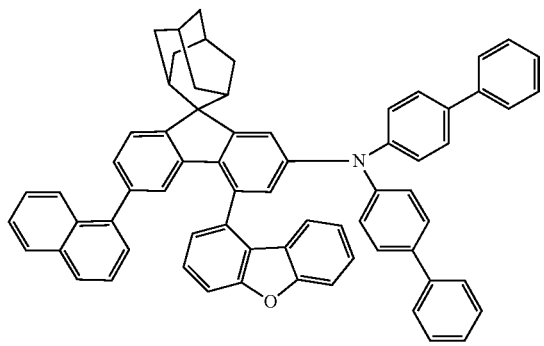
119
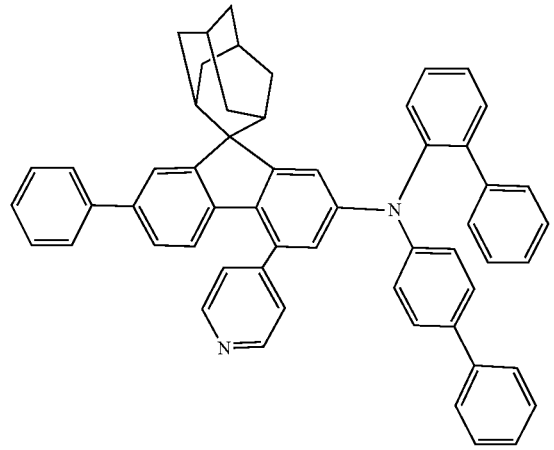
120
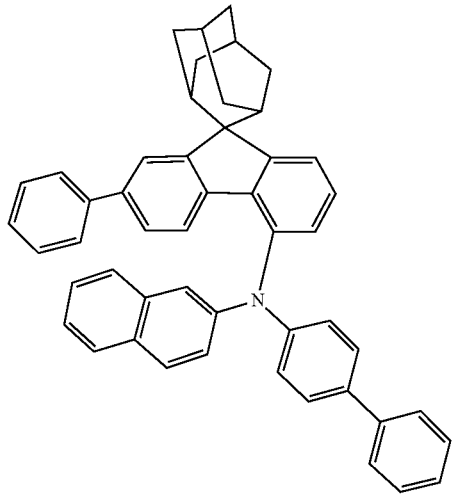
121
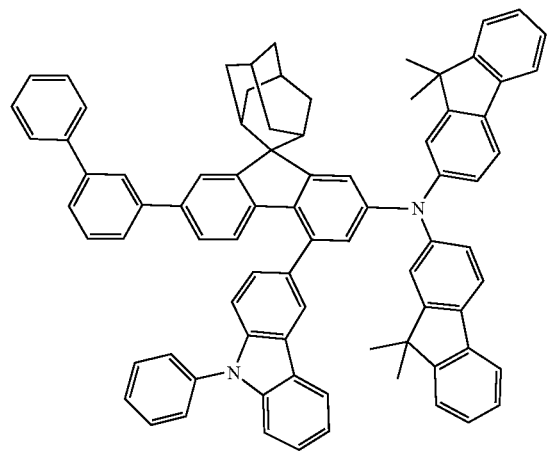
122
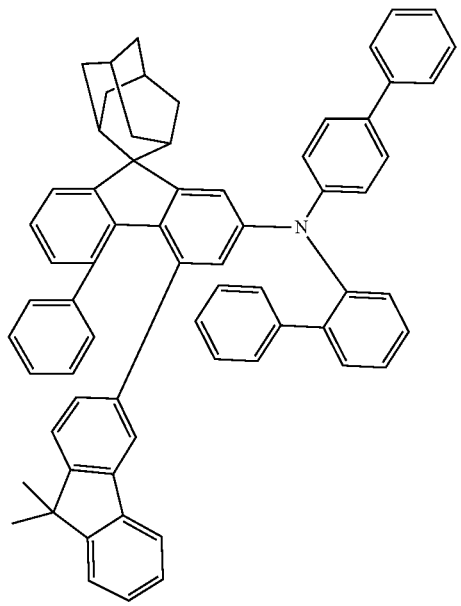

-continued
123
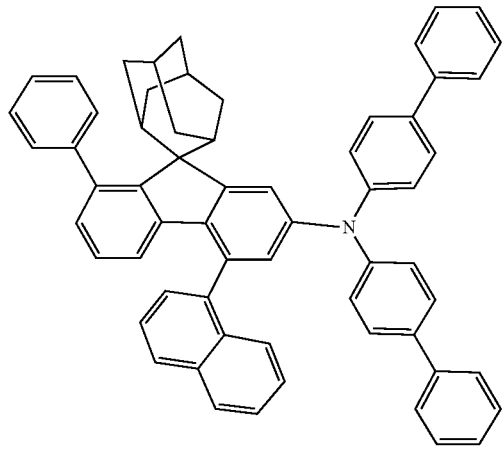
124
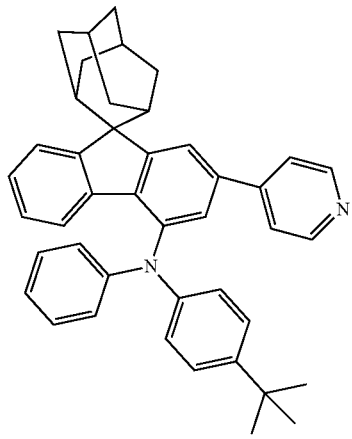
125
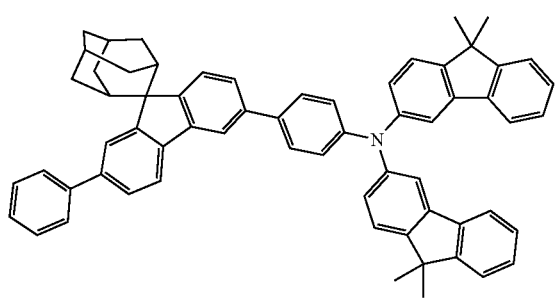
126
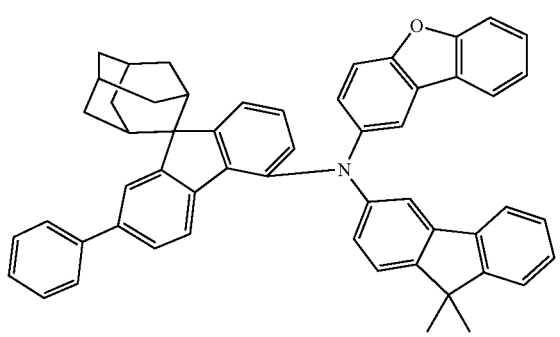
127
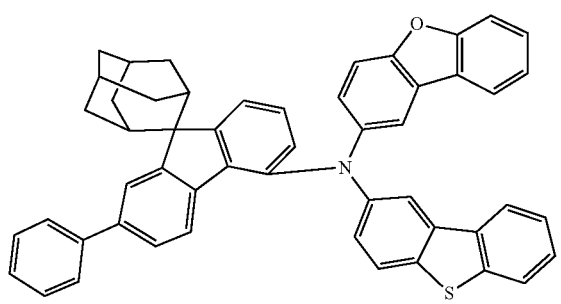
128
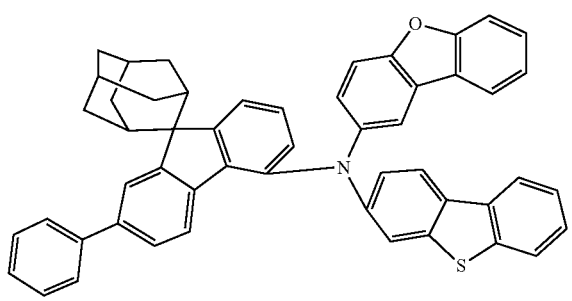
129
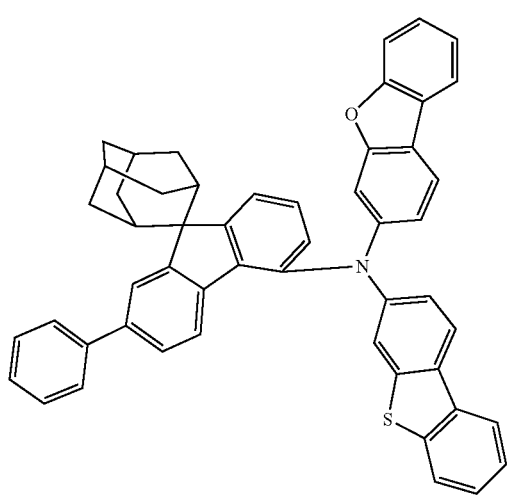
130
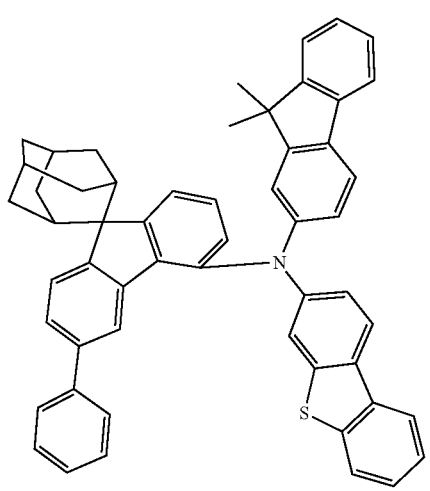

-continued
131
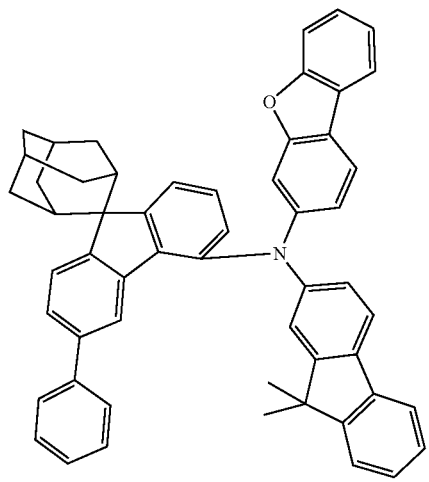
132
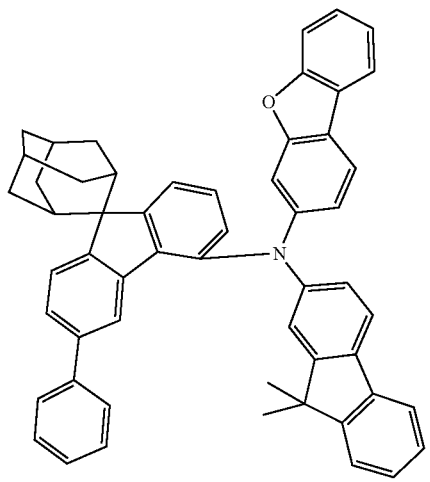
132
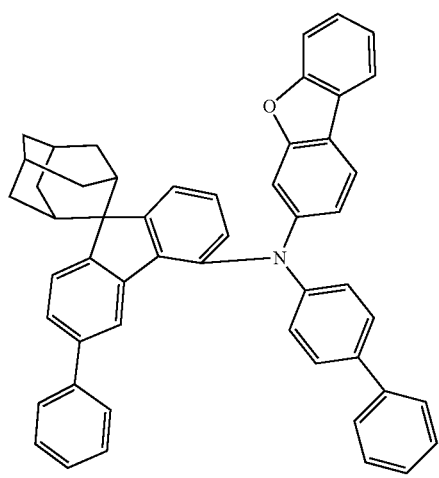
133
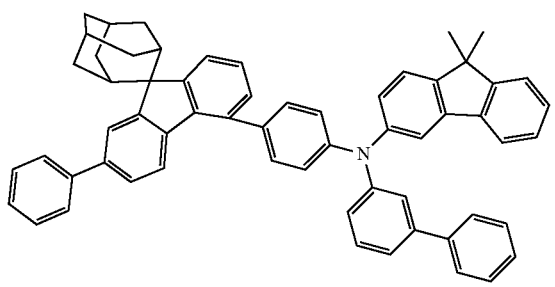
133
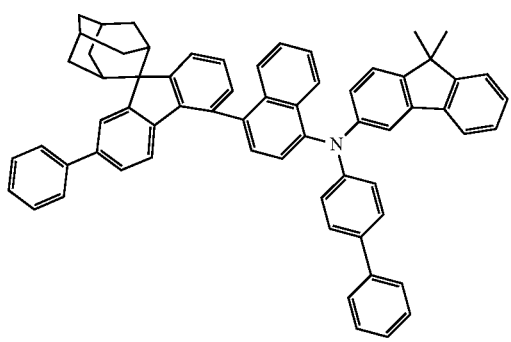

-continued
134
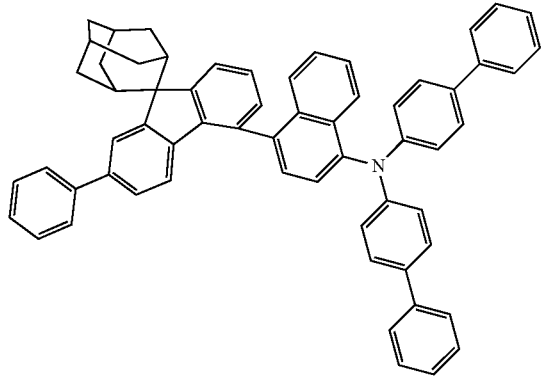
135
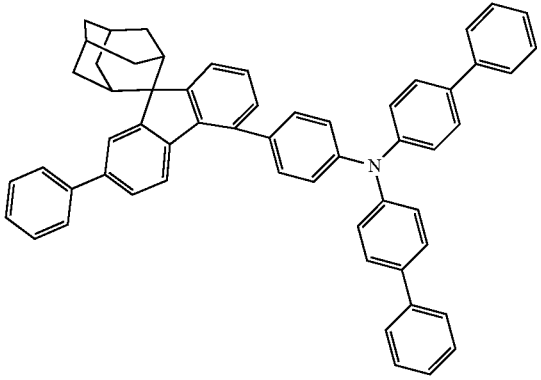
136
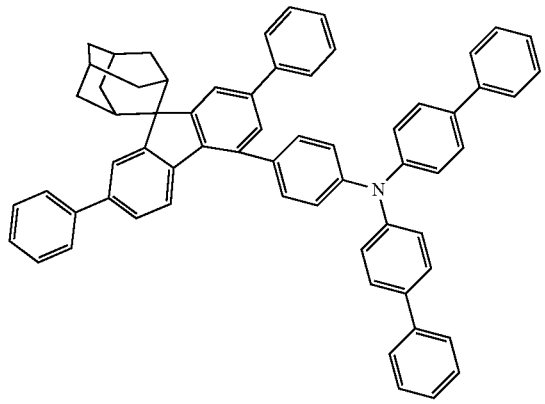
137
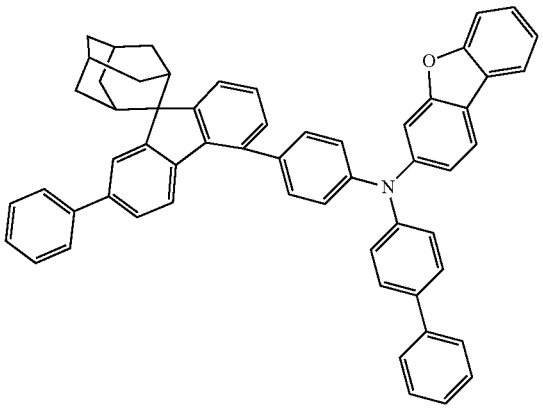
138
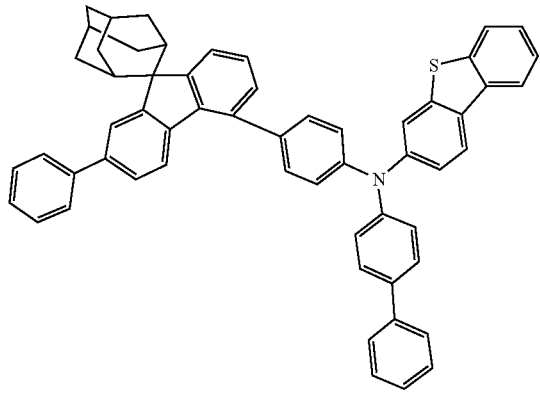
139
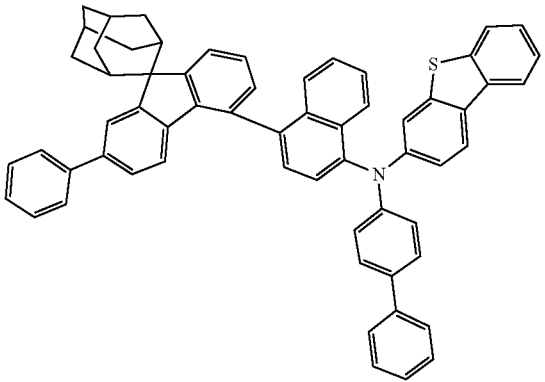
140
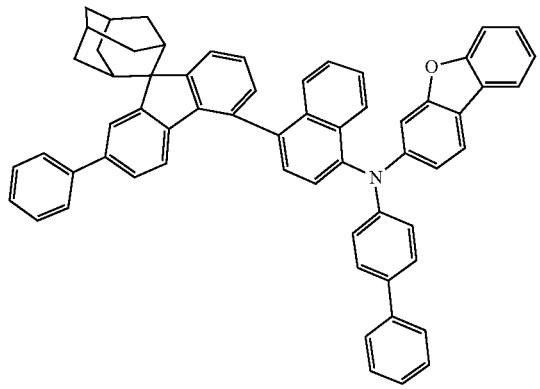
141
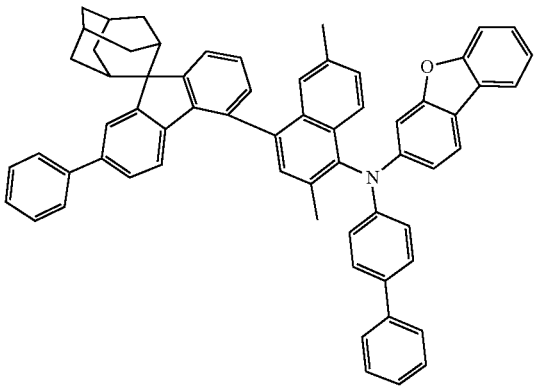

-continued
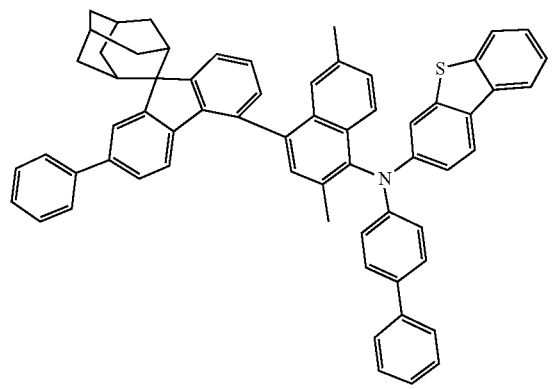
142
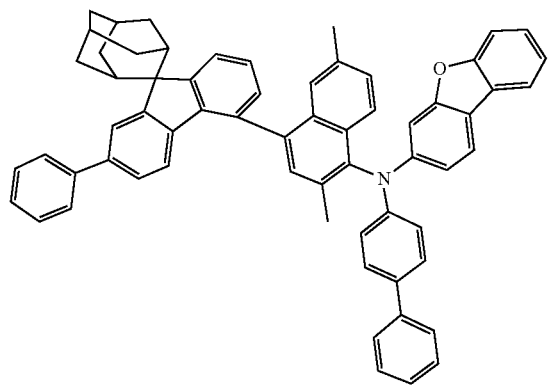
143
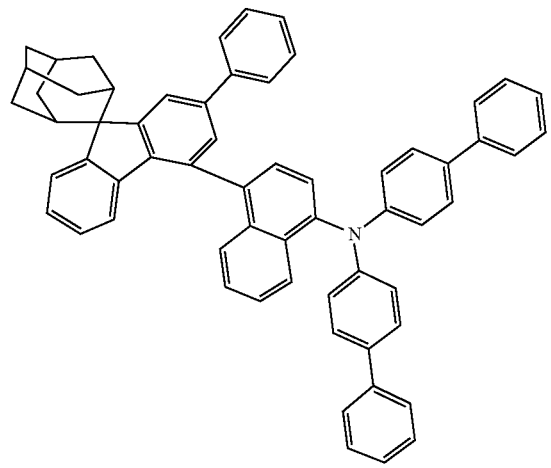
144
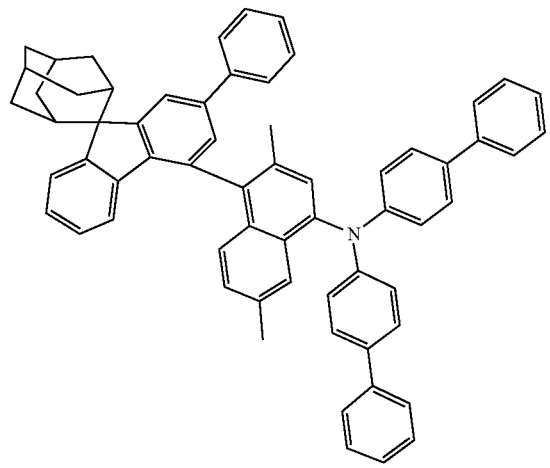
145
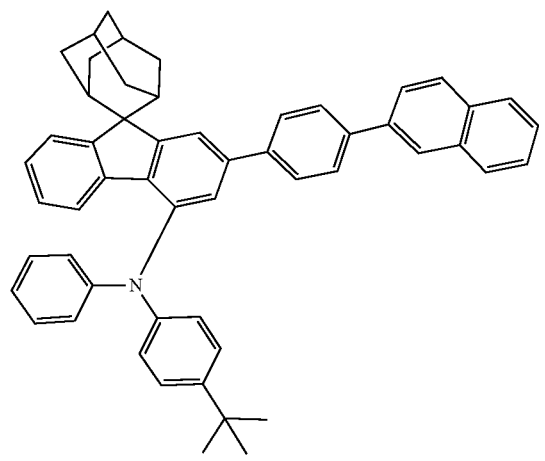
146
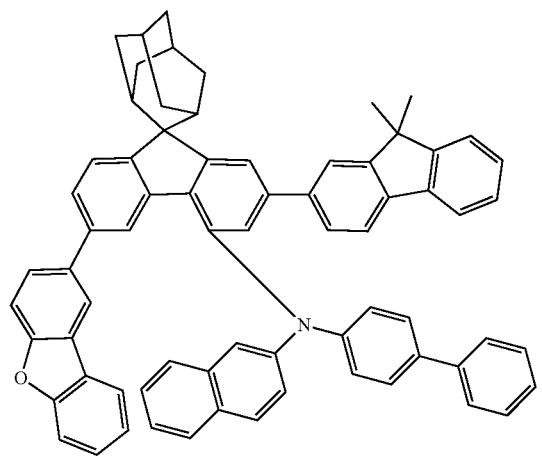
147

-continued
148
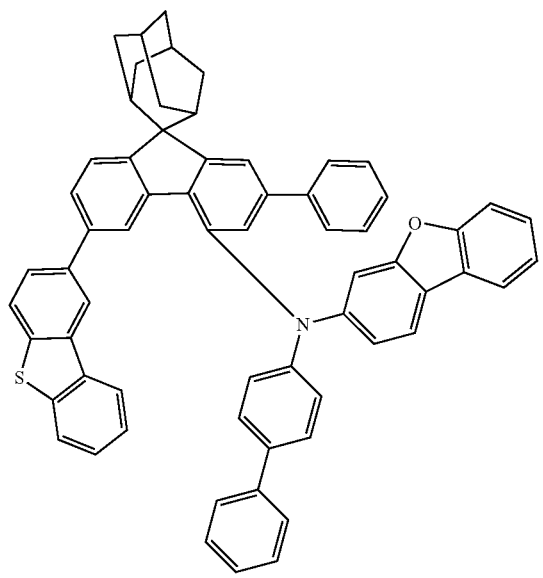
149
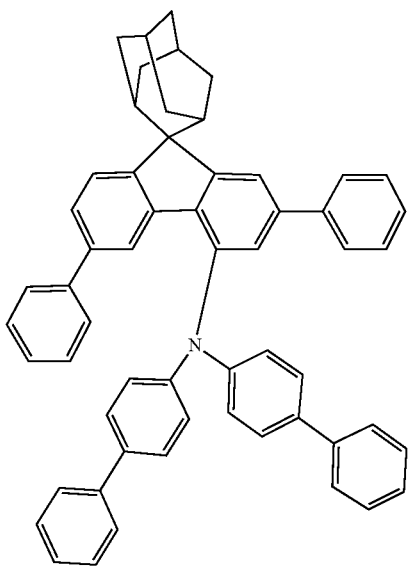
150
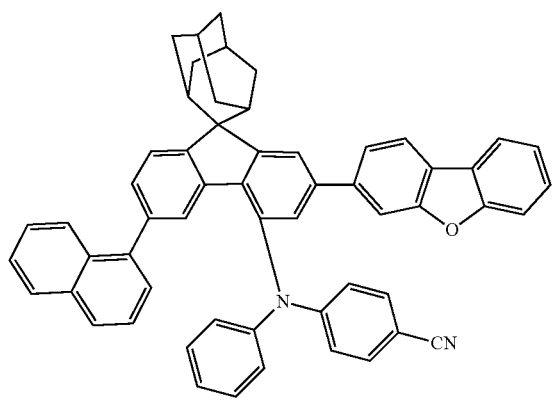
151
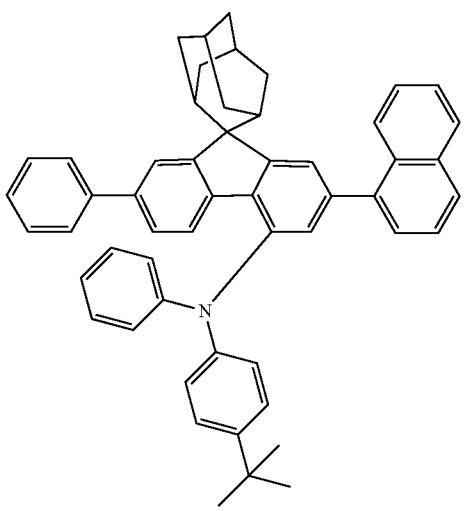
152
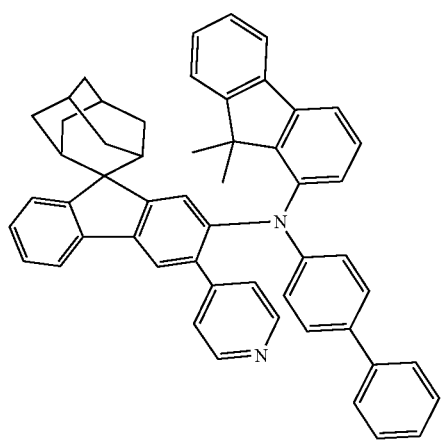
153
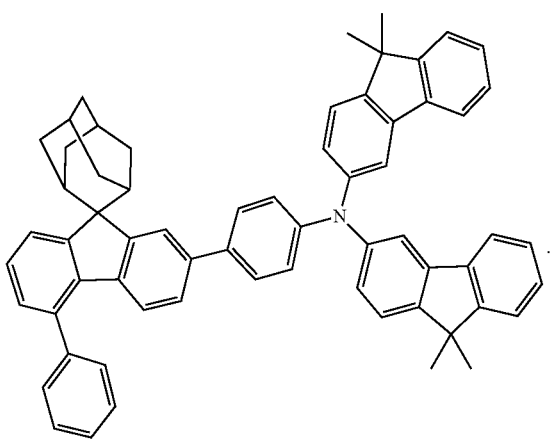

The present disclosure further provides an electronic element which is used for achieving photoelectric conversion or electro-optical conversion. The electronic element includes an anode, a cathode disposed oppositely, and a functional layer disposed between the anode and the cathode; and the functional layer contains the nitrogen-containing compound provided by the present disclosure.

For example, the electronic element is an organic electroluminescent device. As shown in FIG. 1, the organic electroluminescent device includes an anode 100 and a cathode 200 disposed oppositely, and a functional layer 300 disposed between the anode 100 and the cathode 200; and the functional layer 300 contains the nitrogen-containing compound provided by the present disclosure.

Preferably, the organic electroluminescent device is a green organic electroluminescent device or a blue organic electroluminescent device.

Optionally, the functional layer 300 includes an electron blocking layer 322, and the electron blocking layer 322 contains the nitrogen-containing compound provided by the present disclosure. The electron blocking layer 322 can be composed of the nitrogen-containing compound provided by the present disclosure and can also be composed of the nitrogen-containing compound provided by the present disclosure and other materials.

Optionally, the functional layer 300 includes a hole transport layer 321 or a hole injection layer 310, and the hole transport layer 321 or the hole injection layer 310 can contain the nitrogen-containing compound provided by the present disclosure, so that the transport capability of holes in the electronic element is improved.

In one embodiment of the present disclosure, the organic electroluminescent device may include an anode 100, a hole transport layer 321, an electron blocking layer 322, an organic electroluminescent layer 330 as an energy conversion layer, an electron transport layer 350, and a cathode 200 which are sequentially stacked. The nitrogen-containing compound provided by the present disclosure can be applied to the electron blocking layer 322 of the organic electroluminescent device, the luminous efficiency and the service life of the organic electroluminescent device can be effectively improved, and the driving voltage of the organic electroluminescent device is decreased.

Optionally, the anode 100 includes the following anode materials which are preferably materials having a large work function that facilitate hole injection into the functional layer. Specific examples of the anode materials include metals such as nickel, platinum, vanadium, chromium, copper, zinc, and aurum, or their alloys; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene](PEDT), polypyrrole, and polyaniline, but are not limited thereto. It is preferable to include a transparent electrode containing indium tin oxide (ITO) as the anode.

Optionally, the hole transport layer 321 can include one or more hole transport materials, and the hole transport materials can be selected from a carbazole polymer, carbazole connected triarylamine-type compounds or other types of compounds, which are not specially limited in the present disclosure. For example, in one example of the present disclosure, the hole transport layer 321 is composed of a compound NPB.

Optionally, the organic electroluminescent layer 330 may be composed of a single light-emitting material, and may also include a host material and a guest material. Optionally, the organic electroluminescent layer 330 is composed of a host material and a guest material, holes injected into the organic electroluminescent layer 330 and electrons injected into the organic electroluminescent layer 330 can be recombined in the organic electroluminescent layer 330 to form excitons, the excitons transfer energy to the host material, and the host material transfers energy to the guest material, so that the guest material can emit light.

The host material of the organic electroluminescent layer 330 can be a metal chelated compound, a distyryl derivative, an aromatic amine derivative, a dibenzofuran derivative or other types of materials, which is not specially limited in the present disclosure. In one embodiment of the present disclosure, the host material of the organic electroluminescent layer 330 may be a composition of GH-n1 and GH-n2 or $\alpha,\beta$-ADN.

The guest material of the organic electroluminescent layer 330 may be a compound having a condensed aryl ring or its derivative, a compound having a heteroaryl ring or its derivative, an aromatic amine derivative, or other materials, which is not specially limited in the present disclosure. In one embodiment of the present disclosure, the guest material of the organic electroluminescent layer 330 may be $Ir(ppy)_3$ or BD-1.

The electron transport layer 350 can be of a single-layer structure or a multi-layer structure and can include one or more electron transport materials, and the electron transport materials can be selected from a benzimidazole derivative, an oxadiazole derivative, a quinoxaline derivative or other electron transport materials, which are not specially limited in the present disclosure. For example, in one embodiment of the present disclosure, the electron transport layer 350 may be composed of ET-06 and LiQ.

Optionally, the cathode 200 includes the following cathode materials, which is a materials with a small work function that facilitate electron injection into the functional layer. Specific examples of the cathode materials include metals such as magnesium, calcium, sodium, potassium, titanium, indium, yttrium, lithium, gadolinium, aluminum, argentum, tin, and lead, or their alloys; or a multilayer of layers of materials such as LiF/Al, Liq/Al, $LiO_2$/Al, LiF/Ca, LiF/Al, and $BaF_2$/Ca, but are not limited thereto. It is preferable to include a metal electrode containing magnesium (Mg) and argentum (Ag) as the cathode.

Optionally, as shown in FIG. 1, a hole injection layer 310 can also be arranged between the anode 100 and the hole transport layer 321 to enhance the ability of injecting holes into the hole transport layer 321. The hole injection layer 310 may be selected from a benzidine derivative, a starburst arylamine compound, a phthalocyanine derivative or other materials, which is not specially limited in the present disclosure. In one embodiment of the present disclosure, the hole injection layer 310 may be composed of F4-TCNQ.

Optionally, as shown in FIG. 1, an electron injection layer 360 may also be arranged between the cathode 200 and the electron transport layer 350 to enhance the ability of injecting electrons into the electron transport layer 350. The electron injection layer 360 may include an inorganic material such as an alkali metal sulfide, and an alkali metal halide and the like, or may include a complex of an alkali metal and an organic substance. In one embodiment of the present disclosure, the electron injection layer 360 may include Yb.

Optionally, a hole blocking layer 340 can also be arranged between the organic electroluminescent layer 330 and the electron transport layer 350.

Figure 2:
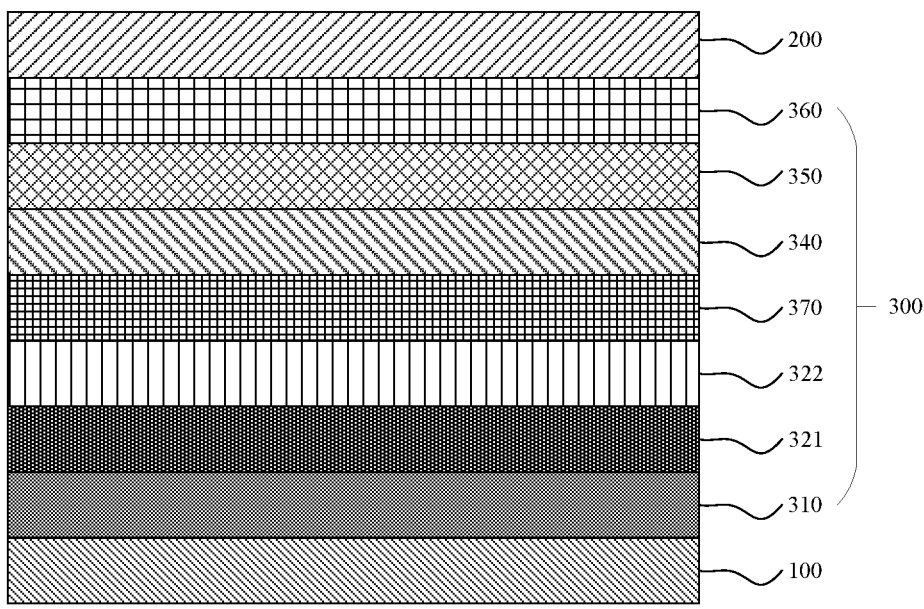
FIG. 2 is a structural schematic diagram of a photoelectric conversion device according to the embodiments of the present disclosure.

For example, the electronic element can be a photoelectric conversion device, as shown in FIG. 2, the photoelectric conversion device can include an anode 100 and a cathode 200 disposed oppositely, and a functional layer 300 disposed between the anode 100 and the cathode 200; and the functional layer 300 contains the nitrogen-containing compound provided in the present disclosure.

Optionally, the functional layer 300 includes an electron blocking layer 322, and the electron blocking layer 322 contains the nitrogen-containing compound provided by the present disclosure. The electron blocking layer 322 can be composed of the nitrogen-containing compound provided by the present disclosure, and can also be composed of the nitrogen-containing compound provided by the present disclosure and other materials.

Optionally, as shown in FIG. 2, the photoelectric conversion device can include an anode 100, a hole transport layer 321, an electron blocking layer 322, a photoelectric conversion layer 370 as an energy conversion layer, an electron transport layer 350 and a cathode 200 which are sequentially stacked. The nitrogen-containing compound provided by the present disclosure can be applied to the electron blocking layer 322 of the photoelectric conversion device, so that the luminous efficiency and the service life of the photoelectric conversion device can be effectively improved, and the open-circuit voltage of the photoelectric conversion device is improved.

Optionally, a hole injection layer 310 may also be arranged between the anode 100 and the hole transport layer 321.

Optionally, an electron injection layer 360 may also be arranged between the cathode 200 and the electron transport layer 350.

Optionally, a hole blocking layer 340 may also be arranged between the photoelectric conversion layer 370 and the electron transport layer 350.

Optionally, the photoelectric conversion device may be a solar cell, especially an organic thin-film solar cell. For example, as shown in FIG. 2, in one embodiment of the present disclosure, the solar cell includes an anode 100, a hole transport layer 321, an electron blocking layer 322, a photoelectric conversion layer 370, an electron transport layer 350 and a cathode 200 which are sequentially stacked, and the electron blocking layer 322 contains the nitrogen-containing compound provided by the present disclosure.

The embodiments of the present disclosure further provide an electronic device, wherein the electronic device includes any one electronic element described in the embodiments of the electronic element. Since the electronic device is provided with any one electronic element described in the embodiments of the electronic element, the electronic device has the same beneficial effects, which will not be repeated here.

Figure 3:
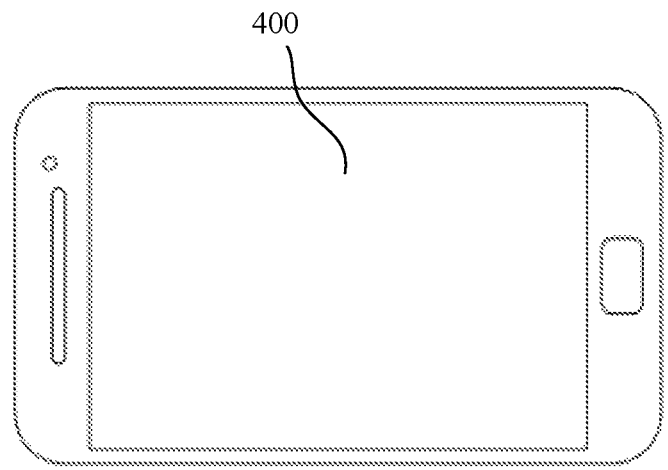
FIG. 3 is a structural schematic diagram of an electronic device according to one embodiment of the present disclosure.

For example, as shown in FIG. 3, the present disclosure provides a first electronic device 400, and the first electronic device 400 includes any one organic electroluminescent device described in the embodiments of the organic electroluminescent device. The first electronic device 400 may be a display device, a lighting device, an optical communication device or other types of electronic devices, for example, it may include but is not limited to, a computer screen, a mobile phone screen, a television, electronic paper, an emergency lighting lamp, an optical module and the like. Since the first electronic device 400 is provided with any one organic electroluminescent device described in the embodiments of the organic electroluminescent device, the first electronic device 400 has the same beneficial effects, which will not be repeated here.

Figure 4:
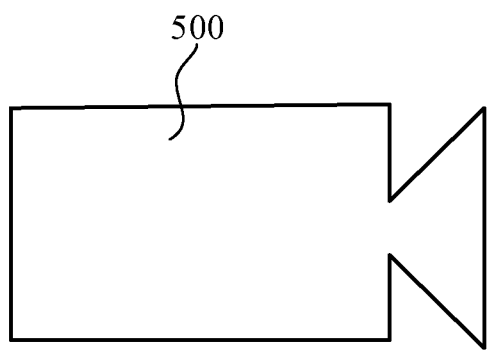
FIG. 4 is a structural schematic diagram of an electronic device according to another embodiment of the present disclosure.

For example, as shown in FIG. 4, the present disclosure provides a second electronic device 500, including any one photoelectric conversion device described in the embodiments of the photoelectric conversion device. The second electronic device 500 may be a solar power generation device, a light detector, a fingerprint identification device, a light module, a CCD camera, or other types of electronic devices. Since the electronic device 500 has the above photoelectric conversion device described in the embodiments of the photoelectric conversion device, the electronic device 500 has the same beneficial effects, which will not be repeated here.

Hereinafter, the present disclosure is further described in detail through examples. However, the following embodiments are only embodiments of the present disclosure, and do not limit the present disclosure.

Synthesis of Compounds

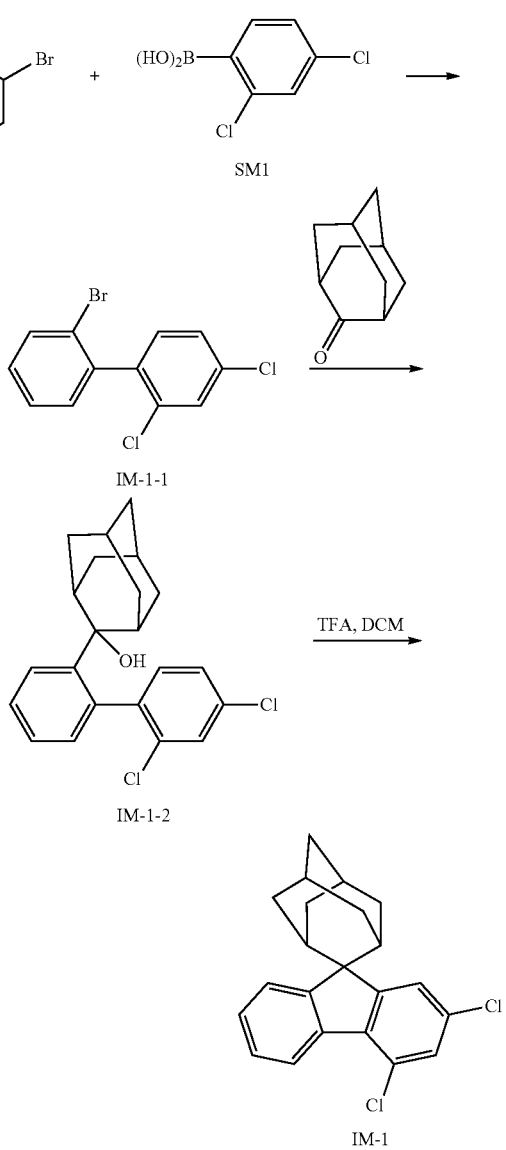

SM1 (100 g, 524.1 mmol), o-bromoiodobenzene (148.26 g, 524.1 mmol), tetrakis(triphenylphosphine)palladium (30.2 g, 26.2 mmol), potassium carbonate (216.9 g, 1572.2 mol), tetrabutylammonium chloride (7.25 g, 26.2 mmol), toluene (800 mL), ethanol (400 mL) and deionized water (200 mL) were added into a three-necked flask, under the protection of nitrogen, the temperature was raised to 78° C., the reaction solution was stirred for 8 h; the reaction solution was cooled to room temperature, toluene (500 mL) was added for extraction, organic phases were mixed and dried over anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified through recrystallization by using a dichloromethane/ethyl acetate (at a volume ratio of 1:3) system to obtain an intermediate IM-1-1 (134.5 g, yield: 85%).

The intermediate IM-1-1 (100 g, 331.13 mmol) was added into a three-necked flask filled with THF (1 L), n-butyllithium (25.45 g, 397.35 mmol) was dropwise added at −80° C. After addition, the temperature of the reaction solution was maintained for 1 hour, then amantanone (39.78 g, 264.90 mmol) was added dropwise. The temperature of the reaction solution was maintained for 1 h, then raised to room temperature, and the reaction solution was stirred overnight. Hydrochloric acid (2 mol/L) was added into the reaction solution to adjust a pH value to be neutral, and then filtered to obtain a white crude product, which was beaten with n-heptane to obtain a white solid intermediate IM-1-2 (86.52 g, yield: 70%).

The intermediate IM-1-2 (86.52 g, 231.77 mmol), trifluoroacetic acid (79.28 g, 695.31 mmol) and dichloromethane (900 mL) were added into a three-necked flask, under the protection of nitrogen, the reaction solution was stirred for 2 h; a sodium hydroxide aqueous solution was added into the reaction solution until the reaction solution was neutral, liquid separation was performed, an organic phase was dried over anhydrous magnesium sulfate, and filtered, and the solvent was removed under reduced pressure; and the obtained crude product was purified by silica gel column chromatography using dichloromethane/n-heptane (at a volume ratio of 1:2) to obtain a white solid intermediate IM-1 (70.82 g, yield: 86%).

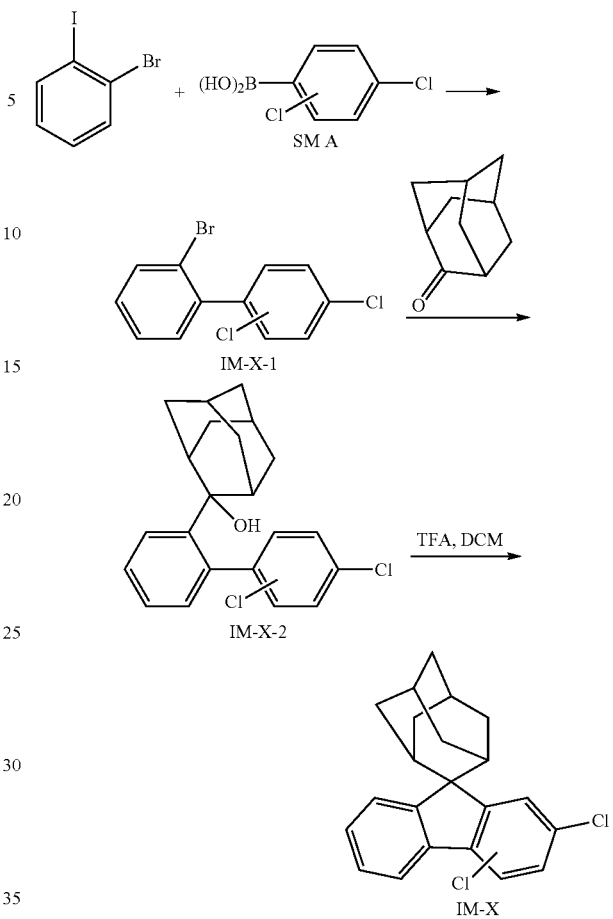

In one embodiment, an intermediate IM-X was obtained through reactions of the above formula, X may be 2 or 3, a reaction process was similar to that of the intermediate IM-1, and SMA in Table 1 was used for replacing SM1 to prepare an intermediate IM-X-1, an intermediate IM-X-2 and the intermediate IM-X. The obtained intermediates are as shown in Table 1.

TABLE 1

| SMA | Intermediate IM-X-1 | Intermediate IM-X-2 | Intermediate IM-X | Mass g/yield % |
|---|---|---|---|---|
| (HO)₂B-⟨Cl,Cl⟩ | IM-2-1 | IM-2-2 | IM-2 | 36.8/41 |
|  |  |  | IM-3 | 32.5/36 |

NMR of an intermediate IM-2:

$^1$HNMR (400 MHz, CD$_2$Cl$_2$), δ (ppm): 8.07 (d, 1H), 7.97 (s, 1H), 7.83 (s, 1H), 7.29-7.26 (m, 1H), 7.19-7.16 (m, 1H), 7.08 (d, 1H), 2.91-2.83 (m, 4H), 2.73-2.39 (m, 4H), 2.19 (s, 2H), 1.92 (d, 2H), 1.56 (s, 2H).

NMR of an intermediate IM-3:

$^1$HNMR (400 MHz, CD$_2$Cl$_2$), δ (ppm): 8.08 (d, 1H), 7.88-7.25 (m, 2H), 7.30-7.26 (m, 1H), 7.19 (d, 1H), 7.11-7.07 (m, 1H), 2.62-2.59 (m, 4H), 2.48-2.45 (m, 4H), 2.03 (s, 2H), 1.89 (d, 2H), 1.56 (s, 2H).

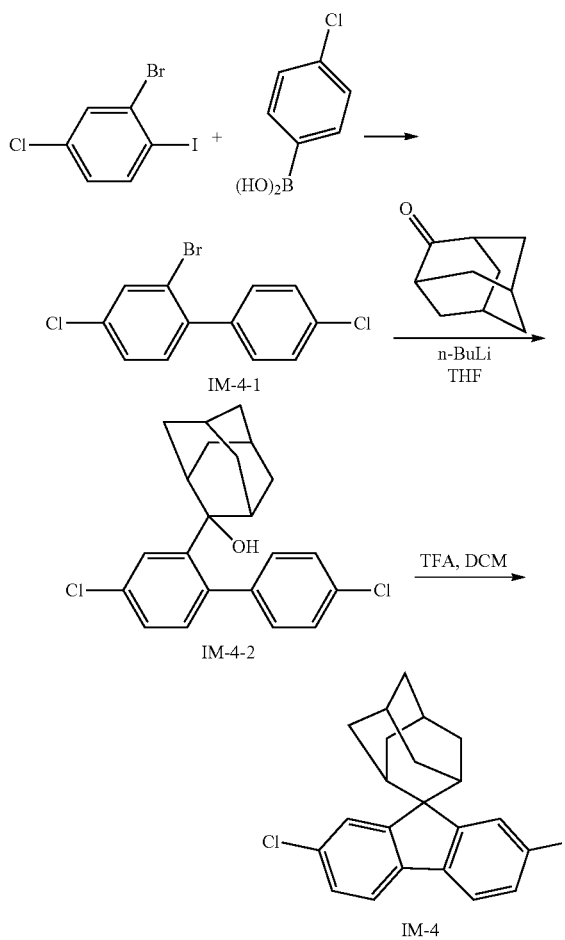

2-bromo-4-chloro-1-iodobenzene (100 g, 315.1 mmol), 4-chlorophenylboronic acid (49.27 g, 315.1 mmol), tetrakis(triphenylphosphine)palladium (18.21 g, 15.7 mmol), potassium carbonate (87.1 g, 630.2 mmol), tetrabutylammonium chloride (3.59 g, 15.7 mmol), toluene (800 mL), ethanol (400 mL) and deionized water (200 mL) were added into a three-necked flask, under the protection of nitrogen, the temperature of the reaction solution was raised to 78° C., and the reaction solution was stirred for 8 h; the resulting reaction solution was cooled to room temperature, toluene (500 mL) was added for extraction, organic phases were mixed, dried over anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified through recrystallization by using a dichloromethane/ethyl acetate system to obtain a white solid intermediate IM-4-1 (75.16 g, yield: 79%).

The intermediate IM-4-1 (100 g, 331.13 mmol) was added into a three-necked flask filled with THF (1 L), n-butyllithium (25.45 g, 397.35 mmol) was added dropwise at −80° C. After addition, the temperature of the reaction solution was maintained for 1 hour, adamantanone (39.78 g, 264.90 mmol) was added dropwise. The temperature of the reaction solution was maintained for 1 hour, then raised to room temperature, and the reaction solution was stirred overnight. Hydrochloric acid (2 mol/L) was added into the reaction solution to adjust a pH value to be neutral, then filtered to obtain a white crude product, and the obtained crude product was beaten with n-heptane to obtain a solid intermediate IM-4-2 (86.52 g, yield: 87%).

The intermediate IM-4-2 (86.52 g, 231.77 mmol), trifluoroacetic acid (79.28 g, 695.31 mmol) and dichloromethane (900 mL) were added into a three-necked flask, and the reaction solution was stirred for 2 h under the protection of nitrogen; a sodium hydroxide aqueous solution was added into the reaction solution until the reaction solution was neutral, liquid separation was performed, an organic phase was dried over anhydrous magnesium sulfate, and filtered, and the solvent was removed under reduced pressure; and the obtained crude product was purified by silica gel column chromatography using dichloromethane/n-heptane (at a volume ratio of 1:2) to obtain a white solid intermediate IM-4 (70.82 g, yield: 86%).

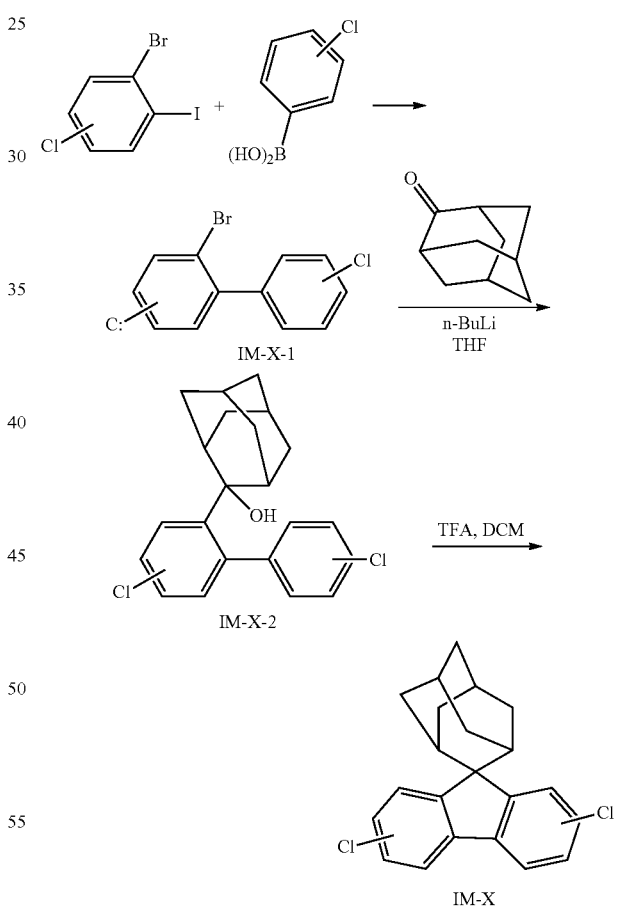

Referring to the synthesis method of the intermediate IM-4, an intermediate IM-5, an intermediate IM-6 and an intermediate IM-17 were synthesized, specifically, a raw material 1 with different structures in Table 2 was used for replacing 2-bromo-4-chloro-1-iodobenzene, and a raw material 2 was used for replacing 4-chlorophenylboronic acid to obtain an intermediate IM-X, X may be 5, 6 or 17, and the obtained intermediate IM-5, intermediate IM-6 and intermediate IM-17 are shown in Table 2.

TABLE 2
| Raw material 1 | 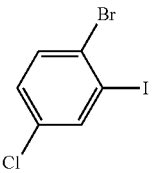 | 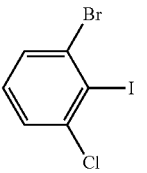 | 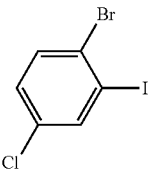 |
|---|---|---|---|
| Raw material 2 | 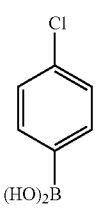 | 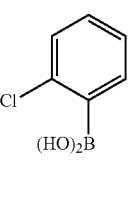 | |
| Intermediate IM-X-1 | 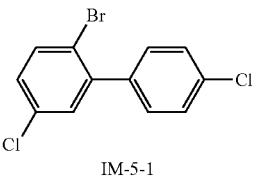 [SMILES: Clc1ccc(-c2cc(Cl)ccc2Br)cc1] IM-5-1 | 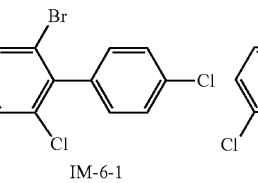 IM-6-1 | 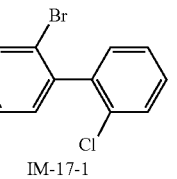 IM-17-1 |
| Intermediate IM-X-2 | 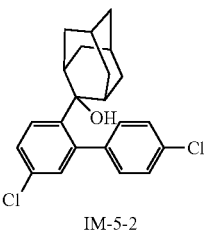 [SMILES: OC1(c2ccc(Cl)cc2-c2ccc(Cl)cc2)C2CC3CC(C2)CC1C3] IM-5-2 | 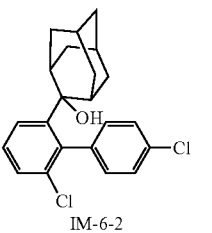 [SMILES: OC1(c2cccc(Cl)c2-c2ccc(Cl)cc2)C2CC3CC(C2)CC1C3] IM-6-2 | 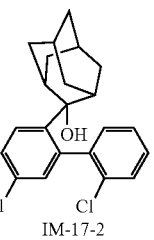 IM-17-2 |
| Intermediate IM-X | 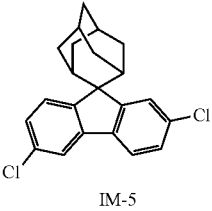 IM-5 | 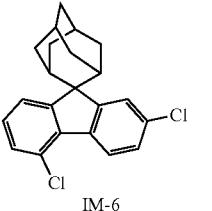 IM-6 | 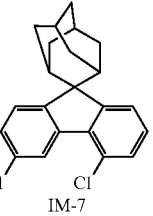 IM-7 |
| Mass/yield of intermediate IM-X | 69.9 g/85% | 69.1 g/84% | 68 g/82% |
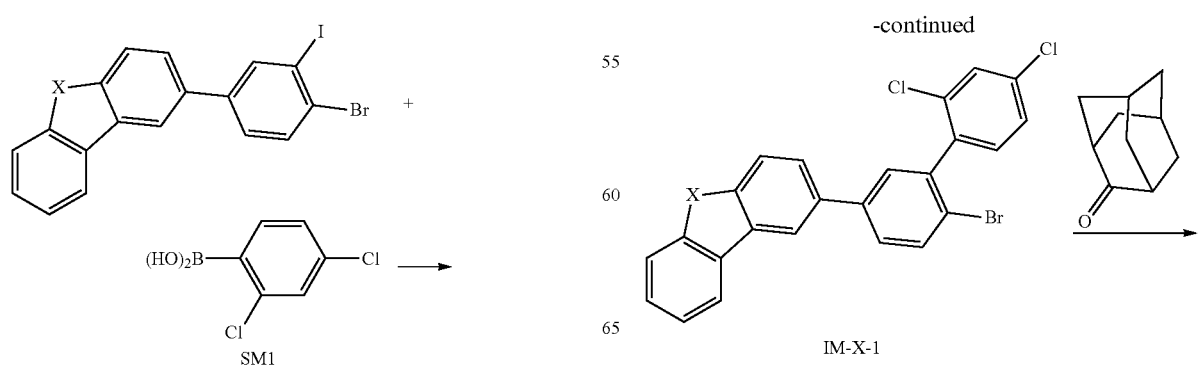

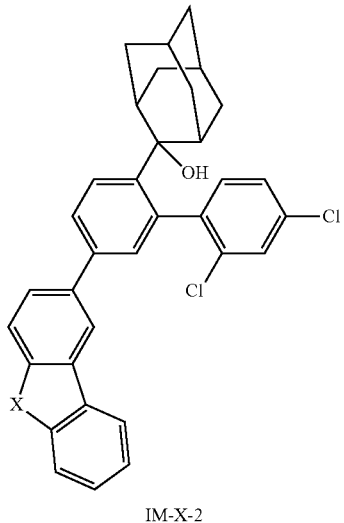

IM-X-2

TFA, DCM →

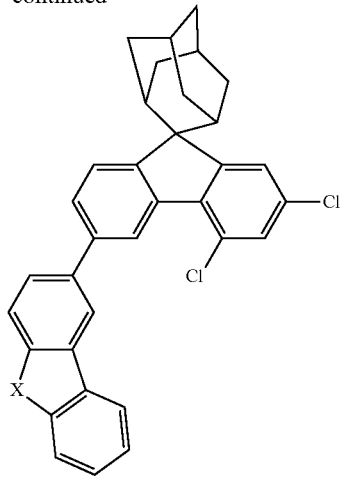

IM-X

Referring to the synthesis method of the intermediate IM-1, an intermediate IM-7 and an intermediate IM-8 were synthesized, specifically, a raw material A with different structures in Table 3 was used for replacing o-bromoiodobenzene, and the obtained intermediate IM-7 and intermediate IM-8 are shown in Table 3.

TABLE 3

| Raw material A | 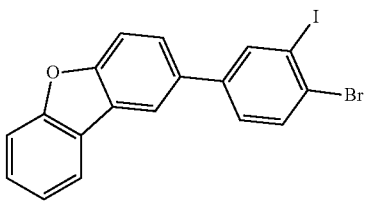 CAS: 2271307-97-0 | 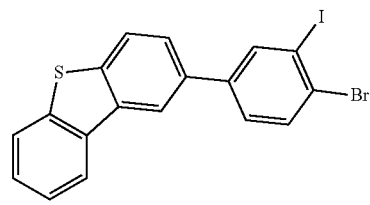 CAS: 2271307-98-1 |
|---|---|---|
| SMI | 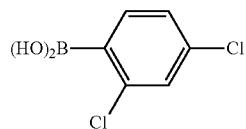 [SMILES: OB(O)c1ccc(Cl)cc1Cl] | |
| Intermediate IM-X-1 | 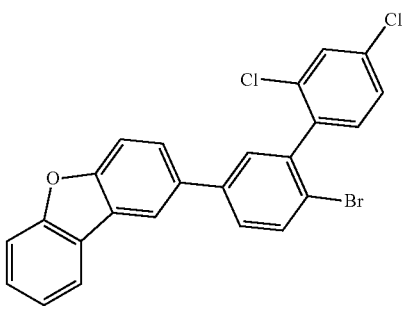 IM-7-1 | 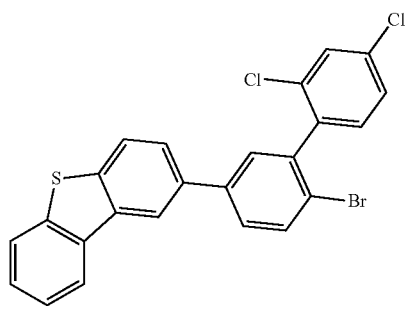 IM-8-1 |

TABLE 3-continued
| Intermediate IM-X-2 | 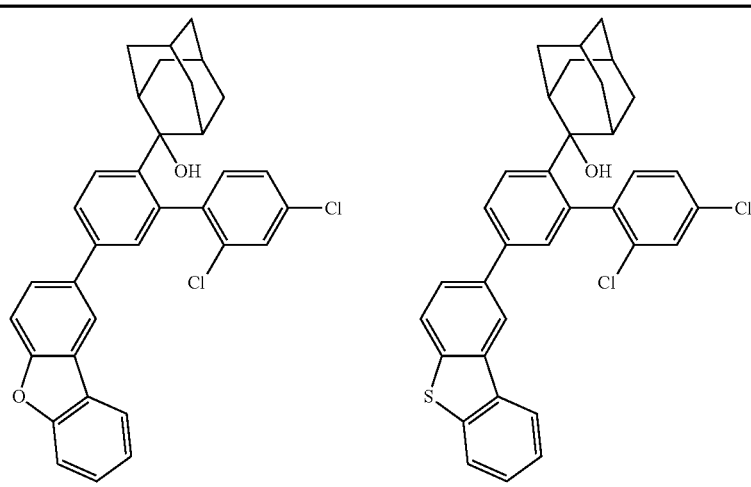 | |
| --- | --- | --- |
| | IM-7-2 | IM-8-2 |
| Intermediate IM-X | 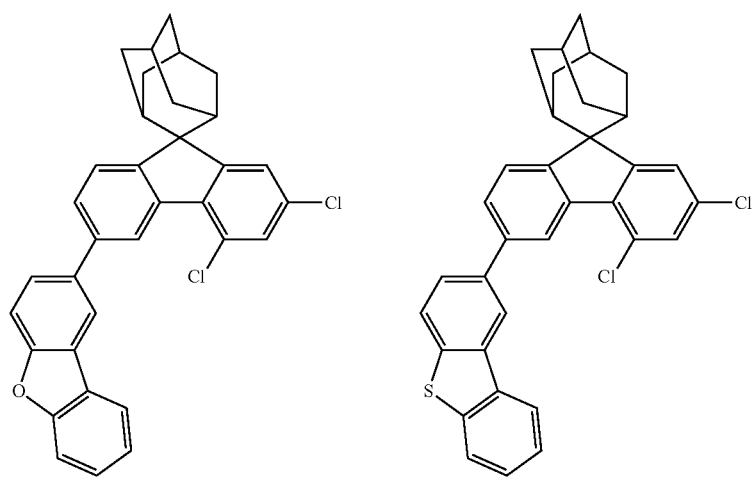 | |
| | IM-7 | IM-8 |
| Mass/yield of intermediate IM-X | 65.7 g/80% | 64.9 g/79% |
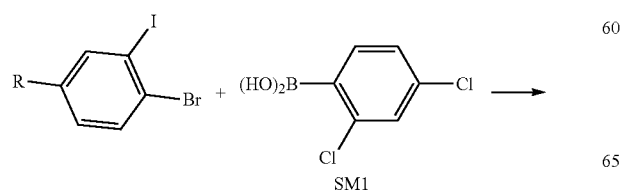

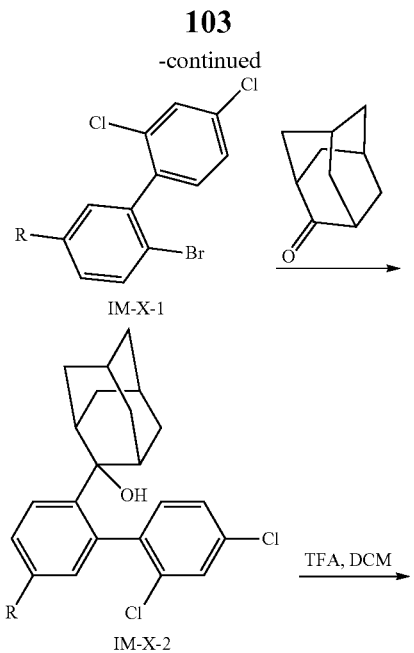

IM-X-1

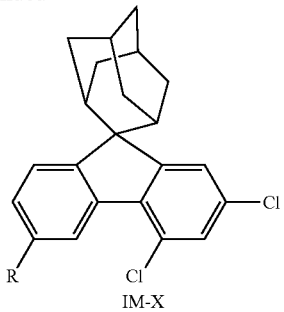

IM-X

Referring to the synthesis method of the intermediate IM-1, an intermediate IM-10 and an intermediate IM-11 were synthesized, specifically, a raw material B with different structures in Table 4 was used for replacing o-bromoiodobenzene to obtain an intermediate IM-X, wherein X can be 10 or 11, and the obtained intermediate IM-10 intermediate IM-11 are shown in Table 4.

TABLE 4

| Raw material B | 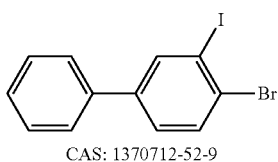 [SMILES: Brc1ccc(-c2ccccc2)cc1I] CAS: 1370712-52-9 | 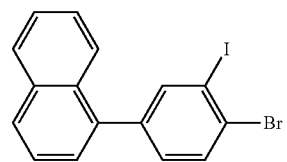 CAS: 1807712-29-3 |
|---|---|---|
| SMI | | 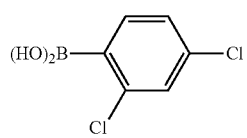 [SMILES: OB(O)c1ccc(Cl)cc1Cl] |
| Intermediate IM-X-1 | 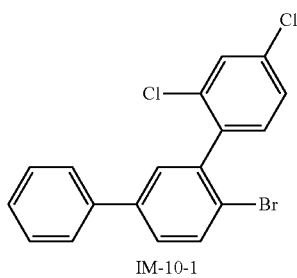 [SMILES: Clc1ccc(-c2cc(-c3ccccc3)ccc2Br)c(Cl)c1] IM-10-1 | 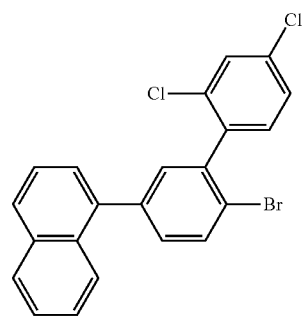 IM-11-1 |

TABLE 4-continued
| Intermediate IM-X-2 | 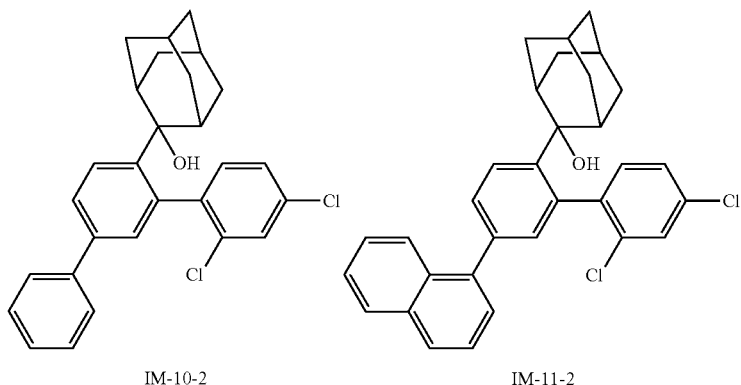 |
| --- | --- |
| | IM-10-2          IM-11-2 |
| Intermediate IM-X | 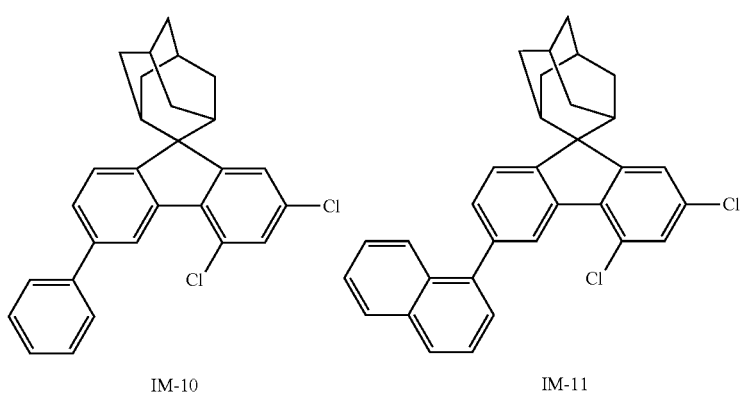 |
| | IM-10          IM-11 |
| Mass/yield of intermediate IM-X | 56.1 g/73%      53.7 g/70% |
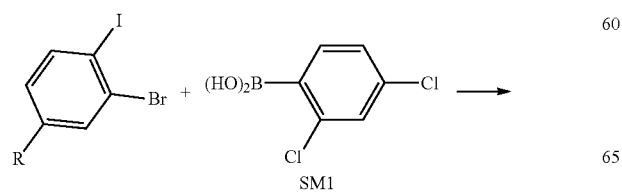

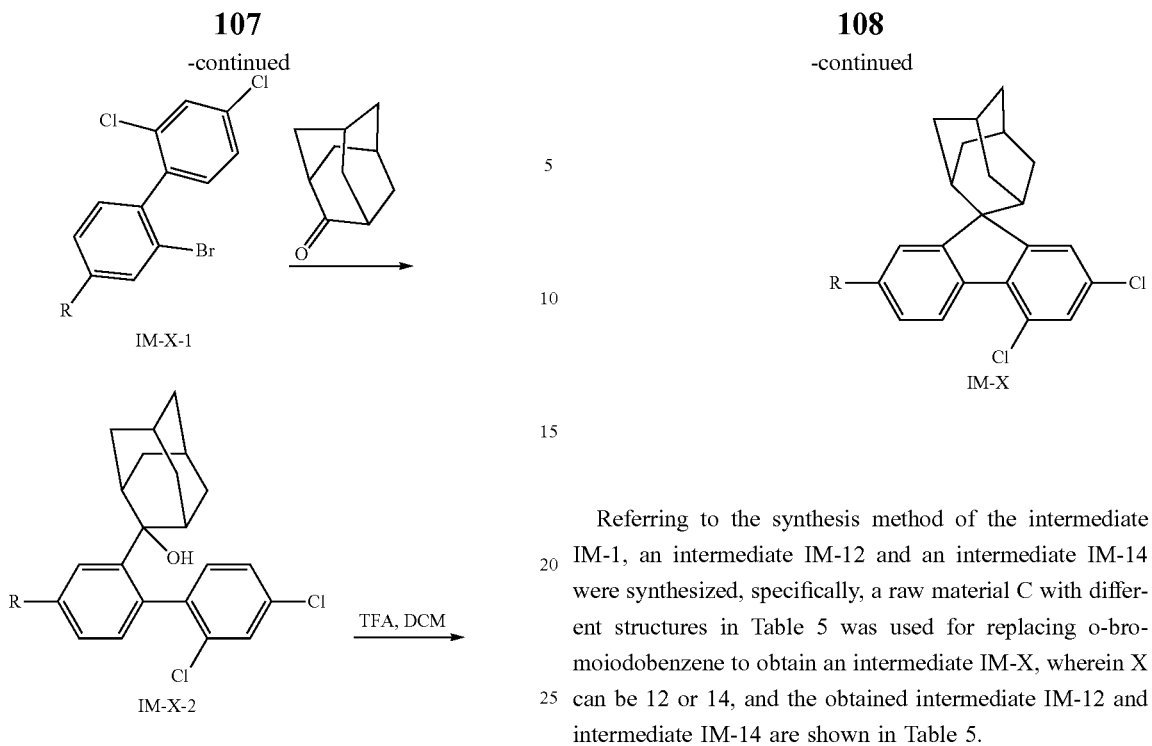
Referring to the synthesis method of the intermediate IM-1, an intermediate IM-12 and an intermediate IM-14 were synthesized, specifically, a raw material C with different structures in Table 5 was used for replacing o-bromoiodobenzene to obtain an intermediate IM-X, wherein X can be 12 or 14, and the obtained intermediate IM-12 and intermediate IM-14 are shown in Table 5.
TABLE 5
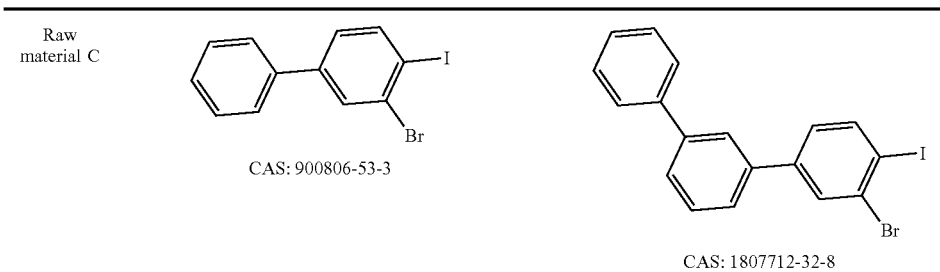
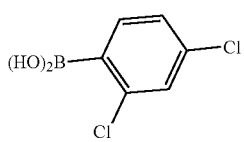
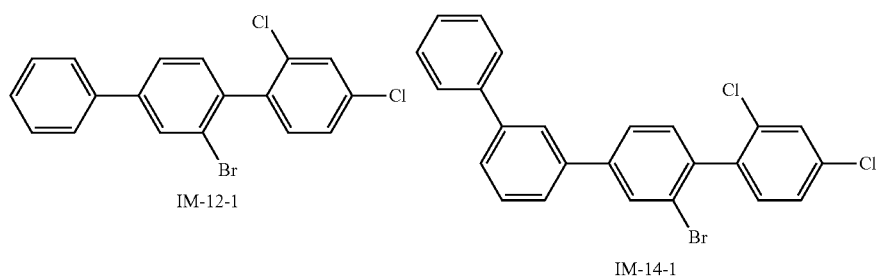

TABLE 5-continued
| Intermediate IM-X-2 | 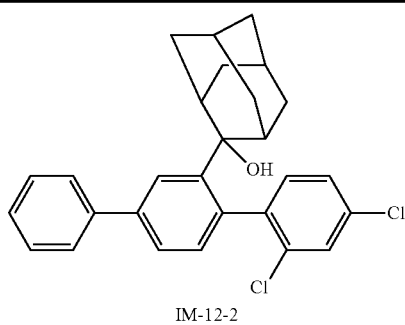 | 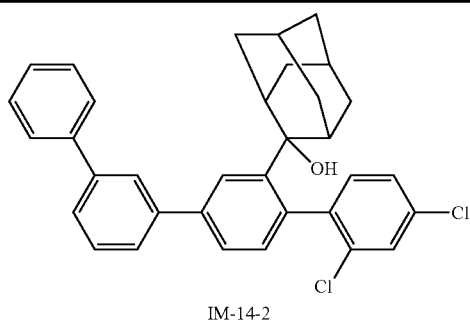 |
|---|---|---|
| | IM-12-2 | IM-14-2 |
| Intermediate IM-X | 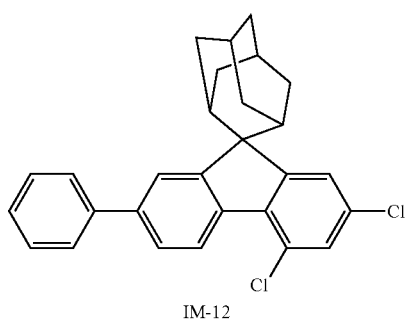 | 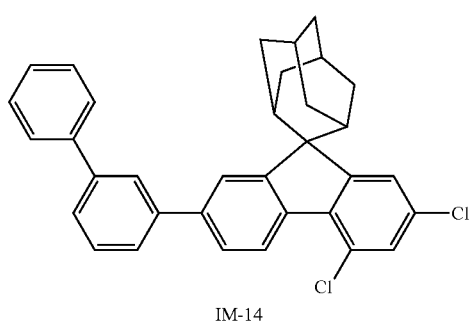 |
| | IM-12 | IM-14 |
| Mass/yield of intermediate IM-X | 53.7 g/70% | 55.3 g/69% |
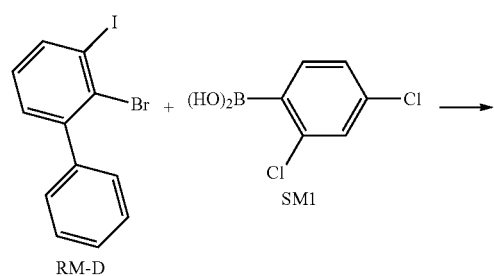
-continued
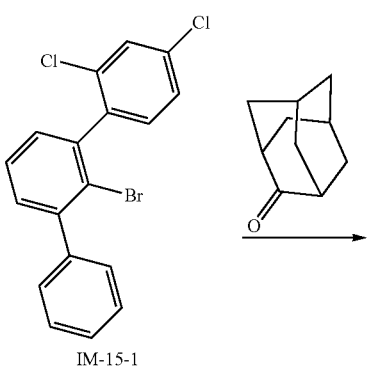

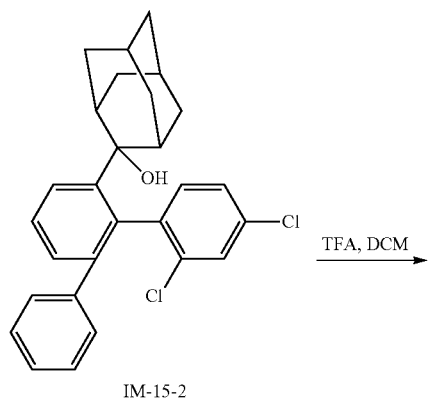

IM-15-2

TFA, DCM

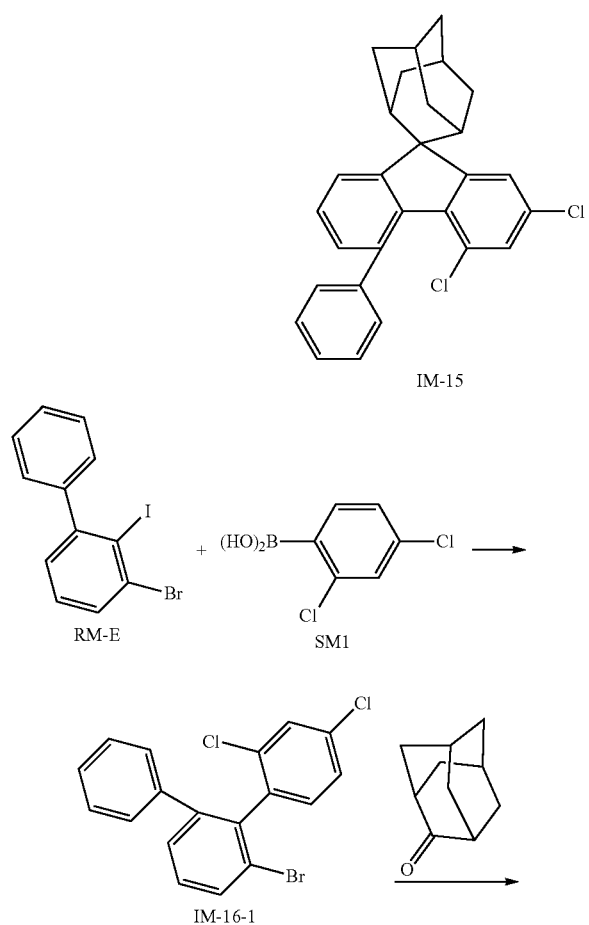

IM-15

RM-E    SM1

IM-16-1

IM-16-2

TFA, DCM

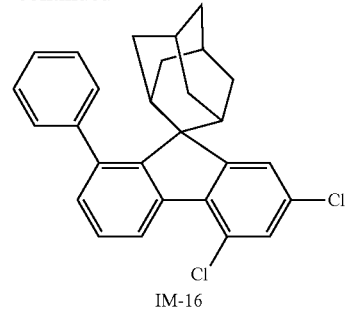

IM-16

Referring to the synthesis method of the intermediate IM-1, an intermediate IM-15 and an intermediate IM-16 were synthesized, a raw material RM-D and a raw material RM-E were respectively used for replacing o-bromoiodobenzene to obtain the intermediate IM-15 and the intermediate IM-16, the mass of the intermediate IM-15 is 51.3 g, the yield of the intermediate IM-15 is 67%, the mass of the intermediate IM-16 is 50.5 g, and the yield of the intermediate IM-16 is 66%.

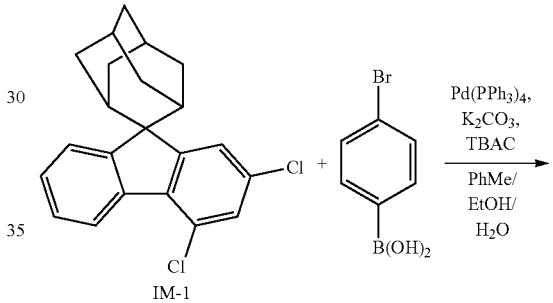

IM-1

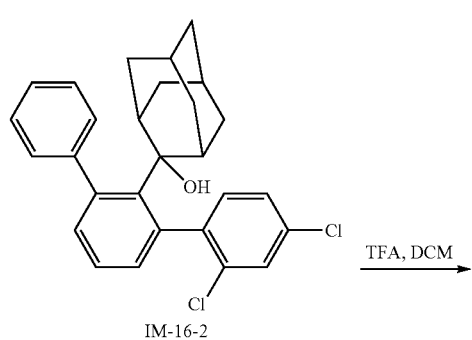

IM-1-A

The intermediate IM-1 (20 g, 56.29 mmol), p-bromophenylboronic acid (11.31 g, 56.29 mmol), tetrakis(triphenylphosphine)palladium (3.25 g, 2.81 mmol), potassium carbonate (23.3 g, 168.8 mmol), tetrabutylammonium chloride (0.78 g, 2.81 mmol), toluene (160 mL), ethanol (40 mL) and deionized water (40 mL) were added into a round-bottom flask, under the protection of nitrogen, the temperature of the reaction solution was raised to 78° C., and the reaction solution was stirred for 12 h; the resulting reaction solution was cooled to room temperature, toluene (100 mL) was added for extraction, organic phases were mixed, dried over anhydrous magnesium sulfate, and filtered, and the solvent was removed under reduced pressure; and the obtained crude product was purified by silica gel column chromatography using n-heptane as a mobile phase, and then purified through recrystallization by using a dichloromethane/ethyl acetate (at a volume ratio of 1:3) system to obtain an intermediate IM-1-A (22.7 g, 85%).

In one embodiment, with reference to the synthesis method of the intermediate IM-1-A, SMD with different structures in Table 6 was used for replacing p-bromophenylboronic acid, so that an intermediate IM-MM shown in Table 6 was synthesized, and each type of compound SMD is corresponding to one only intermediate MM. The synthesized intermediates IM-MM are as shown in Table 6:

TABLE 6

| Intermediate IM-X/intermediate IM-X-A | SMD | Intermediate IM-MM | Mass (g) | Yield (%) |
|---|---|---|---|---|
| 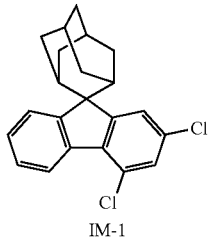 IM-1 | 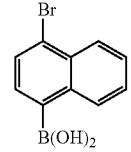 CAS: 145965-14-6 | 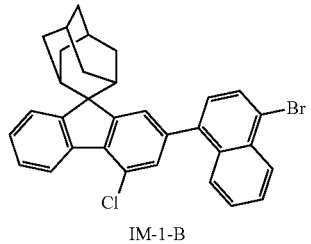 [SMILES: Clc1cc(-c2ccc(Br)c3ccccc23)cc2c1-c1ccccc1C21C2CC3CC(C2)CC1C3] IM-1-B | 20.35 | 83 |
| 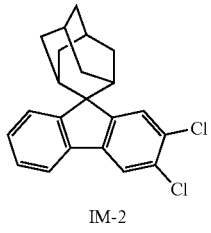 IM-2 | 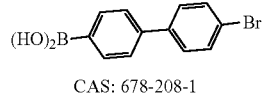 CAS: 678-208-1 | 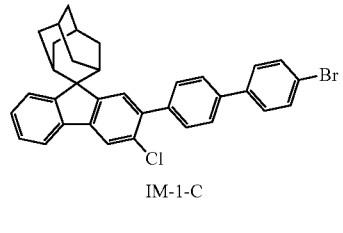 [SMILES: Clc1cc2c(cc1-c1ccc(-c3ccc(Br)cc3)cc1)C1(c3ccccc3-2)C2CC3CC(C2)CC1C3] IM-1-C | 21.32 | 85 |
| 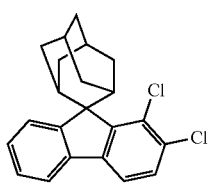 IM-3 | 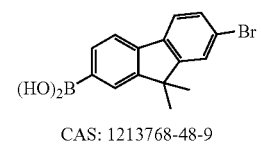 CAS: 1213768-48-9 | 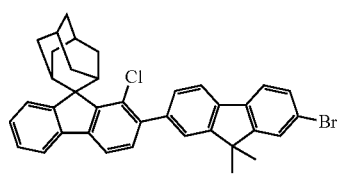 IM-1-D | 20.51 | 84 |
| 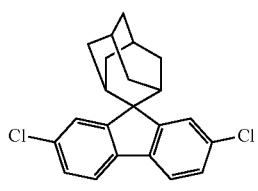 IM-4 | 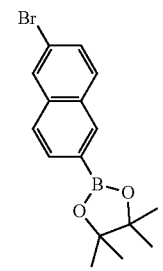 CAS: 1404070-35-4 | 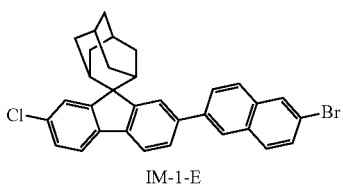 [SMILES: Clc1ccc2c(c1)C1(c3cc(-c4ccc5cc(Br)ccc5c4)ccc3-2)C2CC3CC(C2)CC1C3] IM-1-E | 20.03 | 85 |
| 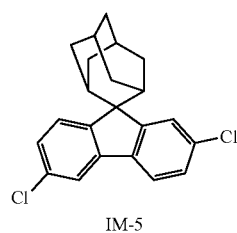 IM-5 | 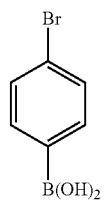 | 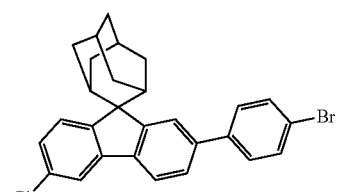 IM-1-F | 21.7 | 81 |

TABLE 6-continued
| Intermediate IM-X/intermediate IM-X-A | SMD | Intermediate IM-MM | Mass (g) | Yield (%) |
|---|---|---|---|---|
| 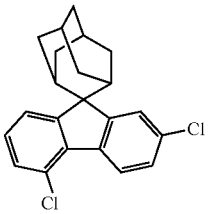 IM-6 | 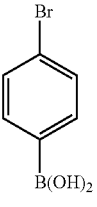 | 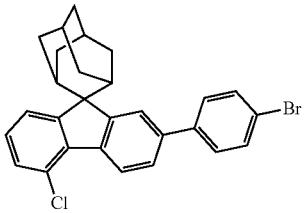 IM-1-G | 21.4 | 80 |
| 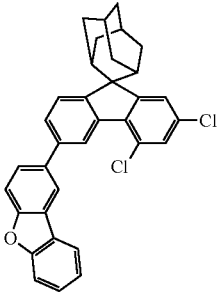 IM-7 | 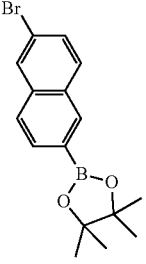 CAS: 1404070-35-4 | 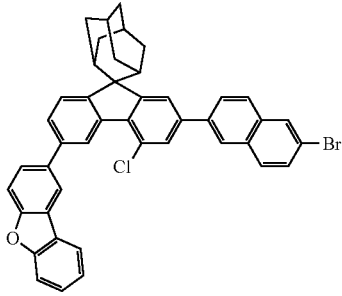 IM-1-H | 22.3 | 75 |
| 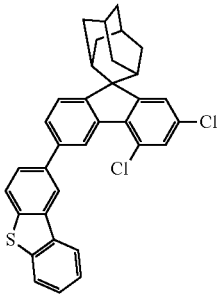 IM-8 | 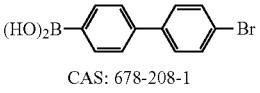 CAS: 678-208-1 | 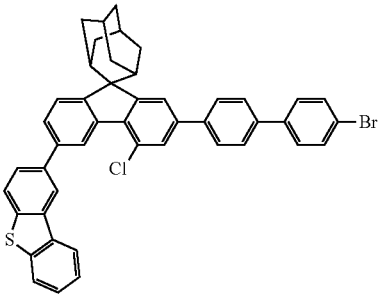 IM-1-I | 20.8 | 73 |
| 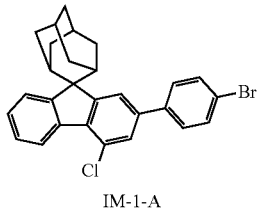 [SMILES: Clc1cc(-c2ccc(Br)cc2)cc2c1-c1ccccc1C21C2CC3CC(C2)CC1C3] IM-1-A | 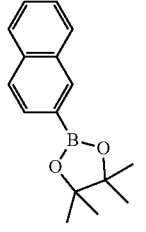 | 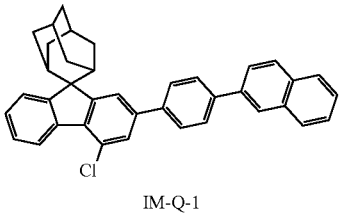 [SMILES: Clc1cc(-c2ccc(-c3ccc4ccccc4c3)cc2)cc2c1-c1ccccc1C21C2CC3CC(C2)CC1C3] IM-Q-1 | 21.0 | 79 |
| 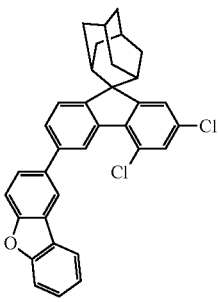 IM-7 | 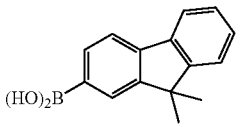 | 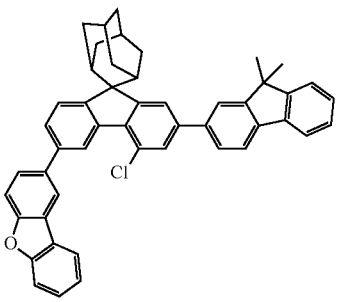 IM-Q-2 | 20.8 | 78 |

TABLE 6-continued

| Intermediate IM-X/intermediate IM-X-A | SMD | Intermediate IM-MM | Mass (g) | Yield (%) |
|---|---|---|---|---|
| IM-8 | B(OH)₂–C₆H₅ | IM-Q-3 | 22.0 | 79 |
| IM-10 | B(OH)₂–C₆H₅ | IM-Q-4 | 21.3 | 81 |
| IM-11 | dibenzofuran-B(OH)₂ | IM-Q-5 | 20.3 | 78 |
| IM-12 | naphthyl-B(OH)₂ | IM-Q-6 | 18.9 | 77 |

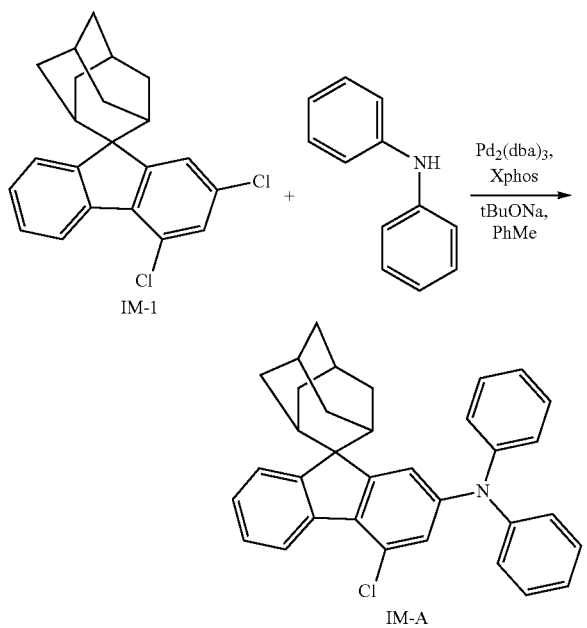

The intermediate IM-1 (20 g, 56.29 mmol), diphenylamine (9.53 g, 56.29 mmol), tris(dibenzylideneacetone)dipalladium (0.52 g, 0.56 mmol), 2-dicyclohexylphosphino-2,4,6-triisopropylbiphenyl (0.46 g, 1.12 mmol), sodium tert-butoxide (8.10 g, 84.4 mmol) and toluene solvent (250 mL) were added into a reaction flask, under the protection of nitrogen, the temperature of the reaction solution was raised to 110° C., and the reaction solution was stirred under heating and refluxing for 3 h. The resulting reaction solution was cooled to room temperature, and extracted by using dichloromethane and water, an organic layer was dried over anhydrous magnesium sulfate, and filtered, the obtained filtrate was allowed to pass through a short silica gel column, the solvent was removed under reduced pressure, and the obtained crude product was purified through recrystallization by using a dichloromethane/n-heptane system (at a volume ratio of 1:3) to obtain an intermediate IM-A (20.6 g, yield: 75%).

In one embodiment, with reference to the synthesis method of the intermediate IM-A, SMB with different structures in Table 7 was used for replacing diphenylamine, so that an intermediate IM-Y shown in the following table 7 was synthesized, and each type of compound SMB is corresponding to one only intermediate IM-Y. The obtained intermediates are as shown in Table 7:

TABLE 7

| Intermediate IM-X | SMB | Intermediate IM-Y | Mass (g) | Yield (%) |
|---|---|---|---|---|
| IM-1 | CAS: 1160294-96-1 | IM-B | 21.3 | 76 |
| | CAS: 1290039-85-8 | IM-C | 22.5 | 77 |

TABLE 7-continued
| Intermediate IM-X | SMB | Intermediate IM-Y | Mass (g) | Yield (%) |
|---|---|---|---|---|
| | 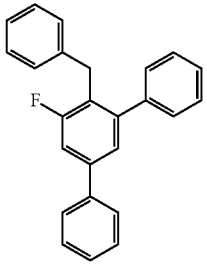<br>CAS: 1228153-91-0 | 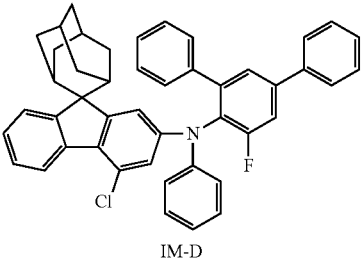<br>IM-D | 20.5 | 75 |
| | 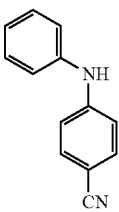<br>CAS: 36602-01-4 | 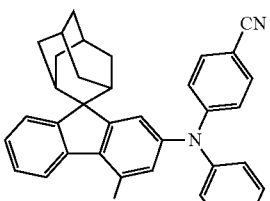<br>IM-E | 19.3 | 74 |
| | 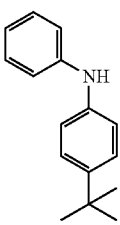<br>CAS: 4496-49-5 | 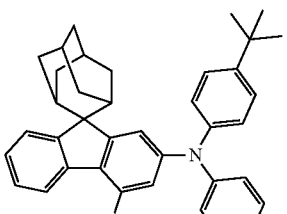<br>IM-F | 17.5 | 71 |
| 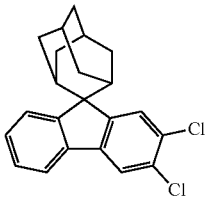<br>Intermediate IM-2 | 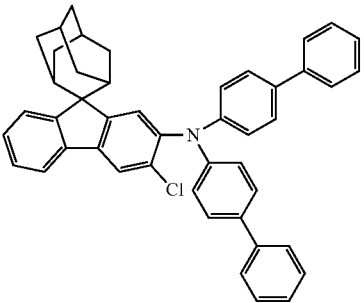<br>CAS: 102113-98-4 | 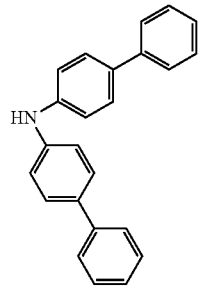<br>IM-G | 18.3 | 70 |
| | 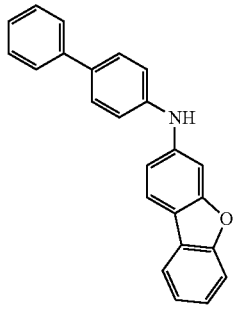<br>CAS: 1290039-85-8 | 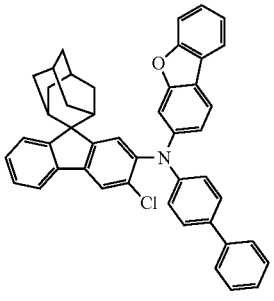<br>IM-G-1 | 17.9 | 68 |

TABLE 7-continued
| Intermediate IM-X | SMB | Intermediate IM-Y | Mass (g) | Yield (%) |
|---|---|---|---|---|
| | 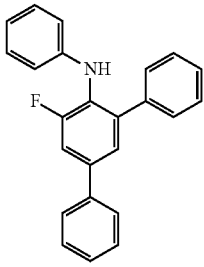<br>CAS: 228153-91-0 | 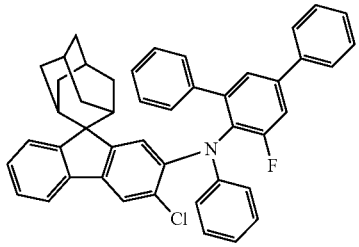<br>IM-G-2 | 16.3 | 70 |
| | 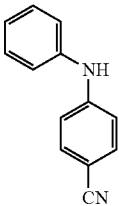<br>CAS: 36602-01-4 | 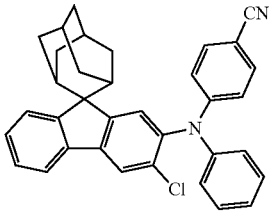<br>IM-G-3 | 17.5 | 72 |
| | 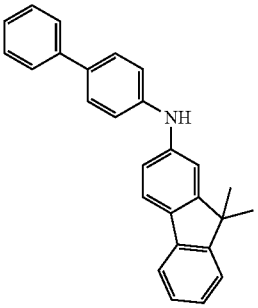<br>CAS: 897671-69-1 | 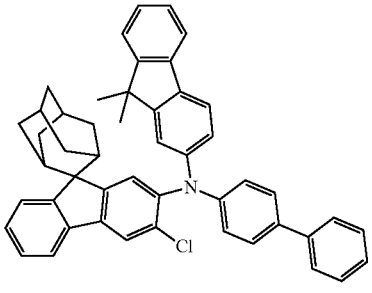<br>IM-G-4 | 18.1 | 72 |
| | 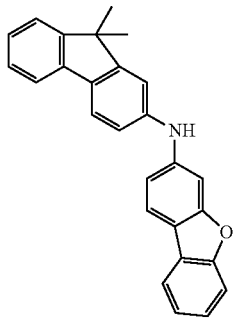<br>CAS: 1427556-50-0 | 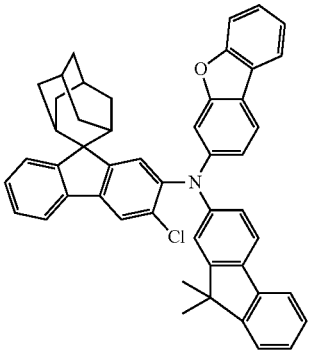<br>IM-H | 18.3 | 70 |

TABLE 7-continued

| Intermediate IM-X | SMB | Intermediate IM-Y | Mass (g) | Yield (%) |
|---|---|---|---|---|
| | CAS: 32228-99-2 | IM-H-1 | 19.5 | 75 |
| | CAS: 897921-59-4 | IM-H-2 | 18.3 | 73 |
| | CAS: 500717-23-7 | IM-H-3 | 17.2 | 70 |
| | CAS: 6336-92-1 | IM-H-4 | 18.9 | 75 |

TABLE 7-continued

| Intermediate IM-X | SMB | Intermediate IM-Y | Mass (g) | Yield (%) |
|---|---|---|---|---|
| | CAS: 1372775-52-4 | IM-H-5 | 18.8 | 73 |
| | CAS: (diphenylamine) | IM-H-6 | 16.2 | 75 |
| | CAS: 4496-49-5 | IM-H-7 | 17.3 | 74 |
| | CAS: 1228153-91-0 | IM-H-8 | 18.8 | 73 |
| | CAS: 147678-90-8 | IM-H-9 | 19.1 | 74 |

TABLE 7-continued
| Intermediate IM-X | SMB | Intermediate IM-Y | Mass (g) | Yield (%) |
|---|---|---|---|---|
| 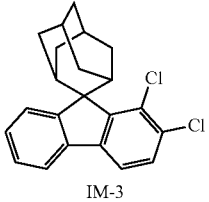 IM-3 | 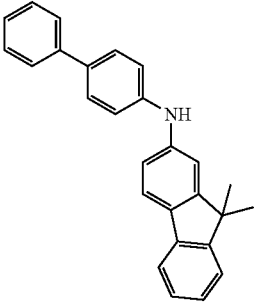 CAS: 897671-69-1 | 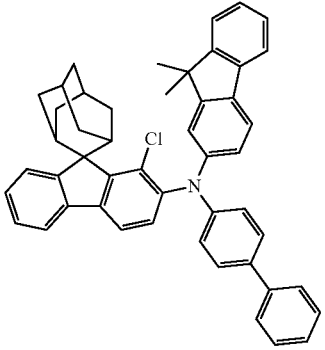 IM-I | 20.6 | 75 |
| | 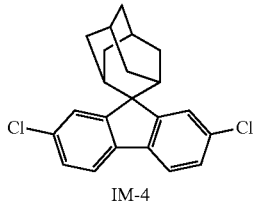 CAS: 32228-99-2 | 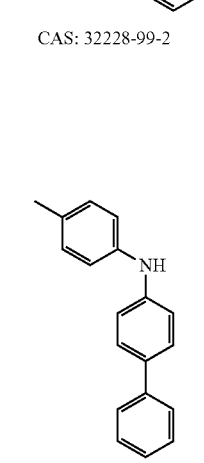 IM-J | 21.6 | 76 |
| 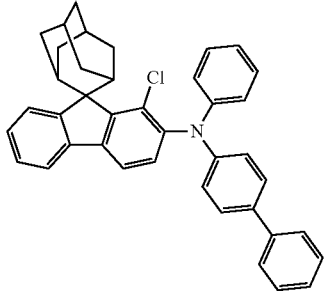 IM-4 | 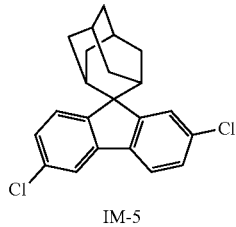 CAS: 147678-90-8 | 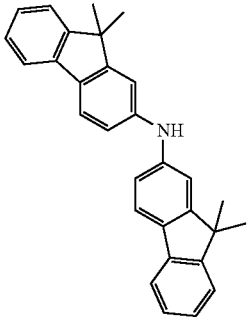 IM-L | 21.3 | 76 |
| 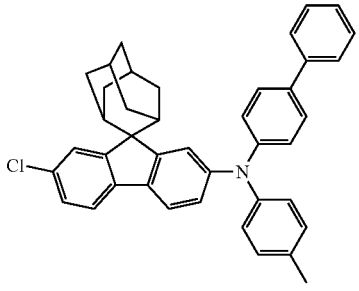 IM-5 | 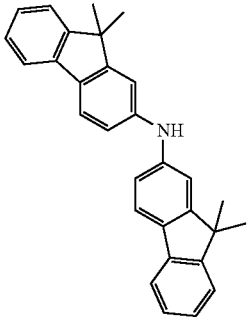 CAS: 500717-23-7 | 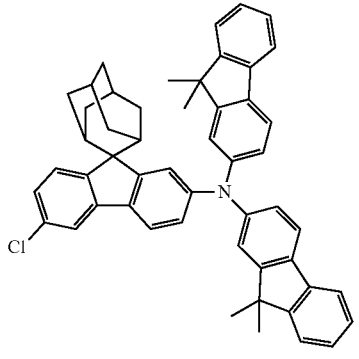 IM-M | 23 | 78 |

TABLE 7-continued
| Intermediate IM-X | SMB | Intermediate IM-Y | Mass (g) | Yield (%) |
|---|---|---|---|---|
| | 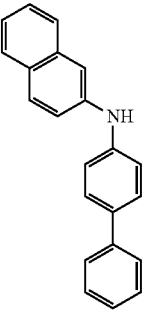<br>CAS: 6336-92-1 | 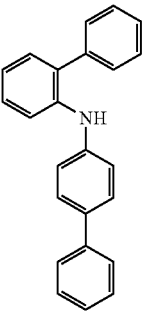<br>IM-N | 26.2 | 73 |
| 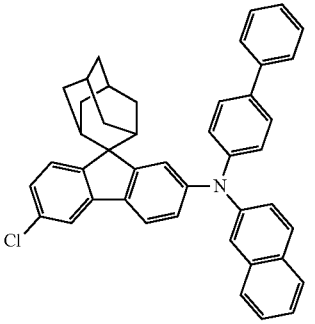<br>IM-6 | 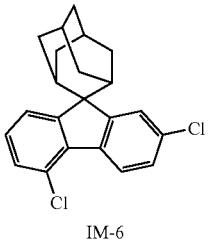<br>CAS: 1372775-52-4 | 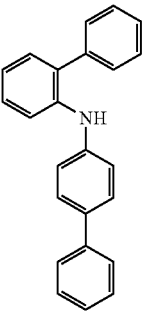<br>IM-P | 23.7 | 75 |
| 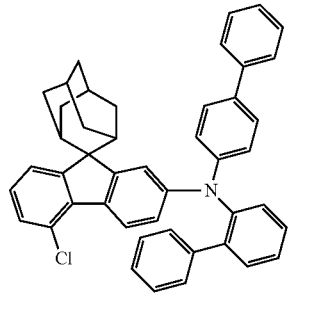<br>IM-1-B | 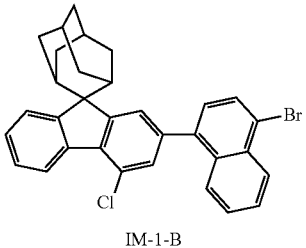<br>CAS: 32228-99-2 | 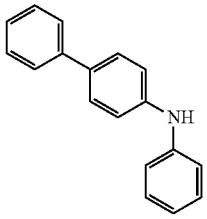<br>IM-Q | 22.5 | 73 |
| 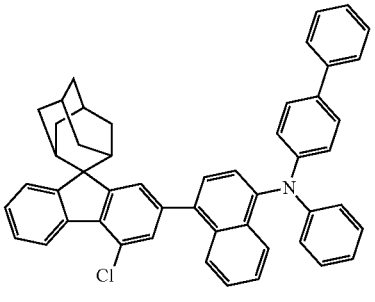<br>IM-1-C | 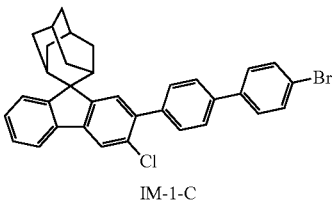<br>CAS: 102113-98-4 | 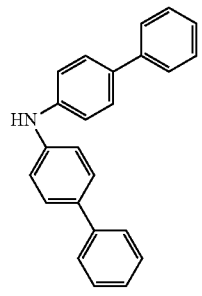<br>IM-R | 20.1 | 71 |

TABLE 7-continued

| Intermediate IM-X | SMB | Intermediate IM-Y | Mass (g) | Yield (%) |
|---|---|---|---|---|
| IM-1-D | | IM-S | 23.9 | 72 |
| IM-1-E | CAS: 147678-90-8 | IM-T | 25.8 | 71 |
| IM-1-F | CAS: 1372775-52-4 | IM-U | 23.6 | 70 |
| IM-1-G | CAS: 500717-23-7 | IM-V | 26.3 | 75 |

TABLE 7-continued
| Intermediate IM-X | SMB | Intermediate IM-Y | Mass (g) | Yield (%) |
|---|---|---|---|---|
| 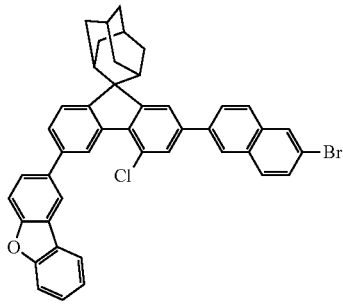 IM-1-H | 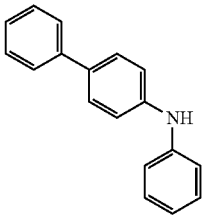 CAS: 32228-99-2 | 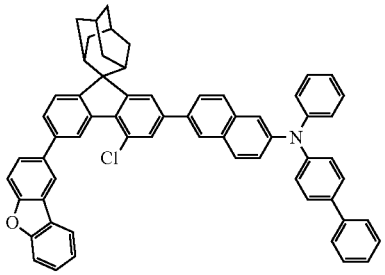 IM-W | 25.3 | 70 |
| 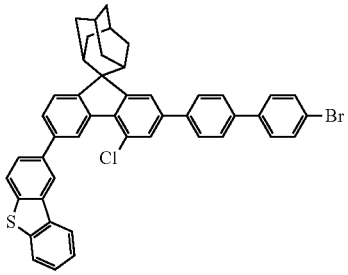 IM-1-I | 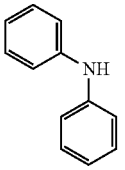 | 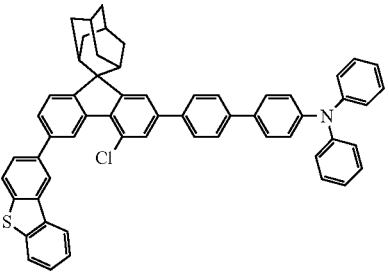 IM-YY | 27.3 | 71 |
| 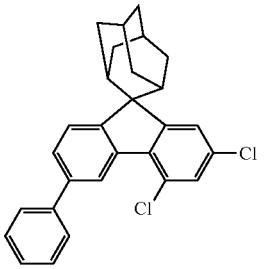 IM-10 | 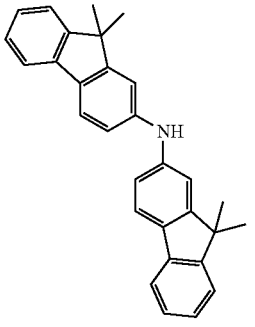 CAS: 500717-23-7 | 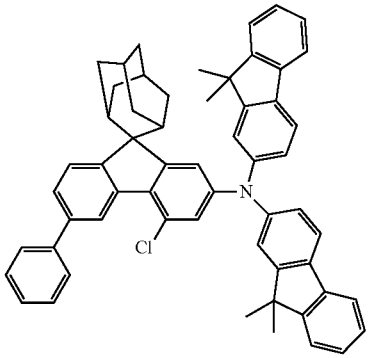 IM-Z-1 | 21.3 | 75 |
| 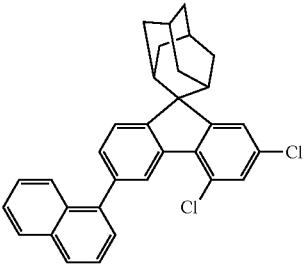 IM-11 | 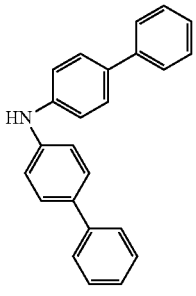 CAS: 102113-98-4 | 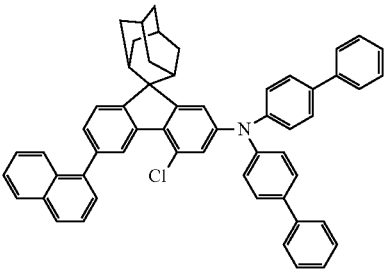 IM-Z-2 | 23.1 | 76 |

TABLE 7-continued
| Intermediate IM-X | SMB | Intermediate IM-Y | Mass (g) | Yield (%) |
|---|---|---|---|---|
| 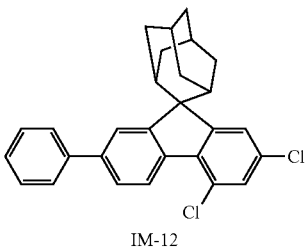 IM-12 | 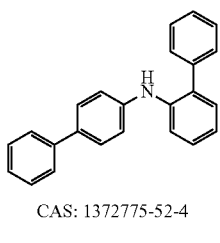 CAS: 1372775-52-4 | 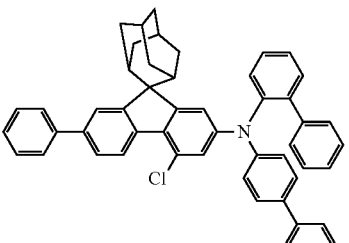 IM-Z-3 | 21.2 | 74 |
| 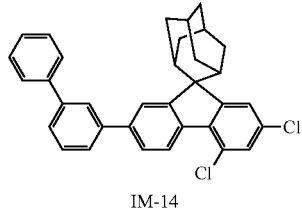 IM-14 | 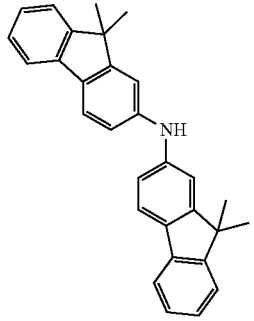 CAS: 500717-23-7 | 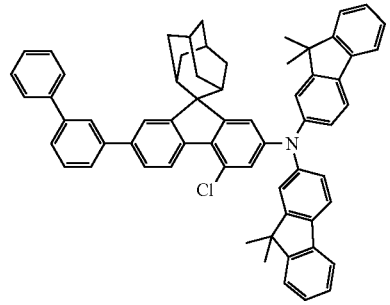 IM-Z-5 | 18.3 | 70 |
| 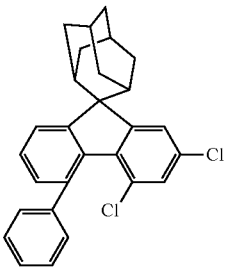 IM-15 | 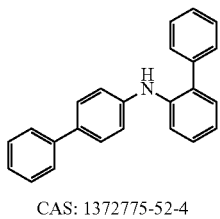 CAS: 1372775-52-4 | 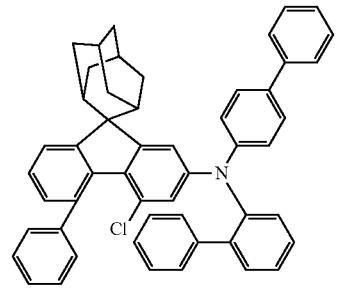 IM-Z-6 | 20.4 | 73 |
| 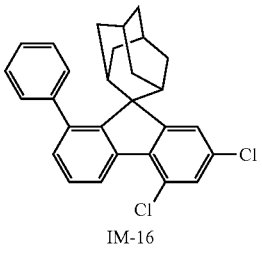 IM-16 | 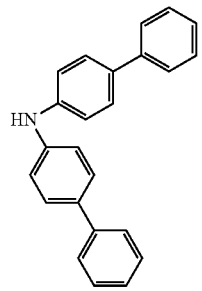 CAS: 102113-98-4 | 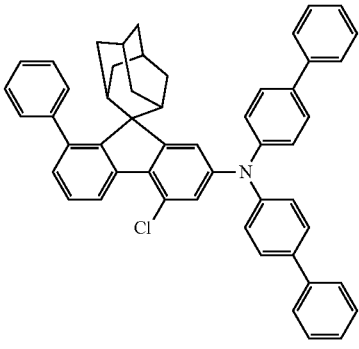 IM-Z-7 | 19.3 | 72 |

TABLE 7-continued

| Intermediate IM-X | SMB | Intermediate IM-Y | Mass (g) | Yield (%) |
|---|---|---|---|---|
| IM-17 | | IM-Q-M | 18.3 | 70 |

Synthesis of Compound 1

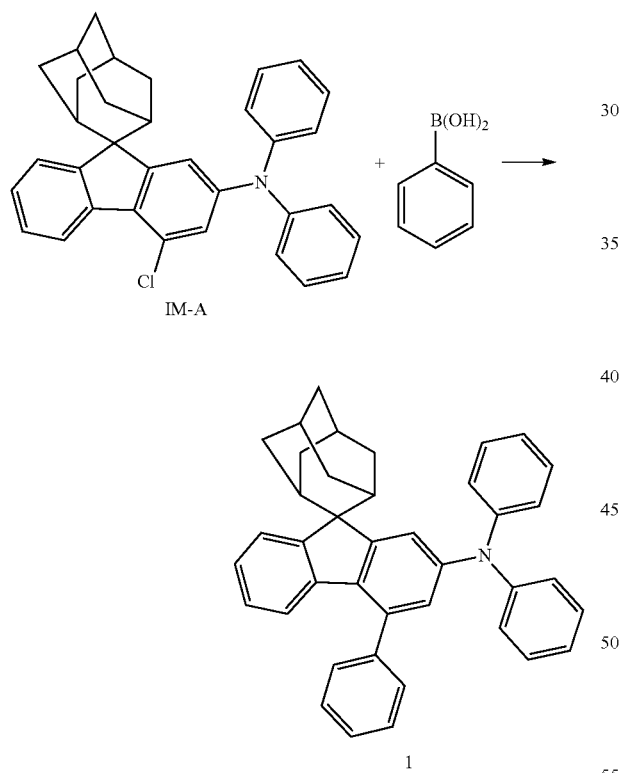

The intermediate IM-A (10 g, 20.4 mmol), phenylboronic acid (2.50 g, 20.4 mmol), tetrakis(triphenylphosphine)palladium (1.18 g, 1.02 mmol), potassium carbonate (8.48 g, 61.4 mmol), tetrabutylammonium chloride (0.28 g, 1.02 mmol), toluene (80 mL), ethanol (40 mL) and deionized water (20 mL) were added into a three-necked flask, under the protection of nitrogen, the temperature of the reaction solution was raised to 78° C., and the reaction solution was stirred for 10 h; the resulting reaction solution was cooled to room temperature, toluene (250 mL) was added for extraction, organic phases were mixed, dried over anhydrous magnesium sulfate, and filtered to obtain a filtrate, and the filtrate was concentrated under reduced pressure to obtain a crude product; and the obtained crude product was purified by silica gel column chromatography using n-heptane as a mobile phase, and then purified through recrystallization by using a dichloromethane/n-heptane (in a volume ratio of 1:3) system to obtain a compound 1 (7.05 g, yield: 65%). m/z=530.2[M+H]$^+$.

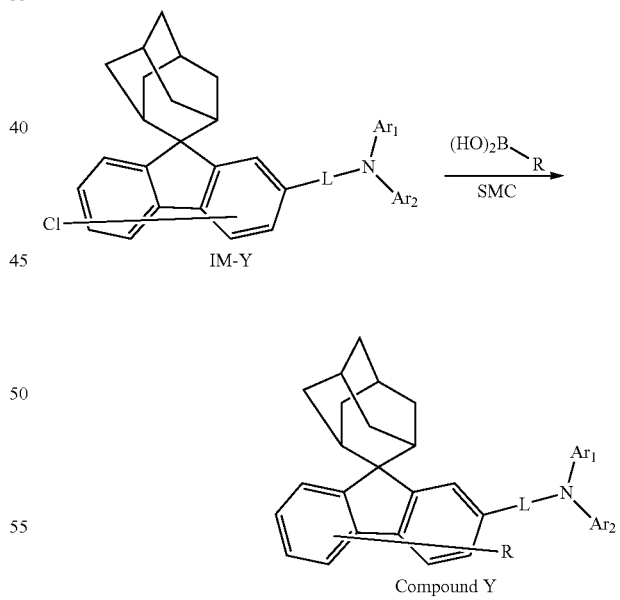

In one embodiment, a compound Y was synthesized with reference to the synthesis method of the compound 1, Y may be 2 to 14, 16 to 18, 20 to 26, or 101 to 123, specifically, phenylboronic acid was replaced with SMC with different structures in Table 8, and each type of compound SMC is corresponding to one only compound Y. The obtained compounds are as shown in Table 8.

TABLE 8
| Intermediate IM-Y | SMC | Compound Y | Mass (g) | Yield (%) | Mass spectrum [M + H] |
|---|---|---|---|---|---|
| 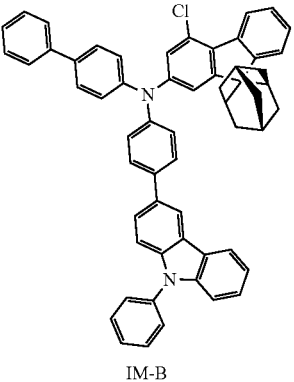 IM-B | 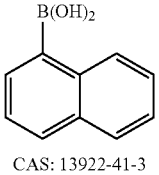 CAS: 13922-41-3 | 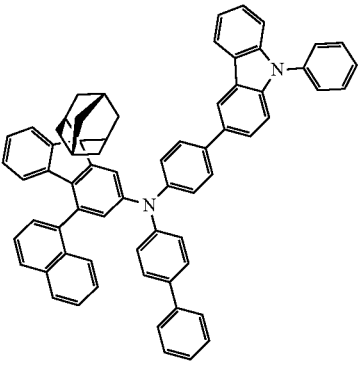 2 | 6.77 | 69 | 897.4 |
| 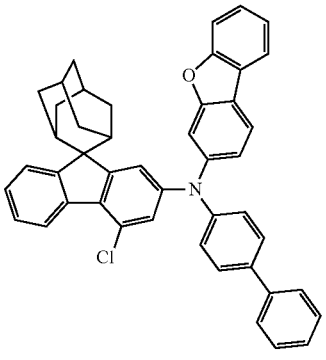 IM-C | 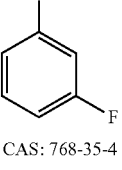 CAS: 768-35-4 | 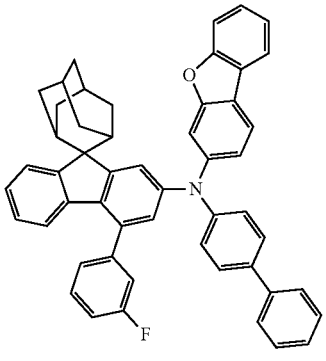 3 | 5.89 | 65 | 714.3 |
| | 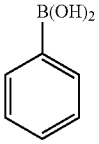 | 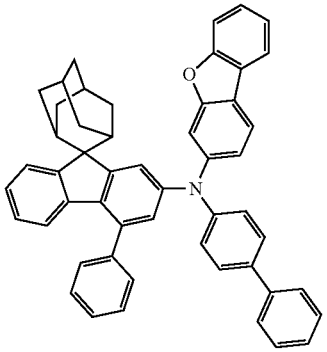 4 | 5.31 | 66 | 696.3 |

TABLE 8-continued
| Intermediate IM-Y | SMC | Compound Y | Mass (g) | Yield (%) | Mass spectrum [M + H] |
|---|---|---|---|---|---|
| 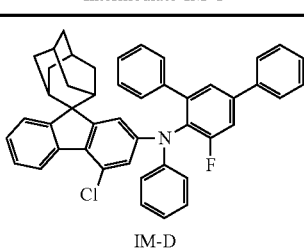<br>IM-D | <br>CAS: 768-35-4 | 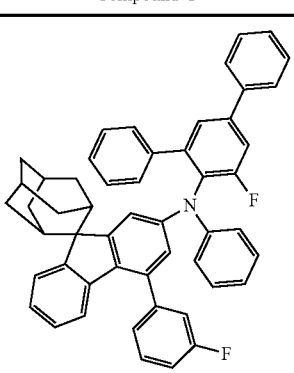<br>5 | 5.96 | 66 | 718.3 |
| | 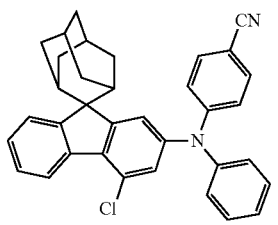<br>CAS: 68572-87-2 | 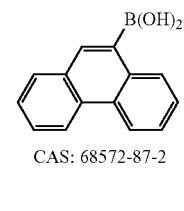 [SMILES: OB(O)c1cc2ccccc2c2ccccc12]<br>6 | 6.35 | 67 | 800.3 |
| 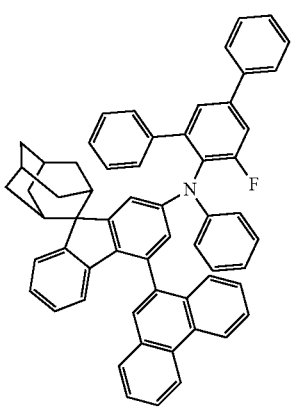<br>IM-E | 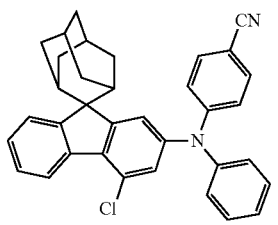<br>CAS: 5122-95-2 | 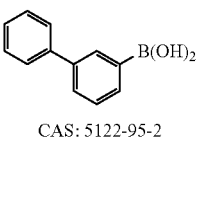 [SMILES: OB(O)c1cccc(-c2ccccc2)c1]<br>7 | 5.86 | 67 | 631.3 |
| | 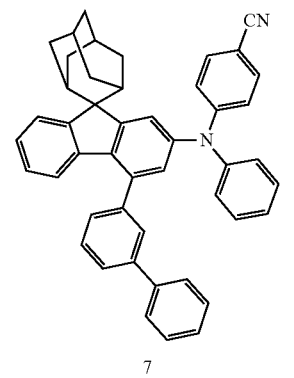<br>CAS: 215527-70-1 | 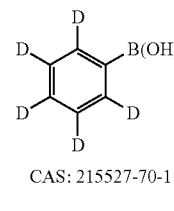<br>8 | 5.23 | 69 | 560.3 |

TABLE 8-continued
| Intermediate IM-Y | SMC | Compound Y | Mass (g) | Yield (%) | Mass spectrum [M + H] |
|---|---|---|---|---|---|
| 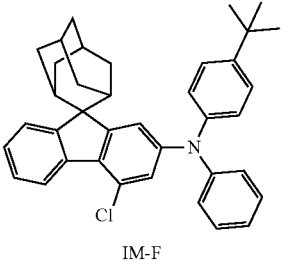 IM-F | 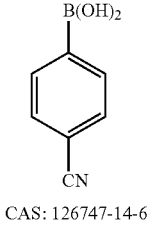 CAS: 126747-14-6 | 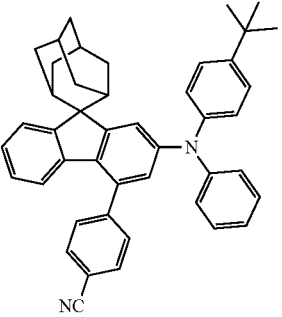 [SMILES: CC(C)(C)c1ccc(N(c2ccccc2)c2cc(-c3ccncc3)c3c(c2)C2(c4ccccc4-3)C3CC4CC(C3)CC2C4)cc1] 9 | 5.36 | 67 | 611.3 |
| | 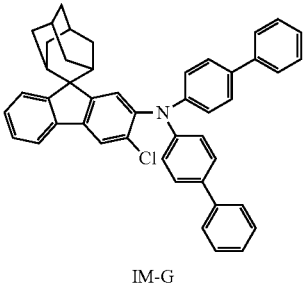 CAS: 1692-15-5 | 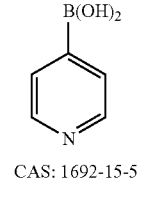 10 | 5.19 | 68 | 587.3 |
| 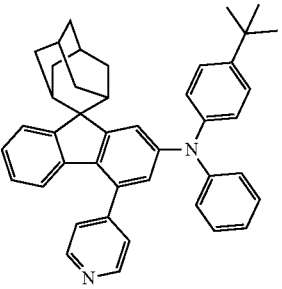 IM-G | 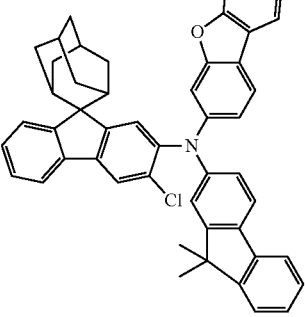 CAS: 100622-34-2 | 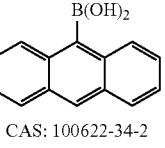 11 | 6.41 | 68 | 782.3 |
| 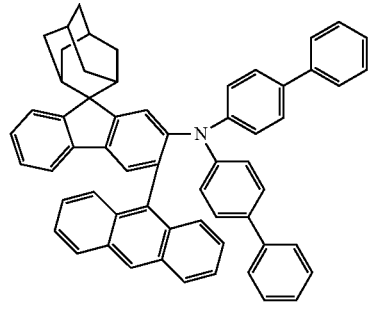 IM-H | 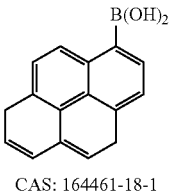 CAS: 164461-18-1 | 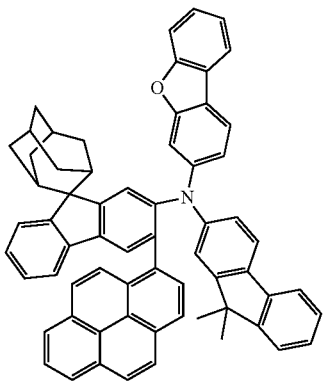 12 | 7.34 | 66 | 860.3 |

TABLE 8-continued

| Intermediate IM-Y | SMC | Compound Y | Mass (g) | Yield (%) | Mass spectrum [M + H] |
|---|---|---|---|---|---|
| IM-I | B(OH)₂, CAS: 123324-71-0 | 13 | 6.38 | 68 | 778.4 |
| IM-J | B(OH)₂, CAS: 1692-15-5 | 14 | 5.75 | 70 | 607.3 |
| IM-L | B(OH)₂, CAS: 4688-76-0 | 16 | 5.76 | 66 | 696.3 |
| IM-M | B(OH)₂, CAS: 100124-06-9 | 17 | 7.09 | 65 | 852.4 |

TABLE 8-continued
| Intermediate IM-Y | SMC | Compound Y | Mass (g) | Yield (%) | Mass spectrum [M + H] |
|---|---|---|---|---|---|
| 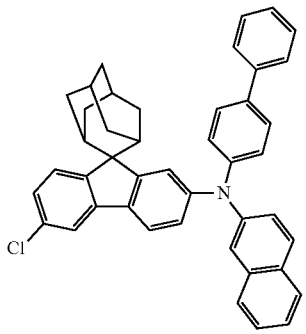<br>IM-N | 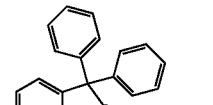<br>CAS: 400607-31-0 | 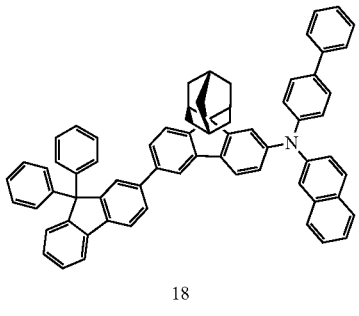 [SMILES: c1ccc(-c2ccc(N(c3ccc4c(c3)C3(c5ccc(-c6ccc7c(c6)C(c6ccccc6)(c6ccccc6)c6ccccc6-7)cc5-4)C4C[C@H]5C[C@@H](C4)C[C@@H]3C5)c3ccc4ccccc4c3)cc2)cc1]<br>18 | 7.19 | 63 | 896.4 |
| 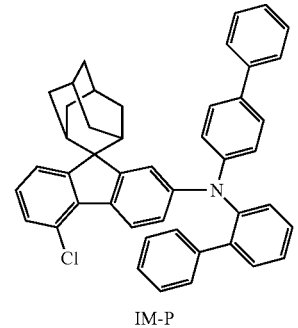 [SMILES: Clc1cccc2c1-c1ccc(N(c3ccc(-c4ccccc4)cc3)c3ccccc3-c3ccccc3)cc1C21C2CC3CC(C2)CC1C3]<br>IM-P | 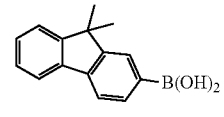<br>CAS: 333432-28-3 | 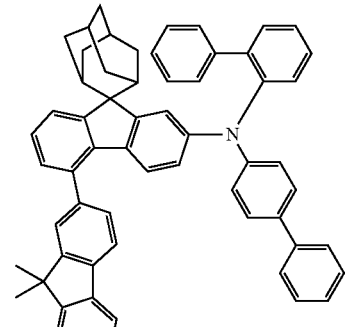<br>20 | 6.69 | 63 | 798.4 |
| 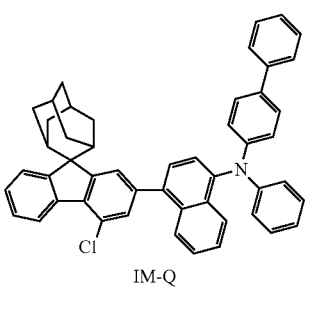<br>IM-Q | 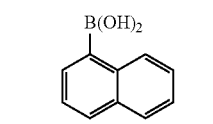<br>CAS: 13922-41-3 | 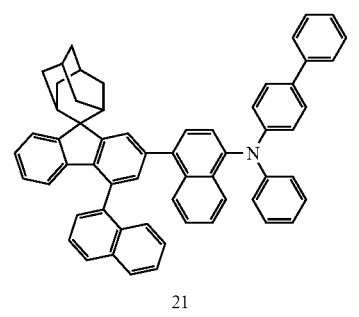 [SMILES: c1ccc(-c2ccc(N(c3ccccc3)c3ccc(-c4cc(-c5cccc6ccccc56)c5c(c4)C4(c6ccccc6-5)C5CC6CC(C5)CC4C6)c4ccccc34)cc2)cc1]<br>21 | 6.35 | 64 | 782.3 |
| 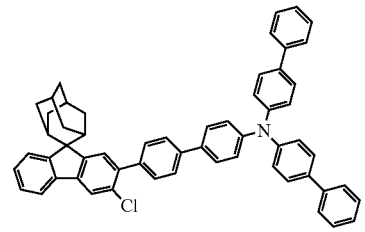<br>IM-R | 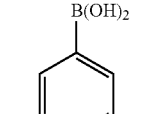<br>CAS: 1692-15-5 | 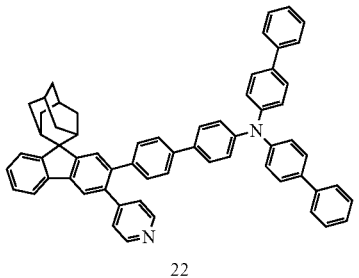 [SMILES: c1ccc(-c2ccc(N(c3ccc(-c4ccccc4)cc3)c3ccc(-c4ccc(-c5cc6c(cc5-c5ccncc5)-c5ccccc5C65C6CC7CC(C6)CC5C7)cc4)cc3)cc2)cc1]<br>22 | 7.01 | 65 | 835.4 |

TABLE 8-continued

| Intermediate IM-Y | SMC | Compound Y | Mass (g) | Yield (%) | Mass spectrum [M + H] |
|---|---|---|---|---|---|
| IM-S | CAS: 5122-95-2 | 23 | 6.69 | 63 | 798.4 |
| IM-T | CAS: 215527-70-1 | 24 | 6.43 | 65 | 751.4 |
| IM-U | CAS: 100124-06-9 | 25 | 7.19 | 66 | 848.3 |
| IM-V | | 26 | 6.86 | 63 | 838.4 |
| IM-G-1 | | 101 | 6.32 | 67 | 696.3 |

TABLE 8-continued
| Intermediate IM-Y | SMC | Compound Y | Mass (g) | Yield (%) | Mass spectrum [M + H] |
|---|---|---|---|---|---|
| 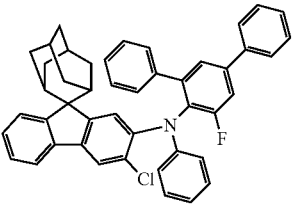<br>IM-G-2 | 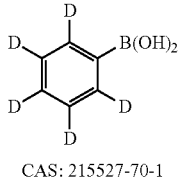<br>CAS: 215527-70-1 | 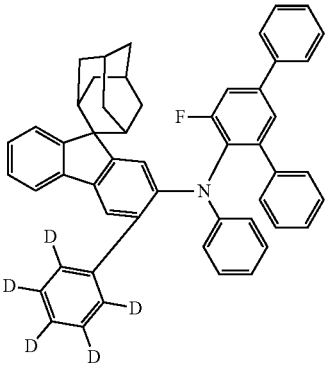<br>102 | 6.13 | 65 | 705.3 |
| 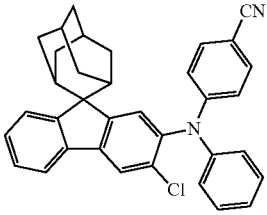<br>IM-G-3 | 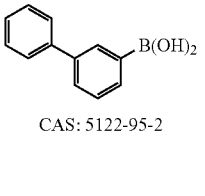<br>CAS: 5122-95-2 | 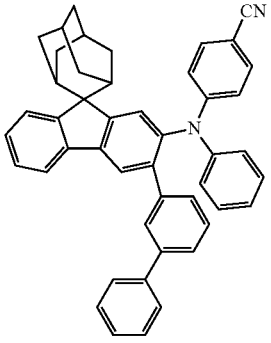<br>103 | 5.79 | 68 | 631.3 |
| 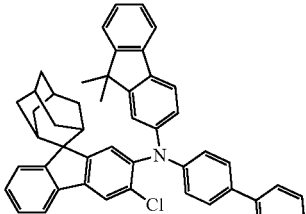<br>IM-G-4 | 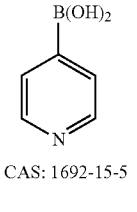<br>CAS: 1692-15-5 | 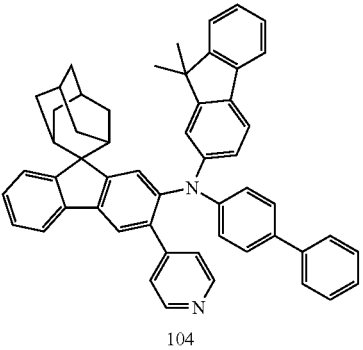 [SMILES: CC1(C)c2ccccc2-c2ccc(N(c3ccc(-c4ccccc4)cc3)c3cc4c(cc3-c3ccncc3)-c3ccccc3C43C4CC5CC(C4)CC3C5)cc21]<br>104 | 6.58 | 65 | 723.3 |
| 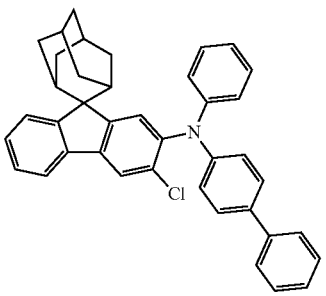<br>IM-H-1 | 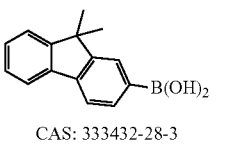<br>CAS: 333432-28-3 | 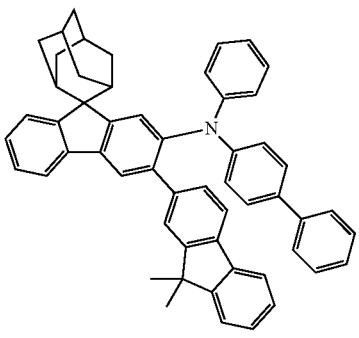<br>105 | 6.32 | 64 | 722.3 |

TABLE 8-continued
| Intermediate IM-Y | SMC | Compound Y | Mass (g) | Yield (%) | Mass spectrum [M + H] |
|---|---|---|---|---|---|
| 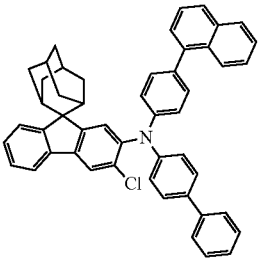<br>IM-H-2 | 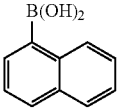<br>CAS: 13922-41-3 | 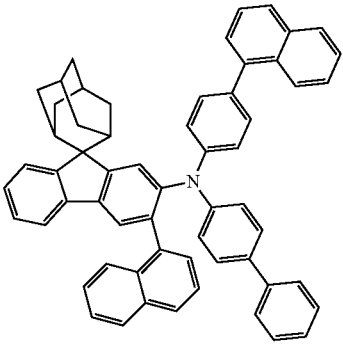<br>106 | 6.85 | 63 | 782.3 |
| 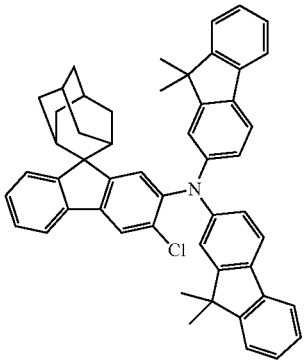<br>IM-H-3 | 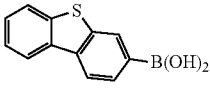<br>CAS: 108847-24-1 | 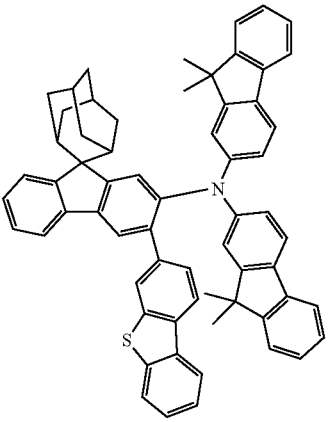<br>107 | 6.93 | 62 | 868.3 |
| 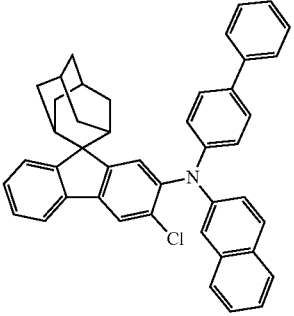<br>IM-H-4 | 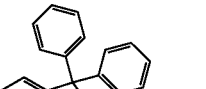<br>CAS: 400607-31-0 | 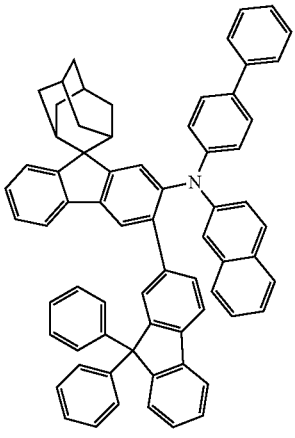<br>108 | 6.32 | 59 | 896.4 |

TABLE 8-continued
| Intermediate IM-Y | SMC | Compound Y | Mass (g) | Yield (%) | Mass spectrum [M + H] |
|---|---|---|---|---|---|
| 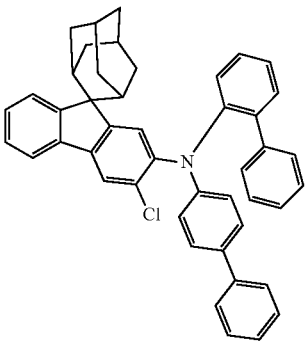<br>IM-H-5 | 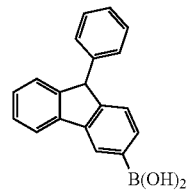<br>CAS: 854952-58-2 | 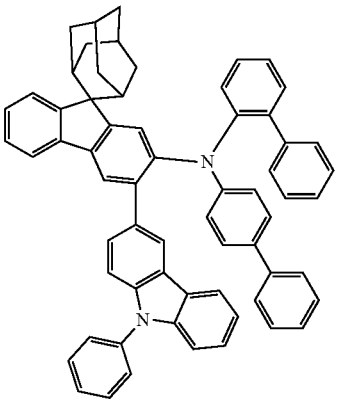<br>109 | 6.15 | 62 | 863.4 |
| 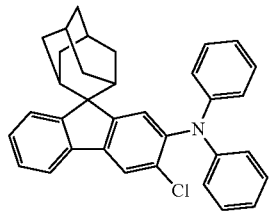<br>IM-H-6 | 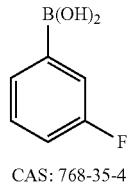<br>CAS: 768-35-4 | 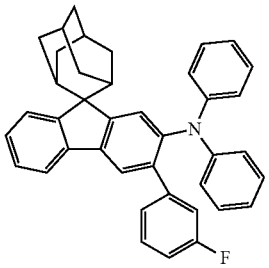<br>110 | 5.83 | 70 | 548.2 |
| 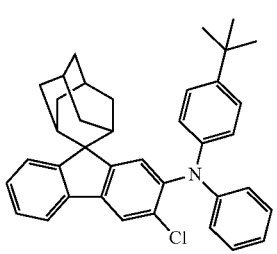<br>IM-H-7 | 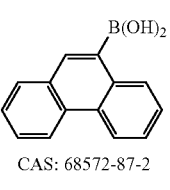<br>CAS: 68572-87-2 | 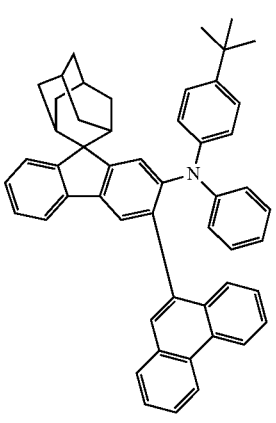<br>111 | 5.54 | 67 | 686.3 |

TABLE 8-continued

| Intermediate IM-Y | SMC | Compound Y | Mass (g) | Yield (%) | Mass spectrum [M + H] |
|---|---|---|---|---|---|
| IM-H-8 | CAS: 5122-94-1 | 112 | 6.32 | 66 | 776.3 |
| IM-H-9 | CAS: 162607-19-4 | 113 | 6.12 | 69 | 711.3 |
| IM-W | | 114 | 8.13 | 65 | 898.3 |
| IM-YY | CAS: 5122-94-1 | 115 | 9.35 | 66 | 940.3 |

TABLE 8-continued
| Intermediate IM-Y | SMC | Compound Y | Mass (g) | Yield (%) | Mass spectrum [M + H] |
|---|---|---|---|---|---|
| 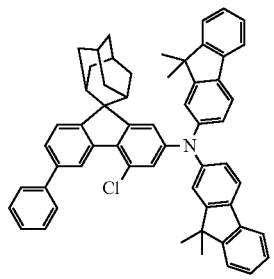 IM-Z-1 | 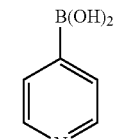 CAS: 1692-15-5 | 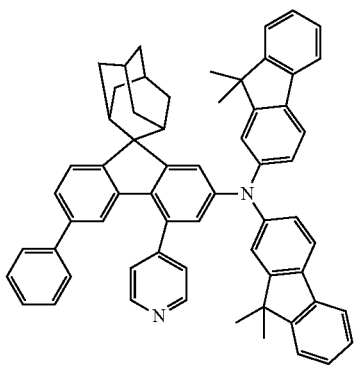 117 | 7.93 | 67 | 839.4 |
| 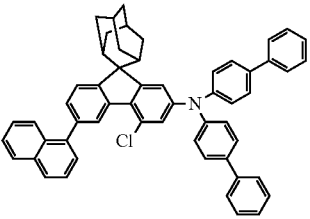 IM-Z-2 | 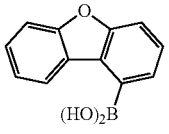 CAS: 162607-19-4 | 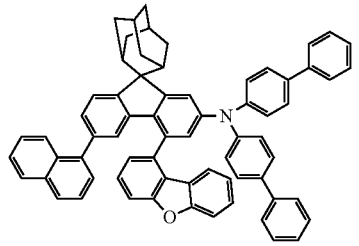 118 | 8.15 | 65 | 898.3 |
| 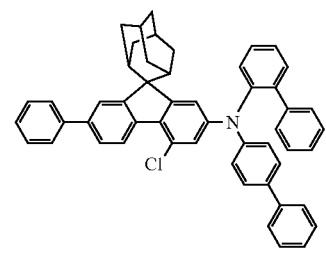 IM-Z-3 | 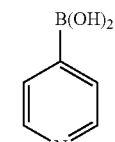 CAS: 1692-15-5 | 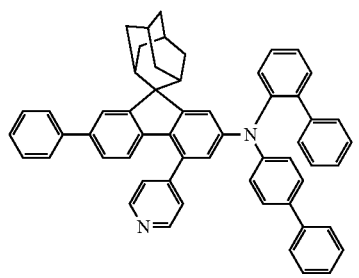 119 | 6.13 | 66 | 759.3 |
| 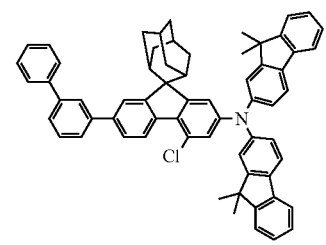 IM-Z-5 | 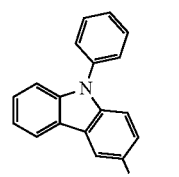 CAS: 854952-58-2 | 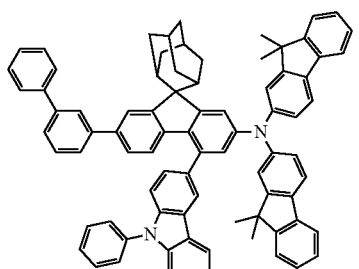 121 | 9.06 | 60 | 1079.5 |

TABLE 8-continued

| Intermediate IM-Y | SMC | Compound Y | Mass (g) | Yield (%) | Mass spectrum [M + H] |
|---|---|---|---|---|---|
| IM-Z-6 | CAS: 333432-28-3 | 122 | 7.66 | 64 | 874.4 |
| IM-Z-7 | CAS: 13922-41-3 | 123 | 7.03 | 69 | 808.3 |
| IM-Q-M | | 116 | 7.94 | 75 | 763.3 |

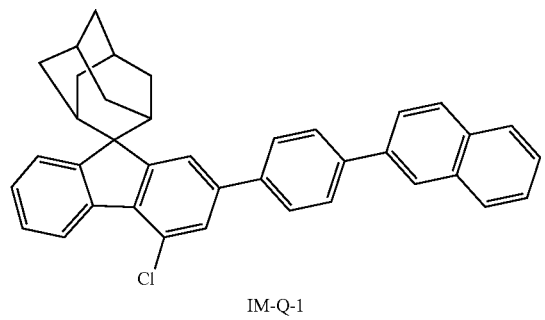

IM-Q-1

+

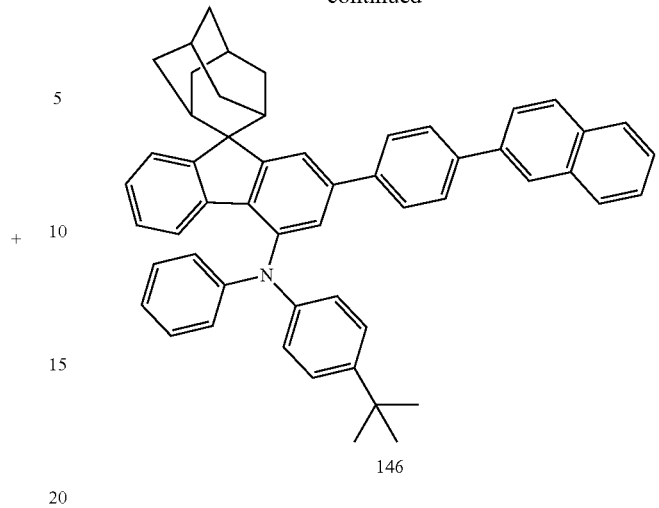

146

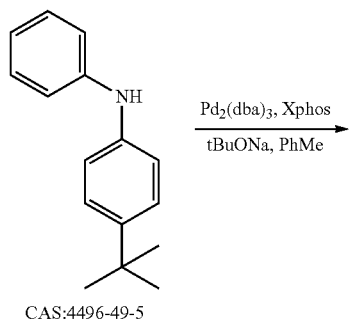

CAS:4496-49-5

→ Pd₂(dba)₃, Xphos
tBuONa, PhMe

An intermediate IM-Q-1 (20 g, 38.3 mmol), SM-L (4496-49-5) (8.6 g, 38.3 mmol), tris(dibenzylideneacetone)dipalladium (0.35 g, 0.38 mmol), 2-dicyclohexylphosphino-2,4,6,-triisopropylbiphenyl (0.35 g, 0.76 mmol), sodium tert-butoxide (5.5 g, 57.3 mmol) and toluene solvent (160 mL) were added into a reaction flask, under the protection of nitrogen, the temperature of the reaction solution was raised to 110° C., and the reaction solution was stirred under heating and refluxing for 3 h. The resulting reaction solution was cooled to room temperature, and extracted by using dichloromethane and water, an organic layer was dried over anhydrous magnesium sulfate, and filtered, the obtained filtrate was allowed to pass through a short silica gel column, the solvent was removed under reduced pressure, and the obtained crude product was purified through recrystallization by using a dichloromethane/n-heptane system (at a volume ratio of 1:3) to obtain a compound 146 (19.1 g, yield: 70%). m/z=712.3[M+H]⁺.

In one embodiment, according to the synthetic method of the compound 146, SMQ with different structures in Table 9 was used for replacing SM-L, and an intermediate IM-Q-X was used for replacing the intermediate IM-Q-1, so that a compound Z was synthesized. Each type of compound SMQ is corresponding to one only compound Z. The obtained compounds are shown in Table 9:

TABLE 9

| Intermediate IM-Q-X | SMQ | Compound Z | Mass (g)/yield (%) | Mass spectrum [M + H] |
|---|---|---|---|---|
| 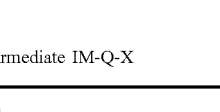<br>IM-Q-2 | 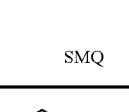<br>CAS: 6336-92-1 | 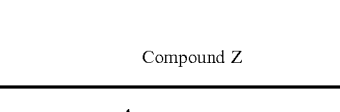<br>147 | 19.6/71 | 938.3 |

TABLE 9-continued

| Intermediate IM-Q-X | SMQ | Compound Z | Mass (g)/yield (%) | Mass spectrum [M + H] |
|---|---|---|---|---|
| IM-Q-3 | CAS: 1290039-85-8 | 148 | 20.9/69 | 878.3 |
| IM-Q-4 | CAS: 102113-98-4 | 149 | 16.7/72 | 758.3 |
| IM-Q-5 | CAS: 36602-01-4 | 150 | 17.6/70 | 771.3 |

TABLE 9-continued

| Intermediate IM-Q-X | SMQ | Compound Z | Mass (g)/yield (%) | Mass spectrum [M + H] |
|---|---|---|---|---|
| 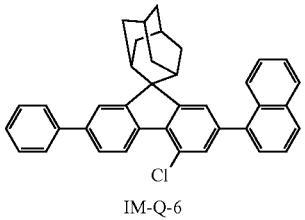 [SMILES: Clc1cc(-c2cccc3ccccc23)cc2c1-c1ccc(-c3ccccc3)cc1C21C2CC3CC(C2)CC1C3]<br>IM-Q-6 | 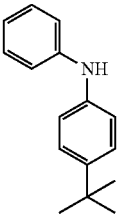<br>CAS: 4496-49-5 | 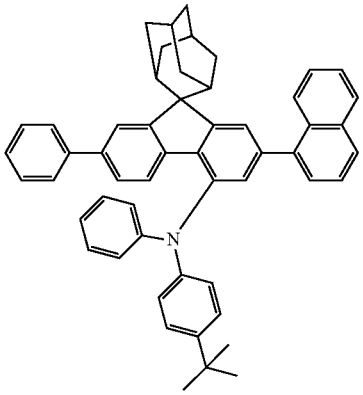<br>151 | 19.3/71 | 712.3 |

NMR Data of Partial Compounds is as Shown in Table 10

TABLE 10

| Compound | NMR data |
|---|---|
| Compound 4 | $^1$HNMR (400 MHz, CD$_2$Cl$_2$): 8.38-8.34 (m, 2H), 8.27 (d, 1H), 7.93-7.86 (m, 10H), 7.70-7.71 (m, 5H), 7.65-7.58 (m, 3H), 7.55 (s, 1H), 7.36 (d, 1H), 7.06 (s, 1H), 7.04 (d, 2H), 6.95 (s, 1H), 2.83 (d, 2H), 2.73 (d, 2H), 2.13 (s, 1H), 2.12 (s, 1H), 1.97 (s, 2H), 1.76 (t, 4H), 1.45 (s, 2H). |
| Compound 16 | $^1$HNMR (400 MHz, CD$_2$Cl$_2$): 8.05 (d, 1H), 8.02-7.99 (m, 2H), 7.96 (s, 1H), 7.94-7.90 (m, 7H), 7.85-7.78 (m, 5H), 7.74 (d, 1H), 7.65 (d, 1H), 7.62 (d, 2H), 7.54 (d, 2H), 7.30 (s, 1H), 6.88-6.82 (m, 5H), 2.23 (m, 3H), 2.84 (d, 2H), 2.76 (d, 2H), 2.12 (s, 1H), 2.11 (s, 1H), 1.96 (s, 2H), 1.75 (t, 4H), 1.45 (s, 2H). |
| Compound 149 | $^1$HNMR (400 MHz, CD$_2$Cl$_2$): 8.17 (s, 1H), 8.00-7.97 (m, 2H), 7.95-7.89 (m, 13H), 7.87-7.78 (m, 10H), 7.60 (s, 1H), 7.34 (d, 1H), 7.18 (s, 1H), 6.84 (d, 4H), 2.86 (d, 2H), 2.74 (d, 2H), 2.16 (s, 1H), 2.14 (s, 1H), 1.94 (s, 2H), 1.76 (t, 4H), 1.45 (s, 2H). |

Organic Electroluminescent Device Manufacture and Evaluation

Example 1: Green Organic Electroluminescent Device

An anode was prepared by the following processes: a substrate with an ITO thickness of 1500 Å (manufactured by Corning) was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and O$_2$:N$_2$ plasma to increase the work function of the anode (the experiment substrate), and remove scum.

F4-TCNQ was vacuum-evaporated on the experiment substrate (the anode) to form a hole injection layer (HIL) with a thickness of 100 Å, and NPB was evaporated on the hole injection layer to form a hole transport layer with a thickness of 1100 Å.

The compound 1 was vacuum-evaporated on the hole transport layer to form an electron blocking layer with a thickness of 350 Å.

GH-n1, GH-n2 and Ir(ppy)$_3$ were co-evaporated on the electron blocking layer at a ratio of 50%:45%:5% (at an evaporation rate) to form a green organic electroluminescent layer (EML) with a thickness of 400 Å.

ET-06 and LiQ were mixed at a weight ratio of 1:1 and the mixture was evaporated to form an electron transport layer (ETL) with a thickness of 300 Å, LiQ was evaporated on the electron transport layer to form an electron injection layer (EIL) with a thickness of 10 Å, and then magnesium (Mg) and argentum (Ag) were mixed at an evaporation rate of 1:9 and the mixture was vacuum-evaporated on the electron injection layer to form a cathode with a thickness of 115 Å.

CP-05 with a thickness of 650 Å was evaporated on the cathode to form an organic capping layer (CPL), thus completing manufacturing of the organic light-emitting device.

Examples 2 to 33

Except that the compound 1 was replaced with compounds shown in the following table 11 when forming an electron blocking layer, an organic electroluminescent element was manufactured by the same method as in Example 1.

Comparative Example 1

Except that the compound 1 was replaced with a compound A-1 when forming an electron blocking layer, an organic electroluminescent device was manufactured by the same method as in Example 1.

Comparative Example 2

Except that the compound 1 was replaced with a compound B-1 when forming an electron blocking layer, an organic electroluminescent device was manufactured by the same method as in Example 1.

Comparative Example 3

Except that the compound 1 was replaced with a compound C-1 when forming an electron blocking layer, an organic electroluminescent device was manufactured by the same method as in Example 1.
The structures of materials used in the above examples and the comparative examples are shown below:
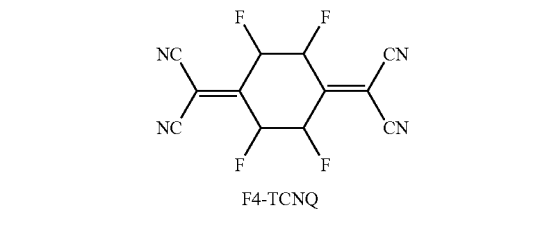
F4-TCNQ
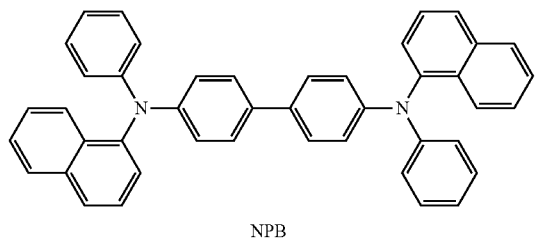
NPB
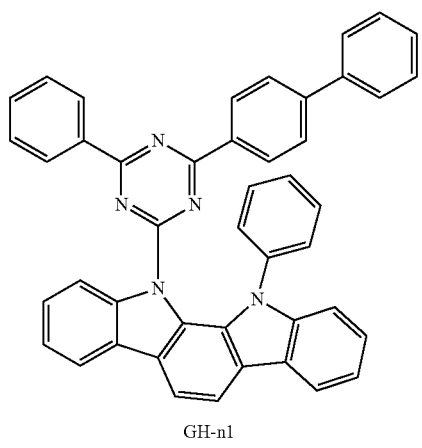
GH-n1
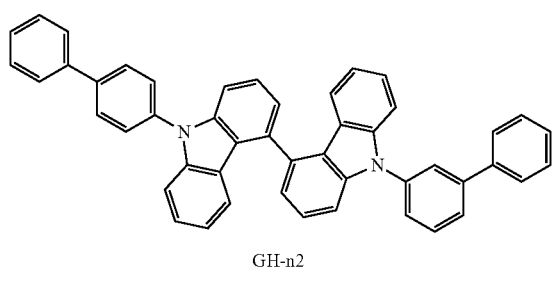
GH-n2
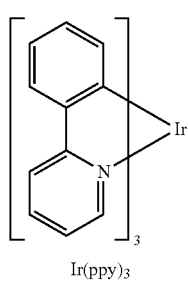
Ir(ppy)$_3$
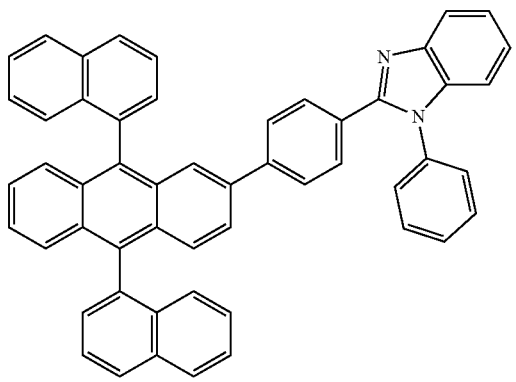
ET-06
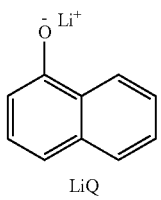
LiQ
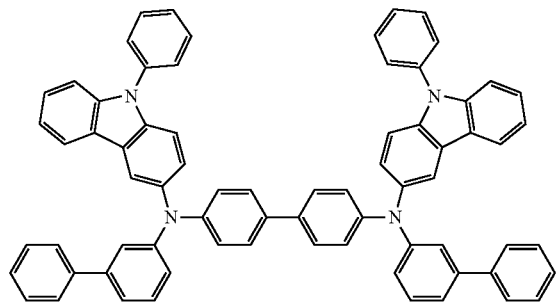
CP-05
Compound A-1
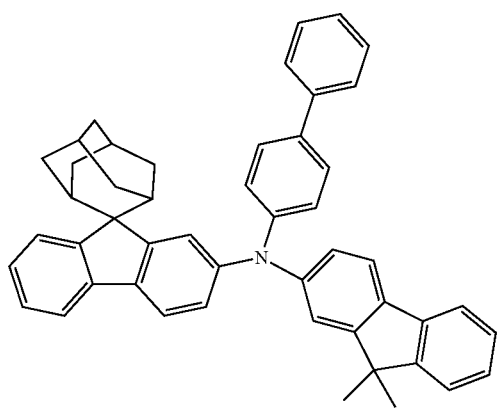

Compound B-1

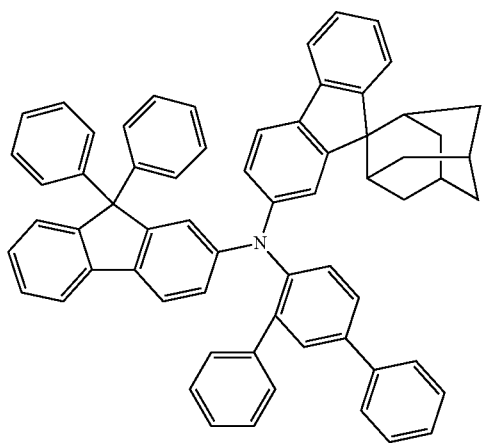

Compound C-1

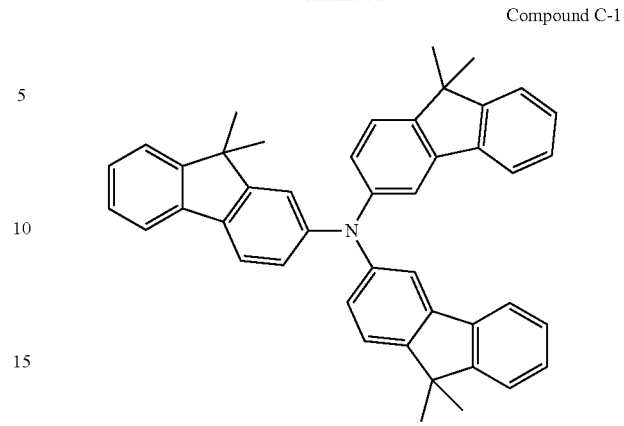

The performance of the manufactured organic electroluminescent device was analyzed under the condition of 20 mA/cm², and the result is shown in the following table 11.

TABLE 11

| Example | Electron blocking layer | Volt (V) | Cd/A | lm/W | CIE-x | CIE-y | EQE % | T95 (hrs)@ 15 mA/cm² |
|---|---|---|---|---|---|---|---|---|
| Example 1 | Compound 1 | 3.86 | 80.00 | 65.11 | 0.22 | 0.73 | 20.00 | 494 |
| Example 2 | Compound 2 | 3.93 | 86.16 | 68.87 | 0.22 | 0.73 | 21.54 | 504 |
| Example 3 | Compound 3 | 3.89 | 80.29 | 64.84 | 0.22 | 0.73 | 20.07 | 498 |
| Example 4 | Compound 4 | 3.89 | 81.90 | 66.14 | 0.22 | 0.73 | 20.48 | 494 |
| Example 5 | Compound 5 | 3.88 | 84.05 | 68.05 | 0.22 | 0.73 | 21.01 | 480 |
| Example 6 | Compound 11 | 3.93 | 83.73 | 66.93 | 0.22 | 0.73 | 20.93 | 495 |
| Example 7 | Compound 12 | 3.86 | 87.02 | 70.82 | 0.22 | 0.73 | 21.76 | 498 |
| Example 8 | Compound 13 | 3.86 | 80.12 | 65.21 | 0.22 | 0.73 | 20.03 | 505 |
| Example 9 | Compound 14 | 3.91 | 83.96 | 67.46 | 0.22 | 0.73 | 20.99 | 470 |
| Example 10 | Compound 17 | 3.88 | 82.95 | 67.16 | 0.22 | 0.73 | 20.74 | 498 |
| Example 11 | Compound 18 | 3.93 | 81.74 | 65.34 | 0.22 | 0.73 | 20.44 | 499 |
| Example 12 | Compound 20 | 3.91 | 81.34 | 65.35 | 0.22 | 0.73 | 20.34 | 500 |
| Example 13 | Compound 21 | 3.92 | 86.12 | 69.02 | 0.22 | 0.73 | 21.53 | 492 |
| Example 14 | Compound 22 | 3.88 | 84.30 | 68.25 | 0.22 | 0.73 | 21.08 | 501 |
| Example 15 | Compound 24 | 3.87 | 80.34 | 65.22 | 0.22 | 0.73 | 20.09 | 490 |
| Example 16 | Compound 109 | 3.92 | 87.90 | 70.44 | 0.22 | 0.73 | 21.98 | 499 |
| Example 17 | Compound 110 | 3.88 | 87.15 | 70.56 | 0.22 | 0.73 | 21.79 | 510 |
| Example 18 | Compound 111 | 3.91 | 87.29 | 70.13 | 0.22 | 0.73 | 21.82 | 499 |
| Example 19 | Compound 112 | 3.92 | 79.04 | 63.34 | 0.22 | 0.73 | 19.76 | 509 |
| Example 20 | Compound 113 | 3.90 | 87.47 | 70.46 | 0.22 | 0.73 | 21.87 | 494 |
| Example 21 | Compound 116 | 3.90 | 89.71 | 72.26 | 0.22 | 0.73 | 22.43 | 510 |
| Example 22 | Compound 117 | 3.92 | 84.71 | 67.89 | 0.22 | 0.73 | 21.18 | 496 |
| Example 23 | Compound 118 | 3.94 | 81.88 | 65.29 | 0.22 | 0.73 | 20.47 | 498 |
| Example 24 | Compound 119 | 3.93 | 84.82 | 67.80 | 0.22 | 0.73 | 21.21 | 494 |
| Example 25 | Compound 121 | 3.89 | 85.95 | 69.41 | 0.22 | 0.73 | 21.49 | 500 |
| Example 26 | Compound 122 | 3.94 | 83.61 | 66.67 | 0.22 | 0.73 | 20.90 | 495 |
| Example 27 | Compound 123 | 3.98 | 80.91 | 61.18 | 0.22 | 0.73 | 30.67 | 495 |
| Example 28 | Compound 146 | 3.89 | 87.52 | 70.68 | 0.22 | 0.73 | 21.88 | 511 |
| Example 29 | Compound 147 | 3.86 | 85.33 | 69.45 | 0.22 | 0.73 | 21.33 | 519 |
| Example 30 | Compound 148 | 3.90 | 89.03 | 71.71 | 0.22 | 0.73 | 22.26 | 525 |
| Example 31 | Compound 149 | 3.90 | 87.35 | 70.36 | 0.22 | 0.73 | 21.84 | 524 |
| Example 32 | Compound 150 | 3.89 | 85.51 | 69.06 | 0.22 | 0.73 | 21.38 | 504 |
| Example 33 | Compound 151 | 3.87 | 86.77 | 70.44 | 0.22 | 0.73 | 21.69 | 529 |
| Comparative example 1 | Compound A-1 | 4.23 | 72.72 | 59.03 | 0.22 | 0.73 | 18.18 | 450 |
| Comparative example 2 | Compound B-1 | 4.37 | 69.52 | 55.95 | 0.22 | 0.73 | 17.38 | 440 |
| Comparative example 3 | Compound C-1 | 4.26 | 68.92 | 56.29 | 0.22 | 0.73 | 17.23 | 436 |

According to the table 11, under the condition of small chromaticity coordinate difference, compared with the comparative examples 1 to 3, the driving voltage of the organic electroluminescent device prepared in the examples 1 to 33 is at least decreased by 0.25 V, the current efficiency (Cd/A) is at least improved by 8.7%, the external quantum efficiency is at least improved by 8.7%, the service life is at least prolonged by 4.4%, and the highest service life can be prolonged by 93 h.

Thus, when the nitrogen-containing compound provided by the present disclosure was used in an electron blocking layer, an organic electroluminescent device with relatively low working voltage can be manufactured.

TABLE 12

| Example | Electron blocking layer | Tg (° C.) | Te (° C.) |
|---|---|---|---|
| Example 1 | Compound 1 | 135 | 234 |
| Example 2 | Compound 2 | 135 | 235 |
| Example 3 | Compound 3 | 136 | 233 |
| Example 4 | Compound 4 | 135 | 223 |
| Example 5 | Compound 5 | 145 | 240 |
| Example 6 | Compound 11 | 143 | 238 |
| Example 7 | Compound 12 | 135 | 222 |
| Example 8 | Compound 13 | 145 | 241 |
| Example 9 | Compound 14 | 145 | 242 |
| Example 10 | Compound 17 | 140 | 231 |
| Example 11 | Compound 18 | 137 | 229 |
| Example 12 | Compound 20 | 138 | 225 |
| Example 13 | Compound 21 | 135 | 216 |
| Example 14 | Compound 22 | 137 | 221 |
| Example 15 | Compound 24 | 141 | 236 |
| Example 16 | Compound 109 | 139 | 227 |
| Example 17 | Compound 110 | 139 | 226 |
| Example 18 | Compound 111 | 136 | 224 |
| Example 19 | Compound 112 | 135 | 210 |
| Example 20 | Compound 113 | 135 | 227 |
| Example 21 | Compound 116 | 136 | 223 |
| Example 22 | Compound 117 | 144 | 241 |
| Example 23 | Compound 118 | 140 | 229 |
| Example 24 | Compound 119 | 144 | 238 |
| Example 25 | Compound 121 | 143 | 237 |
| Example 26 | Compound 122 | 135 | 226 |
| Example 27 | Compound 123 | 135 | 223 |
| Example 28 | Compound 146 | 144 | 244 |
| Example 29 | Compound 147 | 138 | 216 |
| Example 30 | Compound 148 | 138 | 221 |
| Example 31 | Compound 149 | 142 | 239 |
| Example 32 | Compound 150 | 137 | 222 |
| Example 33 | Compound 151 | 139 | 227 |
| Comparative example 1 | Compound A-1 | 133 | 258 |
| Comparative example 2 | Compound B-1 | 111 | 278 |
| Comparative example 3 | Compound C-1 | 117 | 276 |

It can be seen from Table 12 that the compound provided by the present disclosure has lower decomposition possibility in the film forming process of the device through evaporation at high temperature, and has higher crystallization resistance in an electric Joule thermal environment in the operation of the device.

Compared with the compounds in the comparative examples, the compound provided by the present disclosure has the advantage that under the condition of small molecular weight difference, the evaporation temperature (Te) of the compound provided by the present disclosure is reduced due to relatively high steric hindrance. Thus, the compound provided by the present disclosure has better thermal stability.

Example 34: Blue Organic Electroluminescent Device

An anode was prepared by the following processes: an ITO substrate with a thickness of 1500 Å (manufactured by Corning) was cut into a size of 40 mm×40 mm×0.7 mm to be prepared into an experimental substrate with a cathode, an anode and an insulating layer pattern by adopting a photoetching process, and surface treatment was performed by utilizing ultraviolet ozone and $O_2:N_2$ plasma to increase the work function of the anode (the experiment substrate), and remove scum.

F4-TCNQ was vacuum-evaporated on the experiment substrate (the anode) to form a hole injection layer (HIL) with a thickness of 100 Å, and a compound NPB was evaporated on the hole injection layer to form a hole transport layer (HTL) with a thickness of 1050 Å.

The compound 6 was evaporated on the HTL as an electron blocking layer (EBL) with a thickness of 100 Å.

A compound $\alpha,\beta$-ADN was evaporated on the EBL to serve as a host, and meanwhile, BD-1 was doped to form an organic electroluminescent layer (EML) with a thickness of 240 Å, wherein a film thickness ratio of the host to the doping agent is 100:3.

A compound ET-1 was evaporated on the organic electroluminescent layer to form a hole blocking layer (HBL) with a thickness of 50 Å.

ET-06 and LiQ were mixed at a weight ratio of 1:1 and the mixture was evaporated to form an electron transport layer (ETL) with a thickness of 300 Å, LiQ was evaporated on the electron transport layer to form an electron injection layer (EIL) with a thickness of 10 Å, and then magnesium (Mg) and argentum (Ag) were mixed at an evaporation rate of 1:9 and the mixture was vacuum-evaporated on the electron injection layer to form a cathode with a thickness of 115 Å.

In addition, CP-5 with a thickness of 650 Å was evaporated on the cathode to form an organic capping layer (CPL), thus completing manufacturing of the organic light-emitting device.

Examples 35 to 52

Except that the compound 6 was replaced with compounds shown in the following table 13 when forming an electron blocking layer, an organic electroluminescent element was manufactured by the same method as in Example 34.

Comparative Example 6

Except that the compound 6 was replaced with a compound A-2 when forming an electron blocking layer, an organic electroluminescent device was manufactured by the same method as in Example 34.

Comparative Example 7

Except that the compound 6 was replaced with a compound B-2 when forming an electron blocking layer, an organic electroluminescent device was manufactured by the same method as in Example 34.

Comparative Example 8

Except that the compound 6 was replaced with compound C-2 when forming an electron blocking layer, an organic electroluminescent device was manufactured by the same method as in Example 34.

The structures of materials used in the examples and the comparative examples are shown below:

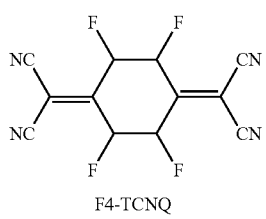
F4-TCNQ
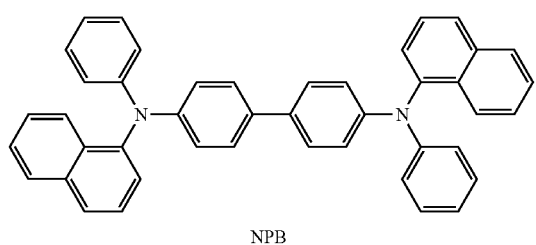
NPB
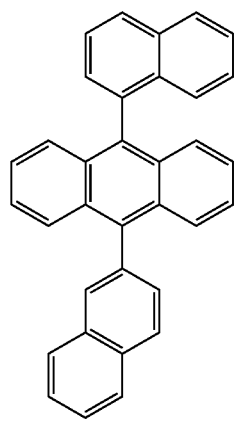
α,β-ADN
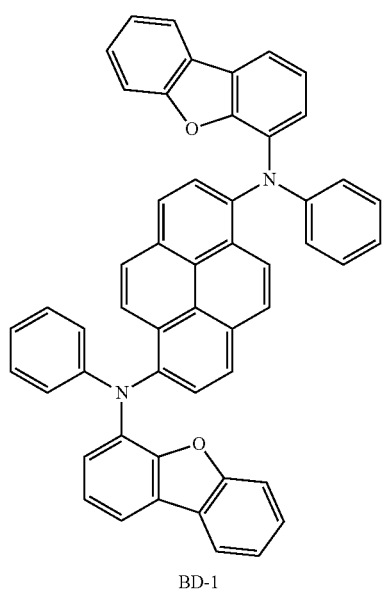
BD-1
-continued
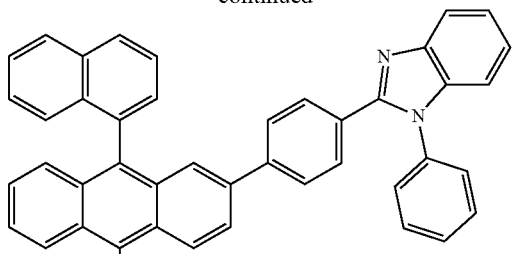
ET-06
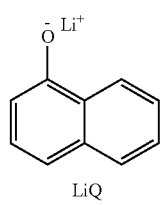
LiQ
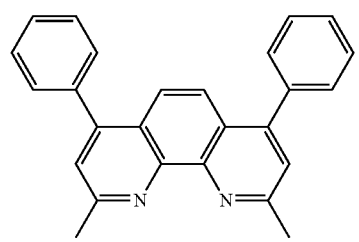
ET-1
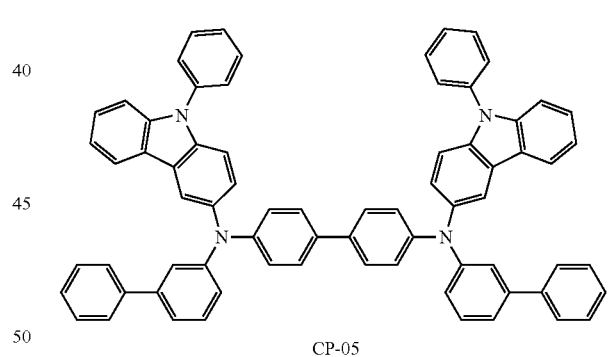
CP-05
Compound A-2
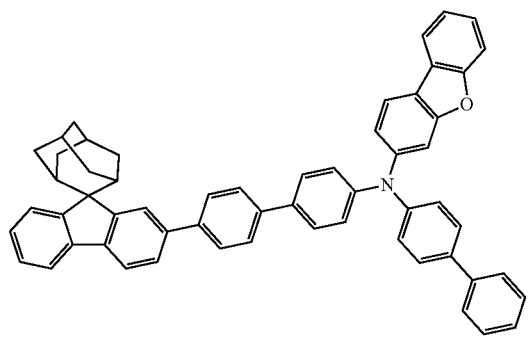

Compound B-2

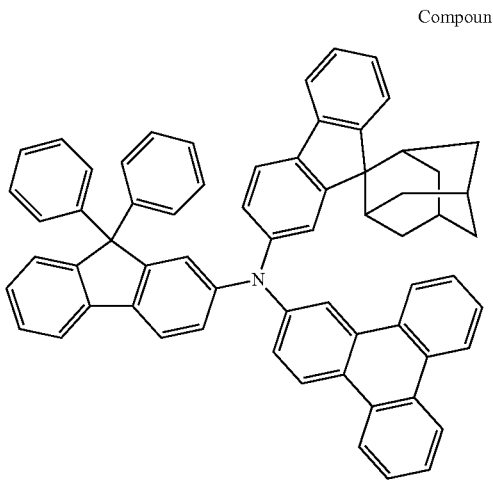

Compoound C-2

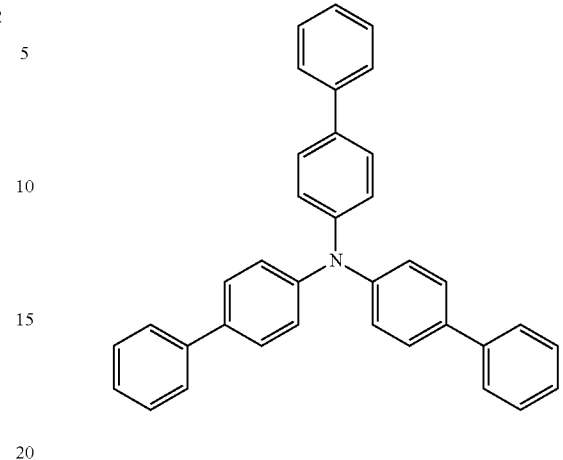

The performance of the manufactured organic electroluminescent device was analyzed under the condition of 20 mA/cm², and the result is shown in the following table 13:

TABLE 13

| Example | Electron blocking layer | Volt (V) | Cd/A | lm/W | CIE-x | CIE-y | EQE % | T95 (hrs)@ 15 mA/cm² |
|---|---|---|---|---|---|---|---|---|
| Example 34 | Compound 6 | 3.87 | 6.71 | 5.45 | 0.14 | 0.05 | 13.80 | 221 |
| Example 35 | Compound 7 | 3.91 | 6.58 | 5.29 | 0.14 | 0.05 | 13.54 | 219 |
| Example 36 | Compound 8 | 3.93 | 6.82 | 5.45 | 0.14 | 0.05 | 14.03 | 206 |
| Example 37 | Compound 9 | 3.86 | 6.56 | 5.34 | 0.14 | 0.05 | 13.49 | 215 |
| Example 38 | Compound 10 | 3.95 | 6.67 | 5.30 | 0.14 | 0.05 | 13.72 | 193 |
| Example 39 | Compound 16 | 3.92 | 6.60 | 5.29 | 0.14 | 0.05 | 13.58 | 229 |
| Example 40 | Compound 23 | 3.95 | 6.66 | 5.30 | 0.14 | 0.05 | 13.70 | 214 |
| Example 41 | Compound 25 | 3.89 | 6.71 | 5.42 | 0.14 | 0.05 | 13.80 | 229 |
| Example 42 | Compound 26 | 3.92 | 6.59 | 5.28 | 0.14 | 0.05 | 13.56 | 222 |
| Example 43 | Compound 101 | 3.92 | 6.82 | 5.47 | 0.14 | 0.05 | 14.03 | 227 |
| Example 44 | Compound 102 | 3.95 | 6.68 | 5.31 | 0.14 | 0.05 | 13.74 | 215 |
| Example 45 | Compound 103 | 3.90 | 6.38 | 5.14 | 0.14 | 0.05 | 13.12 | 207 |
| Example 46 | Compound 104 | 3.95 | 6.47 | 5.15 | 0.14 | 0.05 | 13.31 | 215 |
| Example 47 | Compound 105 | 3.94 | 6.65 | 5.30 | 0.14 | 0.05 | 13.68 | 227 |
| Example 48 | Compound 106 | 3.94 | 6.77 | 5.40 | 0.14 | 0.05 | 13.93 | 217 |
| Example 49 | Compound 107 | 3.95 | 6.40 | 5.09 | 0.14 | 0.05 | 13.16 | 225 |
| Example 50 | Compound 108 | 3.90 | 6.59 | 5.31 | 0.14 | 0.05 | 13.56 | 229 |
| Example 51 | Compound 114 | 3.94 | 6.69 | 5.33 | 0.14 | 0.05 | 13.76 | 224 |
| Example 52 | Compound 115 | 3.94 | 6.37 | 5.08 | 0.14 | 0.05 | 13.10 | 218 |
| Comparative example 4 | Compound A-2 | 4.27 | 5.73 | 4.22 | 0.14 | 0.05 | 11.79 | 162 |
| Comparative example 5 | Compound B-2 | 4.30 | 5.41 | 3.95 | 0.14 | 0.05 | 11.13 | 114 |
| Comparative example 6 | Compound C-2 | 4.44 | 4.94 | 3.50 | 0.14 | 0.05 | 10.16 | 105 |

According to the table 13, under the condition of small hromaticity coordinate difference, compared with the comparative examples 4 to 6, the driving voltage of the organic electroluminescent device prepared in the examples 34 to 52 is at least decreased by 0.32 V, the current efficiency (Cd/A) is at least improved by 11.17%, the external quantum efficiency is at least improved by 11.11%, the service life is at least prolonged by 19.14%, and the highest service life can be prolonged by 124 h.

Thus, the nitrogen-containing compound provided by the present disclosure is low in evaporation temperature, and can be used for manufacturing an organic electroluminescent device with low driving voltage when being used as an electron blocking layer material.

TABLE 14

| Example | Electron blocking layer | Tg (° C.) | Te (° C.) |
|---|---|---|---|
| Example 34 | Compound 6 | 136 | 227 |
| Example 35 | Compound 7 | 145 | 246 |
| Example 36 | Compound 8 | 142 | 244 |
| Example 37 | Compound 9 | 144 | 243 |
| Example 38 | Compound 10 | 136 | 226 |
| Example 39 | Compound 16 | 140 | 241 |
| Example 40 | Compound 23 | 137 | 224 |
| Example 41 | Compound 25 | 138 | 221 |
| Example 42 | Compound 26 | 139 | 239 |
| Example 43 | Compound 101 | 145 | 246 |
| Example 44 | Compound 102 | 143 | 243 |
| Example 45 | Compound 103 | 138 | 227 |
| Example 46 | Compound 104 | 135 | 226 |
| Example 47 | Compound 105 | 135 | 222 |
| Example 48 | Compound 106 | 143 | 243 |
| Example 49 | Compound 107 | 136 | 226 |
| Example 50 | Compound 108 | 137 | 224 |
| Example 51 | Compound 114 | 136 | 234 |
| Example 52 | Compound 115 | 145 | 247 |
| Comparative example 4 | Compound A-2 | 130 | 256 |
| Comparative example 5 | Compound B-2 | 122 | 272 |
| Comparative example 6 | Compound C-2 | 118 | 270 |

It can be seen from Table 14 that the compound provided by the present disclosure has lower decomposition possibility in the film forming process of the device through evaporation at high temperature, and has higher crystallization resistance in an electric Joule thermal environment in the operation of the device.

Compared with the compounds in the comparative examples, the compound provided by the present disclosure has the advantage that under the condition of small molecular weight difference, the evaporation temperature (Te) of the compound provided by the present disclosure is reduced due to relatively high steric hindrance. Thus, the compound provided by the present disclosure has better thermal stability.

The preferable embodiments of the present disclosure are described in detail above in combination with the drawings, however, the present disclosure is not limited to the specific details in the above embodiments, in the technical concept range of the present disclosure, the technical solution of the present disclosure can be subjected to various simple variations, and these simple variations all belong to the protection range of the present disclosure.

In addition, it should be noted that all the specific technical features described in the above specific embodiments can be combined in any appropriate mode without contradiction, and in order to avoid unnecessary repetition, various possible combinations are not described any more in the present disclosure.

In addition, various different embodiments of the present disclosure can also be combined at will, and as long as they do not violate the idea of the present disclosure, they also should be regarded as the contents disclosed by the present disclosure.

What is claimed is:

1. A nitrogen-containing compound, having a structure as shown in a chemical formula 1:

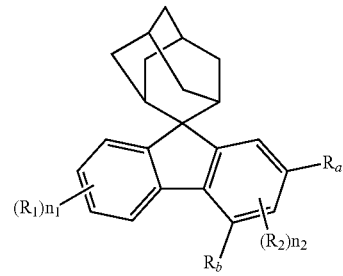

Chemical formula 1

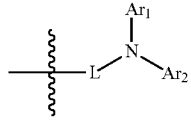

Chemical formula 1-1 wherein

represents a chemical bond;

$R_a$ and $R_b$ are independently selected from hydrogen or a group shown in a chemical formula 1-1, and only one of $R_a$ and $R_b$ is the group shown in the chemical formula 1-1;

L is selected from a single bond or the group consisting of the following groups:

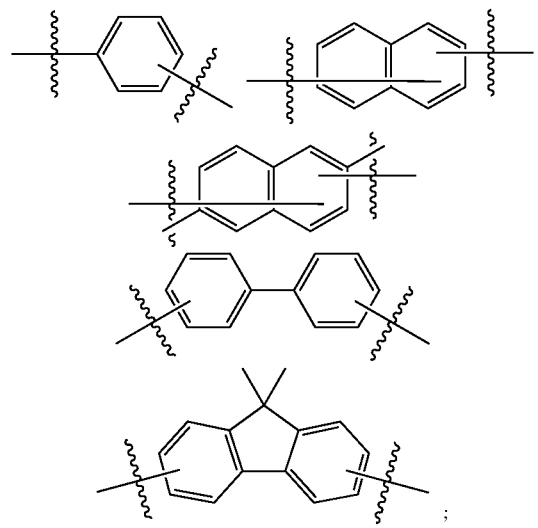

$R_1$ is selected from deuterium, cyano, halogen group, substituted or unsubstituted alkyl with a total carbon atoms number of 1 to 6, substituted or unsubstituted aryl with a total carbon atoms number of 6 to 25, or substituted or unsubstituted heteroaryl with a total carbon atoms number of 5 to 12, and the $R_1$ is not carbazolyl or N-phenylcarbazolyl;

$R_2$ is selected from deuterium, cyano, halogen group, alkyl with a total carbon atoms number of 1 to 6, substituted or unsubstituted aryl with a total carbon atoms number of 6 to 25, or substituted or unsubstituted heteroaryl with a total carbon atoms number of 5 to 18; and at least one of the $R_1$ and the $R_2$ is selected from substituted or unsubstituted aryl, or substituted or unsubstituted heteroaryl;

$n_1$ and $n_2$ are the number of $R_1$ and $R_2$ respectively;

$n_1$ is selected from 0, 1, 2, 3 or 4, and when $n_1$ is greater than 1, any two $R_1$ are the same or different;

$n_2$ is selected from 0, 1, or 2, and when $n_2$ is greater than 1, any two $R_2$ are the same or different;

$n_1+n_2 \geq 1$;

$Ar_1$ and $Ar_2$ are the same or different, and are independently selected from substituted or unsubstituted aryl with a total carbon atoms number of 6 to 30, or substituted or unsubstituted heteroaryl with a total carbon atoms number of 3 to 24, the $Ar_1$ is not 9,9-diphenylfluorenyl, and the $Ar_2$ is not 9,9-diphenylfluorenyl; and the substituents in the L, $R_1$, $R_2$, $Ar_1$ and $Ar_2$ are independently selected from deuterium, halogen group, cyano, heteroaryl with 3 to 20 carbon atoms, aryl with 6 to 20 carbon atoms which can be optionally substituted by 0, 1, 2, 3, 4 or 5 substituents selected from deuterium, fluorine, chlorine, cyano, methyl or tert-butyl, or alkyl with 1 to 10 carbon atoms; and the substituent in the $R_1$ is not carbazolyl;

and the nitrogen-containing compound is not:

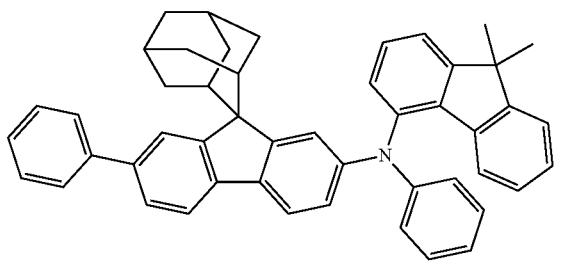

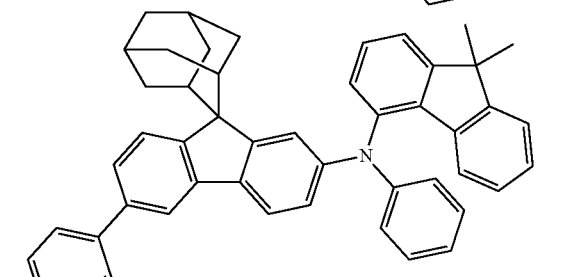

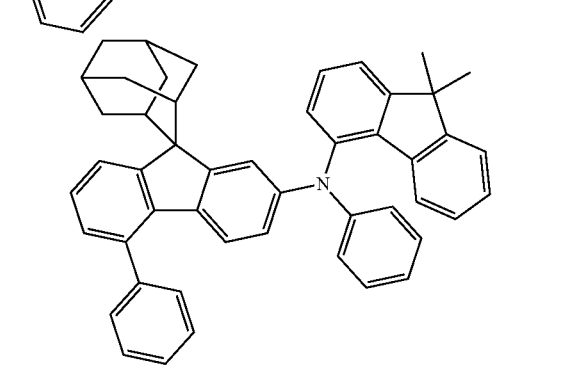

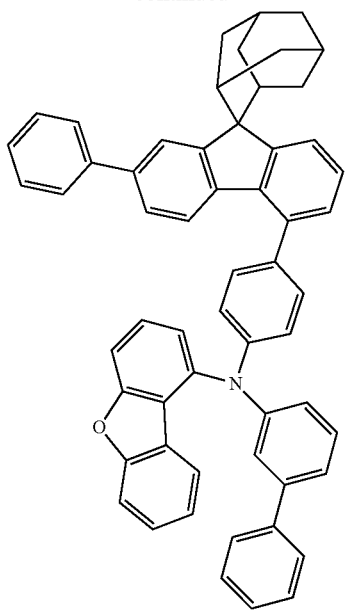

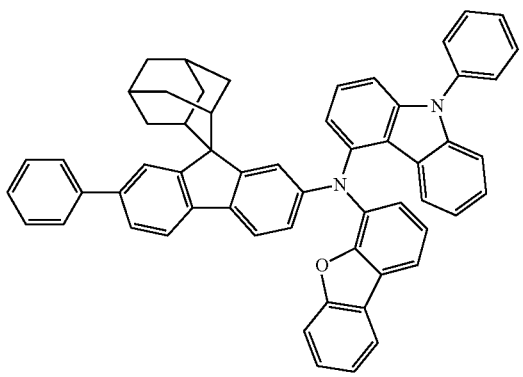

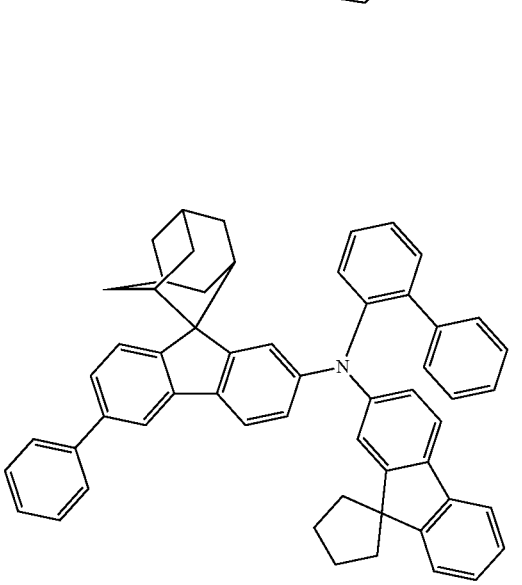

or

-continued

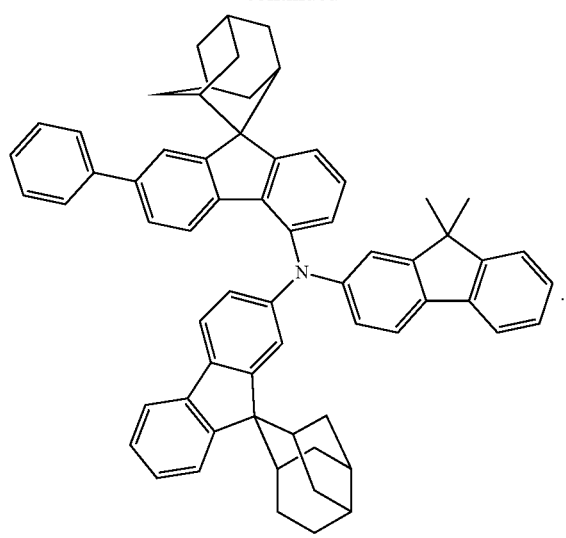

2. The nitrogen-containing compound according to claim 1, wherein $R_1$ is selected from deuterium, halogen group, methyl, ethyl, tert-butyl or the group consisting of the following groups:

-continued

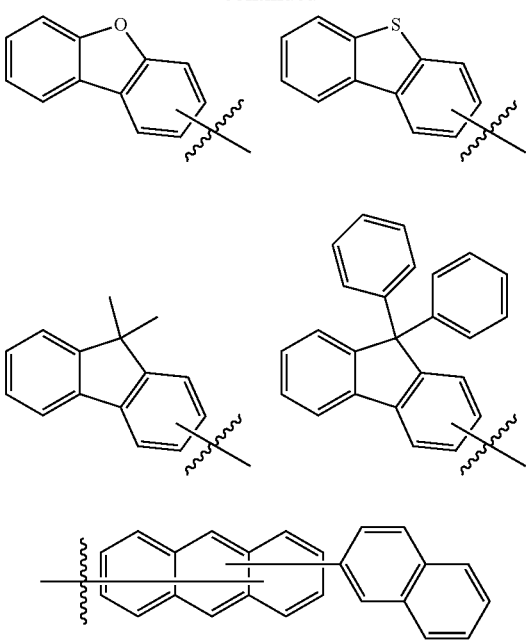

3. The nitrogen-containing compound according to claim 1, wherein $R_2$ is selected from deuterium, halogen group, methyl, ethyl, tert-butyl or the group consisting of the following groups:

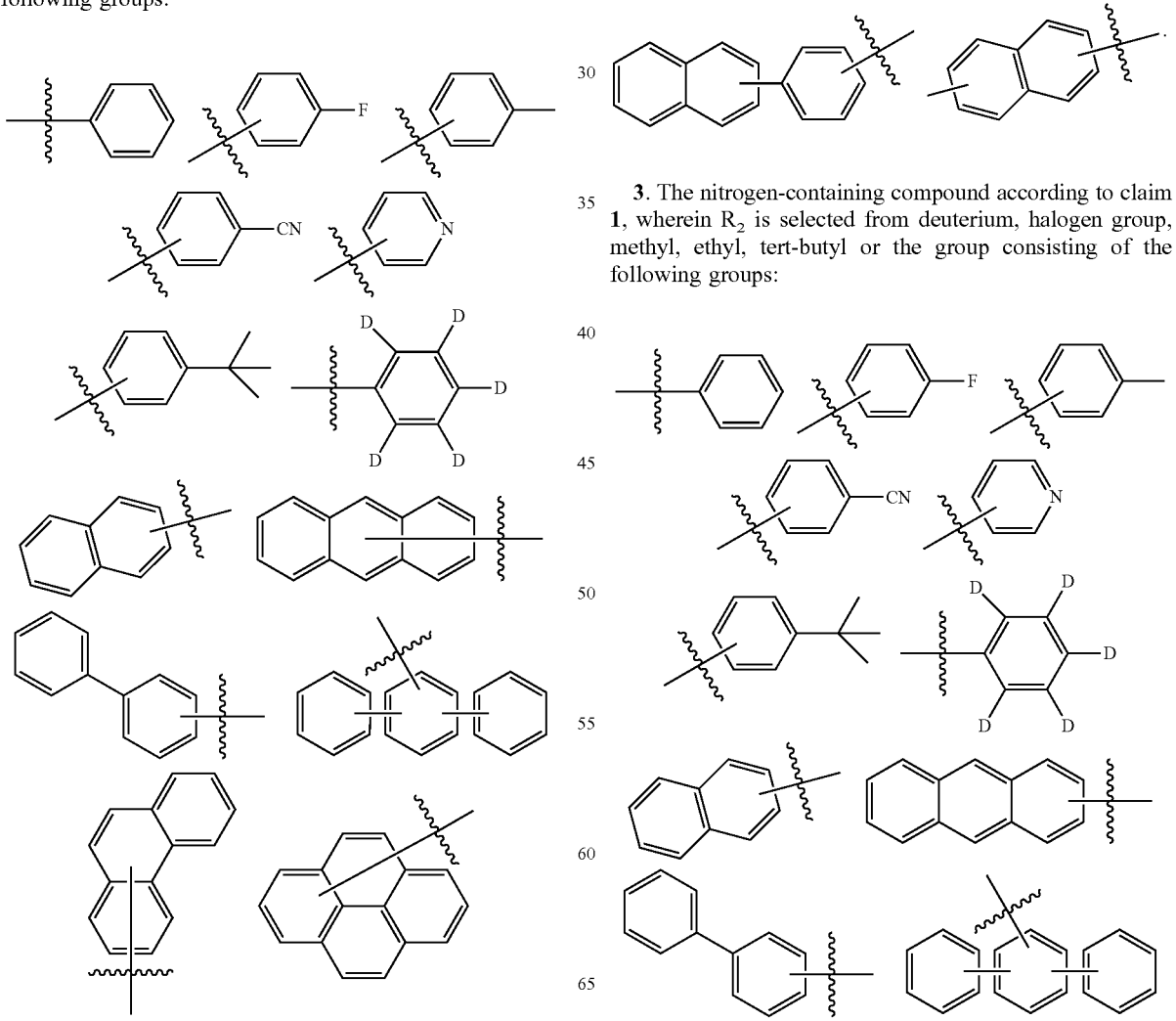

187
-continued
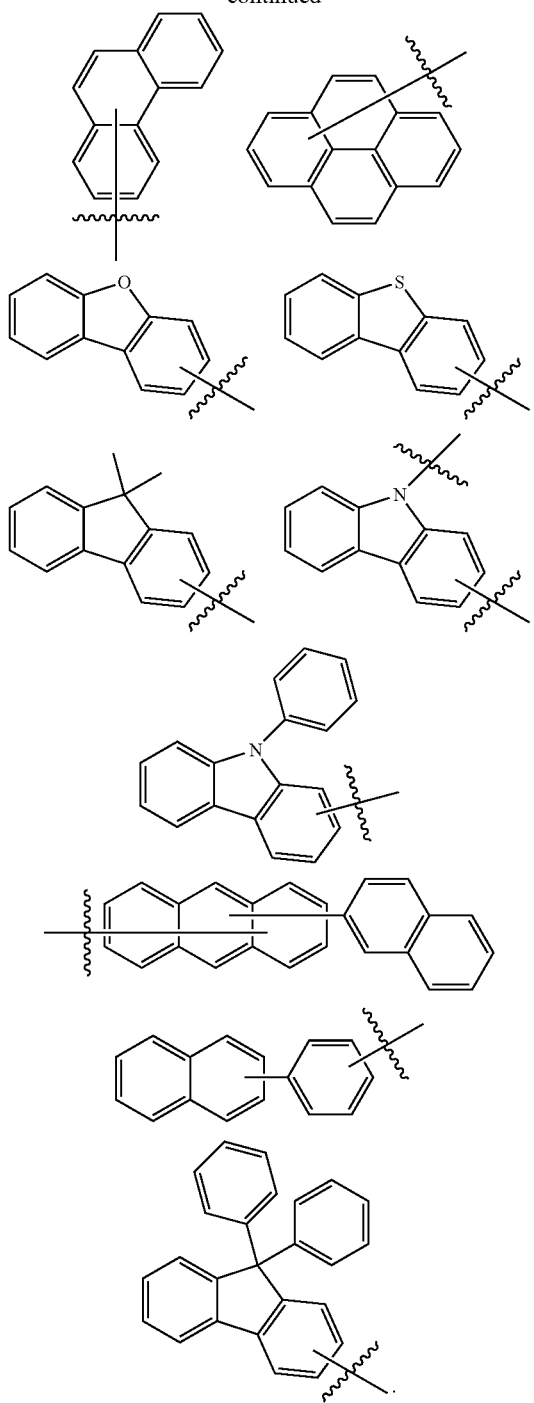
4. The nitrogen-containing compound according to claim 1, wherein Ar₁ and Ar₂ are the same or different, and are independently selected from the group consisting of the following groups:
188
-continued
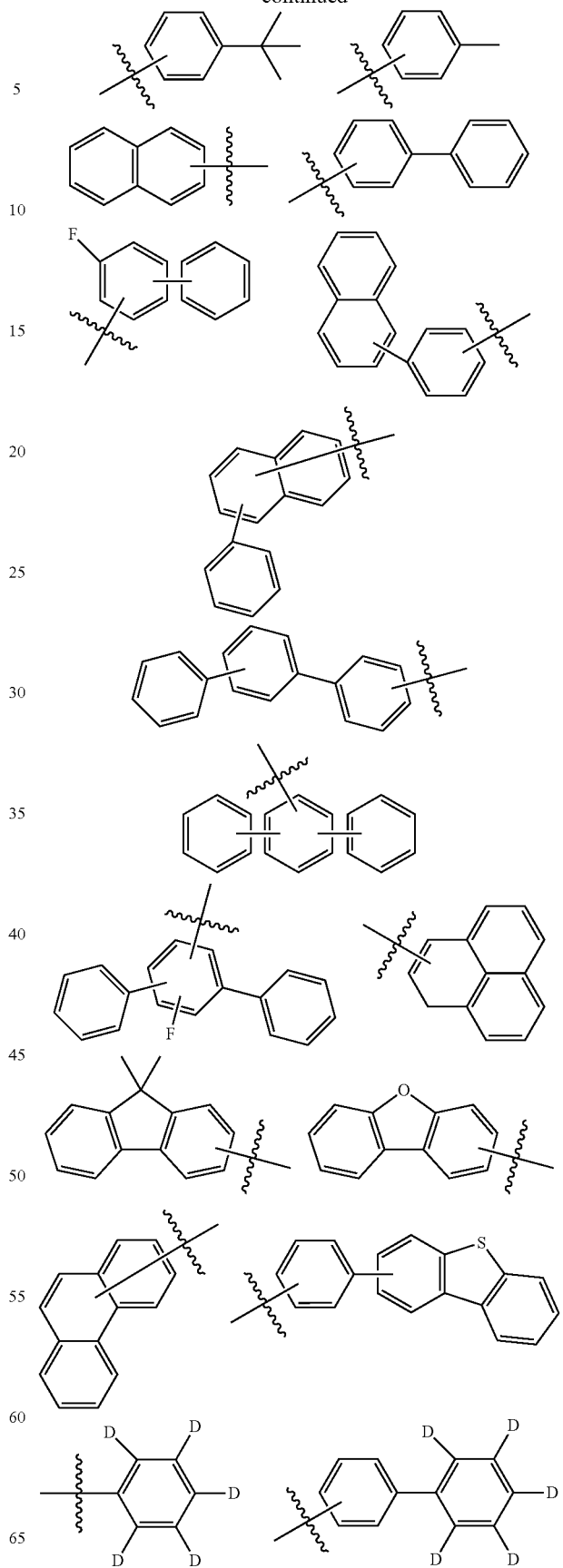
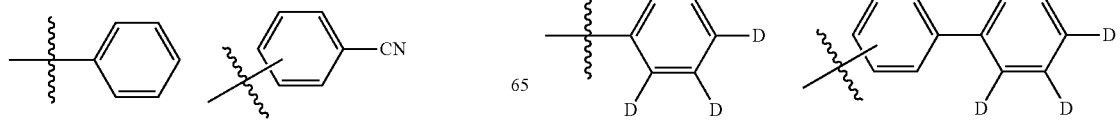

189
-continued
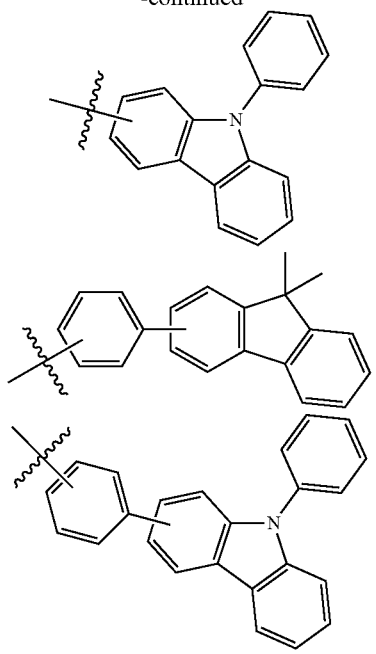
190
-continued
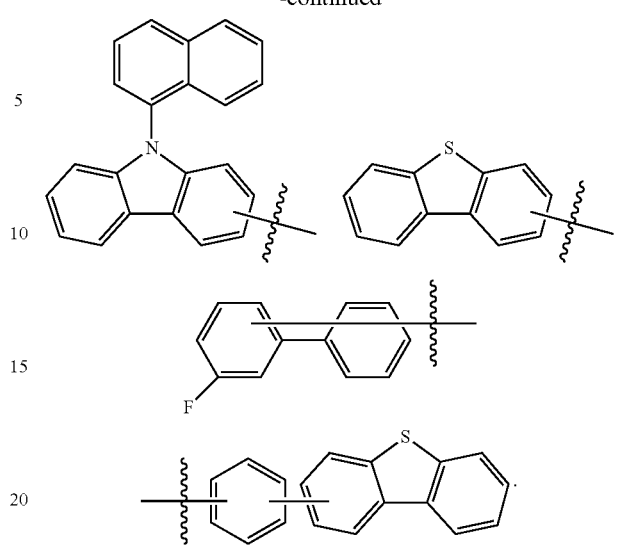
5. The nitrogen-containing compound according to claim 1, wherein the nitrogen-containing compound is selected from the group consisting of the following compounds:
11
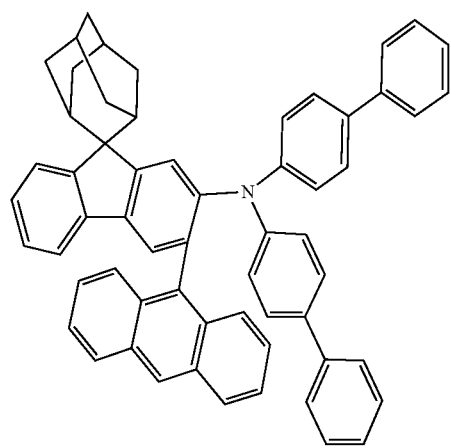
12
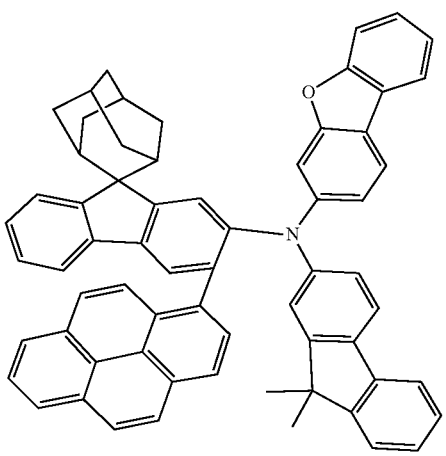
13
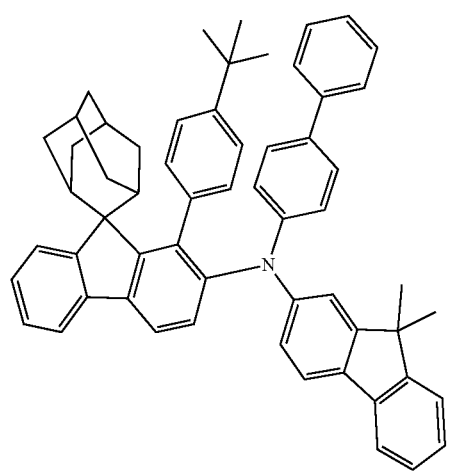
14
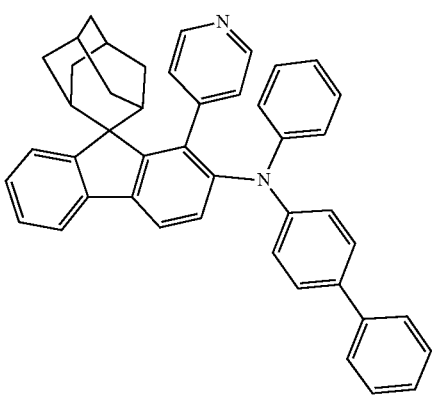

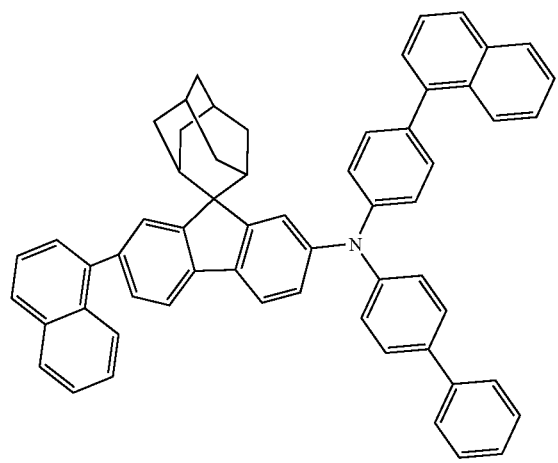
15
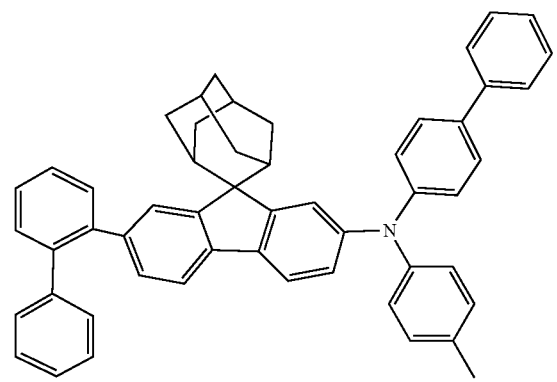
16
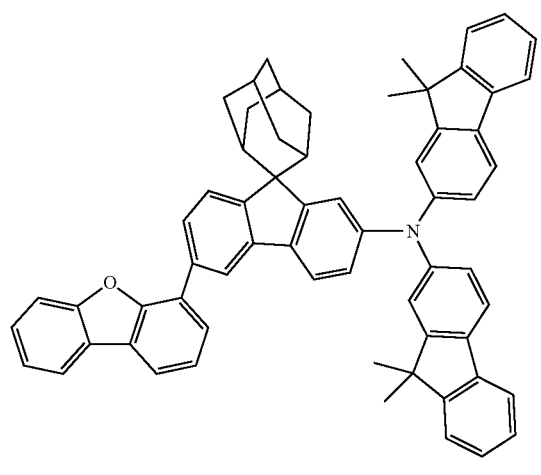
17
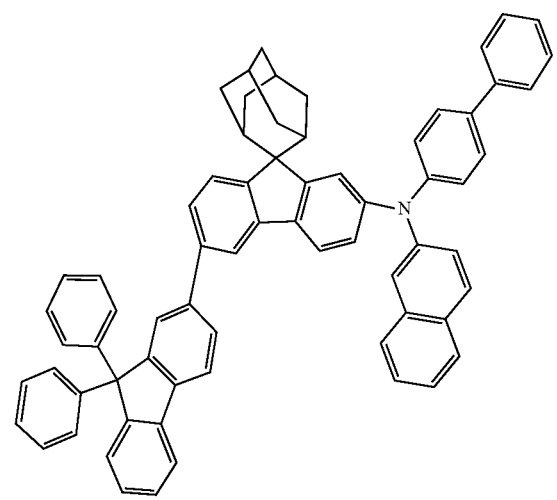
18
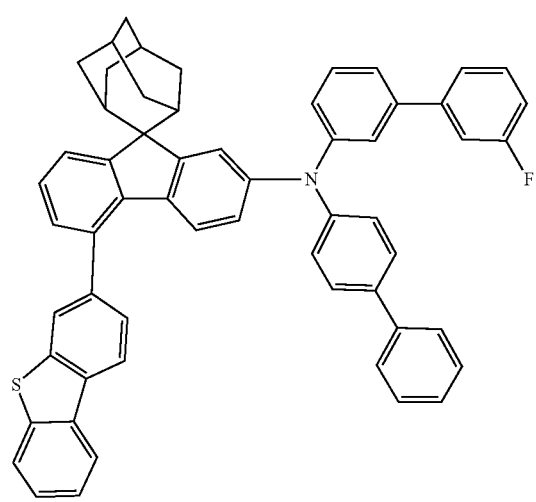
19
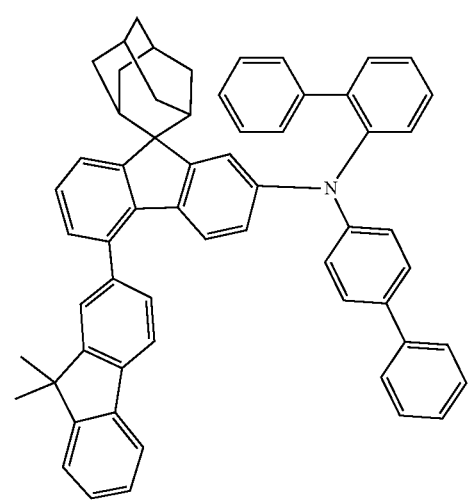
20

-continued
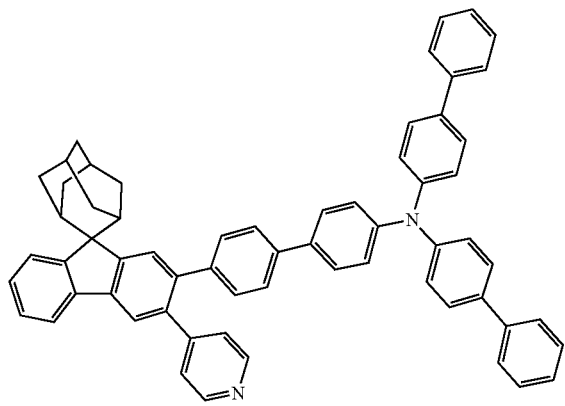
22
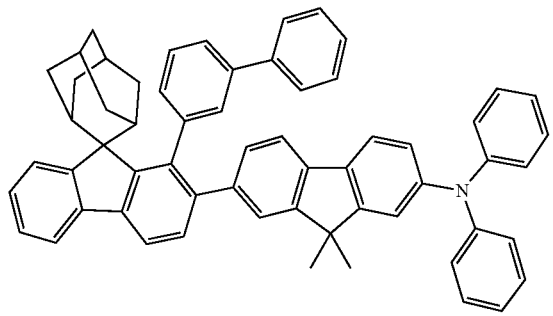
23
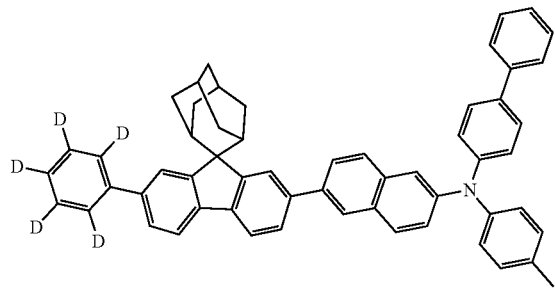
24
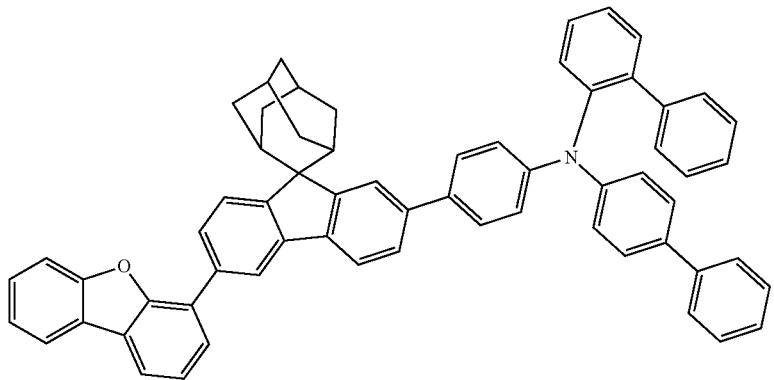
25
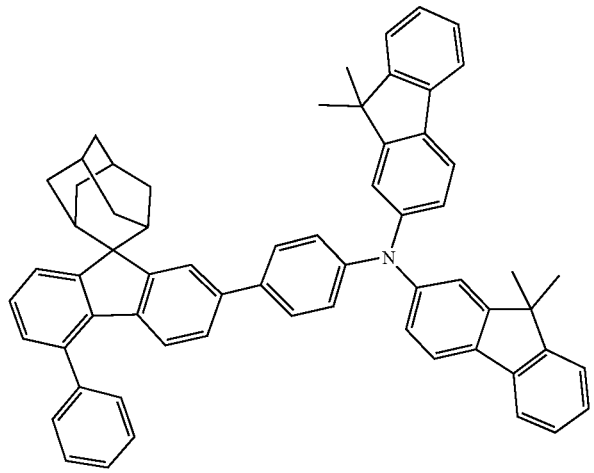
26

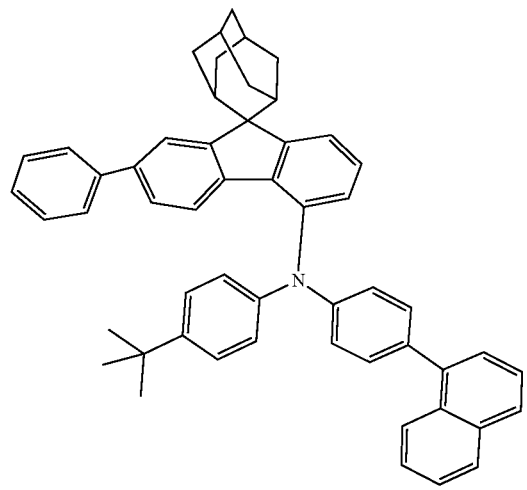
47
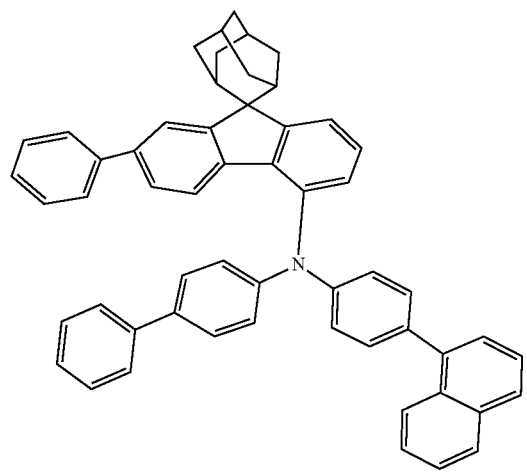
48
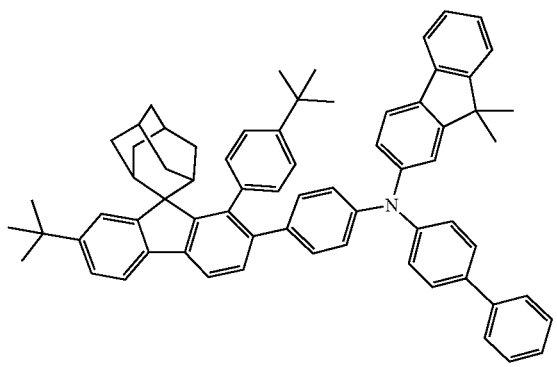
49
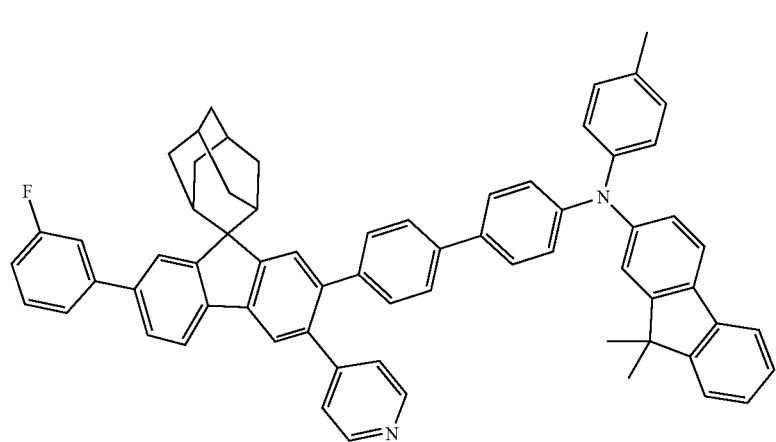
52

-continued
53
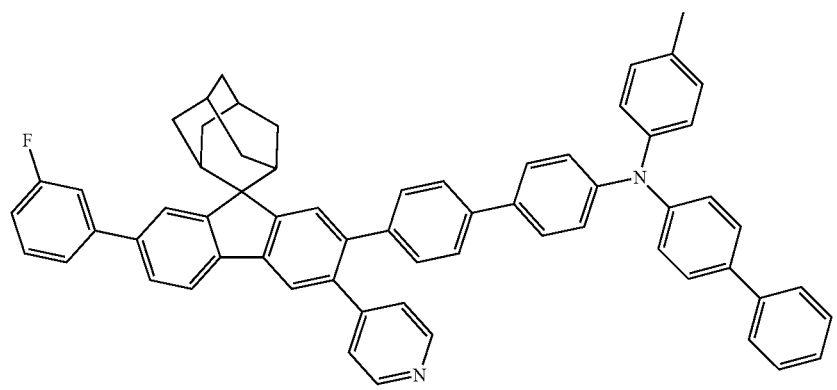
54
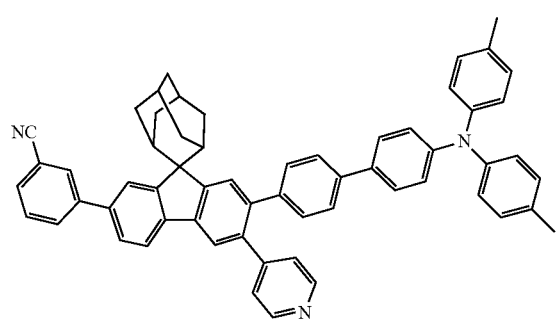
58
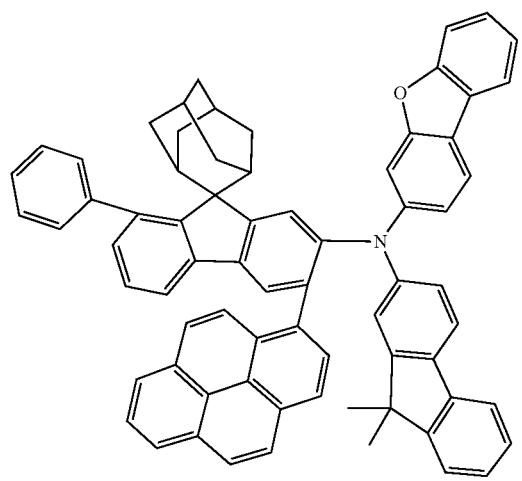
59
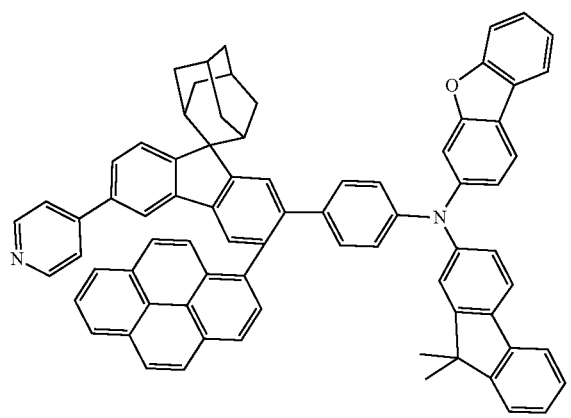

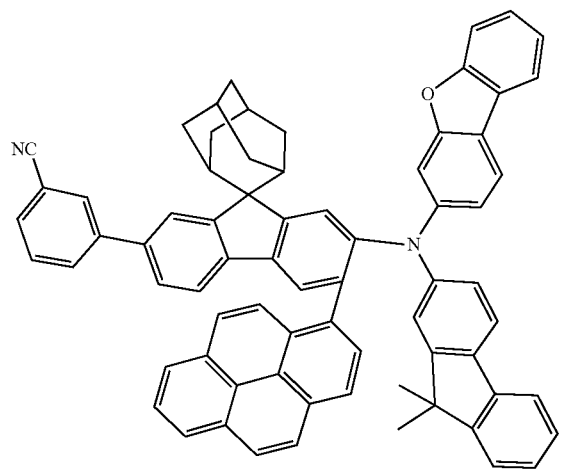
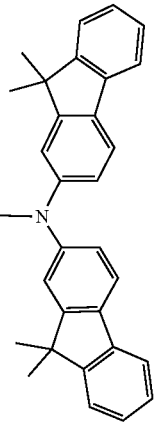
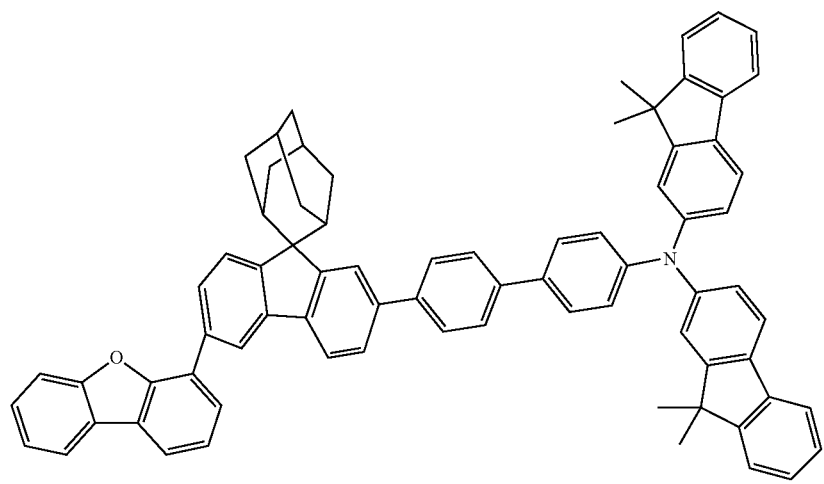
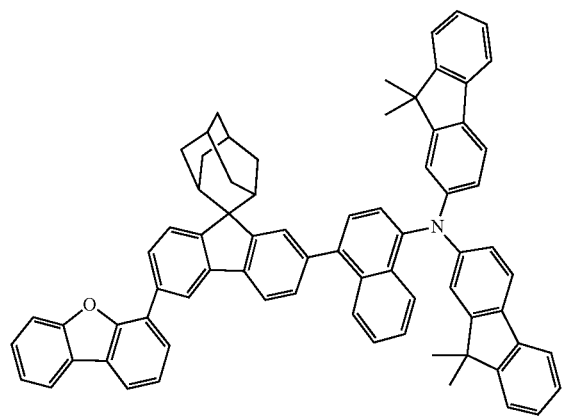

201 202
-continued
| 65 | 66 |
|---|---|
| 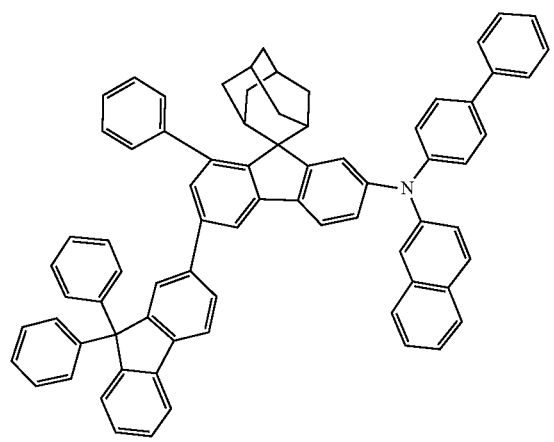 | 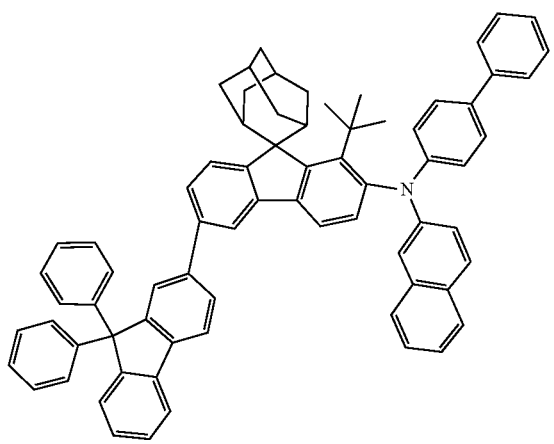 |
76
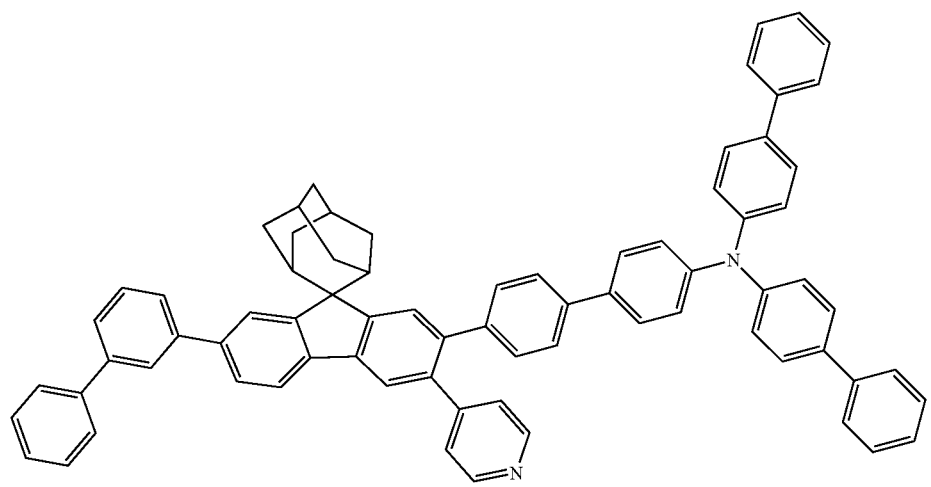
77
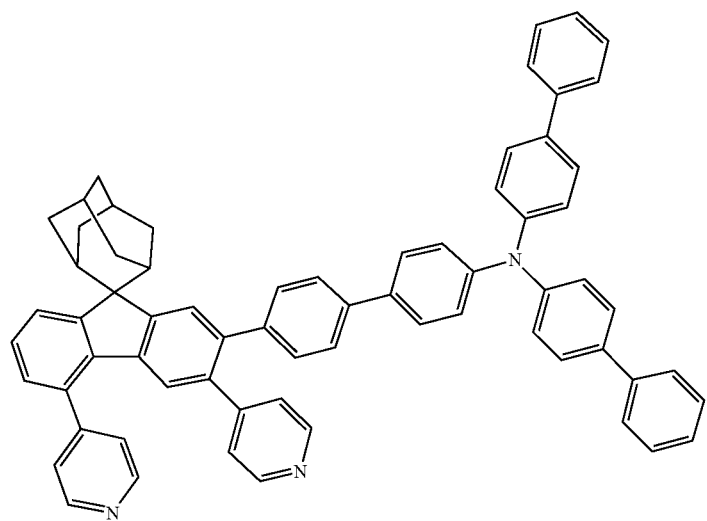

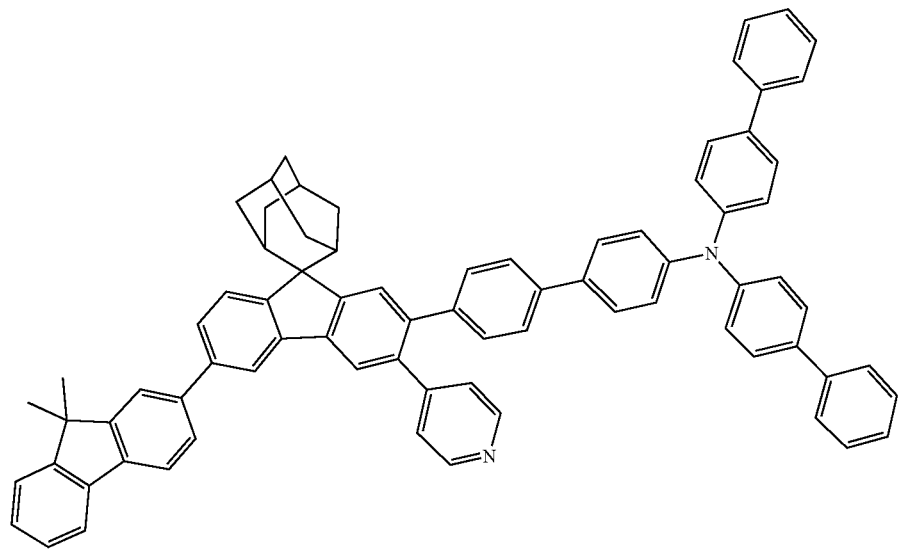
78
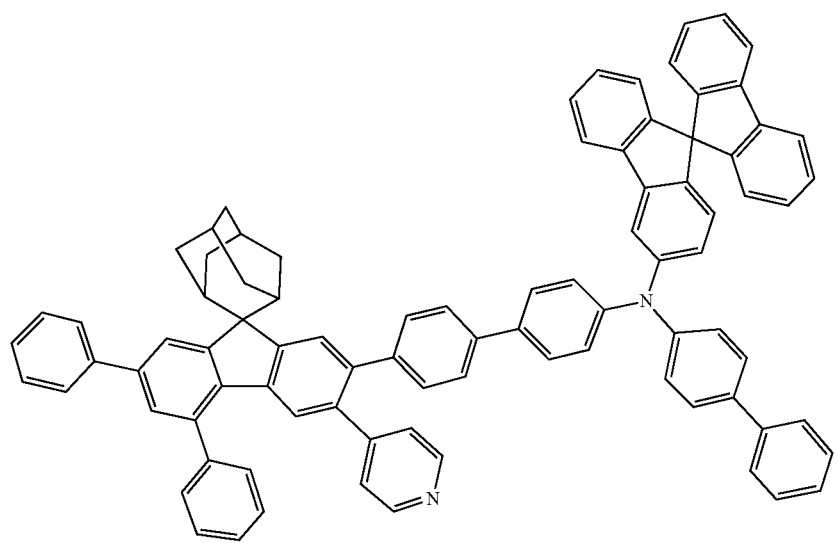
79
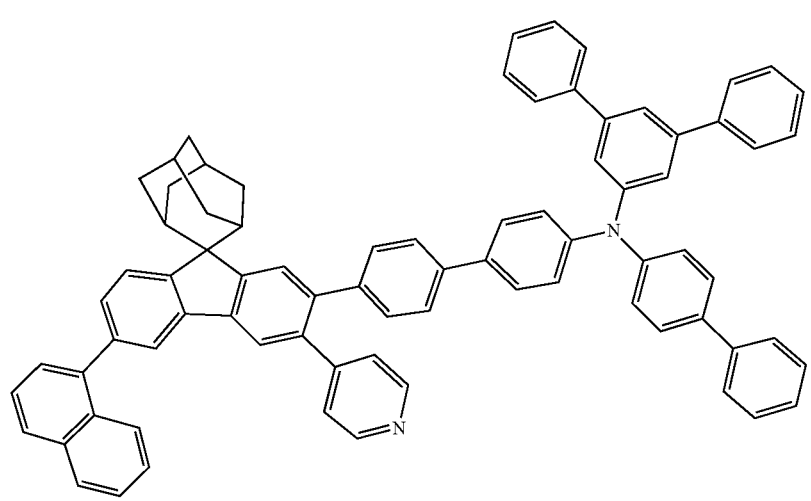
80

81
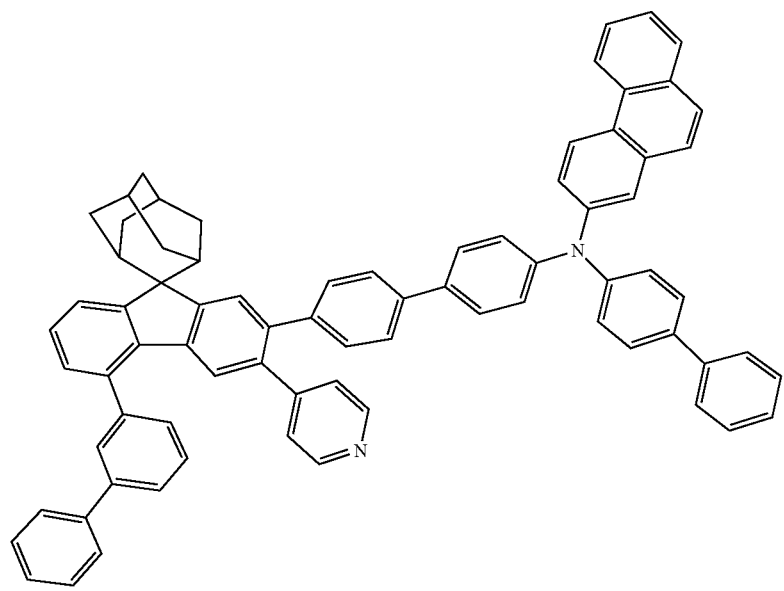
82
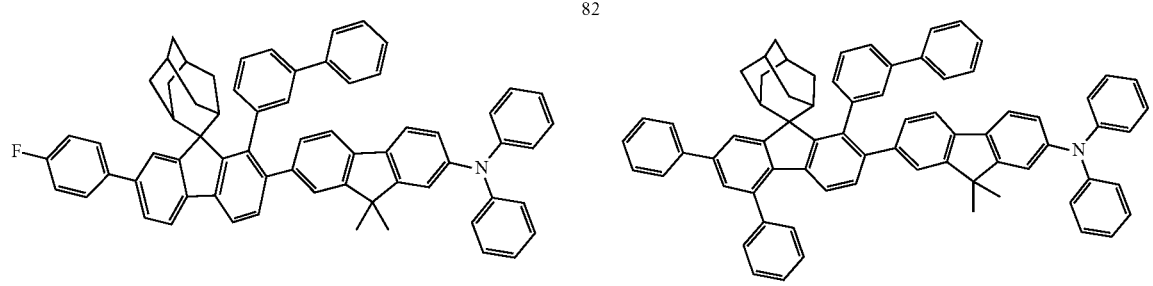
83
85
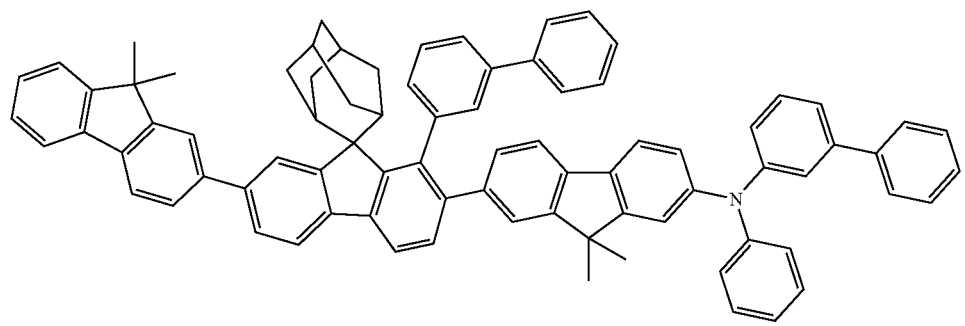
87
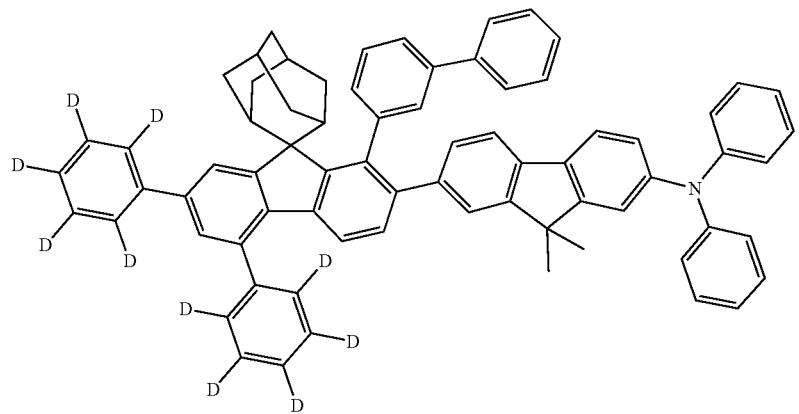

-continued
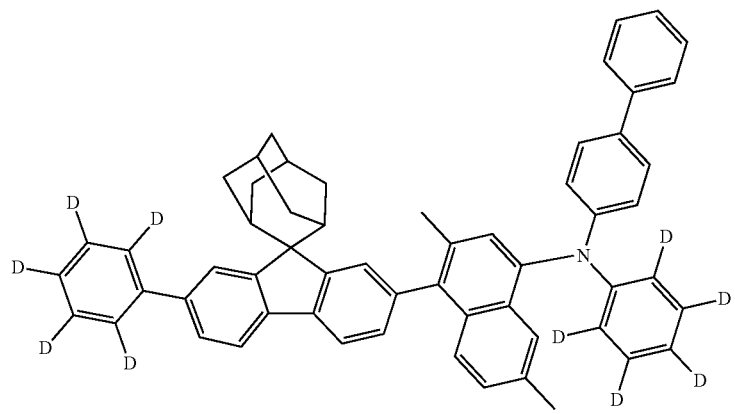
88
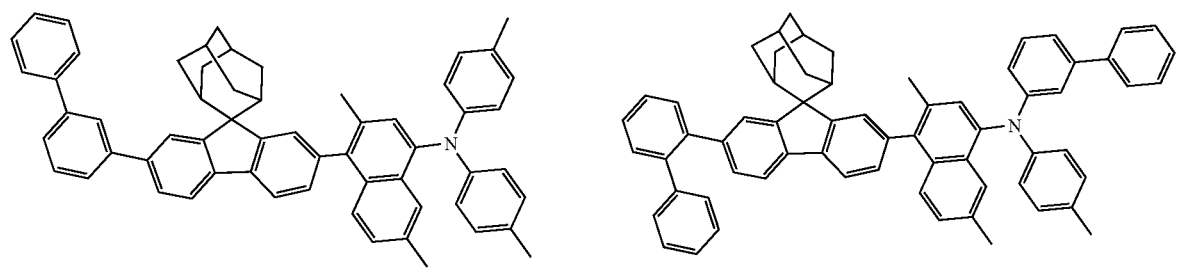
89  90
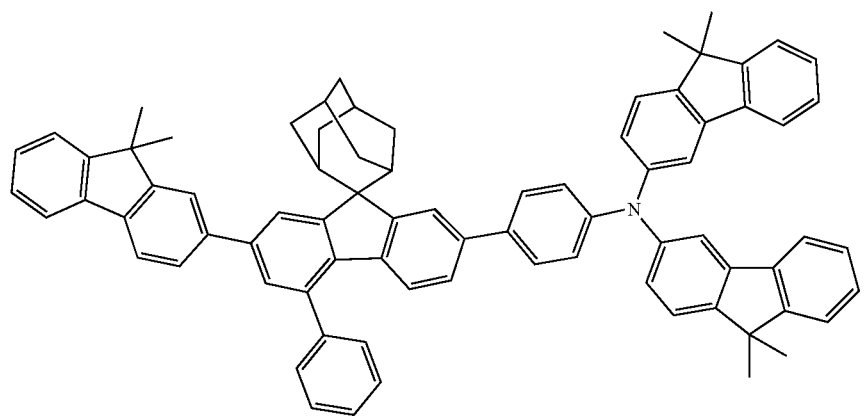
94
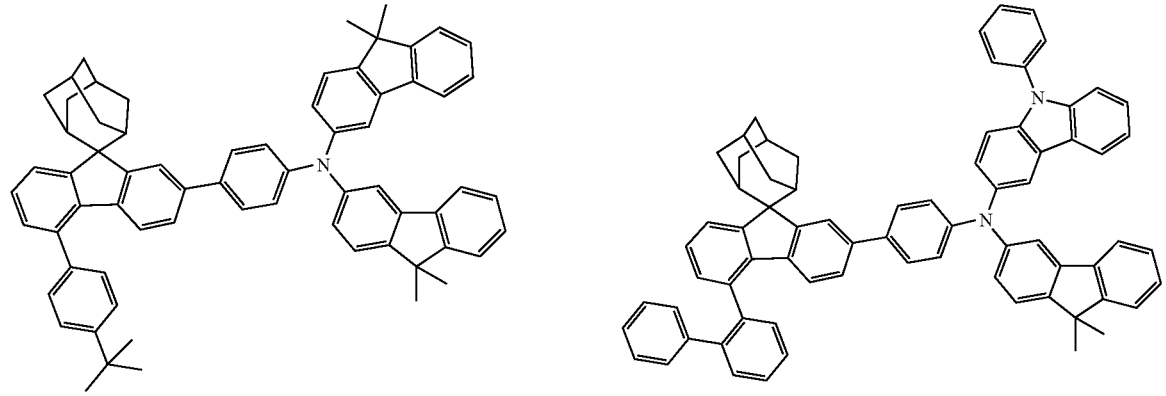
95  96

-continued
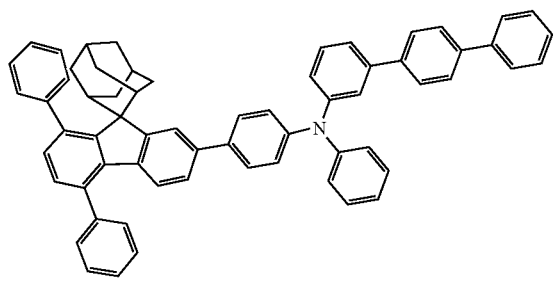
97
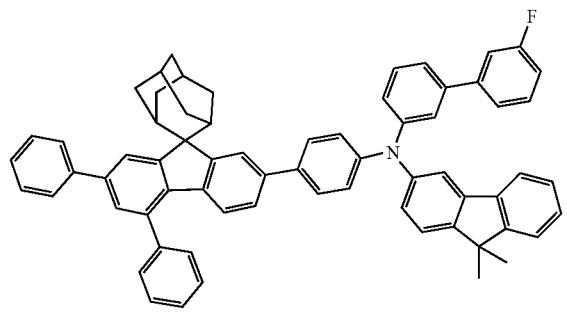
98
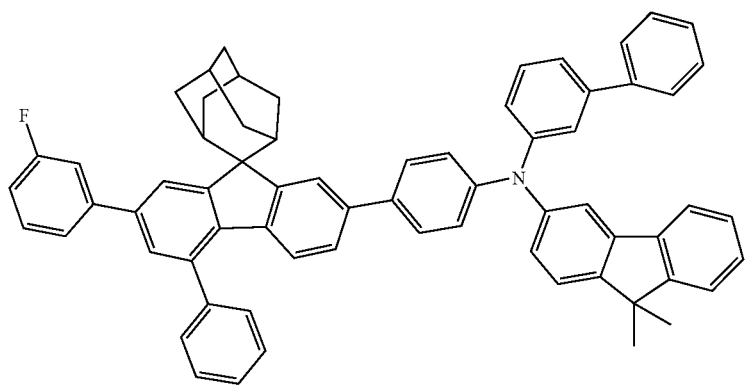
99
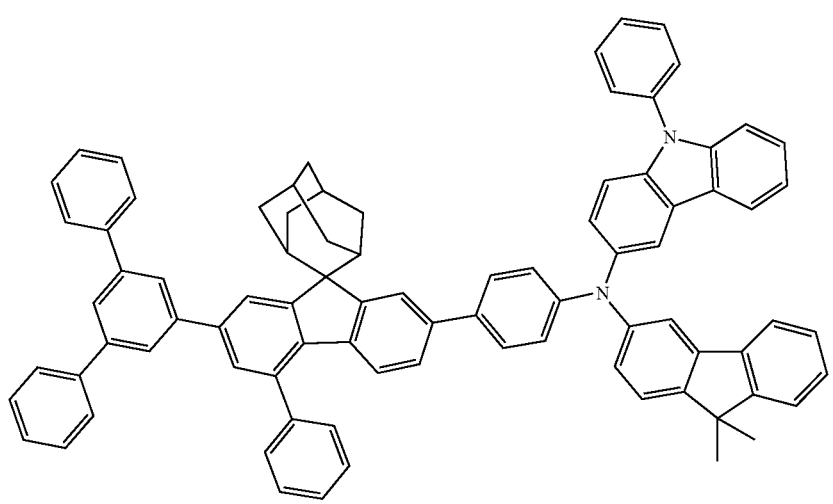
100

-continued
211
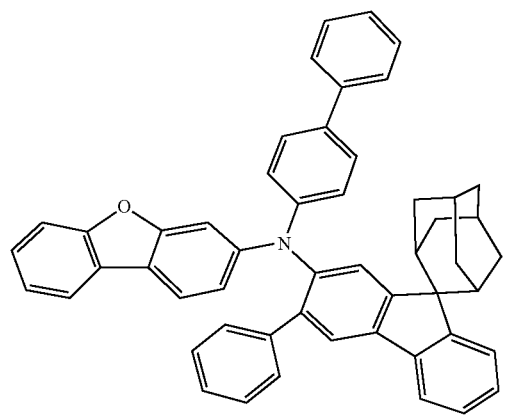
101
212
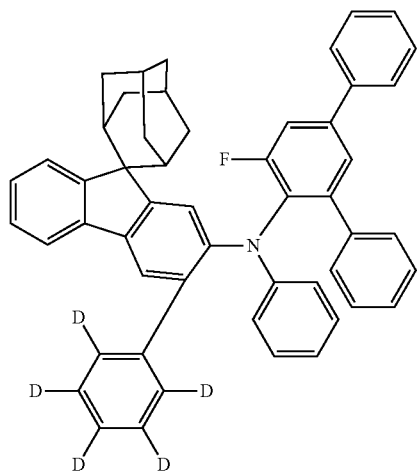
102
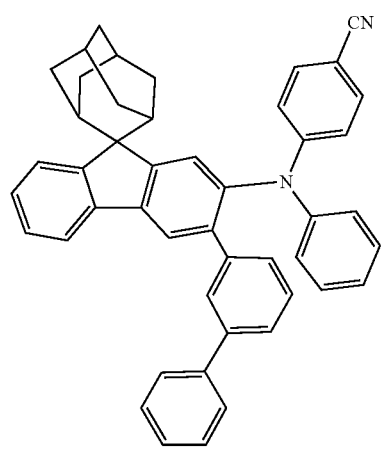
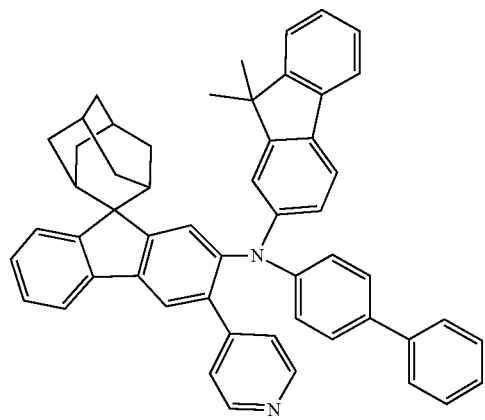
103 104
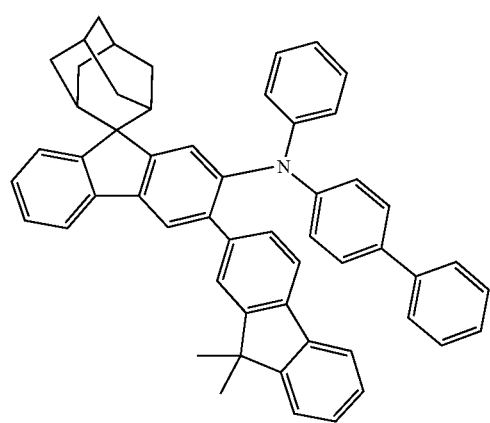
105
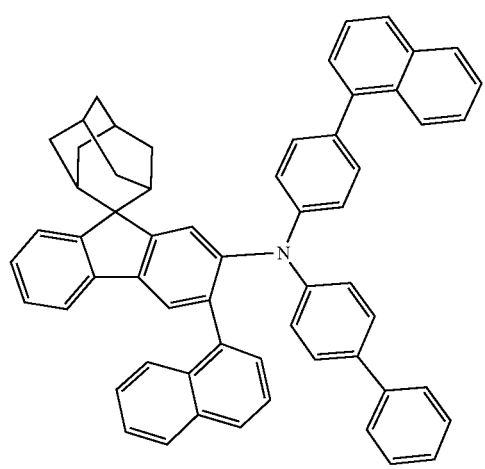
106

107
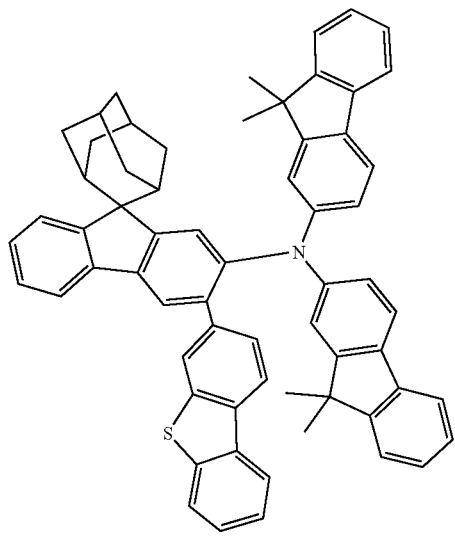
108
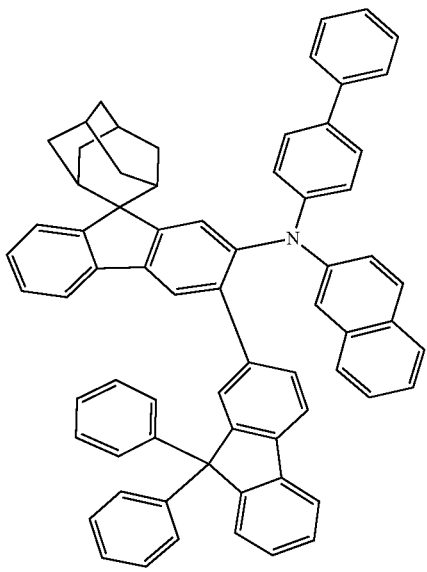
109
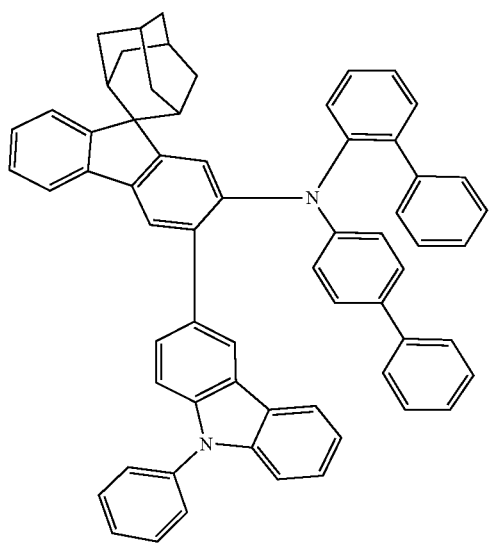
110
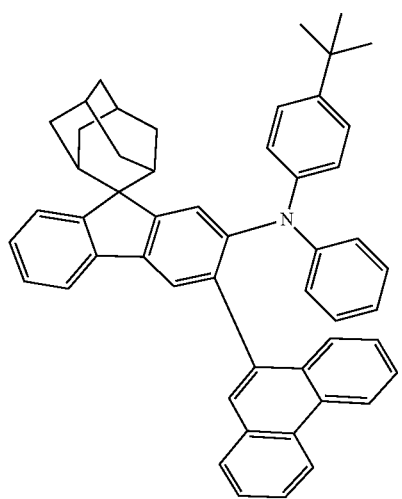
111
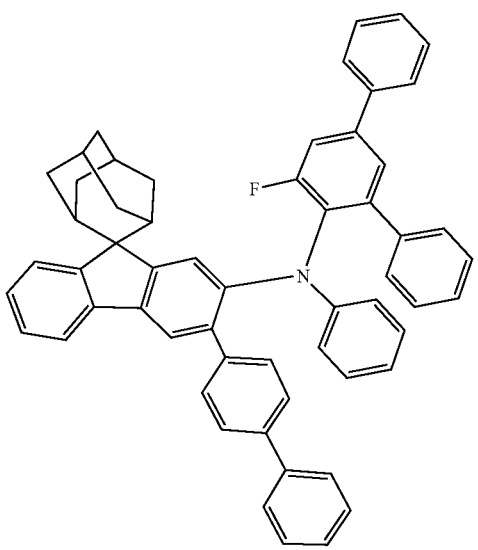
112

-continued
116
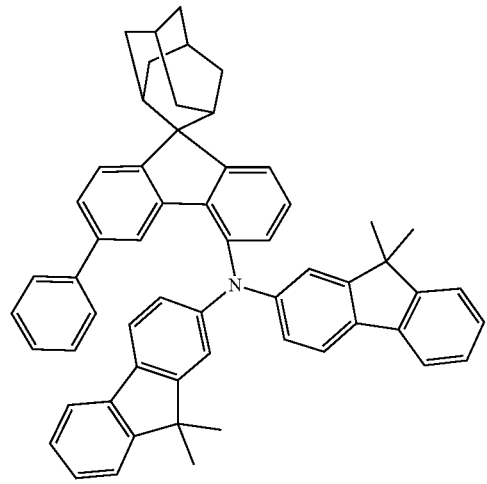
120
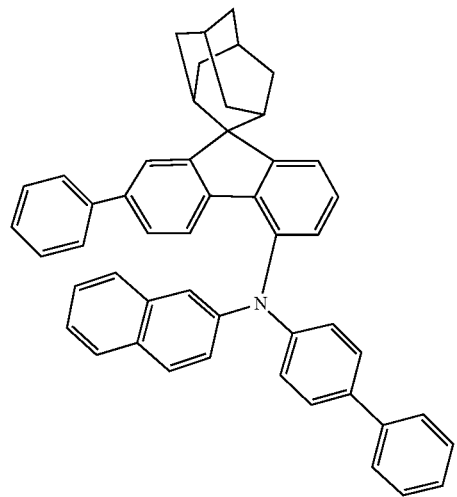
125
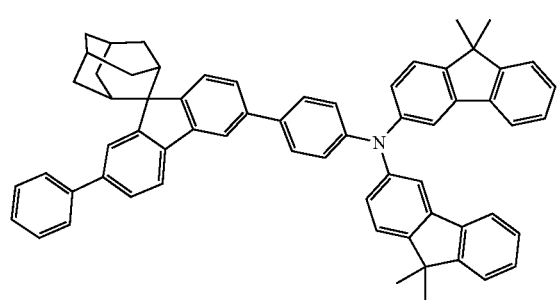
126
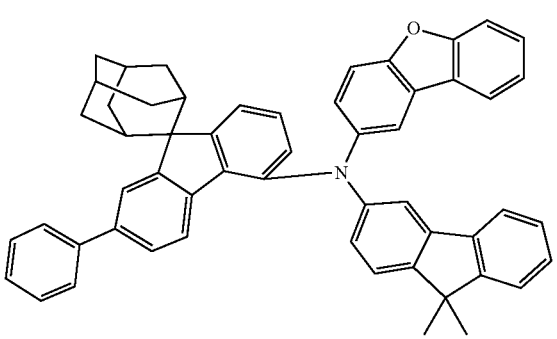
127
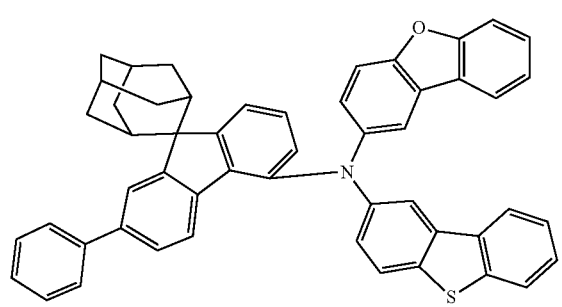
128
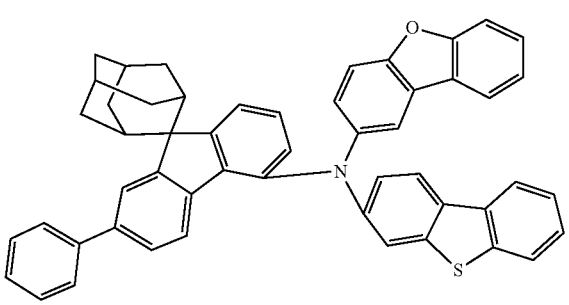

-continued
129
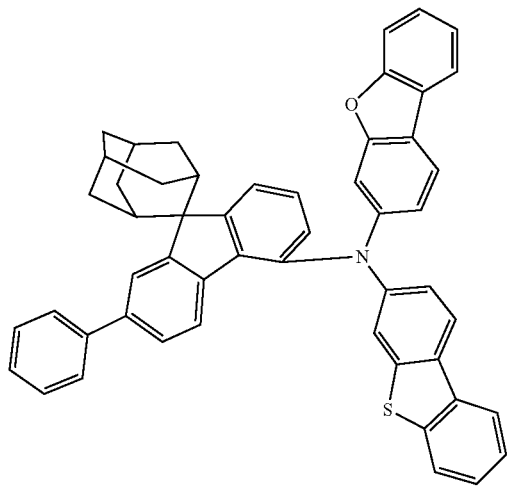
130
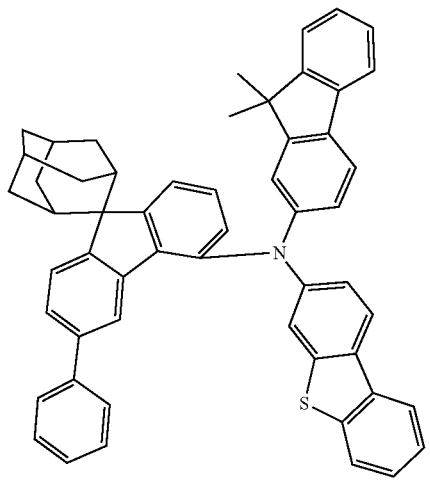
131
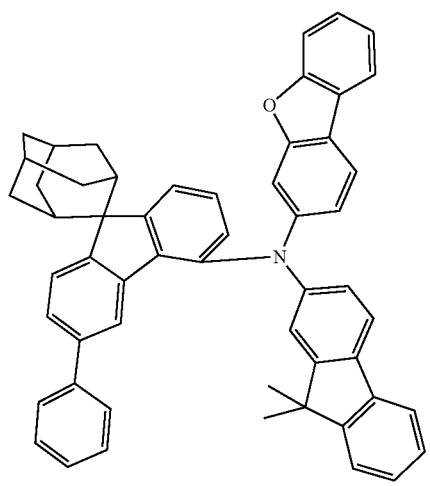
132'
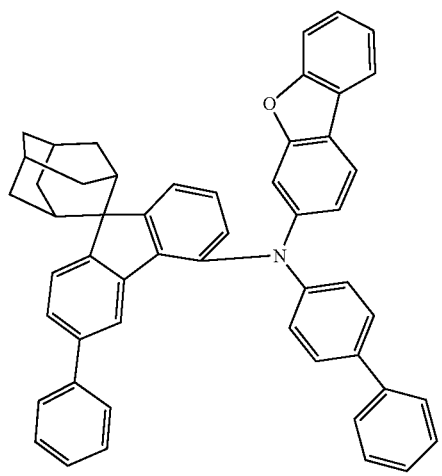
133
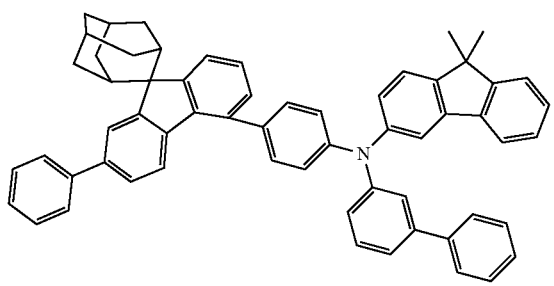

-continued
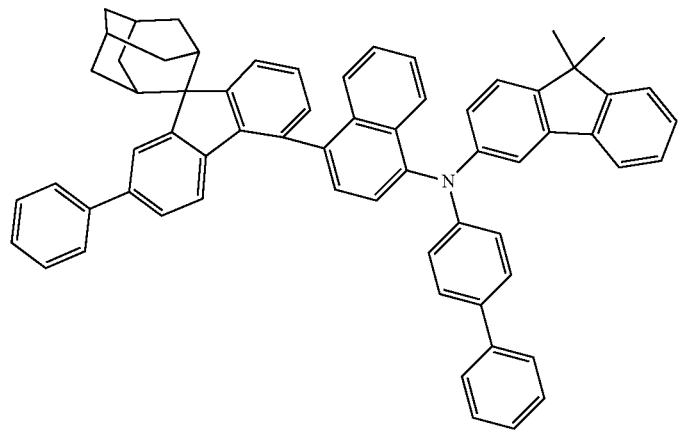
133'
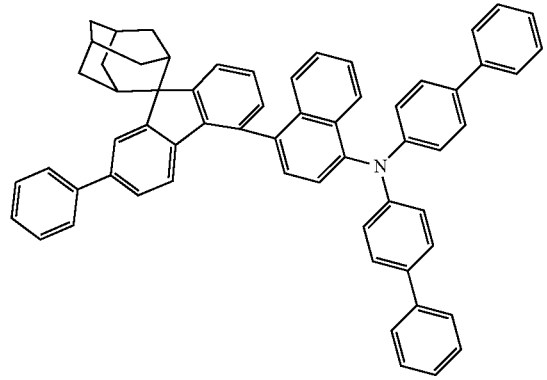
134
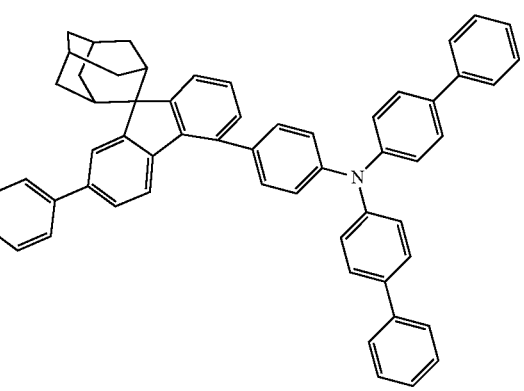
135
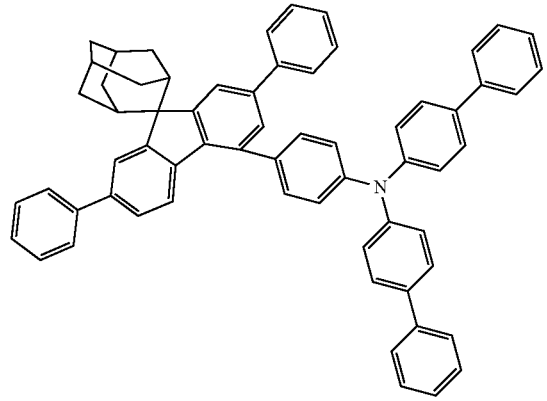
136
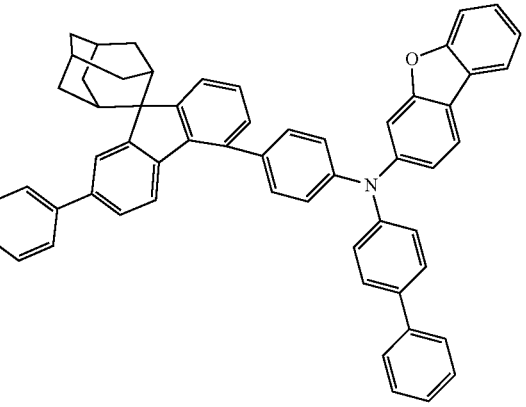
137
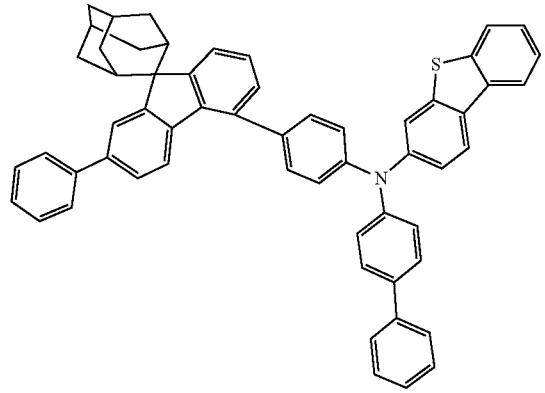
138
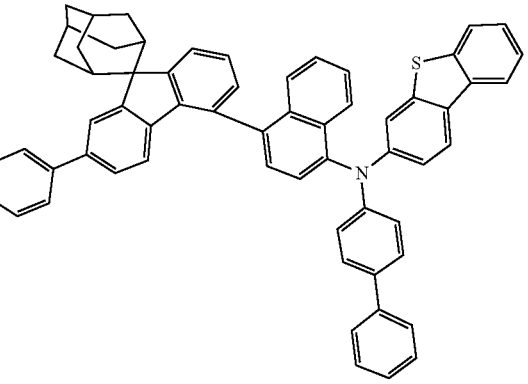
139

-continued

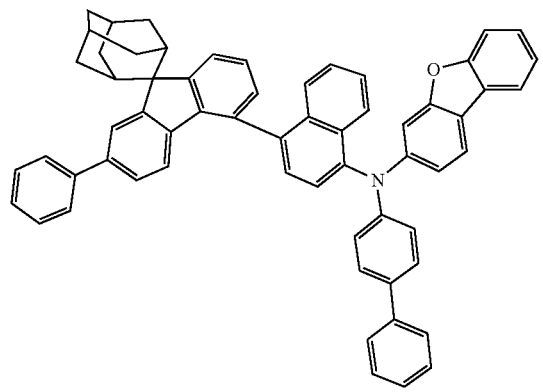
140

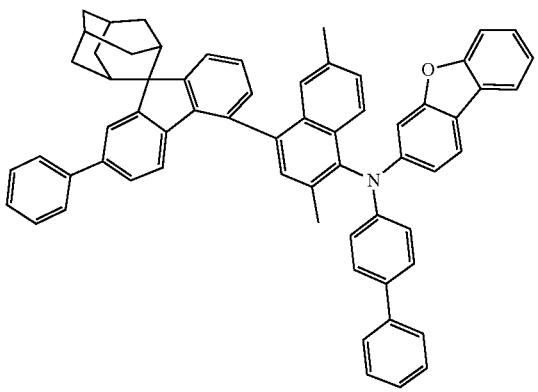
141

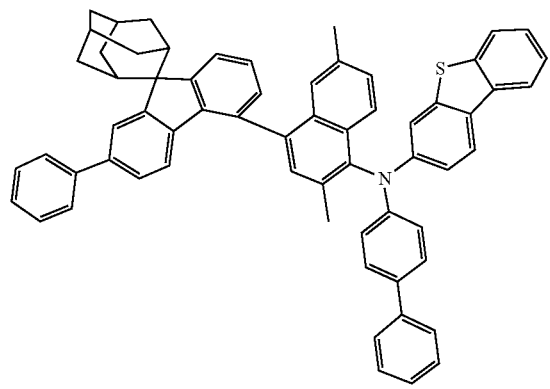
142

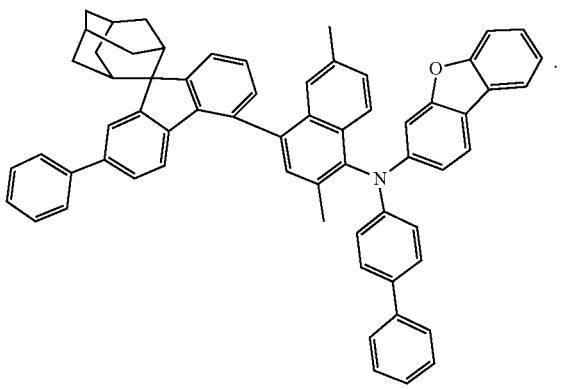
143

6. An electronic element, comprising an anode, a cathode which is disposed oppositely to the anode, and a functional layer disposed between the anode and the cathode; wherein the functional layer contains the nitrogen-containing compound according to claim 1.

7. The electronic element according to claim 6, wherein the electronic element is an organic electroluminescent device or a photoelectric conversion device.

8. An electronic device, comprising the electronic element according to claim 6.

9. The electronic element according to claim 6, wherein the functional layer comprises an electron blocking layer, and the electron blocking layer comprises the nitrogen-containing compound.

10. The electronic element according to claim 7, wherein the organic electroluminescent device is a green organic electroluminescent device or a blue organic electroluminescent device.

* * * * *